(12) United States Patent
Verdine et al.

(10) Patent No.: US 9,744,183 B2
(45) Date of Patent: Aug. 29, 2017

(54) NUCLEIC ACID PRODRUGS AND METHODS OF USE THEREOF

(75) Inventors: Gregory L. Verdine, Boston, MA (US); Meena ., Belmont, MA (US); Naoki Iwamoto, Brighton, MA (US)

(73) Assignee: WAVE LIFE SCIENCES LTD., Singapore (SG)

( * ) Notice: Subject to any disclaimer, the term of this patent is extended or adjusted under 35 U.S.C. 154(b) by 0 days.

(21) Appl. No.: 13/381,323

(22) PCT Filed: Jul. 6, 2010

(86) PCT No.: PCT/US2010/041068
§ 371 (c)(1),
(2), (4) Date: Aug. 23, 2012

(87) PCT Pub. No.: WO2011/005761
PCT Pub. Date: Jan. 13, 2011

(65) Prior Publication Data
US 2012/0316224 A1    Dec. 13, 2012

Related U.S. Application Data

(60) Provisional application No. 61/223,369, filed on Jul. 6, 2009, provisional application No. 61/242,722, filed on Sep. 15, 2009.

(51) Int. Cl.
*A61K 31/70* (2006.01)
*C07F 9/655* (2006.01)
*C07H 21/00* (2006.01)

(52) U.S. Cl.
CPC .......... *A61K 31/70* (2013.01); *C07F 9/65515* (2013.01); *C07H 21/00* (2013.01)

(58) Field of Classification Search
CPC ...................................... C07H 21/00
See application file for complete search history.

(56) References Cited

U.S. PATENT DOCUMENTS

| | | |
|---|---|---|
| 2,878,264 A | 3/1959 | Lunsford |
| 3,484,473 A | 12/1969 | Buckman et al. |
| 3,687,808 A | 8/1972 | Merigan et al. |
| 3,745,162 A | 7/1973 | Helsley |
| 4,022,791 A | 5/1977 | Welch, Jr. |
| 4,113,869 A | 9/1978 | Gardner |
| 4,415,732 A | 11/1983 | Caruthers et al. |
| 4,458,066 A | 7/1984 | Caruthers et al. |
| 4,500,707 A | 2/1985 | Caruthers et al. |
| 4,542,142 A | 9/1985 | Martel et al. |
| 4,659,774 A | 4/1987 | Webb et al. |
| 4,663,328 A | 5/1987 | Lafon |
| 4,668,777 A | 5/1987 | Caruthers et al. |
| 4,725,677 A | 2/1988 | Koster et al. |
| 4,735,949 A | 4/1988 | Domagala et al. |
| 4,840,956 A | 6/1989 | Domagala et al. |
| 4,845,205 A | 7/1989 | Huynh Dinh et al. |
| 4,923,901 A | 5/1990 | Koester et al. |
| 4,973,679 A | 11/1990 | Caruthers et al. |
| 4,981,957 A | 1/1991 | Lebleu et al. |
| 5,047,524 A | 9/1991 | Andrus et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| 5,141,813 A | 8/1992 | Nelson |
| 5,151,510 A | 9/1992 | Stec et al. |
| 5,175,273 A | 12/1992 | Bischofberger et al. |
| 5,212,295 A | 5/1993 | Cook |
| 5,262,530 A | 11/1993 | Andrus et al. |
| 5,292,875 A | 3/1994 | Stec et al. |
| 5,319,080 A | 6/1994 | Leumann |
| 5,359,044 A | 10/1994 | Cook et al. |
| 5,367,066 A | 11/1994 | Urdea et al. |
| 5,432,272 A | 7/1995 | Benner |
| 5,457,187 A | 10/1995 | Gmeiner et al. |
| 5,457,191 A | 10/1995 | Cook et al. |
| 5,459,255 A | 10/1995 | Cook et al. |
| 5,484,908 A | 1/1996 | Froehler et al. |
| 5,502,177 A | 3/1996 | Matteucci et al. |
| 5,506,212 A | 4/1996 | Hoke et al. |
| 5,512,668 A | 4/1996 | Stec et al. |
| 5,521,302 A | 5/1996 | Cook |
| 5,525,711 A | 6/1996 | Hawkins et al. |
| 5,552,540 A | 9/1996 | Haralambidis |
| 5,576,302 A | 11/1996 | Cook et al. |

(Continued)

FOREIGN PATENT DOCUMENTS

| | | |
|---|---|---|
| CN | 1345328 A | 4/2002 |
| DE | 1144279 B | 2/1963 |
| DE | 133885 A1 | 1/1979 |
| EA | 008940 B1 | 10/2007 |
| EP | 0 002 322 A2 | 6/1979 |
| EP | 192521 A1 | 8/1986 |
| EP | 269258 A2 | 6/1988 |
| EP | 0506242 A1 | 9/1992 |
| EP | 0531447 A1 | 3/1993 |
| EP | 0604409 A1 | 7/1994 |

(Continued)

OTHER PUBLICATIONS

Poijarvi. Nucleosides, Nucleotides & Nucleic Acids, 2001, 20 (1 & 2), 77-91.*
Adams, S.P. et al., Hindered dialkylamino nucleoside phosphite reagents in the synthesis of two DNA 51-mers, Journal of the American Chemical Society, 105:661-663 (1983).
Agrawal, S. and Tang, J.Y., GEM 91—an antisense oligonucleotide phosphorothioate as a therapeutic agent for AIDS, Antisense Research and Development, 2(4):261-266 (1992).
Altschul, S.F. et al., Basic local alignment search tool, Journal of Molecular Biology, 215(3):403-410 (1990).

(Continued)

*Primary Examiner* — Noble Jarrell
(74) *Attorney, Agent, or Firm* — Choate, Hall & Stewart LLP; Brenda Herschbach Jarrell; Danielle M. Nihan

(57) ABSTRACT

Described herein are nucleic acid prodrugs and nucleic acid prodrugs comprising chiral phosphorous moieties. Also described herein are methods of making and using nucleic acid prodrugs and nucleic acid prodrugs comprising chiral phosphorous moieties.

23 Claims, 6 Drawing Sheets

(56) References Cited

U.S. PATENT DOCUMENTS

| | | |
|---|---|---|
| 5,587,361 A | 12/1996 | Cook et al. |
| 5,587,469 A | 12/1996 | Cook et al. |
| 5,594,121 A | 1/1997 | Froehler et al. |
| 5,596,091 A | 1/1997 | Switzer |
| 5,599,797 A | 2/1997 | Cook et al. |
| 5,607,923 A | 3/1997 | Cook et al. |
| 5,614,617 A | 3/1997 | Cook et al. |
| 5,620,963 A | 4/1997 | Cook et al. |
| 5,635,488 A | 6/1997 | Cook et al. |
| 5,643,889 A | 7/1997 | Suhadolnik et al. |
| 5,643,989 A | 7/1997 | Van De Grampel et al. |
| 5,646,267 A | 7/1997 | Stec et al. |
| 5,654,284 A | 8/1997 | Cook et al. |
| 5,661,134 A | 8/1997 | Cook et al. |
| 5,681,940 A | 10/1997 | Wang et al. |
| 5,681,941 A | 10/1997 | Cook et al. |
| 5,708,161 A | 1/1998 | Reese |
| 5,712,378 A | 1/1998 | Wang |
| 5,734,041 A | 3/1998 | Just et al. |
| 5,750,692 A | 5/1998 | Cook et al. |
| 5,795,765 A | 8/1998 | Izu et al. |
| 5,824,503 A | 10/1998 | Kurome et al. |
| 5,851,840 A | 12/1998 | Sluka et al. |
| 5,852,188 A | 12/1998 | Cook |
| 5,856,465 A | 1/1999 | Stec et al. |
| 5,883,237 A | 3/1999 | Stec et al. |
| 5,898,031 A | 4/1999 | Crooke |
| 5,908,772 A | 6/1999 | Mitta et al. |
| 5,914,396 A | 6/1999 | Cook et al. |
| 5,932,450 A | 8/1999 | Dattagupta et al. |
| 5,936,080 A | 8/1999 | Stec et al. |
| 5,976,855 A | 11/1999 | Svendsen et al. |
| 5,998,602 A | 12/1999 | Torrence et al. |
| 6,004,813 A | 12/1999 | Serlupi-Crescenzi et al. |
| 6,015,886 A | 1/2000 | Dale et al. |
| 6,015,887 A | 1/2000 | Teng |
| 6,017,700 A | 1/2000 | Horn et al. |
| 6,031,092 A | 2/2000 | Just et al. |
| 6,056,973 A | 5/2000 | Allen et al. |
| 6,057,371 A | 5/2000 | Glennon |
| 6,066,500 A | 5/2000 | Bennett et al. |
| 6,080,543 A | 6/2000 | Engel et al. |
| 6,107,094 A | 8/2000 | Crooke |
| 6,124,445 A | 9/2000 | Imbach et al. |
| 6,140,096 A | 10/2000 | Kofod et al. |
| 6,146,829 A | 11/2000 | Cook et al. |
| 6,147,200 A | 11/2000 | Manoharan et al. |
| 6,159,728 A | 12/2000 | Stockley et al. |
| 6,160,109 A | 12/2000 | Just et al. |
| 6,166,197 A | 12/2000 | Cook et al. |
| 6,191,266 B1 | 2/2001 | Wang |
| 6,207,646 B1 | 3/2001 | Krieg et al. |
| 6,214,805 B1 | 4/2001 | Torrence et al. |
| 6,222,025 B1 | 4/2001 | Cook et al. |
| 6,235,887 B1 | 5/2001 | Froehler et al. |
| 6,239,116 B1 | 5/2001 | Krieg et al. |
| 6,239,265 B1 | 5/2001 | Cook |
| 6,242,589 B1 | 6/2001 | Cook et al. |
| 6,248,519 B1 | 6/2001 | Engel et al. |
| 6,265,172 B1 | 7/2001 | St. Clair et al. |
| 6,270,968 B1 | 8/2001 | Dalbøge et al. |
| 6,271,004 B1 | 8/2001 | Warthoe |
| 6,300,069 B1 | 10/2001 | Missel et al. |
| 6,306,627 B1 | 10/2001 | Decker |
| 6,316,024 B1 | 11/2001 | Allen et al. |
| 6,316,626 B1 | 11/2001 | Swayze et al. |
| 6,322,985 B1 | 11/2001 | Kashi et al. |
| 6,326,199 B1 | 12/2001 | Cook et al. |
| 6,339,066 B1 | 1/2002 | Bennett et al. |
| 6,344,356 B1 | 2/2002 | Stemmer |
| 6,369,209 B1 | 4/2002 | Manoharan et al. |
| 6,369,237 B1 | 4/2002 | Verdine et al. |
| 6,380,368 B1 | 4/2002 | Froehler et al. |
| 6,383,808 B1 | 5/2002 | Monia et al. |
| 6,407,223 B1 | 6/2002 | Stec et al. |
| 6,440,943 B1 | 8/2002 | Cook et al. |
| 6,451,524 B1 | 9/2002 | Ecker |
| 6,455,308 B1 | 9/2002 | Freier |
| 6,468,983 B2 | 10/2002 | Silverman et al. |
| 6,500,945 B2 * | 12/2002 | Cook .......................... 536/26.7 |
| 6,506,594 B1 | 1/2003 | Barany et al. |
| 6,506,894 B1 | 1/2003 | Reese et al. |
| 6,528,262 B1 | 3/2003 | Gilad et al. |
| 6,528,640 B1 | 3/2003 | Beigelman et al. |
| 6,538,126 B1 | 3/2003 | Cho et al. |
| 6,559,279 B1 | 5/2003 | Manoharan et al. |
| 6,562,960 B1 | 5/2003 | Baxter et al. |
| 6,582,936 B1 | 6/2003 | Serafini et al. |
| 6,608,186 B1 | 8/2003 | Miculka et al. |
| 6,610,837 B1 | 8/2003 | Guzaev et al. |
| 6,613,873 B1 | 9/2003 | Buchardt et al. |
| 6,617,438 B1 | 9/2003 | Beigelman et al. |
| 6,632,600 B1 | 10/2003 | Short |
| 6,639,062 B2 | 10/2003 | Manoharan et al. |
| 6,649,750 B1 | 11/2003 | Capaldi et al. |
| 6,682,889 B1 | 1/2004 | Wang et al. |
| 6,699,979 B2 | 3/2004 | Cook |
| 6,737,520 B2 | 5/2004 | Manoharan et al. |
| 6,762,281 B2 | 7/2004 | Manoharan et al. |
| 6,767,739 B2 | 7/2004 | Crooke et al. |
| 6,809,195 B1 | 10/2004 | Sanghvi et al. |
| 6,811,975 B2 | 11/2004 | Cook et al. |
| 6,861,518 B2 | 3/2005 | Just et al. |
| 6,867,294 B1 | 3/2005 | Sanghvi et al. |
| 6,933,146 B2 | 8/2005 | Helliwell et al. |
| 6,933,288 B2 | 8/2005 | Migawa et al. |
| 6,936,432 B2 | 8/2005 | Gopalan et al. |
| 6,949,520 B1 | 9/2005 | Hartmann et al. |
| 6,995,259 B1 | 2/2006 | Vargeese et al. |
| 7,015,315 B1 | 3/2006 | Cook et al. |
| 7,018,793 B1 | 3/2006 | Short |
| 7,019,127 B2 | 3/2006 | Reese et al. |
| 7,022,833 B2 | 4/2006 | Reese |
| 7,045,610 B2 | 5/2006 | Dempcy et al. |
| 7,049,122 B2 | 5/2006 | Chang et al. |
| 7,067,497 B2 | 6/2006 | Hanecak et al. |
| 7,101,993 B1 | 9/2006 | Cook et al. |
| 7,119,184 B2 | 10/2006 | Manoharan et al. |
| RE39,464 E | 1/2007 | Cook et al. |
| 7,160,920 B2 | 1/2007 | Garvey et al. |
| 7,205,399 B1 | 4/2007 | Vargeese et al. |
| 7,214,491 B2 | 5/2007 | Yadav et al. |
| 7,227,014 B2 | 6/2007 | Crooke et al. |
| 7,259,150 B2 | 8/2007 | Crooke et al. |
| 7,264,932 B2 | 9/2007 | Latham et al. |
| 7,271,156 B2 | 9/2007 | Krieg et al. |
| 7,288,376 B2 | 10/2007 | Sarma et al. |
| 7,303,895 B1 | 12/2007 | O'Regan et al. |
| 7,304,081 B2 | 12/2007 | Yao et al. |
| 7,381,527 B2 | 6/2008 | Sarma et al. |
| 7,399,845 B2 | 7/2008 | Seth et al. |
| 7,407,943 B2 | 8/2008 | Crooke et al. |
| 7,414,116 B2 | 8/2008 | Milton et al. |
| 7,425,545 B2 | 9/2008 | Crooke et al. |
| 7,427,672 B2 | 9/2008 | Imanishi et al. |
| 7,432,249 B2 | 10/2008 | Crooke |
| 7,432,250 B2 | 10/2008 | Crooke |
| 7,495,088 B1 | 2/2009 | Brakel et al. |
| 7,501,091 B2 | 3/2009 | Munoz et al. |
| 7,507,808 B2 | 3/2009 | Dobie |
| 7,511,131 B2 | 3/2009 | Crooke et al. |
| 7,517,520 B2 | 4/2009 | Manolova et al. |
| 7,534,879 B2 | 5/2009 | van Deutekom |
| 7,537,767 B2 | 5/2009 | Bachmann et al. |
| 7,547,684 B2 | 6/2009 | Seth et al. |
| 7,598,031 B2 | 10/2009 | Liew |
| 7,598,227 B2 | 10/2009 | Crooke et al. |
| 7,629,321 B2 | 12/2009 | Crooke |
| 7,662,558 B2 | 2/2010 | Liew |
| 7,666,854 B2 | 2/2010 | Seth et al. |
| 7,666,888 B2 | 2/2010 | Bartberger et al. |
| 7,683,036 B2 | 3/2010 | Esau et al. |
| 7,695,902 B2 | 4/2010 | Crooke |
| 7,696,345 B2 | 4/2010 | Allerson et al. |

(56) References Cited

U.S. PATENT DOCUMENTS

| | | |
|---|---|---|
| 7,723,508 B2 | 5/2010 | Crooke et al. |
| 7,732,590 B2 | 6/2010 | Bhanot et al. |
| 7,732,660 B2 | 6/2010 | Helliwell et al. |
| 7,741,305 B2 | 6/2010 | Crooke et al. |
| 7,749,700 B2 | 7/2010 | Baird et al. |
| 7,750,131 B2 | 7/2010 | Seth et al. |
| 7,750,141 B2 | 7/2010 | Crooke et al. |
| 7,750,731 B2 | 7/2010 | Poulsen et al. |
| 7,759,318 B1 | 7/2010 | Perera et al. |
| 7,776,344 B2 | 8/2010 | Hartmann et al. |
| 7,776,874 B2 | 8/2010 | Yao et al. |
| 7,777,023 B2 | 8/2010 | Vargeese et al. |
| 7,803,930 B2 | 9/2010 | Crooke et al. |
| 7,812,003 B2 | 10/2010 | Safe et al. |
| 7,838,287 B2 | 11/2010 | Goldsmith et al. |
| 7,863,252 B2 | 1/2011 | Crooke et al. |
| 7,884,086 B2 | 2/2011 | Bennett et al. |
| 7,884,117 B2 | 2/2011 | Zhang et al. |
| 7,888,324 B2 | 2/2011 | Crooke et al. |
| 7,893,039 B2 | 2/2011 | Swayze et al. |
| 7,919,472 B2 | 4/2011 | Monia et al. |
| 7,947,658 B2 | 5/2011 | Aronin et al. |
| 7,951,934 B2 | 5/2011 | Freier |
| 7,973,015 B2 | 7/2011 | van Ommen et al. |
| 8,008,011 B2 | 8/2011 | Schmutz et al. |
| 8,008,459 B2 | 8/2011 | Goldsmith et al. |
| 8,039,235 B2 | 10/2011 | Lin et al. |
| 8,058,288 B2 | 11/2011 | Yao et al. |
| 8,067,173 B2 | 11/2011 | Liew |
| 8,076,303 B2 | 12/2011 | Iyer et al. |
| 8,084,437 B2 | 12/2011 | Freier et al. |
| 8,084,600 B2 | 12/2011 | Natt et al. |
| 8,088,582 B2 | 1/2012 | Sampath et al. |
| 8,093,222 B2 | 1/2012 | Freier et al. |
| 8,093,225 B2 | 1/2012 | Mamet |
| 8,101,348 B2 | 1/2012 | Tuschl et al. |
| 8,101,358 B2 | 1/2012 | Liew |
| 8,101,585 B2 | 1/2012 | Yu et al. |
| 8,101,743 B2 | 1/2012 | Brown-Driver et al. |
| 8,106,025 B2 | 1/2012 | Bennett et al. |
| 8,110,358 B2 | 2/2012 | Liew |
| 8,110,558 B2 | 2/2012 | Bennett et al. |
| 8,114,597 B2 | 2/2012 | Liew |
| 8,124,745 B2 | 2/2012 | Allerson et al. |
| 8,133,674 B2 | 3/2012 | Liew |
| 8,133,675 B2 | 3/2012 | Liew |
| 8,133,876 B2 | 3/2012 | Bennett et al. |
| 8,138,328 B2 | 3/2012 | Crooke et al. |
| 8,143,230 B2 | 3/2012 | Bhanot et al. |
| 8,148,072 B2 | 4/2012 | Liew |
| 8,158,598 B2 | 4/2012 | Bhanot et al. |
| 8,178,506 B2 | 5/2012 | Lollo et al. |
| 8,188,059 B2 | 5/2012 | Bhanot et al. |
| 8,206,923 B2 | 6/2012 | Garza Gonzalez et al. |
| 8,207,263 B2 | 6/2012 | Popot et al. |
| 8,257,922 B2 | 9/2012 | Liew |
| 8,258,289 B2 | 9/2012 | Bhanot et al. |
| 8,383,660 B2 | 2/2013 | Chang et al. |
| 8,415,465 B2 | 4/2013 | Freier |
| 8,470,987 B2 | 6/2013 | Wada et al. |
| 8,501,414 B2 | 8/2013 | Danzer et al. |
| 8,557,549 B2 | 10/2013 | Chang et al. |
| 8,592,566 B2 | 11/2013 | Iwamura et al. |
| 8,632,963 B2 | 1/2014 | Shah et al. |
| 8,633,206 B2 | 1/2014 | Promo et al. |
| 8,647,742 B2 | 2/2014 | Dendukuri et al. |
| 8,648,186 B2 | 2/2014 | Monteleone |
| 8,669,058 B2 | 3/2014 | Liew |
| 8,674,044 B2 | 3/2014 | Popot et al. |
| 8,679,750 B2 | 3/2014 | Hayden et al. |
| 8,680,063 B2 | 3/2014 | Aronin et al. |
| 8,729,036 B2 | 5/2014 | Zamore et al. |
| 8,735,417 B2 | 5/2014 | Altman et al. |
| 8,750,507 B2 | 6/2014 | Roosta et al. |
| 8,754,107 B2 | 6/2014 | George et al. |
| 8,759,507 B2 | 6/2014 | Van Deutekom |
| 8,822,671 B2 | 9/2014 | Shimizu et al. |
| 8,859,755 B2 | 10/2014 | Wada et al. |
| 8,877,435 B2 | 11/2014 | Helliwell et al. |
| 8,883,969 B2 | 11/2014 | Ide et al. |
| 8,952,145 B2 | 2/2015 | Freier |
| 8,957,040 B2 | 2/2015 | Bennett et al. |
| 8,957,042 B2 | 2/2015 | Safe et al. |
| 8,975,389 B2 | 3/2015 | Manoharan et al. |
| 8,987,222 B2 | 3/2015 | Aronin et al. |
| 8,993,738 B2 | 3/2015 | Prakash et al. |
| 9,006,198 B2 | 4/2015 | Bennett et al. |
| 9,040,674 B2 | 5/2015 | Benson et al. |
| 9,121,020 B2 | 9/2015 | Feinstein et al. |
| 9,126,927 B2 | 9/2015 | Yao et al. |
| 9,127,123 B2 | 9/2015 | Livingston et al. |
| 9,284,344 B2 | 3/2016 | Kim et al. |
| 9,308,252 B2 | 4/2016 | Suckow et al. |
| 9,394,333 B2 | 7/2016 | Wada et al. |
| 9,453,228 B2 | 9/2016 | Kandimalla et al. |
| 9,480,740 B2 | 11/2016 | Reed et al. |
| 2001/0055761 A1 | 12/2001 | Kanemoto et al. |
| 2002/0013792 A1 | 1/2002 | Imielinski et al. |
| 2002/0137921 A1 | 9/2002 | Cook |
| 2003/0045705 A1 | 3/2003 | Cook et al. |
| 2003/0049662 A1 | 3/2003 | Monia et al. |
| 2003/0235845 A1 | 12/2003 | van Ommen et al. |
| 2004/0063647 A1 | 4/2004 | Johnson |
| 2005/0059619 A1 | 3/2005 | Krieg et al. |
| 2005/0096284 A1 | 5/2005 | McSwiggen |
| 2005/0159375 A1 | 7/2005 | Srivastava et al. |
| 2005/0239102 A1 | 10/2005 | Verdine et al. |
| 2005/0277133 A1 | 12/2005 | McSwiggen |
| 2005/0277609 A1 | 12/2005 | Krieg et al. |
| 2006/0003962 A1 | 1/2006 | Ahluwalia et al. |
| 2006/0035858 A1 | 2/2006 | Geary et al. |
| 2006/0063730 A1 | 3/2006 | Monia et al. |
| 2006/0099616 A1 | 5/2006 | van Ommen et al. |
| 2006/0147952 A1 | 7/2006 | van Ommen et al. |
| 2006/0211644 A1 | 9/2006 | Krieg et al. |
| 2007/0149462 A1 | 6/2007 | Iyer et al. |
| 2007/0161547 A1 | 7/2007 | Bhat et al. |
| 2007/0282097 A1 | 12/2007 | Ohgi et al. |
| 2007/0287831 A1 | 12/2007 | Seth et al. |
| 2008/0064867 A1 | 3/2008 | Leuck et al. |
| 2008/0209581 A1 | 8/2008 | van Ommen et al. |
| 2008/0221303 A1 | 9/2008 | Katzhendler et al. |
| 2009/0023675 A1 | 1/2009 | McSwiggen et al. |
| 2009/0053148 A1 | 2/2009 | Kandimalla et al. |
| 2009/0053205 A1 | 2/2009 | Kandimalla et al. |
| 2009/0060898 A1 | 3/2009 | Kandimalla et al. |
| 2009/0093425 A1 | 4/2009 | Dowdy et al. |
| 2009/0162316 A1 | 6/2009 | Verdine et al. |
| 2009/0186410 A1 | 7/2009 | Aronin et al. |
| 2009/0228998 A1 | 9/2009 | van Ommen et al. |
| 2009/0263413 A1 | 10/2009 | Iwamura et al. |
| 2010/0038543 A1 | 2/2010 | Toda et al. |
| 2010/0215642 A1 | 8/2010 | Lan et al. |
| 2010/0273999 A1 | 10/2010 | Jung et al. |
| 2011/0009477 A1 | 1/2011 | Yu et al. |
| 2011/0039334 A1 | 2/2011 | Bennett et al. |
| 2011/0136765 A1 | 6/2011 | Promo et al. |
| 2011/0178284 A1 | 7/2011 | Wada et al. |
| 2011/0201599 A1 | 8/2011 | Bahceci et al. |
| 2011/0257251 A1 | 10/2011 | Gude-Rodriguez et al. |
| 2011/0294124 A1 | 12/2011 | Wada et al. |
| 2011/0294869 A1 | 12/2011 | Petersen |
| 2012/0136039 A1 | 5/2012 | Aronin et al. |
| 2012/0208864 A1 | 8/2012 | Bhanot et al. |
| 2012/0246747 A1 | 9/2012 | Tuschl et al. |
| 2012/0308609 A1 | 12/2012 | Gibbon et al. |
| 2013/0046008 A1 | 2/2013 | Bennett et al. |
| 2013/0072671 A1 | 3/2013 | Van Deutekom |
| 2013/0178612 A1 | 7/2013 | Wada et al. |
| 2013/0184450 A1 | 7/2013 | Wada et al. |
| 2013/0197061 A1 | 8/2013 | Hohjoh et al. |
| 2013/0302806 A1 | 11/2013 | Van Deutekom |
| 2014/0142160 A1 | 5/2014 | Lee et al. |
| 2014/0194610 A1 | 7/2014 | Verdine et al. |

(56) References Cited

U.S. PATENT DOCUMENTS

| | | |
|---|---|---|
| 2014/0213635 A1 | 7/2014 | Van Deutekom |
| 2014/0275212 A1 | 9/2014 | van Deutekom |
| 2014/0323707 A1 | 10/2014 | Seth et al. |
| 2014/0350076 A1 | 11/2014 | van Deutekom |
| 2014/0357698 A1 | 12/2014 | Van Deutekom et al. |
| 2014/0357855 A1 | 12/2014 | Van Deutekom et al. |
| 2014/0373188 A1 | 12/2014 | Zamore et al. |
| 2014/0378527 A1 | 12/2014 | van Deutekom |
| 2015/0051389 A1 | 2/2015 | Seth et al. |
| 2015/0096064 A1 | 4/2015 | Tuschl et al. |
| 2015/0166999 A1 | 6/2015 | Gemba |
| 2015/0197540 A1 | 7/2015 | Shimizu et al. |
| 2015/0211006 A1 | 7/2015 | Butler et al. |
| 2015/0218559 A1 | 8/2015 | Van Deutekom et al. |
| 2015/0275208 A1 | 10/2015 | Oestergaard et al. |
| 2015/0322434 A1 | 11/2015 | van Deutekom |
| 2015/0329859 A1 | 11/2015 | Bennett et al. |
| 2015/0361424 A1 | 12/2015 | van Deutekom |
| 2016/0138022 A1 | 5/2016 | Kandimalla et al. |
| 2016/0186178 A1 | 6/2016 | Radovic-Moreno et al. |

FOREIGN PATENT DOCUMENTS

| | | | |
|---|---|---|---|
| EP | 0655088 A1 | 5/1995 | |
| EP | 0779893 A2 | 6/1997 | |
| EP | 0831854 | 4/1998 | |
| EP | 0973945 A1 | 1/2000 | |
| EP | 1100807 A1 | 5/2001 | |
| EP | 1185305 A1 | 3/2002 | |
| EP | 1244682 A1 | 10/2002 | |
| EP | 1311526 A1 | 5/2003 | |
| EP | 1418179 A2 | 5/2004 | |
| EP | 1499627 A2 | 1/2005 | |
| EP | 1539188 A2 | 6/2005 | |
| EP | 1556077 A2 | 7/2005 | |
| EP | 1560840 A2 | 8/2005 | |
| EP | 1562971 A2 | 8/2005 | |
| EP | 1670810 A2 | 6/2006 | |
| EP | 1670896 A2 | 6/2006 | |
| EP | 1795536 A1 | 6/2007 | |
| EP | 1957507 A2 | 8/2008 | |
| EP | 198438 | 10/2008 | |
| EP | 2021472 A2 | 2/2009 | |
| EP | 2066684 | 6/2009 | |
| EP | 2149571 A1 | 2/2010 | |
| EP | 2170917 A2 | 4/2010 | |
| EP | 2173760 A2 | 4/2010 | |
| EP | 2176280 A2 | 4/2010 | |
| EP | 2282744 A1 | 2/2011 | |
| EP | 2285819 A1 | 2/2011 | |
| EP | 1097162 | 5/2011 | |
| EP | 2320895 A2 | 5/2011 | |
| EP | 2360166 A1 | 8/2011 | |
| EP | 2399588 A1 | 12/2011 | |
| EP | 2462153 A2 | 6/2012 | |
| EP | 2479182 A1 | 7/2012 | |
| EP | 14193887.8 | 11/2014 | |
| EP | 14198167.0 | 12/2014 | |
| EP | 15182401.8 | 8/2015 | |
| EP | 15191074.2 | 10/2015 | |
| EP | 15191075.9 | 10/2015 | |
| EP | 15191076.7 | 10/2015 | |
| GB | 1448437 A | 9/1976 | |
| GB | 2016273 A | 9/1979 | |
| JP | 2003/238586 A | 8/2003 | |
| JP | 2009-190983 A | 8/2009 | |
| JP | 04348044 B2 | 10/2009 | |
| JP | 04348077 B2 | 10/2009 | |
| JP | 2010/241836 A | 10/2010 | |
| JP | 2010/265304 A | 11/2010 | |
| JP | A03-074398 | 3/2011 | |
| JP | 2011/088935 A | 5/2011 | |
| JP | 2011/225598 A | 11/2011 | |
| WO | WO-9110671 A1 | 7/1991 | |
| WO | WO-91/16331 A1 | 10/1991 | |
| WO | WO-9117755 A1 | 11/1991 | |
| WO | WO-9308296 A1 | 4/1993 | |
| WO | WO-94/17093 A1 | 8/1994 | |
| WO | WO96/07392 * | 3/1996 | ............ C07H 21/00 |
| WO | WO-96/07392 A2 | 3/1996 | |
| WO | WO-96/14329 A1 | 5/1996 | |
| WO | WO-9619572 | 6/1996 | |
| WO | WO-9637504 | 11/1996 | |
| WO | WO-96/39413 A1 | 12/1996 | |
| WO | WO-97/06183 A1 | 2/1997 | |
| WO | WO-97/14710 A1 | 4/1997 | |
| WO | WO 97/47637 * | 12/1997 | ............ C07H 19/10 |
| WO | WO-97/47637 A1 | 12/1997 | |
| WO | WO-9803542 A1 | 1/1998 | |
| WO | WO-98/18810 A1 | 5/1998 | |
| WO | WO-98/39334 A1 | 9/1998 | |
| WO | WO-9846794 A1 | 10/1998 | |
| WO | WO-9853801 A1 | 12/1998 | |
| WO | WO-9905160 | 2/1999 | |
| WO | WO-9912034 A1 | 3/1999 | |
| WO | WO-99/56755 A1 | 11/1999 | |
| WO | WO-99/58118 A2 | 11/1999 | |
| WO | WO-0000499 A1 | 1/2000 | |
| WO | WO-0004034 A2 | 1/2000 | |
| WO | WO-0006588 | 2/2000 | |
| WO | WO-00/23444 A1 | 4/2000 | |
| WO | WO-00/37658 A2 | 6/2000 | |
| WO | WO-0031110 A1 | 6/2000 | |
| WO | WO-0055179 A1 | 9/2000 | |
| WO | WO-00/58329 A1 | 10/2000 | |
| WO | WO-0076554 A1 | 12/2000 | |
| WO | WO-01/02415 A1 | 1/2001 | |
| WO | WO-01/22990 A2 | 4/2001 | |
| WO | WO-01/27126 A2 | 4/2001 | |
| WO | WO-0140515 A1 | 6/2001 | |
| WO | WO-0149701 A1 | 7/2001 | |
| WO | WO-01/64702 A1 | 9/2001 | |
| WO | WO-01/85751 A1 | 11/2001 | |
| WO | WO-01/88198 A1 | 11/2001 | |
| WO | WO-0214340 A1 | 2/2002 | |
| WO | WO-02/24906 A1 | 3/2002 | |
| WO | WO-0220544 A1 | 3/2002 | |
| WO | WO-0222635 A1 | 3/2002 | |
| WO | WO-02/32450 A2 | 4/2002 | |
| WO | WO-02057425 A2 | 7/2002 | |
| WO | WO-02097134 A2 | 12/2002 | |
| WO | WO-03/002065 A2 | 1/2003 | |
| WO | WO-03004602 A2 | 1/2003 | |
| WO | WO-03011887 A2 | 2/2003 | |
| WO | WO-03012057 A2 | 2/2003 | |
| WO | WO-03014306 A2 | 2/2003 | |
| WO | WO-03014307 A2 | 2/2003 | |
| WO | WO-03018600 A2 | 3/2003 | |
| WO | WO-03066633 A1 | 8/2003 | |
| WO | WO-03097662 A1 | 11/2003 | |
| WO | WO-2004/000351 A1 | 12/2003 | |
| WO | WO-03099840 A1 | 12/2003 | |
| WO | WO-03100017 A2 | 12/2003 | |
| WO | WO-03106477 A1 | 12/2003 | |
| WO | WO-2004/007718 A2 | 1/2004 | |
| WO | WO-2004/016805 A2 | 2/2004 | |
| WO | WO-2004010956 A2 | 2/2004 | |
| WO | WO-2004/024919 A1 | 3/2004 | |
| WO | WO-2004/042018 A2 | 5/2004 | |
| WO | WO-2004041889 A2 | 5/2004 | |
| WO | WO-2004/044134 A2 | 5/2004 | |
| WO | WO-2004/044136 A2 | 5/2004 | |
| WO | WO-2004/044141 A2 | 5/2004 | |
| WO | WO-2004/044181 A2 | 5/2004 | |
| WO | WO-2004/055162 A2 | 7/2004 | |
| WO | WO-2004/083432 A1 | 9/2004 | |
| WO | WO-2004/083446 A2 | 9/2004 | |
| WO | WO-2004/085454 A1 | 10/2004 | |
| WO | WO-2004093783 A2 | 11/2004 | |
| WO | WO-2005000201 A2 | 1/2005 | |
| WO | WO-2005005599 A2 | 1/2005 | |
| WO | WO-2005/014609 A2 | 2/2005 | |
| WO | WO-2005013901 A2 | 2/2005 | |
| WO | WO-2005/023828 A1 | 3/2005 | |

(56) References Cited

FOREIGN PATENT DOCUMENTS

| | | |
|---|---|---|
| WO | WO-2005/028494 A1 | 3/2005 |
| WO | WO-2005019418 A2 | 3/2005 |
| WO | WO-2005023825 A2 | 3/2005 |
| WO | WO-2005023995 A2 | 3/2005 |
| WO | WO-2005/039630 A2 | 5/2005 |
| WO | WO-2005/042018 A2 | 5/2005 |
| WO | WO-2005/042716 A2 | 5/2005 |
| WO | WO-2005/070859 A1 | 8/2005 |
| WO | WO-2005/085272 A1 | 9/2005 |
| WO | WO-2005/092909 A1 | 10/2005 |
| WO | WO-2006020676 A2 | 2/2006 |
| WO | WO-2006/022323 A1 | 3/2006 |
| WO | WO-2006/029258 A2 | 3/2006 |
| WO | WO-2006031461 A2 | 3/2006 |
| WO | WO-2006044531 A2 | 4/2006 |
| WO | WO-2006/065751 A2 | 6/2006 |
| WO | WO-2006/066260 A2 | 6/2006 |
| WO | WO-2006/080596 A1 | 8/2006 |
| WO | WO-2006/091915 A2 | 8/2006 |
| WO | WO-2007/005941 A2 | 1/2007 |
| WO | WO-2007027775 A2 | 3/2007 |
| WO | WO-2007/059041 A2 | 5/2007 |
| WO | WO-2007/064291 A1 | 6/2007 |
| WO | WO-2007/070598 A2 | 6/2007 |
| WO | WO-2007064954 A2 | 6/2007 |
| WO | WO-2007/131232 A2 | 11/2007 |
| WO | WO-2007131237 A2 | 11/2007 |
| WO | WO-2007/131238 A2 | 11/2007 |
| WO | WO-2007/134014 A2 | 11/2007 |
| WO | WO-2007136988 A2 | 11/2007 |
| WO | WO-2007/139190 A1 | 12/2007 |
| WO | WO-2007143315 A2 | 12/2007 |
| WO | WO-2007143316 A2 | 12/2007 |
| WO | WO-2007143317 A2 | 12/2007 |
| WO | WO-2007146511 A2 | 12/2007 |
| WO | WO-2008/008476 A1 | 1/2008 |
| WO | WO-2008017081 A1 | 2/2008 |
| WO | WO-2008/049085 A1 | 4/2008 |
| WO | WO-2008/068638 A2 | 6/2008 |
| WO | WO-2008066776 A2 | 6/2008 |
| WO | WO-2008/098104 A1 | 8/2008 |
| WO | WO-2008118883 A1 | 10/2008 |
| WO | WO-2008/139262 A2 | 11/2008 |
| WO | WO-2008/148801 A2 | 12/2008 |
| WO | WO-2009046141 A2 | 4/2009 |
| WO | WO-2009117589 A1 | 9/2009 |
| WO | WO-2009124238 A1 | 10/2009 |
| WO | WO-2009143387 A2 | 11/2009 |
| WO | WO-2009143390 A2 | 11/2009 |
| WO | WO-2009143391 A2 | 11/2009 |
| WO | WO-2009143463 A2 | 11/2009 |
| WO | WO-2009/146123 A2 | 12/2009 |
| WO | WO-2009148605 A2 | 12/2009 |
| WO | WO-2010/003133 A1 | 1/2010 |
| WO | WO-2010/039543 A2 | 4/2010 |
| WO | WO-2010/042636 A2 | 4/2010 |
| WO | WO-2010036696 A1 | 4/2010 |
| WO | WO-2010036698 A1 | 4/2010 |
| WO | WO-2010/048552 A2 | 4/2010 |
| WO | WO-2010/064146 A2 | 6/2010 |
| WO | WO-2010/072831 A1 | 7/2010 |
| WO | WO-2010080953 A1 | 7/2010 |
| WO | WO-2010091301 A1 | 8/2010 |
| WO | WO-2010107838 A1 | 9/2010 |
| WO | WO-2010/118263 A1 | 10/2010 |
| WO | WO-2010/129853 A2 | 11/2010 |
| WO | WO-2010/141471 A2 | 12/2010 |
| WO | WO-2011/005761 A1 | 1/2011 |
| WO | WO-2011017521 A2 | 2/2011 |
| WO | WO-2011/034072 A1 | 3/2011 |
| WO | WO-2011038288 A1 | 3/2011 |
| WO | WO-2011/045702 A1 | 4/2011 |
| WO | WO-2011085271 A2 | 7/2011 |
| WO | WO-2011/108682 A1 | 9/2011 |
| WO | WO-2011127175 A1 | 10/2011 |
| WO | WO-2011127307 A1 | 10/2011 |
| WO | WO-2011139911 A2 | 11/2011 |
| WO | WO-2012/030683 A2 | 3/2012 |
| WO | WO-2012/039448 A1 | 3/2012 |
| WO | WO-2012/073857 A1 | 6/2012 |
| WO | WO-2012151324 A1 | 11/2012 |
| WO | WO-2013/012758 A1 | 1/2013 |
| WO | WO-2014/010250 A1 | 1/2014 |
| WO | WO-2014/010718 A1 | 1/2014 |
| WO | WO-2014/012081 A2 | 1/2014 |
| WO | WO-2014/025805 A1 | 2/2014 |
| WO | WO-2015/010135 A2 | 1/2015 |
| WO | WO-2015/051366 A2 | 4/2015 |
| WO | WO-2015/089511 A2 | 6/2015 |
| WO | WO-2015/107425 A2 | 7/2015 |
| WO | WO-2015/108046 A1 | 7/2015 |
| WO | WO-2015/108047 A1 | 7/2015 |
| WO | WO-2015/108048 A1 | 7/2015 |
| WO | WO-2016/079181 A1 | 5/2016 |
| WO | WO-2016/079183 A1 | 5/2016 |

OTHER PUBLICATIONS

Altschul, S.F. et al., Gapped BLAST and PSI-BLAST: a new generation of protein database search programs, Nucleic Acids Research, 25(17):3389-3402 (1997).

Alul, R.H. et al., Oxalyl-CPG: a labile support for synthesis of sensitive oligonucleotide, Nucleic Acids Research, 19(7):1527-1532 (1991).

Alvarez, K. et al., Photocleavable Protecting Groups as Nucleobase Protections Allowed the Solid-Phase Synthesis of Base-Sensitive Sate-Prooligonucleotides, Journal of Organic Chemistry, (1999).

Austin, C. et al., Assesment of heat-sensitive thiophosphate protecting groups in the development of thermolytic DNA oligonucleotide prodrugs, Tetrahedron, 66(1):68-79 (2010).

Barber, I. et al., The Prooligonucleotides Approach I: Esterase-Mediated Reversibility of Dithymidine S-Alkyl Phosphorothiolates to Dithymidine Phosphorothioates, Bioorganic and Medicinal Chemistry Letters, 5(6):563-568 (1995).

Barber, I. et al., The Prooligonucleotides Approach II: Synthesis and stability studies of chimeric oligonucleotide models, Bioorganic and Medicinal Chemistry Letters, 5(14):1441-1444 (1995).

Bayever, E. et al., Systematic administration of a phosphorothioate oligonucleotide with a sequence complementary to p53 for acute myelogenous leukemia and myelodysplastic syndrome: intial results of a phase I trial, Antisense Research Development, 3(4):383-390 (1993).

Beaucage, S.L. and Iyer, R.P., Advances in the Synthesis of Oligonucleotides by the Phosphoramidite Approach, Tetrahedron, 46:2223 (1992).

Benner, S.A. and Sismour, A.M., Synthetic biology, Nature Reviews Genetics, 6(7):553-543 (2005).

Bisbal, C. and Silverman, R.H., Diverse functions of RNase L and implication in pathology, Biochimie, 89(6-7):789-798 (2007).

Bodor, N. et al., A convenient synthesis of (acyloxy)alkyl .alpha.-ethers of phenols, The Journal of Organic Chemistry, 48(26):5280-5284 (1983).

Bohringer, M. et al., Why Pentose and not Hexose Nucleic Acids? Part II: Oligonucleotides of 2'3'-dideoxy-β-d-glucopyranosyl ('homo-DNA') production, Helvetica Chiminca Acta, 75:1416-1477 (1992).

Bologna, J. et al., Uptake and Quantification of Intracellular Concentration of Lipophilic Pro-Oligonucleotides in HeLa Cells, Antisense and Nucleic Acid Drug Development, 12(1):33-41 (2002).

Brooks, P.C. et al., Insulin-like Growth Factor Receptor Cooperates with Integrin βvβ5 to Promote Tumor Cell Dissemination in Vivo, The Journal of Clinical Investigation, 99(6):1390-1398 (1997).

Bundgaard, H., Design of Prodrugs, Elsevier, 7-9 and 21-24 (1985).

Chatgilialoglu, C. and Snieckus, V., Chemical Synthesis: Gnosis to Prognosis, Kluwer Academic, 293 (1996).

Chiu, Y. and Rana, T.M., siRNA function in RNAi: A chemical modification analysis, A Publication of the RNA Society, 9:1034-1048 (2003).

(56) References Cited

OTHER PUBLICATIONS

Cieslak, J. et al., Thermolytic 4-methylthio-1-butyl group for phosphate/thiophosphate protection in solid-phase synthesis of DNA oligonucleotides, Journal of Organic Chemistry, 69(7):2509-2515 (2004).
Coughlin, J.E. et al., Orally bioavailable anti-HBV dinucleotide acyloxyalkyl prodrugs, Bioorganic and Medicinal Chemistry Letters, 20(5):1783-1786 (2010).
Cox, J.R. and Ramsay, O.B., Mechanisms of Nucleophilic Substitution in Phosphate Esters, (1964).
Crary, S.M. et al., Specific phosphorothioate substitutions probe the active site of Bacilus subtilis ribonuclease P, A Publication of the RNA Society, 8:933-947 (2002).
Devereux, J. et al., A comprehensive set of sequence analysis programs for the VAX, Nucleic Acids Research, 12(1):387-395 (1984).
Dietz, G.P.H. et al., Delivery of bioactive molecules into the cell: the Trojan horse approach, Molecular and Cellular Neuroscience, 27(2): 85-131 (2004).
Egli, M. et al., Crystal structure of homo-DNA and natures choice of pentose over hexose in the genetic system, Journal of the American Chemical Society, 128(33):10847-56 (2006).
Epton, R., Innovation and Perspectives in Solid Phase Synthesis, Peptides, Proteins and Nucleic Acids, 21:157-162 (1994).
Eschenmoser, A et al., Why pentose- and not hexose-nucleic acids? Introduction to the problem, conformational analysis of oligonucleotide single strands containing 2?, 3?-dideoxyglucopyranosyl building blocks ('homo-DNA'), and reflections on the conformation of A-and B-DNA, Helvetica Chimica Acta, 75:218-259 (1992).
Fernando, F. et al., Lewis acid deprotection of silyl-protected oligonucleotides and base-sensitive oligonucleotide analogues, Tetrahedron Letters, 45(33):6287-6290 (2004).
Frederiksen, J.K. et al., Separation of RNA Phosphorothioate Oligonucleotides by HPLC, Methods of Enzymology, 468:289-309 (2009).
Gosselin, G. et al., New insights regarding the potential of the pronucleotide approach in antiviral chemotherapy, 43(1):196-208 (1996).
Gough, G.R. et al., Recovery and recycling of synthetic units in the construction of oligodeoxyribonucleotides on solid supports, Tetrahedron Letters, 22:4177-4180 (1981).
Grajkowski, A. et al., Design and Development of Thermolytic DNA Oligonucleotide Prodrugs, Annals of the New York Academy of Sciences, 1058:26-38 (2005).
Grajkowski, A. et al., Solid-Phase Synthesis of Thermolytic DNA Oligonucleotides Functionalized with a Single 4-Hydroxy-1-butyl or 4-Phosphato-/Thiophosphato-1-butyl Thiophosphate Protecting Group, Journal of Organic Chemistry, 72(3):805-518 (2007).
Grajkowski, A. et al., Thermolytic CpG-containing DNA oligonucleotides as potential immunotherapeutic prodrugs, Nucleic Acids Research, 33(11):3550-3560 (2005).
Groebke, K. et al., Why pentose and not hexose nucleic acids? Part V. Purine-purine pairing in homo-DNA: guanine, isoguanine, 2,6-diaminopurine and xanthine. Heletica Chimica Acta. 81:375-474 (1998).
Guerlavais-Dagland, T et al., Fluoride-labile protecting groups for the synthesis of base-sensitive methyl-Sate oligonucleotide prodrugs, European Journal of Organic Chemistry, 2003(12):2327-2335 (2003).
Guga, P., P-chiral oligonucleotides in biological recognition processes, Current Topics in Medicinal Chemistry, 7:695-713 (2007).
Hacia, J.G. et al., Phosphorothioate oligonucleotide-direc ed triple helix formation, Biochemistry, 33:5367-5369 (1994).
Henry, A.A. and Romesberg, F.E., Beyond A, C, G and T: augmenting natures alphabet, Current Opinion in Chemical Biology, 7(6):723-733 (2003).
Heuberger, B.D. and Switzer, C., Journal of the American Chemical Society, 130(2):412-413 (2008).
Hirao, I., Unnatural base pair systems for DNA/RNA-based biotechnology, Current Opinion in Chemical Biology,10:622-627 (2006).
Hunziker, J. et al., Why Pentose-And Not Hexose-Nucleic Acids? Part III. Oligo(2?,3?-dideoxy-?-D-glucopyranosyl)nucleotides. ('Homo-DNA'): Base-Pairing Properties, Helvetica Chimica Acta, 76(1):259-352 (1993).
International Search Report for PCT/US2010/041068, 1 page, (Sep. 1, 2010).
International Search Report for PCT/US2011/064287, 2 pages (Apr. 12, 2012).
Iwamoto, N. et al., Stereocontrolled solid-phase synthesis of oligonucleoside H-phosphonates by an oxazaphospholidine approach, Angewandte Chemie International Edition, 48(3):496-499 (2009).
Iyer, R.P. et al., A novel nucleoside phosphoramidite synthon derived from 1R, 2S-ephedrine, Tetrahedron Asymmetry 6(5):1051-1054 (1995).
Iyer, R.P. et al., Acyloxyaryl prodrugs of oligonucleoside phosphorothioates, Bioorganic and Medicinal Chemistry Letters, 6(16):1917-1922 (1996).
Iyer, R.P. et al., Bioreversible oligonucleotide conjugates by site-specific derivatization, Bioorganic and Medicinal Chemistry Letters, 7:871-876 (1997).
Iyer, R.P. et al., Stereospecific Bio-Reversibility of Dinucleoside S-Alkyl Phosphorothiolates to Dinucleoside Phosphorothioates, Bioorganic & Medicinal Chemistry Letter, 4(20):2471-2476 (1994).
Iyer, R.P., et al., 3H-1,2-Benzodithiole-3-one 1,1-Dioxide as an Improved Sulfurizing Reagent in the Solid-Phase Synthesis of Oligodeoxyribonucleoside Phosphorothioates, Journal of the American Chemical Society, 112(3):1253-1254 (1990).
Iyer, R.P., et al., Prodrugs of Oligonucletides: The Acyloxyalkyl Esters of Oligodeoxyribonucleoside Phosphorothioates, Bioorganic Chemistry, 23:1-21 (1995).
Iyer, R.P., et al., Solid-phase stereoselective synthesis of oligonucleoside phosphorothioates: The nucleoside bicyclic oxazaphospholidines as novel synthons, Tetrahedron Letters, 39:2491-2494 (1998).
Joyce, G.F. et al., The case for an ancestral genetic system involving simple analogues of the nucleotide, Proceedings of the National Academy of Sciences, 84:4398-4402 (1987).
Klose, J. et al., Preparation of 2-(2-Cyanoethyl)-sulfanyl-1H-isoindole-1,3-(2H)-dione and related sulfur transfer reagents, Tetrahedron, 53(42):14411-14416 (1997).
Kool, E.T., Replacing the Nucleobases in DNA with Designer Molecules, Accounts of Chemical Research, 35:936-943 (2002).
Krieg, A.M. et al., P-Chirality-Dependent Immune Activiation by Phosphorothioate CpG Oligodeoxynucleotides, Oligonucleotides, 13:491-499 (2003).
Krueger, A.T. et al., Synthesis and properties of size-expanded DNAs: toward designed, functional genetic systems, Accounts of Chemical Research, 40:141-150 (2007).
Limbach, P.A. et al., Summary: the modified nucleosides of RNA, Nucleic Acids Research, 22(12):2183-2196 (1994).
Lu, Y. and Just, G., Stereoselective synthesis of dithymidine phosphorothioates using d-xylose derived chiral auxiliaries, Tetrahedron, 57(9):1677-1687 (2001).
Lu, Y. et al., Stereoselective Synthesis of R(P)- and S(P)-Dithymidine Phosphorothioates via Chiral Indolooxazaphosphorine Intermediates Derived from Tryptophan This work was financially supported by Natural Science and Engineering Research Council of Canada (NSERC). We thank Nadim Saadeh and Dr. Orval Mamer, McGill University biomedical mass spectroscopy unit, for recording mass spectra, Angewandte Chemie International Edition, 39(24):4521-4524 (2000).
Martin, P., A New Access to 2?-O-Alkylated Ribonucleosides and Properties of 2?-O-Alkylated Oligoribonucleotides, Helvetic Chimica Acta, 78(2):486-504 (1995).
Mauritz, R.P. et al., Elucidation of the Hydrolytical Properties of aHydroxybenzylphosphonates as a New Potential Pro-Oligonucleotide Concept, Nucleosides and Nucleotides, 18(6-7):1417-1418 (1999).

(56) References Cited

OTHER PUBLICATIONS

Mauritz, R.P. et al., Synthesis of 3',5'-Dithymidylyl-α-hydroxyphosphonate Dimer Building Blocks for Oligonucleotide Synthesis—A New Pro-oliguncleotide, Nucleosides Nucleotides and Nucleic Acids, 16(7-9):1209-1212 (1997).

McLaughlin, L., The introduction of reporter groups at multiple and/or specific sites in DNA containing phosphorothioate diesters, (1989).

Mignet, N. et al., Synthesis and evaluation of glucuronic acid derivatives as alkylating agents for the reversible masking of internucleoside groups of antisense oligonucleotides, Carbohydrate Research, 303:17-24 (1997).

Mignet, N. et al., The Prooligonucleotide Approach. V: Influence of the phosphorus atom environment on the hydrolysis of enzymolabile dinucleoside phosphotriesters, Bioorganic and Medicinal Chemistry Letters, 7(11):851-854 (1997).

Morales-Rojas, H. and Kool, E.T., A porphyrin C-nucleoside incorporated into DNA, Organic Letters, 4:4377-4380 (2002).

Morvan, F. et al., Cellular uptake and intracellular quantification of fluorescent labeled T20 Me-SATE prooligonucleotides, Nucleosides Nucleotides Nucleic Acids, 20(4-7):1165-1168 (2001).

Morvan, F. et al., Kinetics study of the biotransformation of an oligonucleotide prodrug in cells extract by matrix-assisted laser desorption/ionization time-of-flight mass spectrometry, 20(2-4):1159-1163 (2001).

Morvan, F. et al., The Oligonucleotide Prodrug Approach: The Pro-Oligonucleotides, Pharmaceutical Aspects of Oligonucleotides, 79-97 (2000).

Nilsson, J. et al., Chemoselectivity in oxidative coupling of bifunctional nucleophiles with dinucleoside H-phosphonate and dinucleoside H-phosphonothioate diesters, Nucleosides, Nucleotides & Nucleic Acids, 22(5-8):1467-1469 (2003).

Nukaga, Y. et al., Stereocontrolled Solid-Phase Synthesis of Phosphorothioate Oligoribonucleotides Using 2'-O-(2-Cyanoethoxymethyl)-nucleoside 3'-O-Oxazaphospholiidine Monomers, Journal of Organic Chemistry, 77(18):7913-7222 (2012).

Oka, N. and Wada, T., Stereocontrolled synthesis of oligonucleotide analogs containing chiral internucleotidic phosphorus atoms, Chemical Society Reviews, 40(12):5829-5843 (2011).

Oka, N. et al., An oxazaphospholidine approach for the stereocontrolled synthesis of oligonucleoside phosphorothioates, Journal of the America Chemical Society, 125(27):8307-8317 (2003).

Oka, N. et al., Diastereocontrolled Synthesis of Dinucleoside Phosphorothioates Using a Novel Class of Activators, Dialkyl(cyanomethyl)ammonium Tetrafluoroborates, Journal of the American Chemical Society, 124(18):4962-4963 (2002).

Oka, N. et al., Solid-Phase Synthesis of Stereoregular Oligodeoxyribonucleoside Phosphorothioates Using Bicyclic Oxazaphospholidine Derivatives as Monomer Units, Journal of the American Chemical Society, 130(47):16031-16037 (2008).

Oka, N. et al., Stereocontrolled Synthesis of Oligoribonucleoside Phosphorothioates by an Oxazaphospholidine Approach, Organic Letters, 11(14):967-970 (2009).

Otting, G. et al., Why Pentose- and Not Hexose-Nucleid Acids? Part IV. 'Homo-DNA': 1H-, 13C-, 31P-, and 15N-NMR-Spectroscopic Investigation of ddGlc(A-A-A-A-A-T-T-T-T-T) in Aqueous Solution, Helvetica Chimica Acta, 76(8):2701-2756 (1993).

Padmanabhan, S. et al., Anti-HBV nucleotide prodrug analogs: Synthesis, bioreversibility, and cytotoxicity studies, Bioorganic and Medicinal Chemistry Letters, 16(15):1491-1494 (2006).

Peyrottes, S. et al., SATE pronucleotide approaches: an overview, Mini-Reviews Medicinal Chemistry, 4(4):395-408 (2004).

Poijarvi, P. et al., 2,2-Bis(ethoxycarbonyl)- and 2-(Alkylaminocarbonyl)-2-cyano-Substituted 3-(Pivaloyloxy)propyl Groups as Biodegradable Phosphate Protections of Oligonucleotides, Bioconjugate Chemistry, 16(6):1564-1567 (2005).

Poijarvi, P. et al., The chemical stability of S-(2-acylthioethyl) and S-acyloxymethyl protected thymidylyl-3',5'-thymidine phosphoromonothiolates and their deacylation products in aqueous solution, Nucleosides Nucleotides and Nucleic Acids, 20(1-2):77-91 (2001).

Poijarvi, P. et al., Towards Nucleotide Prodrugs Derived from 2,2-Bis(hydroxymethyl)malonate and Its Congeners: Hydrolytic Cleavage of 2-Cyano-2-(hydroxymethyl)-3-methoxy-3-oxopropyl and 3-(Alkylamino)-2-cyano-2-(hydroxymethyl)-3-oxopropyl Protections from the Internucleosidic Phosphodiester and Phosphorothioate Linkages, Helvetica Chimica Acta, 85(7):1869-1876 (2002).

Poijarvi, P. et al., Towards Oligonucleotide Pro-Drugs: 2,2-Bis(ethoxycarbonyl) and 2-(Alkylaminocarbonyl)-2-cyano Substituted 3-(Pivaloyloxy)Propyl Groups as Biodegradable Protecting Groups for Internucleosidic Phosphoromonothioate Linkages, Letters in Organic Chemistry, 1(2):183-188 (2004).

Poijarvi, P., Prodrug Approaches of Nucleotides and Oligonucleotides, Current Medicinal Chemistry, 13(28):3441-3465 (2006).

Schoning, K.-U. et al., Chemical Etiology of Nucleic Acid Structure: The ?-Threofuranosyl-(3'?2') Oligonucleotide System, Science, 290(5495):1347-1351 (2000).

Schultz, C., Prodrugs of Biologically Active Phospate Esters, Bioorganic and Medicinal Chemistry, 11(6):885-898 (2003).

Schulz, W.G. and Cai, S.L., Synthetic Genetics, Chemical and Engineering News, 5 (2012).

Seela, F. and Kretschmer, U., Diastereomerically pure Rp and Sp dinucleoside H-phosphonates. The stereochemical course of their conversion into P-methylphosphonates, phosphorothioates and [18O] chiral phosphates, Journal of Organic Chemistry, 56:3861-3869 (1991).

She, X. et al., Synergy between anti-endoglin (CD105) monoclonal antibodies and TGF-beta in suppression of growth of human endothelial cells, International Journal of Cancer, 108: 251-257 (2004).

Silverman, R.H., A scientific journey through the 2-5A/RNase L system, Cytokine Growth Factor Reviews, 18(5-6):381-388 (2007).

Spinelli, N. et al., Use of Allylic Protecting Groups for the Synthesis of Base-Sensitive Prooligonucleotides, European Journal of Organic Chemistry, 2002(1):49-56 (2002).

Stec, W.J. et al., Diastereomers of Nucleoside 3'-O-(2-Thio-1,3,2-oxathia(selena)phospholanes): Building Blocks for Stereocontrolled Synthesis of Oligo(nucleoside phosphorothioate)s, Journal of the American Chemical Society, 117(49):12019-12029 (1995).

Stec, W.J. et al., Novel route to oligo(deoxyribonucleoside phosphorothioates). Stereocontrolled synthesis of P-chiral oligo(deoxyribonucleoside phosphorothioates), Nucleic Acids Research, 19(21):5883-5888 (1991).

Stein, C.A. and Cheng, Y.C., Antisense oligonucleotides as therapeutic agents—is the bullet really magical?, Science, 261(5124):1004-12 (1993).

Suska, A. et al., Antisense oligonucleotides: Stereocontrolled synthesis of phosphorothioate oligonucleotides, Pure and Applied Chemistry, 65(4):707-714 (1993).

Tang, J. et al., Enzymatic Synthesis of Stereoregular (All Rp) Oligonucleotide Phosphorothioate and Its Properties, Nucleosides Nucleotides, 14(3-5):985-990 (1995).

Tawarada, R. et al., Mechanistic studies on oxidative condensation of a thymidine 3?-H-phosphonate derivative with 3?-O-acetylthymidine, Archive for Organic Chemistr, (3):264-273 (2009).

Tosquellas, G. et al., Firstsynthesis of alternating SATE-phosphotriester/phosphodiester prooligonucleotides on solid support, Bioorganic and Medicinal Chemistry Letters, 8(20):2013-2018 (1998).

Tosquellas, G. et al., Prooligonucleotides exhibit less serum-protein binding than phosphodiester and phosphorothioate oligonucleotides, Nucleosides Nucleotides Nucleic Acids, 19(5-6):995-1003 (2000).

Tosquellas, G. et al., The pro-oligonucleotide approach: solid phase synthesis and preliminary evaluation of model pro-dodecathymidylates, Nucleic Acids Research, 26(9):2069-2074 (1998).

(56) References Cited

OTHER PUBLICATIONS

Tosquellas, G. et al., The Prooligonucleotide Approach III: Synthesis and bioreversibility of a chimeric phosphorodithioate prooligonucleotide, Bioorganic and Medicinal Chemistry Letters, 6(4):457-462 (1996).
Tosquellas, G. et al., The Prooligonucleotide Approach IV : Synthesis of chimeric prooligonucleotides with 6 enzymolabile masking groups and unexpected desulfurization side reaction, Bioorganic and Medicinal Chemistry Letters, 7(3):263-268 (1997).
Tsai, C.H. et al., Enzymatic synthesis of DNA on glycerol nucleic acid templates without stable duplex formation between product and template, Proceedings of the National Academy of Science, 104(37):14598-14603 (2007).
Uznanski, B. et al., Stereochemistry of base-catalyzed ring opening of 1,3,2-oxathiaphospholanes. Absolute configuration of 2-{N-[(Rc)-1-(.alpha.-naphthyl)ethyl]amino}-2-thiono-1,3,2-oxathiaphospholanes and O,S-dimethyl N-[(Rc)-1-(.alpha.-naphthyl)ethyl]phosphoramidothioates, Journal of the American Chemical Society, 114(26):10197-10202 (1992).
Vives, E. et al., Lipophilic pro-oligonucleotides are rapidly and efficiently internalized in HeLa cells, Nucleic Acids Research, 27(20):4071-4076 (1999).
Vu, H. and Hirschbein, B.L., Internucleotide Phosphite Sulfurization With Tetraethylthiuram Disulfide. Phosphorothioate Oligonucleotide Synthesis Via Phosphoramidite Chemistry, Tetrahedron Letters, 32(26):3005-3008 (1991).
Wada, T. et al., Chemical synthesis and properties of stereoregulated phosphorothioate RNAs, Nucleic Acids Symposium Series, 51:119-120 (2007).
Wada, T. et al., Stereocontrolled synthesis of phosphorothioate DNA by an oxazaphospholidine approach, Nucleic Acids Research Supplement, 3:109-110 (2003).
Wagner, C.R. et al., Pronucleotides: toward the in vivo delivery of antiviral and anticancer nucleotides, Medicinal Research Reviews, 20(6):417-451 (2000).
Wilk, A. and Stec, W.J., Analysis of oligo(deoxynucleoside phosphorothioate)s and their diastereomeric composition, Nucleic Acids Research, 23(3):530-534 (1995).
Wilk, A. et al., Deoxyribonucleoside Cyclic N-Acylphosphoramidites as a New Class of Monomers for the Stereocontrolled Synthesis of Oligothymidylyl- and Oligodeoxycytidylyl-Phosphorothioates, Journal of the American Chemical Society, 122:2149-2156 (2000).
Wright, P. et al., Large scale synthesis of oligonucleotides via phosphoramidite nucleosides and a high-loaded polystyrene support, Tetrahedron Letters, 34:3373-3736 (1993).
Written Opinion for PCT/US2010/041068, 11 pages, (Sep. 1, 2010).
Written Opinion for PCT/US2011/064287, 16 pages (Apr. 12, 2012).
Xiang, Y. et al., Effects of RNase L mutations associated with prostate cancer on apoptosis induced by 2',5'-oligoadenylates, Cancer Research, 63(20):6795-6801 (2003).
Zhang, L. et al., A simple glycol nucleic acid, Journal of the American Chemical Society,127(12):4174-4175 (2005).
Zhang, R.S. et al., Synthesis of two mirror image 4-helix junctions derived from glycerol nucleic acid, Journal of the American Chemical Society, 130(18):5846-5847 (2008).
Zon, G and Stec, W.J., Phosphorothioate oligonucleotides, Oligonucleotides and Analogues: A Practical Approach, 87-108 (1991).
Ekstein, F., Oligonucleotides and Analogues a Practical Approach, IRL Press at Oxford University Press, 1-26 (1991).
International Search Report for PCT/US2013/050407, 5 pages (Jan. 9, 2014).
Written Opinion for PCT/US2013/050407, 12 pages (Jan. 9, 2014).
Lesnikowski et al., Studies on Stereospecific Formation of P-Chiral Internucleotide Linkage. Synthesis of (RP, RP)- and (SP, SP)- Thymidylyl (3', 5') Thymidylyl (3', 5') Thymidine DI (O,O- Phosphorothioate) Using 2-Nitrobenzyl Group as a New S-Protection, Tetrahedron Letters 30(29) 3821-3824 (1989).

Tamura et al., Preparation of Stereoregulated Antisense Oligodeoxyribonucleoside Phoshorothioate and Interaction with its Complementary DNA and RNA, 17(1-3): 269-282 (1998).
Bachelin et al., Structure of a Stereoregular Phosphorothioate DNA/RNA duplex, Nat. Struct. Biol., 5(4): 271-276 (1998).
Fujii et al., Acylphosphonates. 7.1 A New Method for Stereospecific and Stereoselective Generation of Dideoxyribonucleoside Phosphorothioates via the Acylphosphonate Intermediates, Tetrahedron, 43: 3395-3407 (1987).
Jin et al., Stereoselective Synthesis of Dithymidine Phosphorothioates Using Xylose Derivatives as Chiral Auxiliaries, J. Org. Chem., 63: 3647-3654 (1998).
Koziolkewicz et al., Stability of Stereoregular Oligo-(nucleoside Phosphorothioate)s in Human Plasma: Diastereoselectiviy of Plasma 3'-Exonuclease, Antisense Nucl. Acid Drug Dev., 7: 43-48 (1997).
Koziolkewicz et al., Stereodifferentiation—the effect of P chirality of oligo(nucleoside phosphorothioates) on the activity of bacterial RNase H, Nucl. Acids Res., 23(24): 5000-5005 (1995).
Nawrot et al., DNA Oligonucleotides Containing Stereodefined Phosphorothioate Linkages in Selected Positions, Current Protocols in Nucleic Acid Chemistry, UNIT 4.34: 4.34.1-4.34.15 (2009).
Stec et al., Oxathiaphospholane Method of Stereocontrolled Synthesis of Diribonucleoside 3', 5'-Phosphorothiptes, J. Org. Chem., 61: 6713-6716 (1996).
Stec et al., Stereocontrolled Synthesis of Oligo (nucleoside phosphorothioate)s , Angew. Chem. Int. Ed. Engl., 33:709-722 (1994).
Stec et al., Stereospecific Synthesis of P-Chiral Analogs of Oligonucleotides, Methods in Molecular Biology, 20: 285-313 (1993).
Stec, Oligo(nucleoside Phosphorothioate)s: The Quest of P-Chirality, in Phosphorus, Sulfur, and Silicon and the Related Elements, 177(6): 1775-1778 (2002).
Stec et al., Synthesis of Phosphorothioate Oligonucleotides with Stereodefined Phsphorothioate Linkages, Current Protocols in Nucleic Acid Chemistry, Unit 4.17: 4.17.14.17.28 (2003).
Zon, Automated synthesis of phosphorus—sulfur analogs of nucleic acids—25 years on: potential therapeutic agents and proven utility in biotechnology, New J. Chem., 34: 795-804 (2010).
Forster, A.C. and Symons, R.H. Self-cleavage of plus and minus RNAs of a virusoid and a structural model for the active sites, Cell, 49(2): 211-220 (1987).
Isis Pharmaceuticals, Intellectual Property: Capturing Value From Innovation, Isis' Annual Meeting of Stockholders and Open House, Intellectual Property Poster, 1 page (2011). Received from Internet <http://www.isispharm.com/Site_Gfx/pdf/11-AnMtg_IntellectualProperty_TAB.pdf>.
Isis Pharmaceuticals, Intellectual Property: Capturing Value From Innovation, Isis' Annual Meeting of Stockholders and Open House, Intellectual Property Poster, 1 page (2012). Received from Internet <http://www.isispharm.com/Site_Gbdpdf/2012_Annual_Meeting_IP_Poster.pdf>.
Agrawal, S. et al., Mixed-backbone oligonucleotides as second generation antisense oligonucleotides: in vitro and in vivo studies, Proc. Natl. Acad. Sci. USA, 94: 2620-2625 (1997).
Frazier, K.S. Antisense Oligonucleotide Therapies: The Promise and the Challenges from a Toxicologic Pathologist's Perspective, Toxicology Pathology, 43: 78-89 (2015).
Henry, S.P. et al., Activation of the Alternative Pathway of Complement by a Phosphorothioate Oligonucleotide: Potential Mechanism of Action, The Journal of Pharmacology and Experimental Therapeutics, 281(2): 810-816 (1997).
Wang, J.-C. et al., A stereoselective synthesis of dinucleotide phosphorothioate triesters through a chiral indol-oxazaphosphorine intermediate, Tetrahedron Letters, 38(5):705-708 (1997).
Adarsh, et al., Organelle Specific Targeted Drug Delivery—A Review, International Journal of Research in Pharmaceutical and Biomedical Sciences, 2(3): 895-912 (2011).
Sonveaux, E., Protecting Groups in Oligonucleotide Synthesis, Protocols for Oligonucleotide Conjugates, Methods in Molecular Biology, Edited by Agrawal, S., Humana Press, 26: 1-71 (1994).
Aldaye, F.A. et al., Assembling materials with DNA as the guide, Science, 321(5897): 1795-1799 (2008).

(56) References Cited

OTHER PUBLICATIONS

Almer et al., Synthesis of Stereochemically Homogeneous Oligoribonucleoside All-Rp-Phosphorothioates by Combining H-Phosphonate Chemistry and Enzymatic Digestion, J. Chem. Soc., Chem. Commun., 1459-1460 (1994).

Almer, et al. A New Approach to Stereospecific Synthesis of P-chiral Phosphorothioates. Preparation of Diastereomeric Dithymidyl-(3'-5') Phosphorothioates, Chem. Commun., (3): 290-1 (2004).

Almer, et al. Solid Support Synthesis of all-Rp-oligo(ribonucleoside phosphorothioate)s, Nucleic Acids Res., 24(19): 3811-3820 (1996).

Almer, H. et al., Synthesis of Diribonucleoside Phosphorothioates via Sterospecific Sulfurization of H-Phosphonate Diesters, 57(23): 6163-6169 (1992).

Aristarkhova, L.N. et al., Investigation in the field of thiosulfonic acids. 28. alkyl esters of cyclopentane- and cyclohexanethiosulfonic acids, Journal of Organic Chemistry of the USSR, 6: 2454-2458 (1970).

Athyros, V.G. et al., Antisense technology for the prevention or the treatment of cardiovascular disease: the next blockbuster?, Expert Opin. Investig. Drugs, 17(7): 969-72 (2008).

Current Protocols in Nucleic Acid Chemistry, Edited by Beaucage, S.L. et al., Chapter 2: Protection of Nucleosides for Oligonucleotide Synthesis, 2.0.1.-2.16.31 (2012).

Methods in Enzymology, Edited by Widder, K. and Green, R., Drug and Enzyme Targeting, Academic Press, 112: 309-396 (1985).

Baek, M-S. et al., In Vitro Metabolic Stabilities and Metabolism of 2'-O-(Methoxyethyl) Partially Modified Phosphorothioate Antisense Oligonucleotides in Preincubated Rat or Human Whole Liver Homogenates, Oligonucleotides, 20(6): 309-316 (2010).

Ballas, Z.K. et al., Induction of NK Activity in Murine and Human Cells by CpG Motifs in Oligodeoxynucleotides and Bacterial DNA, J. Immunoll., 57: 1840-1845 (1996).

Barnes, P.J. and Peterson, S. Efficacy and Safety of Inhaled Corticosteroids in Asthma, Am. Rev. Respir. Dis., 148: SI-S26 (1993).

Battistini et al., Stereoselective Synthesis of Cyclic Dinucloetide Phosphorothioates, Tetrahedron, 49(5): 1115-1132 (1993).

Beal, P.A. et al., Second Structural Motif for Recognition of DNA by Oligonucleotide-Directed Triple-Helix Formation, Science, 251: 1360-1363 (1991).

Berge, S.M. et al., Pharmaceutical salts, J. Pharm. Sci., 66(1):1-19 (1997).

Besch, R. et al, Specific Inhibition of ICAM-1 Expression Mediated by Gene Targeting with Triplex-forming Oligonucleotides, J. Biol. Chem., 277(26): 32473-32479 (2002).

Block, E. et al., Allium Chemistry: Synthesis and Sigmatropic Rearrangements of Alk(en)yl 1-Propenyl Disulfide S-Oxides from Cut Onion and Garlic, Journal of the Ameican Chemical Society, 118(12): 2799-2810 (1996).

Bock, L.C. et al., Selections of single-stranded DNA molecules that bind and inhibit human thrombin, Nature, 355: 564-566 (1992).

Bode, C. et al. CpG DNA as a vaccine adjuvant, Expert Rev. Vaccines, 10(4): 499-511 (2011).

Boudreau, R.L. et al., Nonallele-specific silencing of mutant and wild-type huntingtin demonstrates therapeutic efficacy in Huntington's disease mice, 17(6): 1053-1063 (2009).

Brown, J.W.S. and Simpson, C.G., Splice Site Selection in Plant Pre-mRNA Splicing, Ann. Rev. Plant Physiol. Plant Mol. Biol., 49: 77-95 (1998).

Bundgaard, H., (C) Means to Enhance Penetration. (1) Prodrugs as a means to improve the delivery of peptide drugs, Advanced Drug Delivery Reviews, 8:1-38 (1992).

Bundgaard, H., Design and Application of Prodrugs, 5: 113-191 (1991).

Bunnell. B.A. et al., Targeted Delivery of Antisense Oligonucleotides by Molecular Conjugates, Somatic Cell and Molecular Genetics, 18(6):559-569 (1992).

Carbone, G.M. et al., Selective inhibition of transcription of the Ets2 gene in prostate cancer cells by a triplex-forming oligonucleotide, Nucl. Acid. Res., 31: 833-843 (2003).

Carrillo, H., and Lipman, D.J., The multiple sequence alignment problem in biology, SIAM J. Appl. Math., 48(5):1073-1082 (1988).

Check, E., RNA interference: hitting the on switch, Nature, 448(7156): 855-858 (2007).

Cooney, M., et al., Site-Specific Oligonucleotide Binding Represses Transcription of the Human c-myc Gene in Vitro, Science, 241: 456-459 (1988).

Cosstick, R. and Eckstein, F., Synthesis of d(GC) and d(CG) Octamers Containing Alternating Phosphorothioate Linkages: Effect of the Phosphorothioate Group on the B-Z Transition, Biochemistry, 24: 3630-3638 (1985).

Cullen, K.A. et al., Ambulatory surgery in the United States, 2006, National Health Statistics Reports, 11: 1-28 (Jan. 28, 2009—Revised Sep. 4, 2009).

Davis, B.G. et al., Altering the specificity of subtilisin *Bacillus lentus* through the introduction of positive charge at single amino acid sites, Bioorganic & Medicinal Chemistry, 7(11): 2303-2311 (1999).

Dellinger, D.J. et al., Streamlined Process for the Chemical Synthesis of RNA Using 2'-O-Thionocarbamate-Protected Nucleoside Phosphoramidites in the Solid Phase, J. Am. Chem. Soc., 133: 11540-11556 (2011).

Djukanovic, R. et al., Mucosal Inflammation in Asthma, Am. Rev. Respir. Dis., 142: 434-457 (1990).

Dorman et al., Synthesis of Oligodeoxynucleotides and Oligodeoxynucleotide Analogs using Phosphoramidite Intermediates, Tetrahedron, 40(1):95-102 (1984).

Dua, P. et al., Patents on SELEX and therapeutic aptamers, Recent Patents on DNA & Gene Sequences, 2(3):172-186 (2008).

Eaton, W.A. et al., Submillisecond kinetics of protein folding, Curr. Opin. Chem. Biol., 1:10-14 (1997).

Eckstein, F. Phosphorothioates, Essential Components of Therapeutic Oligonucleotides, Nucleic Acid Therapeutics, 1-14 (2014).

El Harchaoui, K. et al., Current and future pharmacologic options for the management of patients unable to achieve low-density lipoprotein-cholesterol goals with statins, Am. J. Cardiovasc. Drugs, 8(4): 233-242 (2008).

Elbashir, S.M. et al., Duplexes of 21-nucleotide RNAs mediate RNA interference in cultured mammalian cells, Nature, 411: 494-498 (2001).

Elbashir, S.M. et al., Functional anatomy of siRNAs for mediating efficient RNAi in *Drosophila melanogaster* embryo lysate, The EMBO Journal, 20(23): 6877-6888 (2001).

Ellington, A.D. and Szostak, J.W., In vitro selection of RNA molecules that bind specific ligands, Nature, 346: 818-822 (1990).

Eschenmoser, A., Chemical etiology of nucleic acid structure, Science, 284(5423):2118-24 (1999).

Eschenmoser, A., Towards a Chemical Etiology of the Natural Nucleic Acids' Structure, Chemical Synthesis, Edited by Chatgilialoglu, C. and Snieckus, V., Kluwer Academic Publishers, 293-340 (1996).

Famulok, M. Oligonucleotide aptamers that recognize small molecules, Curr. Opin. Struct. Biol., 9: 324-329 (1999).

Fendrich et al., Determination of the Absolute P-configuration of a Phthalidyl Phosphonate Thymidine-Thymidine Dimer, Nucleosides Nucleotides Nucleic Acids., 22(5-8): 1127-1129 (2003).

Fire, A. et al., Potent and specific RNA interference by double-stranded RNA in *Caenorhadbditis elegans*, Nature, 391: 806-811 (1998).

Forster, A.C. and Symons, R.H. Self-Cleavage of Virusoid RNA is performed by the Proposed 55-Nucleotide Active Site, Cell, 49(2): 211-20 (1987).

Frank-Kamenetsky, M. et al., Therapeutic RNAi targeting PCSK9 acutely lowers plasma cholesterol in rodents and LDL cholesterol in nonhuman primates. Proc. Natl. Acad. Sci. USA., 105(33): 11915-11920 (2008).

Freier, S.M. et al., Improved free-energy parameters for predictions of RNA duplex stability, Proc. Nat. Acad. Sci. USA, 83: 9373-9377 (1986).

(56) References Cited

OTHER PUBLICATIONS

Froehler, B.C. et al., Synthesis of DNA via deoxynucleoside H-phosphonate intermediates, Nucleic Acids Research, 14(13): 5399-5407 (1986).

Fujii et al., Acylphosphonates. 5.1A new method for stereospecific generation of phosphorothioate via aroylphosphonate intermediate, Tetrahedron Letters, 27(8): 935-938 (1986).

Garegg, P.J. et al., Nucleoside H-Phosphonates. III. Chemical Synthesis of Oligodeoxyribonucleotides by the Hydrogenphosphonate Approach, Tetrahedron Letters, 27(34): 4051-4054 (1986).

Gauglitz, G.G. et al., Hypertrophic Scarring and Keloids: Pathomechanisms and Current Emerging Treatment Strategies, Mol. Med., 17(1-2): 113-125 (2011).

Goraczmiak, R. et al., Gene silencing by synthetic U1 Adaptors, Nature Biotechnology 27(3): 257-263 (2008).

Graham, M.J. et al., Antisense inhibition of proprotein convertase subtilisin/kexin type 9 reduces serum LDL in hyperlipidemic mice, J. Lipid Res., 48(4): 763-767 (2007).

Green, L.S. et al., Inhibitory DNA Ligands to Platelet-Derived Growth Factor B-Chain, Biochemistry, 35: 14413-14424 (1996).

Green, L.S. et al., Nuclease-resistant nucleic acid ligands to vascular permeability factor/vascular endothelial growth factor, Chem. Biol., 2(10): 683-695 (1995).

Griffiths-Jones, S. et al., miRBase: microRIVA sequences, targets and gene nomenclature, Nucleic Acids Research, 34 (Database Issue): D140-D144 (2006).

Griffiths-Jones, S. The microRNA Registry, Nucleic Acids Research, 32 (Database Issue): D109-D111 (2004).

Gude, L. et al., Mapping Targetable Sites on Human Telomerase RNA Pseudoknot/Template Domain Using 2'-OMe RNA-interacting Polynucleotide (RIPtide) Microarrays, J. Biol. Chem., 287(22): 18843-18853 (2012).

Guga et al., Oxathiaphospholane Approach to the Synthesis of P-Chiral, Isotopomeric Deoxy(ribonucleoside phosphorothioate)s and Phosphates Labeled with an Oxygen Isotope. Angew Chem., 113(3): 630-633 (2001).

Guga et al., Unusual Thermal Stability of RNA/[RP-PS]-DNA/RNA Triplexes Containing a Homopurine DNA Strand, Biophys J., 92(7): 2507-2515 (2007).

Guzaev, A.P., Reactivity of 3H-1,2,4-dithiazole-3-thiones and 3H-1,2-dithiole-3-thiones as sulfurizing agents for oligonucleotide synthesis, Tetrahedron Letters, 52: 434-437 (2011).

Hanagata, N., Structure-dependent immunostimulatory effect of CpG oligodeoxynucleoties and their delivery system, Int. J. Nanomedicine, 7: 2181-95 (2012).

Harper, S.Q. et al., RNA interference improves motor and neuropathological abnormalities in a Huntington's disease mouse model, Proc. Natl. Acad. Sci. USA, 102(16): 5820-5825 (2005).

Hau, P. et al., Results of G004, a phase lib actively controlled clinical trial with the TGF-b2 targeted compound AP 12009 for recurrent anaplastic astrocytoma, Journal of Clinical Oncology, 2006 ASCO Annual Meeting Proceedings (Post-Meeting Edition), 24(18, Jun. 20 Supplement): 1566 (2006).

Hayashi, S. et al., Studies on Antitumor Substances, Chemical & Pharmaceutical Bulletin, 12(11): 1271-1276 (1964).

Herbert, B-S. et al., Nonradioactive detection of telomerase activity using the telomeric repeat amplification protocol, Nat. Protoc., 1(3): 1583-1590 (2006).

Herdewijn, Oligonucleotide Synthesis, Methods in Molecular Biology, 288: 1-435 (2005).

Higuchi, T. et al., Pro-drugs as Novel Delivery Systems, ACS Symposium Series, 14 (1975).

Hohjoh, H., Disease-Causing Allele-Specific Silencing by RNA Interference, Pharmaceuticals, 6: 522-535 (2013).

International Search Report for PCT/IB2009/007923, 4 pages (Sep. 6, 2010).

International Search Report for PCT/US2012/046805, 2 pages (Sep. 19, 2012).

Iwamoto et al., Stereocontrolled Synthesis of H-phosphonate DNA, Nucleic Acids Symposium Series, (50):159-60 (2006).

Jiang, J. et al., Allele-Specific Silencing of Mutant Myh6 Transcripts in Mice Suppresses Hypertrophic Cardiomyopathy, Science, 342: 111-114 (2013).

Jin et al., A Stereoselective Synthesis of Dinucleotide Boranophosphate, Using Chiral Indole-Oxazaphosphorine Intermediates, Tetrahedron Letters, 39: 6433-6436 (1998).

Johansson et al., Studies towards synthesis of dinucleoside arylphosphonates with metal complexing properties, Nucleosides Nucleotides & Nucleic Acids, 22(5-8): 1459-61 (2003).

Johansson et al., Synthesis of dinucleoside pyridylphosphonates involving palladium(o)-catalysed phosphorus-carbon bond formation as a key step, Chem. Commun., 2564-2565 (2001).

Johansson et al., The case for configurational stability of H-phosphonate diesters in the presence of diazabicyclo[5.4.0]undec-7-ene (DBU), Bioorg Med Chem., 9(9): 2315-22 (2001).

Jopling, C.L. et al., Modulation of Hepatitis C Vicus RNA Abundance by a Liver-Specific MicroRNA, Science, 309: 1577-1581 (2005).

Joyce, G.F. The antiquity of RNA-based evolution, Nature, 418(6894): 214-221 (2002).

Kakeya, N. et al., Studies on Prodrugs of Cephalosporins. I. Synthesis and Biological Properties of Glycyloxybenzoyloxymethyl and Glycylaminobenzoyloxymethyl Esters of 7-[2-(2-Aminothiazol-4-yl)-(Z)-2-methoxyiminoacetamido]-3-methyl-3-cephem-4-carboxylic Acid, Chem. Pharm. Bull., 32(2): 692-698 (1984).

Kamada, A.K. et al., Issues in the Use of Inhaled Glucocorticoids, Am. J. Respir. Crit. Care. Med., 153: 1739-1748 (1996).

Kawasaki, A et. al., Uniformly Modified 2'-Deoxy-2'-fluoro Phosphorothioate Oligonucleotides as Nuclease-Resistant Antisense Compounds with High Affinity and Specificity for RNA Targets, J. Med. Chem., 36: 831-841 (1993).

Kers et al., A new type of nucleotide analogue with 4-pyridylphosphonate internucleotide linkage, Tetrahedron Letters, 40(22): 4263-4266 (1999).

Kim, N.W. et al., Specific Association of Human Telomerase Activity with Immortal Cells and Cancer, Science, 226: 2011-2015 (1994).

Kim, S-H. and Cech, T.R., Three-dimensional model of the active site of the selfsplicing rRNA precursor of Tetrahymena, Proc. Natl. Acad. Sci. U S A., 84(24): 8788-8792 (1987).

Kordasiewicz, H.B. et al., Sustained therapeutic reversal of Huntington's disease by transient repression of huntingtin synthesis, Neuron, 74(6): 1031-1044 (2012).

Kozikowski, A.P. et al., Chemistry of the main group metals: A stereoselective synthesis of allyl vinyl thioethers for the thio-claisen reaction, Journal of Organometallic Chemistry, 164(3): C33-C37 (1979).

Kraszewski et al., Studies on Reactions of Nucleoside H-phosphonates with Bifunctional Reagents. Part 1. Reaction with amino alcohols, J. Chem. Soc., Perkin Trans., 1: 1699-1704 (1993).

Krieg, A.M. et al., CpG motifs in bacterial DNA trigger direct B-cell activation, Nature, 374: 546-549 (1995).

Krutzfeldt, J. et al., Silencing of microRNAs in vivo with 'antagomirs', Nature, 438: 685-689 (2005).

LaPlanche, L.A. et al., Phosphorothioate-modified oligodeoxyribonucleotides. III. NMR and UV spectroscopic studies of the Rp-Rp, Sp-Sp, and Rp•Sp duplexes, [d(GGsAATI'CC)2, derived from diastereomeric 0-ethyl phosphorothioates, Nucleic Acids Research, 14(22): 9081-9093 (1986).

Latimer, L.J.P. et al, Synthetic repeating sequence DNAs containing phosphorothioates: nuclease sensitivity and triplex formation, Nucleic Acids Research, 17(4): 1549-1561 (1989).

Laurent et al., Chiral and steric effects in the efficient binding of alpha-anomeric deoxyoligonucleoside N-alkylphosphoramidates to ssDNA and RNA, Nucleic Acids Res., 27(21): 4151-9 (1999).

Lavergne, T. et al., A Base-Labile Group for 2'-OH Protection of Ribonucleosides: A Major Challenge for RNA Synthesis, Chem. Eur. J, 14, 9135-9138 (2008).

(56) References Cited

OTHER PUBLICATIONS

Lesnikowski, Z. J. et al., Octa(thymidine methanephosphonates) of partially defined sterochemistry: synthesis and effect of chirality at phosphorus on binding to pentadecadeoxyriboadenylic acid, Nucleic Acids Research, 18(8): 2109-2115 (1990).
Li L.C., Small RNA Mediated Gene Activation, RNA and the Regulation of Gene Expression: A Hidden Layer of Complexity, Edited by Kevin V. Morris, Chapter 13, Caister Academic Press (2008).
Li, L-C. et al., Small dsRNAs induce transcriptional activation in human cells, Proc. Natl. Acad. Sci. USA, 103(46): 17337-17342 (2006).
Li-Tsang, C.W. et al., Prevalence of hypertrophic scar formation and its characteristics among the Chinese population, Burns, 31: 610-616 (2005).
Lima, W. et al., Single-Stranded ssRNAi Activate RNAi in Animals, Cell, 150: 883-894 (2012).
Lima, W.F. et al., The influence of antisense oligonucleotide-induced RNA structure on *Escherichia coli* RNase H1 activity, J. Biol. Chem., 272(29):18191-9 (1997).
Lin et al., Synthesis and resolution of dinucleotide (TpAZT) phosphoramidates, Synthetic Commun., 33(14): 2553-2562 (2003).
Lu, X. et al., Antisense-Mediated Inhibition of Human Immunodeficiency Virus (HIV) Replication by Use of an HIV Type 1-Based Vector Results in Severely Attenuated Mutants Incapable of Developing Resistance, Journal of Virology, 78(13): 7079-7088 (2004).
Machytka et al., Extension of the Applicability of &I-Values for the Configurational Assignment of Diastereomeric Phosphate-Modified Dideoxynucleotides, Nucleosides and Nucleotides, 17(12): 2311-2322 (1998).
Machytka et al., Synthesis and NMR characterization of diastereomeric CPSMeG derivatives, Nucleosides Nucleotides Nucleic Acids., 19(5-6): 903-15 (2000).
Maher III, L.J., et al., Inhibition of DNA Binding Proteins by Oligonucleotide-Directed Triple Helix Formation, Science, 245: 725-730 (1989).
Mann, M.J. et al., Therapeutic applications of transcription factor decoy oligonucleotides, J. Clin. Invest., 106:1071-1075 (2000).
Mannironi, C. et al., In Vivo Selection of Dopamine RNA Ligands, Biochemistry, 36: 9726-9734 (1997).
Martin, P., Stereoselective Synthesis of 2'-O-(2-Methoxyethypribonucleosides: Neighboring-Group Participation of the Methoxyethoxy Group in the Ribosylation Step, Helv. Chim. Acta, Abstract Only, 79: 1930-1938 (1996).
Masahiro, T. et al., Nematicidal and antimicrobial constituents from *Allium grayi* Regel and *Allium fistulosum* L. var. *caespitosum*, Agricultural and Biological Chemistry, 52(9): 2383-2385 (1988).
Maung, J. et al., Alternatives to 1-H-tetrazole in the preparation of phosphonate diesters and phosphonamidates from phosphonyl dichlorides, Tetrahedron Lett., 45: 6497-6499 (2004).
McBride, J.L. et al., Prelinical Safety of RNAi-Mediated HTT Suppression in the Rhesus Macaque as a Potential Therapy for Huntington's Disease, Molecular Therapy, 19: 1-11 (2011).
Medical News Today, AVI BioPharma Announces FDA Clears IND Applications for Clinical Trials of RNA Therapeutic Agents for Treatment of Ebola and Marburg Viruses, Accessed Apr. 2, 2015, 2 pages (Dec. 30, 2008).
Merki, E. et al., Antisense oligonucleotide directed to human apolipoprotein B-100 reduces lipoprotein(a) levels and oxidized phospholipids on human apolipoprotein B-1 00 particles in lipoprotein(a) transgenic mice, Circulation, 118(7): 743-53 (2008).
Mesmaeker, A.D. Backbone modifications in oligonucleotides and peptide nucleic acid systems, Current Opinion in Structural Biology, 5: 343-355 (1995).
Milkowski, J.D. et al., Thiol Protection with the Acetamidomethyl Group: S-Acetamidomethyl-l-cysteine Hydrochloride, Organic Syntheses, 6: 5 (1988).
Monteys, A.M. et al., Single nucleotide seed modification restores in vivo tolerability of a toxic artificial miRNA sequence in the mouse brain, Nucleic Acids Res., 42(21): 13315-13327 (2014).
Morcos, P.A., Achieving targeted and quantifiable alteration of mRNA splicing with Morpholino oligos, Biochem. Biophys. Res. Commun., 358(2): 521-527 (2007).
Moser, H. E. et al., Sequence-Specific Cleavage of Double Helical DNA by Triple Helix Formation, Science, 238: 645-650 (1987).
Nielsen, N.M. and Bundgaard, H. Glycolamide Esters as Biolabile Prodrugs of Carboxylic Acid Agents: Synthesis, Stability, Bioconversion, and Physicochemical Properties, Journal of Pharmaceutical Sciences, 77(4): 285-298 (1988).
Nieuwlandt, D. et al., In Vitro Selection of RNA Ligands to Substance P, Biochemistry, 34: 5651-5659 (1995).
Nilsson et al., Chemical and Stereochemical Aspects of Oxidative Coupling of H-Phosphonate and H-Phosphonothioate Diesters. Reactions with N,N-,N,O and O,O-Binucleophiles, Letters in Organic Chemistry, 2(2): 188-197 (2005).
Nilsson et al., Controlling Stereochemistry During Oxidative Coupling. Preparation of Rp or Sp Phosphoramidates from One P-chiral Precursor, Chem. Commun., (22): 2566-7 (2004).
Nowotny, M. et al., Structure of human RNase H1 complexed with an RNA/DNA hybrid: insight into HIV reverse transcription, Mol Cell, 28(2):264-76 (2007).
O'Connell, D. et al., Calcium-dependent oligonucleotide antagonists specific for L-selectin, Proc. Natl. Acad. Sci. USA, 93: 5883-5887 (1996).
Ohgi, T. et al., A New RNA Synthetic Method with a 2'-O-(2-Cyanoethoxymethyl) Protecting Group, Org. Lett., 7(16): 3477-3480 (2005).
Ohkubo et al., Synthesis of oligodeoxyribonucleotides containing hydroxymethylphosphonate bonds in the phosphoramidite method and their hybridization properties, Tetrahedron Letters, 46(51): 8953-8957 (2005).
Oka, N. et al., Stereocontrolled synthesis of dinucleoside boranophosphates by an oxazaphospholidine method, Nucleic Acids Symposium Series, (49): 131-132 (2005).
Ostergaard, M. et al., Rational design of antisense oligonucleotides targeting single nucleotide polymorphisms for potent and allele selective suppression of mutant Huntingtin in the CNS, Nucleic Acids Research, 41(21), 9634-9650 (2013).
Pan, Q-W. et al., New therapeutic opportunities for Hepatitis C based on small RNA, World J. Gastroenterol., 13(33): 4431-4436 (2007).
Patil et al., Syntheses and properties of oligothymidylate analogs containing stereoregulated phosphorothioate and phosphodiester linkages in an alternating manner, Bioorganic & Medicinal Chemistry Letters, 4(22): 2663-2666 (1994).
Perrino, E. et al., New sulfurated derivatives of valproic acid with enhanced histone deacetylase inhibitory activity, Bioorganic & Medicinal Chemistry Letters, 18(6): 1893-1897 (2008).
Pfister, E.L. et al., Five siRNAs targeting three SNPs may provide therapy for three-quarters of Huntington's disease patients, 19(9): 774-778 (2009).
Pitsch, S. et al., Reliable Chemical Synthesis of Oligoribonucleotides (RNA) with 2'-0-[(Triisopropylsil)oxy]methyl(2'-0-tom)-Protected Phosphoramidites, Helvetica Chimica Acta, 84: 3773-3795 (2001).
Pon, R. T., Solid-Phase Supports for Oligonucleotide Synthesis, Current Protocols in Nucleic Acid Chemistry, 3.1.1-3.1.28 (2000).
Potter, B.V.L. et al., Synthesis and Configurational Analysis of Dinucleoside Phosphate Isotopically Chiral at Phosphorus. Stereochmical Course of *Penicillium citrum* Nuclease P1 Reaction, Biochemistry, 22: 1369-1377 (1983).
Prakash, T.P. et al., Z -0-[2-(Methylthio )ethyl]-Modified Oligonucleotide: An Analogue of 2'-0-[2-(Methoxy)-ethyl]-Modified Oligonucleotide with Improved Protein Binding Properties and High Binding Affinity to Target RNA, Biochemistry, 41: 11642-11648 (2002).
Prhavc, M. et al., 2'-0[2[2-(N,N-Dimethylamino)ethoxy]ethyl] Modified Oligonucleotides: Symbiosis of Charge Interaction Factors and Stereoelectronic Effects, Organic Letters, 5(12): 2017-2020 (2003).
Puri, N. et al, Targeted Gene Knockout by 2'-O-Aminoethyl Modified Triplex Forming Oligonucleotides, J. Biol. Chem., 276: 28991-28998 (2001).

(56) References Cited

OTHER PUBLICATIONS

Ravikumar, V.T. et al., Unylinker: An Efficient and Scaleable Synthesis of Oligonucleotides Utilizing a Universal Linker Molecule: A Novel Approach to Enhance the Purity of Drugs, Org. Process Res. Dev., 12(3): 399-410 (2008).
Reese, C.B. and Yan, H., Solution phase synthesis of ISIS 2922 (Vitravene) by the modified H-phophane approach, J. Chem. Soc., Perkin Trans. I, 2619-2633 (2002).
Reither, S. and Jeltsch, A., Specificity of DNA triple helix formation analyzed by a FRET assay, BMC Biochemistry, 3: 9 pages (2002).
Revankar, G. R. and Rao, T.S., DNA with Altered Bases, DNA and Aspects of Molecular Biology, Comprehensive Natural Products Chemistry, 7.09: 313-339 (1999).
Robinson, D.S. et al., Predominant TH2-Like Bronchoalveolar T-Lymphocyte Population in Atopic Asthma, The New England Journal of Medicine, 326: 298-304 (1992).
Seidman, M.M. and Glazer, P.T. The potential for gene repair via triple helix formation, The Journal of Clinical Investigation, 112(4): 487-494 (2003).
Sergueeva et al., Synthesis of Dithymidine Boranophosphates via Stereospecific Boronation of H-phosphonate Diesters and Assignment of their Configuration, Tetrahedron Letters, 40: 2041-2044 (1999).
Seth, P.P. et al., An Exocyclic Methylene Group Acts as a Bioisostere of the 2'Oxygen Atom in LNA, J. Am. Chem. Soc, 132(42): 14942-14950 (2010).
Skotte, N.H. et al., Allele-specific suppression of mutant huntingtin using antisense oligonucleotides: providing a therapeutic option for all Huntington disease patients, PLoS One, 9(9): e107434 1-18 (2014).
Small, L.D. et al.,Comparison of Some Properties of Thiolsulfonates and Thiolsulfinates, Journal of the American Chemical Society, 71(10): 3565-3566 (1949).
Smith, A. et al., The murine haemopexin receptor, Biochem. J., 276: 417-425 (1991).
Sobkowski, et al. Stereochemistry of internucleotide bond formation by the H?phosphonate method. 1. Synthesis and 31P NMR analysis of 16 diribonulceoside (3'-5')-H-phosphonates and the corresponding phosphorothioates, Nucleosides Nucleotides Nucleic Acids, 24(10-12): 1469-84 (2005).
Stawinski et al., Nucleoside H-phosphonates. 14. Synthesis of nucleoside phosphoroselenoates and phosphorothioselenoates via stereospecific selenization of the corresponding H-phosphonate and H-phosphonothioate diesters with the aid of new selenium-transfer reagent, 3H-1,2-benzothiaselenol-3-one, J. Org. Chem., 59(1): 130-136 (1994).
Stawinski et al., Stereospecific oxidation and oxidative coupling of H-phosphonate and H-phosphonothioate diesters, Tetrahedron Letters, 33(22):3185-3188 (1992).
Stawinski, J. and Stromberg, R. Di- and Oligonucleotide Synthesis Using H-Phosphonate Chemistry, Methods in Molecular Biology, 288: 81-100 (2005).
Stawinski, J. and Thelin, M., 3-*H*-2,1-benzoxathiol-3-one 1-oxide—A New Reagent for Stereospecific Oxidation of Nucleoside H-Phosphonothioate Diesters, Tetrahedron Letters, 33(22): 3189-3192 (1992).
Stawinski, J. and Thelin, M., 3*H*-1,2-benzothiaselenol-3-one. A new selenizing reagent for nucleoside H-phosphonate and H-phosphonothioate diesters, Tetrahedron Letters, 33(47): 7255-7258 (1992).
Stec et al., Deoxyribonucleoside 3'-O-(2-Thio- and 2-Oxo-"spiro"-4,4-pentamethylene-1,3,2-oxathiaphospholane)s:? Monomers for Stereocontrolled Synthesis of Oligo(deoxyribonucleoside phosphorothioate)s and Chimeric PS/PO Oligonucleotides, J. Am. Chem. Soc., 120(29): 7156-7167 (1998).
Stec, W.J. et al., Stereodependent inhibition of plasminogen activator inhibitor type 1 by phosphorothioate oligonucleotides: proof of sequence specificity in cell culture and in vivo rat experiments, Antisense Nucleic Acid Drug Dev., 7(6):567-73 (1997).
Sureshbabu, V.V. et al., Synthesis of tetrazole analogues of amino acids using Fmoc chemistry: isolation of amino free tetrazoles and their incorporation into peptides, Tetrahedron Letters, 48(39): 7038-7041 (2007).
Takeno, H. et al., Selection of an RNA Molecule that Specifically Inhibits the Protease Activity of Subtilisin, J. Biochem., 125: 1115-1119 (1999).
Thayer, J.R. et al., Separation of oligonucleotide phosphorothioate distereoisomers by pellicular anion-exchange chromatography, Journal of Chromatography A, 1218: 802-808 (2011).
Tomoskozi et al., Stereospecific conversion of H-phosphonates into phosphoramidates. The use of vicinal carbon-phosphorus couplings for configurational determination of phosphorus, Tetrahedron, 51(24): 6797-6804 (1995).
Tuerk, C. and Gold, L., Systematic Evolution of Ligans by Exponential Enrichment: RNA Ligands to Bacteriophage T4 DNA Polymerase, Science, 249: 505-510 (1990).
Turner, D.H. et al, Improved Parameters for Prediction of RNA Structure, Cold Spring Harbor Symposia on Quantitative Biology, LII: 123-133 (1987).
Turner, D.H. et al., Free Energy Increments for Hydrogen Bonds in Nucleic Acid Base Pairs, J. Am. Chem. Soc., 109: 3783-3785 (1987).
Uphoff, K.W. et al., In vitro selection of aptamers: the death of pure reason, Curr. Opin. Struct. Biol., 6: 281-288 (1996).
Van Der Veken, P. et al., Irreversible inhibition of dipeptidyl peptidase 8 by dipeptide-derived diaryl phosphonates, Journal of Medicinal Chemistry, 50(23): 5568-5570 (2007).
Vasquez, K.M. et al., Chromosomal mutations induced by triplex-forming oligonucleotides in mammalian cells, Nucl. Acids Res. 27(4): 1176-1181 (1999).
Verma, S. and Eckstein, F., Modified Oligonucleotides: Synthesis and Strategy for Users, Annu. Rev. Biochem., 67: 99-134 (1998).
Vermeulen, A. et al., Double-Stranded Regions Are Essential Design Components of Potent Inhibitors of Risc Function, RNA, 13: 723-730 (2007).
Vlassov, V.V. et al., Transport of oligonucleotides across natural and model membranes, Biochimica et Biophysica Acta, 1197: 95-108 (1994).
Vuyisich, M. and Beal, P.A., Regulation of the RNA-dependent protein kinase by triple helix formation, Nuc, Acids Res., 28(12): 2369-74 (2000).
Wada et al., Stereocontrolled Synthesis of Phosphorothioate RNA by the Oxazaphospholidine Approach, Nucleic Acids Symp. Ser., 48: 57-58 (2004).
Wan et al., Synthesis of Second Generation Antisense Oligonucleotides Containing Chiral Phosphorothioate Linkages and Evaluation of their Biophysical Properties and Biological Activity, 10th Annual Meeting of the Oligonucleotide Therapeutics Society, abstract received by Applicant Oct. 7, 2014, poster setup prior to presentation (first known to Applicant late Oct. 12, 2014, PST), poster presentation Oct. 13, 2014.
Wan, W.B. et al., Synthesis, biophysical properties and biological activity of second generation antisense oligonucleoties containing chiral phosphorothioate linkages, Nucleic Acid Research, 27 pages, online advance access (2014).
Wang H, et al., Therapeutic gene silencing delivered by a chemically modified siRNA against mutant SOD 1 slows ALS progression, The Journal of Biological Chemistry, 283(23):15845-15852 (2008).
Warby, S.C. et al., CAG expansion in the Huntington disease gene is associated with a specific and targetable predisposing haplogroup, Am. J. Hum. Genet., 84(3): 351-366 (2009).
Weidner, J.P. et al., Alkyl and Aryl Thiolsulfonates, Journal of Medicinal Chemistry, 7(5): 671-673 (1964).
Weiser, T.G., et al., An estimation of the global volume of surgery: a modeling strategy based on available data, Lancet, 372(9633): 139-144 (2008).
Wengel, J., Synthesis of 3'-C- and 4'-C-Branched Oligodeoxynucleotides and the Development of Locked Nucleic Acid (LNA), Ace. Chem. Res., 32: 301-310 (1999).

(56) References Cited

OTHER PUBLICATIONS

Widdison, W. C. et al., Semisynthetic Maytansine analogues for the targeted treatment of cancer, Journal of Medicinal Chemistry, 49(14): 4392-4408 (2006).
Written Opinion for PCT/IB2009/007923, 8 pages (Sep. 6, 2010).
Written Opinion for PCT/US2012/046805, 9 pages (Sep. 19, 2012).
Xiong, H.Y. et al., The human splicing code reveals new insights into the genetic determinants of disease, Science, 347(6218): 144 (2015).
Xu, L. et al., Cyclic ADP-ribose analogues containing the methylenebisphosphonate linkage: effect of pyrophosphate modifications on Ca2+ release activity, J. Med. Chem., 48(12): 4177-4181 (2005).
Yamada, O. et al., Diastereoselective Synthesis of 3,4-Dimethoxy-7-morphinanone: A Potential Route to Morphine, Organic Letters, 2(18): 2785-2788 (2000).
Yamamoto, S. et al., Unique Palindromic Sequences in Synthetic Oligonucleotides are Required to Induce INF and Augment INF-Mediated Natural Killer Activiry, J. Immunol., 148(12): 4072-4076 (1992).
Zhao, J. et al., Genome-wide Identification of Polycomb-Associated RNAs by RIP-seq, Molecular Cell, 40: 939-953 (2010).
Zlatev et al., Phosphoramidate dinucleosides as hepatitis C virus polymerase inhibitors, J Med Chem., 51(18): 5745-57 (2008).
Aldrich Chemical Co. Catalog, 2007-2008 Issue, only page 1719 supplied: see first full entry at col. 1 (S-methyl methanethiosulfonate), Milwaukee, WI.
Communication Relating to the Results of the Partial International Search of PCT/IB2015/000395, Annex to Form PCT/ISA/206, 3 pages (Aug. 24, 2015).
Engelhardt, J.A. et al., Scientific and Regulatory Policy Committee Points-to-consider Paper*: Drug-induced Vascular Injury Associated with Nonsmall Molecule Therapeutics in Preclinical Development: Part 2. Antisense Oligonucleotides, Toxicologic Pathology, XX: 1-10 (2015).
Frazier, K. et al., Potential Mechanisms of vascular toxicity in Monkeys with antisense oligonucleotides, TIDES oligo confrence, 1-25 (May 15, 2014).
Inagawa, T. et al., Inhibition of human immunodeficiency virus type 1 replication by P-stereodefined oligo(nucleoside phosphorothioate)s in a long-term infection model, FEBS Letters, 528(1-3): 48-52 (2002).
Kay, C. et al., Huntingtin Haplotypes Provide Prioritized Target Panels for Allele-Specific Silencing in Huntington Disease Patients of European Ancestry, Molecular Therapy, Accepted Article Preview Online (Jul. 23, 2015).
Koziolkiewicz, M. et al., Effect of P-chirality of oligo(deoxyribonucleoside phosphorothioate)s) on the activity of terminal deoxyribonucleotidyl transferase, FEBS Letters, 434(1-2): 77-82 (1998).
Liang, X-h. et al., Identification and characterization of intracellular proteins that bind oligonucleotides with phosphorothioate linkages, Nucleic Acids Research 43(5): 2927-2945, Supplemental Data pp. 1-20 (2015).
Liu, W. et al., Increased Steady-State Mutant Huntingtin mRNA in Huntington's Disease Brain, Journal of Huntington's Disease 2: 491-500 (2013).
Lu, Y., Recent advances in the stereocontrolled synthesis of antisense phosphorothioates, Mini Reviews in Medicinal Chemistry, 6(3): 319-330 (2006).
Pharmacology Review(s), Application Number: 203568Orig1s000, Center for Drug Evaluation and Research, Food and Drug Administration, Department of Health & Human Services, 2013.
Senn, J.J. et al., Non-CpG-Containing Antisense 2-Methoxyethyl Oligonucleotides Activate a Proinflammatory Response Independent of Toll-Like Receptor 9 or Myeloid DifferentiationFactor 88, The Journal of Pharmacology and Experimental Therapeutics, 314: 972-979 (2005).
Sheehan, J.P. and Phan, T.M. Phosphorothioate Oligonucleotides Inhibit the Intrinsic Tenase Complex by an Allosteric Mechanism, Biochemistry, 40: 4980-4989 (2001).
Singhrao, S.K. et al., Increased Complementl Biosynthesis by Microglia and Complement Activation on Neurons in Huntington's Disease, Experimental Neurology, 159: 362-376 (1999).
Walker, J.R. et al., Structure of the Ku heterodimer bound to DNA and its implications for double-strand break repair, Nature, 412: 607-614 (2001).
Wild, E. et al., Quantification of mutant huntingtin protein in cerebrospinal fluid from Huntington's disease patients, The Journal of Clinical Investigation, 125(5): 1979-1986 (2015).
Xu, D. and Esko, J.D., Demystifying Heparan Sulfate- Protein Interactions, Annu. Rev. Biochem., 83: 129-157 (2014).
Yanai, H. et al., Suppression of immune responses by nonimmunogenic oligodeoxynucleotides with high affinity for high-mobility group box proteins (HMGBs), PNAS Early Edition, 1-6 (2011).
Ganguly, A.K. et al., Structure of Halomicin B, J.C.S. Chem. Comm., 395-396 (1974).
Amarzguioui et al., Tolerance for mutations and chemical modifications in a siRNA, Nucleic Acids Research 31(2): 589-595 (2003).
Arai, K. et al., Synthesis and properties of novel 2'-O-alkoxymethyl-modified nucleic acids, Bioorganic & Medicinal Chemistry Letters, 21(21): 6285-6287 (2011).
Bobkov, G.V. et al., Phosphoramidite building blocks for efficient incorporation of 2'-O-aminoethoxy(and propoxy)methyl nucleosides into oligonucleotides, Tetrahedron, 64: 6238-6251 (2008).
Braasch et al., RNA Interference in Mammalian Cells by Chemically-Modified RNA, Biochemistry 42(26): 7967-7975 (2003).
Burgers et al., Absolute configuration of the diastereomers of adenosine 5'-O-(1- thiaotriphosphate): Consequences for the stereochemistry of polymerization by DNA-dependent RNA polymerase from *Escherichia coli*, Proceedings of the National Academy of Sciences of the United States of America 75(10): 4798-4800 (1978).
CAS RN 78-96-6, Entered STN: Nov. 16, 1984.
Clark, J.H, Flouride IOn as a Base in Organic Synthesis, Chemical Reviews, 1980 American Chemical Society 80(5): 429-452 (1980).
Documents submitted to the U.S. Securities and Exchange Commission (SEC), Wave Life Sciences Ltd. CIK#: 0001631574 (2015-). Additional documents available through EDGAR of SEC, URL: <http://www.sec.gov/cgi-bin/browse-edgar?company=wave+life+sciences&owner=exclude&action=getcompany>.
Egli, M. et al., Probing the Influence of Stereoelectronic Effects on the Biophysical Properties of Oligonucleotides: Comprehensive Analysis of the RNA Affinity, Nuclease Resistance, and Crystal Structure of Ten 2'-0-Ribonucleic Acid Modifications, Biochemistry, 44: 9045-9057 (2005).
File Registry on STN, RN 18217-60-2, Entered STN: Nov. 16, 1984.
File Registry on STN, RN 871246-91-2, Entered STN: Jan. 5, 2006.
Gijsen, H.J.M et al., Development of two diastereoselective rougtes towards trans-4-aminomethyl-piperidin-3-o1 building blocks, Tetrahedron 64(10): 2456-2464 (2008).
Guo, M. et al., Solid-phase stereoselective synthesis of 2'-0-methyl-oligo-ribonucleoside phosphorothioates using nucleoside bicyclic oxazaphospholidines, Biorganic & Medicinal Chemistry Letters, 8(18):2539-2544 (1998).
Hansen et al., Azaribofuranoside Analogues as Designed Inhibitors of Purine Nucleoside Phosphorylase, Synthesis and Biological Evaluation, Acta Chemis Scandinavica 52: 1214-1222 (1998).
International Preliminary Report on Patentability and Written Opinion of the Searching Authority for PCT/JP2011/055018 (Oct. 11, 2012) with English Translation thereof.
International Preliminary Report on Patentability for Application No. PCT/JP2010/065900, 6 pages (Mar. 29, 2012).
International Preliminary Report on Patentability for Application No. PCT/JP2010/065900, 7 pages (Apr. 19, 2012). (English Translation).
International Preliminary Report on Patentability for Application No. PCT/JP2011/071559, 7 pages (Apr. 25, 2014).

(56) References Cited

OTHER PUBLICATIONS

International Preliminary Report on Patentability for PCT/JP2013/004303, 1 page (Jan. 13, 2015).
International Search Report for PCT/IB2015/000395, 7 pages (Oct. 30, 2015).
International Search Report for PCT/JP11/71559, 3 pages (Dec. 20, 2011).
International Search Report for PCT/JP2010/065900, 1 page (Sep. 15, 2010).
International Search Report for PCT/JP2011/077313, 2 pages (Jan. 10, 2012).
International Search Report for PCT/JP2011/55018 (Mar. 29, 2011).
International Search Report for PCT/JP2013/004303, 3 pages (Aug. 13, 2013).
Kihara, M et al., New norepinephrine potentiators: synthesis and structure-actvity relastionships of a series of 4-phenyl-1,2,3,4-tetrahydroisoquinolin-4-ols, Chemical & Pharmaceutical Bulletin 42(1): 67-73 (1994).
Kiviniemi, A. et al., Solid-Supported 2'-O-Glycoconjugation of Oligonucleotides by Azidation and Click Reactions, Bioconjugate Chemistry, 22(6): 1249-1255 (2011).
Machine Translation of JP 2010-265304 (2010). <http://dossier1.ipdl.inpit.go.jp/AIPN/odse_top_dn.ipdl?N0000=7400>.
Matysiak, S et al., Acetals as New 2'-O-Protecting Functions for the Synthesis of the Oligoribonucleotides: Synthesis of Uridine Building Blocks and Evaluatino of Their Relative Acid Stability, Helvetica Chimica Acta 81: 1545-1566 (1998).
Misaki, S et al., Dehydration of 2-Trifluoromethyl-3,3,3-Trifluoropropanil with Base, Journal of Flourine Chemistry 24: 531-533 (1984).
Oka, N. et al., Stereocontrolled synthesis of oligonucleoside phosphorothioates and PO/PS-chimeric oligonucleotides by using oxazaphospholidine derivatives, Nucleic Acids Symposium Series, 52: 335-336 (2008).
Parrish et al., Functional Anatomy of a dsRNA Trigger: Differential Requirement for the Two Trigger Strands in RNA Interference, Molecular Cell, 6:1077-1087 (2000).
Pontiggia, R. et al., 2-C-Methyluridine modified hammerhead riboxyme against the estrogen receptor, Bioorganic & Medicinal Chemistry Letters, 20: 2806-2808 (2010).
Pontiggia, R. et al., DNAzymes and ribozymes carrying 2'-C-methyl nucleotides, Nucleic Acids Sumposium Series, 52: 521-522 (2008).
Potter et al, Stereospecificity of nucleases towards phosphorothioate-substituted RNA: stereochemistry of transcription by T7 RNA polymerase, Nucleinc Acids Research, 15(10): 4145-4162 (1987).
Puri, N. et al., The Synthesis and Reactivity of New 2-(N,N-Diisoprophylamino)-3-Methylsulfonyl-1,3,2-Benzoxazaphospholes. The Utility of the 5-Chloro analogue in the One-Pot Synthesis of Oligothiophosphates: [ApsppA, ApspppA, ppp5'A2'ps5'A, m7GpsppA, Apspppp, Apspp], Tetrahedron 51(10): 2991-3014 (1995).
Rozners, E. et al., Evaluation of 2'-hydroxyl protection in RNA-synthesis using the H-phosphonate approad, Nucleic Acids Research, 22(1): 94-99 (1994).
Sakatsume, O. et al., Solid Phase Synthesis of Oligoribonucleotides by the Phosphoramidite Approach Using 2'-O-1-(2-Chloroethoxy)Ethyl Protection, Tetrahedron, 47(41): 8717-8728 (1991).
Saneyoshi, H. et al., A General Method for the Synthesis of 2'-0-Cyanoethylated Oligoribonucleotides Having Promising Hybridization Affinity for DNA and RNA and Enhanced Nuclease Resistance, The Journal of Organic Chemistry, 70(25): 10453-10460 (2005).
Sierzchala et al., Oxathiaphospholane Method of Stereocontrolled Synthesis of Diribonucleoside 3', 5'—Phosphorotioates, Journal of Organic Chemistry 61(19): 6713-6716 (1996).
Umemoto, T et al., Oligoribonucleotide Synthesis by the use of 1-(2-cyanoethoxy)ethyl (CEE) as a 2'-hydroxy protecting group, Tetrahedron Letters 45: 9529-9531 (2004).
Usman, N et al., Automated Chemical Synthesis of Long Oligoribonucleotides Using 2'-O-Siylylated Ribonucleoside 3'-O-Phosphoramidites on a Controlled-Pore Glass Support, J. Am. Chem. Soc. 109(25): 7845-7854 (1987).
Wada, Takeshi, Chapter I Development of nucleic acid medicines, 3.3 Chemical synthesis of phosphorous atom-modified nucleic acids, CMC Publication., Fronteir of Development of Nucleic Acid Medicine: 67-75 (2009).
Welz et al., 5-(Benzylmercapto)-1H-tetrazole as activator for 2'-O-TBDMS phosphoramidite building blocks in RNA synthesis, Tetrahedron Letters, 43: 795-797 (2002).
Wong, Chui Ming, Synthesis of anisomycin. Part I. The stereospecific synthesis of N-benzoyl-2-(p-methoxybenzyl)-3-hydroxy-4-carboxamido pyrrolidine and the absolute configuration of anisomycin, Canadian journal of Chemistry 46: 1101-1104 (1968).
Written Opinion for PCT/IB2015/000395, 10 pages (Oct. 30, 2015).
Written Opinion for PCT/JP11/55018, 3 pages (Mar. 29, 2011).
Written Opinion for PCT/JP11/71559, 6 pages (Dec. 20, 2011).
Written Opinion for PCT/JP2010/065900, 5 pages (Sep. 15, 2010).
Written Opinion for PCT/JP2013/004303, 6 pages (Aug. 13, 2013).
Wu, X. et al., Synthesis of 5'-C- and 2'-O-(Bromoalkyl)-Substituted Ribonucleoside Phosphoramidites for the Post-synthetic Functionalization of Oligonucleotides on Solid Support, Helvetica Chimica Acta, 83: 1127-1144 (2000).
Yamakage, S-i. et al., 1-(2-Chloroethoxy)Ethyl Group for the Protection of 2'-Hydroxyl Group in the Synthesis of Oligoribonucleotides, Tetrahedron Letters, 30(46): 6361-6364 (1989).
Yu, S. et al., A One-Pot Formal [4 + 2] Cycloaddition Approach to Substituted Piperidines, Indolizidines, and Quinolizidines. Total Synthesis of Indolizidine (−)-209l, Journal of Organic Chemicals, 70:7364-7370 (2005).
Guerciolini, R., Allele-selective Silencing of Mutant Huntingtin by Stereopure Oligonucleotides, WAVE Life Sciences, Huntington's Disease Society of America, HDSA Presentation 2016 (Jun. 3, 2016).
Iwamoto, N. et al., Optimization of Therapeutic Phosphorothioate Oligonucleotides by P-Chirality Control, WAVE Life Sciences, PSJ Congress: The Pharmaceutical Society of Japan, (Mar. 25-28, 2016).
Meena, Control of Human RNase H Mediated Cleavage by Stereopure Phosphorothioate Oligonucleotides, WAVE Life Sciences, TIDES Meeting (May 3-6, 2015).
Meena, Development of Allele Specific Antisense Oligonucleotides, WAVE Life Sciences, TIDES Meeting (May 11, 2016).
Meena, Development of Allele Specific Antisense Oligonucleotides, WAVE Life Sciences, ACS Central Regional Meeting (CERM), Covington, KY (May 19, 2016).
Meena, et al., Therapeutic Implications of Controlling P-Chirality in Phosphorothioate Oligonucleotides, TIDES Poster (May 12-15, 2014).
Meena, Optimization of Antisense Drugs by P-Stereochemistry Control, WAVE Life Sciences, OTS Annual Meeting 2014, Oligonucleotide Therapeutics Society (Oct. 12-14, 2014).
Zhang, J. et al., Optimization of Exon Skipping Therapies for Duchenne Muscular Dystrophy, WAVE Life Sciences, PPMD: Parent Project Muscular Dystrophy Meeting, Orlando, FL (Jul. 25, 2016).
Ager, D.J. The Peterson olefination reaction, Organic Reactions, 38: 1-223(2004).
Agrawal, S. and Kandimalla, E.R., Antisense and/or Immunostimulatory Oligonucleotide THerapeutics, Current Cancer Drug Targets, Bentham Science, 1(3):1 page URL: <http:www.eurekaselect.com/65087/article>[Retrieved Apr. 3, 2016].
Block, S.S. and Weidner, J.P, Vibrational Behavior and Structure of Disulfide Dioxides (Thiolsulfonates), Applied spectroscopy, 20(2): 71-73 (1966).
Boczkowska, M. et al., Stereodefined Phosphorothioate Analogues of DNA: Relative Thermodynamic Stability of the Model PS-DNA/DNA and PS-DNA/RNA complexes, Biochemistry, 41: 12483-12487 (2002).

(56) References Cited

OTHER PUBLICATIONS

Bonora, G.M. et al., Large scale, liquid phase synthesis of oligonucleotides by the phosphoramidite approach, Nucleic Acids Research, 21(5): 1213-1217 (1993).
Bumcrot, D et al., RNAi therapeutics: a potential new class of pharmaceutical drugs, Nat. Chem. Bio., 2: 711-9 (2006).
Campbell. J. et al., Hybrid polymer/MOF membranes for Organic Solvent Nanofiltration (OSN): Chemical modification and the quest for perfection, Journal of Membrance Science, 503: 166-176 (2016).
CAS Registry No. 1225524-67-3; STN Entry Date May 28, 2010; α-[(2-methylphenyl)methyl]-Pyrrolidinemethanol.
CAS Registry No. 1225524-68-4; STN Entry Date May 28, 2010; α-[(4-methylphenyl)methyl]-2-Pyrrolidinemethanol.
CAS Registry No. 1225545-00-5; STN Entry Date May 28, 2010; α-[(2,4,6-trimethylphenyl)methyl]-2-Pyrrolidinemethanol.
CAS Registry No. 1225554-20-0; STN Entry Date May 28, 2010; α-[(4-ethylphenyl)methyl]-2-Pyrrolidinemethanol.
CAS Registry No. 1225594-74-0; STN Entry Date May 28, 2010; α-[(2-chloro-6-fluorophenyl)methyl]-2-Pyrrolidinemethanol.
CAS Registry No. 1225682-42-7; STN Entry Date May 30, 2010; α-[(4-chlorophenyl)methyl]-2-Pyrrolidinemethanol.
CAS Registry No. 1226037-41-7; STN Entry Date May 30, 2010; α-[(3-chlorophenyl)methyl]-2-Pyrrolidinemethanol.
CAS Registry No. 1226118-97-3; STN Entry Date May 30, 2010; α-[(3-bromophenyl)methyl]-2-Pyrrolidinemethanol.
CAS Registry No. 1226119-02-3; STN Entry Date May 30, 2010; α-[(4-bromophenyl)methyl]-2-Pyrrolidinemethanol.
CAS Registry No. 1226146-65-1; STN Entry Date May 30, 2010; α-[(2,4-dimethylphenyl)methyl]-2-Pyrrolidinemethanol.
CAS Registry No. 1226160-20-8; STN Entry Date May 30, 2010; α-[(2,5-dimethylphenyl)methyl]-2-Pyrrolidinemethanol.
CAS Registry No. 122178-36-4; STN Entry Date May 30, 2010; α-[(2-fluorophenyl)methyl]-2-Pyrrolidinemethanol.
CAS Registry No. 1226188-06-2; STN Entry Date May 30, 2010; α-[(4-(1-methylethyl)phenyl)]methyl]-2-Pyrrolidinemethanol.
CAS Registry No. 1226204-20-1; STN Entry Date May 30, 2010; α-[(3-methylphenyl)methyl]-2-Pyrrolidinemethanol.
CAS Registry No. 1226231-44-2; STN Entry Date May 30, 2010; α-[(2-chlorophenyl)methyl]-2-Pyrrolidinemethanol.
CAS Registry No. 1226352-28-8; STN Entry Date May 30, 2010; α-[(2,4-dichlorophenyl)methyl]-2-Pyrrolidinemethanol.
CAS Registry No. 1226352-38-0; STN Entry Date May 30, 2010; α-[(3,4-dichlorophenyl)methyl]-2-Pyrrolidinemethanol.
CAS Registry No. 1226413-27-9; STN Entry Date May 30, 2010; α-[(phenylmethyl]-2-Pyrrolidinemethanol.
CAS Registry No. 1226419-15-3; STN Entry Date May 30, 2010; α-[(4-fluorophenyl)methyl]-2-Pyrrolidinemethanol.
CAS Registry No. 1263282-82-1; STN Entry Date Feb. 21, 2011; (S)-[(dipheny)methyl]-2-Pyrrolidinemethanol.
Crooke, S.T. and Geary, R.S. Clinical pharmacological properties of mipomersen (Kynamro), a second generation antisense inhibitor of apolipoprotein B, Br. J. Clin. Pharmacol., 76: 269-276 (2012).
Crooke, S.T., Molecular mechanisms of action of antisense drugs, Biochemica et Biophysica Acta, 1489: 31-44 (1999).
De Koning, M.C. et al., Simple and Efficient Solution-Phase Synthesis of Oligonucleotides Using Extractive Work-Up, Organic Process Research & Developmen, 10: 1238-1245 (2006).
Deleavey, G.F. and Damha, M.J., Designing chemically modified oligonucleotides for targeted gene silencing. Chem. Bio., 19: 937-54 (2012).
Eckstein, F. et al., Stereochemistry of polymerization of DNA-dependent RNA-polymerase from *Escherichia coli*: an investigation with a diastereomeric ATP-analogue, Proc. Natl. Acad. Sci. USA, 73: 2987-90 (1976).
Gaffney, P.R.J. et al., Liquid-Phase Synthesis of 2'-Methyl-RNA on a Homostar Support through Organic-Solvent Nanofiltration, Chem. Eur. J., 21: 1-10 (2015).
Hammond, S.M. and Wood, M.J. Genetic therapies for RNA mis-splicing diseases, Trends Genet., 27:196-205 (2001).

Hartmann, B. et al., Sequence effects on energetic and structural properties of phosphorothioate DNA: a molecular modelling study, Nucleic Acids Research, 27(16): 3342-3347 (1999).
Hartmann, G. et al., Delineation of a CpG Phosphorothioate Oligodeoxynucleotide for Activating Primate Immune Responses in Vitro and In Vivo, The Journal of Immunology, 164(3): 1617-1624 (2000).
Heger, W. et al., Embryotoxic effects of thalidomide derivatives on the non-human primate Callithrix jacchus; 3. Teratogenic potency of the EM 12 enantiomers, Arch. Toxicol., 62: 205-208 (1988).
International Preliminary Report on Patentability for PCT/JP2013/069107, 10 pages (Jan. 15, 2015).
International Search Report of PCT/JP2013/069107, 2 pages (Oct. 1, 2013).
Jahns, H., et al., Stereochemical bias introduced during RNA synthesis modulates the activity of phosphorothioate siRNAs, Nat. Commun., 6: 6317 (2015).
Karwowski, B. et al., Stereocontrolled Synthesis of LNA Dinucleoside Phosphorothioate by the Oxathiaphospholane Approach, Bioorganic & Medicinal Chemistry Letters, 11: 1001-1003 (2001).
Kim, D. et al., Immunostimulation and anti-DNA antibody production by backbone modified CpG-DNA, Biochemical and Biophysical Research Communicationes, 379: 362-367 (2009).
Kim, S. et al., Liquid-Phase RNA Synthesis by Using Alkyl-Chain-Soluble Support, Chem. Eur. J., 19: 8615-8620 (2013).
Koziolkiewicz, M., et al., Stereodifferentiation—the effect of P chirality of oligo(nucleoside phosphorothioates) on the activity of bacterial RNase H, Nucleic Acids Res., 23: 5000-5 (1995).
Krieg, A.M. et al., P-chirality-dependent immune activation by phosphorothioate CpG oligodeoxynucleotides, Oligonucleotides, 13(6): 491-499 (2003).
Kungurtsev, V. et al., Solution-Phase Synthesis of Short Oligo-2'-deoxyribonucleotides by Using Clustered Nucleosides as a Soluble Support, Eur. J. Org. Chem., 6687-6693 (2013).
Kwon, H-J. et al., NF-kappaB-dependent regulation of tumor necrosis factor-alpha gene expression by CpG-oligodeoxynucleotides, Biochem. Biophys. Res. Commun., 311(1): 129-138 (2003).
Levin, A.A. et al., Basic Principles of the Pharmacokinetics of Antisense Oligonucleotide Drugs, Antisense Drug Technology: Principles, Strategies, and Applications, Second Edition, Capter 7: 183-215 (2008).
Lima, W.F., et al., Human RNase H1 discriminates between subtle variations in the structure of the heteroduplex substrate, Mol. Pharmacol., 71: 83-91 (2007).
Linton, M.F., et al., Transgenic Mice Expressing High Plasma Concentrations of Human Apolipoproteins B100 and Lipoprotein (a), J. Clin. Invest., 92: 3029-37 (1993).
Matsuno, Y. et al., Synthetic Method for Oligonucleotide Block by Using Alkyl-Chain-Soluble Support, Org. Lett., 18: 800-803 (2016).
Meade, M.F., et al., Efficient delivery of RNAi prodrugs containing reversible charge-neutralizing phosphotriester backbone modifications, Nat. Biotech., 32: 1256-61 (2014).
Molenkamp, B.G. et al., Local Administration of PF-3512676 CpG-B Instigates Tumor-Specific DC8+ T-Cell Reactivity in Melanoma Patients, Clin. Cancer Res., 14(14): 4532-4542 (2008).
Molina, A.G. et al., Acetylated and methylated β-Cyclodextrins asViable Soluble Supports for the Synthesis of Short 2'-Oligodeoxyribo-nucleotides in Solution, Molecules, 17: 12102-12120 (2012).
Molina, A.G. et al., Assembly of Short Oligoribonucleotides from Commercially Available Building Blocks on a Tetrapodal Soluble Support, Current Organic Synthesis, 12: 1-6 (2015).
Molina, A.G. et al., Solution phase synthesis of short of short oligoribonucleotides on a precipitative tetrapodal support, Beilstein Journal of Organic Chemistry, 10: 2279-2285 (2014).
Molina, A.G., Synthesis of Short Oligonucleotides on a Soluble Support by the Phosphoramidite Method, University of Turku, 1-66 (2015).
Nielsen, J. and Caruthers, M.H., Directed Arbuzov-type reactions of 2-cyano-1, 1-dimethylethyl deoxynucleoside phosphites, J. Am. Chem. Soc., 110: 6275-6 (1988).

(56) References Cited

OTHER PUBLICATIONS

Nukaga, Y. et al., Stereocontrolled Solid-Phase Synthesis of Phosphate/Phosphorothioate (PO/PS) Chimeric Oligodeoxyribonucleotides on an Automated Synthesizer Using an Oxazaphospholidine-Phosphoramidite Method, J. Org. Chem., A-J, 10 pages (Publication Date (Web): Mar. 3, 2016).
Pérez, B. et al., Antisense Mediated Splicing Modulation for Inherited Metabolic Diseases: Challenges for Delivery, Nucleic Acid Therapies, 24(1): 48-56 (2014).
Regan, J.R. et al., A Rapid Molecular Approach for Chromosomal Phasing, PLOS ONE, 1-15 (2015).
Sharma, V.K. et al. Antisense oligonucleotides: modifications and clinical trials, Med. Chem. Commun., 5: 1454-71 (2014).
Sproat, B.S., RNA Synthesis Using 2'-O-(Tert-Butyldimethylsiyl) Protection, Methods in Molecular Biology, 288: 17-31 (2005).
Stec, W.J. and Zon, G., Stereochemical Sudies of the Formation of Chiral Internucleotide Linkages by Phosphormadite COupling in the Synthesis of Oligodeocyribonucleotides, Tetrahedron Letters, 25(46): 5279-5282 (1984).
Stec, W.J. et al., Automated Solid-Phase Synthesis, Separation, and Stereochemistry of Phosphorothioate Analogues of Oligodeocyribonucleotides, J. Am. Chem. Soc., 106: 6077-6079 (1984).
Swayze, E.E. and Bhat, B., The medicinal chemistry of oligonucleotides Crooke, S.T. (ed) Antisense Drug Technology: Principles, Strategies, and Applications, CRC Press, Boca Raton, FL: 143-82 (2007).
Swayze, E.E. et al., Antisense oligonucleotides containing locked nucleic acid improve potency but cause significant hepatotoxcity in animals, Nucleic Acids Research, 35(20: 687-700 (2007).
Takahashi, D. et al., Novel diphenylmethyl-Derived Amide Protecting Group for Efficient liquid-Phase Peptide Synthesis: Ajiphase, Org. Lett., 14(17): 4514-4517 (2012).
Tam, Journal of Hematotherapy & Stem Cell Research, 12: 467-471 (2003).
U.S. Food and Drug Administration, Development of New Stereoisomeric Drugs, 8 pages (May 1, 1992). URL: http://www.fda.gov/Drugs/guidanceComplianceRegulatoryInformation/Guidances/ucm122883.htm [Retrieved Jun. 15, 2016].
Wave Life Sciences Poster, Therpeutic Implications of Controlling P-Chirality in Phosphorothioate Oligonucleotides, TIDES, San Diego (May 3-6, 2014).
Xiong, H.Y. et al., The human splicing code reveals new insights into the genetic determinants of disease, Science, 347(6218): 144, 12548061-8 (2015).
Yu, D. et al., Stereo-Enriched Phosphorothioate Oligodeoxynucleotides: Synthesis, Biophysical and Biological Properties, Bioorganic & Medicinal Chemitry, 8: 275-284 (2000).
Yu, R.Z. et al., Cross-species comparison of in vivo PK/PD relationships for second-generation antisense oligonucleotides targeting apolipoprotein B-100, Biochem. Pharmacol., 77: 910-919 (2009).
Aartsma-Rus, A. et al., Targeted exon skipping as a potential gene correction therapy for Duchenne muscular dystrophy, Neuromuscular Disorders, 12: S71-S77 (2002).
Brill, W. et al., Thioalkylation of Nucleoside-H-Phosphonates and Its Application to Solid Phase Synthesis of Oligonucleotides, Tetrahedron Letters, 36(5):703-706 (1995).
Change, W. et al., Systematic chemical modifications of single stranded siRNAs significantly improved CTNNB1 mRNA silencing, Bioorg. Med. Chem. Lett., 1-5 (2016), http://dx.doi.org/10.1016/j.bmcl.2016.07.064.
Documents submitted to and/or received from the United States Securities and Exchange Commission; downloaded from EDGAR (Dec. 17, 2015-Oct. 4, 2016).
Schmitz, C. et al., Synthesis of P-Sterogenic Phosphoramidite and Phosphorodiamidite Ligands and Their Application in Asymmetric Cataysis, Eur. J. Org. Chem., 6205-6230 (2015).
WAVE Life Sciences Press Release, WAVE life Sciences Added to the Russell 2000® Index, 2 pages (Jun. 27, 2016).
WAVE Life Sciences Press Release, WAVE Life Sciences Announces Plan to Deliver Six Clinical Programs by 2018, 6 pages (Jan. 29, 2016).
WAVE Life Sciences Press Release, WAVE Life Sciences Announces Pricing of Initial Public Offering, 3 pages (Nov. 11, 2015).
WAVE Life Sciences Press Release, WAVE Life Sciences Appoints Dr. Michael Panzara as Head of Neurology Franchise, 4 pages (Jul. 12, 2016).
WAVE Life Sciences Press Release, WAVE Life Sciences Appoints Keith Regnante as Chief Financial Officer, 4 pages (Aug. 17, 2016).
WAVE Life Sciences Press Release, WAVE Life Sciences Appoints Roberto Guerciolini, M. Senior Vice President and Head of Early Development, 2 pages (Apr. 7, 2015).
WAVE Life Sciences Press Release, WAVE Life Sciences Closed $18 Million Series A Financing to Advance Stereopure Nucleic Acid Therapeutics, 3 pages (Feb. 2, 2015).
WAVE Life Sciences Press Release, WAVE Life Sciences Enters Collaboration with Pfizer to Develop Genetically Targeted Therapies for the Treatment of Metabolic Diseases, 5 pages (May 5, 2016).
WAVE Life Sciences Press Release, WAVE Life Sciences Expands Stereopure Synthetic Chemistry Platform Capabilities, Augments Patent Portfolio with Addition of Single-Stranded RNAi (ssRNAi), 3 pages (Jun. 8, 2015).
WAVE Life Sciences Press Release, WAVE Life Sciences Raises $66 Million in Series B Financing, 3 pages (Aug. 18, 2015).
WAVE Life Sciences Press Release, WAVE Life Sciences Receives Orphan Drug Designation from FDA for its Lead Candidate Designed to Treat Huntington's Disease, 5 pages (Jun. 21, 2016).
WAVE Life Sciences Press Release, WAVE Life Sciences Reports First Quarter 2016 Financial Results and Provides Business Update, 9 pages (May 16, 2016).
WAVE Life Sciences Press Release, WAVE Life Sciences Reports Fourth Quarter and Full Year 2015 Financial Results and Provides Business Update, 10 pages (Mar. 30, 2016).
WAVE Life Sciences Press Release, WAVE Life Sciences Reports Second Quarter 2016 Financial Results and Provides Business Update, 10 pages (Aug. 15, 2016).
WAVE Life Sciences Press Release, WAVE Life Sciences to Advance Next-Generation Nucleic Acid Therapies to Address Unmet Need in Duchenne Muscular Dystrophy, 6 pages (May 9, 2016).
WAVE Life Sciences Press Release, WAVE Life Sciences to Present at the Deutsche Bank 41st Annual Health Care Conference, 2 pages (Apr. 29, 2016).
WAVE Life Sciences Press Release, WAVE Life Sciences to Present at the Jefferies 2016 Healthcare Conference, 2 pages (Jun. 1, 2016).
WAVE Life Sciences Press Release, WAVE Life Sciences to Present at the JMP Securities Life Sciences Conference, 2 pages (Jun. 15, 2016).
WAVE Life Sciences Press Release, WAVE Life Sciences to Present at the LEERINK Partner 5th Annual Global Healthcare Conference, 2 pages (Feb. 3, 2016).
WAVE Life Sciences Press Release, WAVE Life Sciences to Present at the Leerink Partners Rare Disease & Immuno-Oncology Roundtable, 2 pages (Sep. 14, 2016).
WAVE Life Sciences Press Release, WAVE Life Sciences to Present at the SunTrust Robinson Humphrey 2016 Orphan Drug Day Conference, 2 pages (Feb. 16, 2016).
Yamato, K. et al., Enhanced specificity of HPV16 E6E7 siRNA by RNA-DNA chimera modification, Cancer Gene Therapy, 18: 587-597 (2011).
Yu, D. et al., Single-Stranded RNAs Use RNAi to Potently and Allele-Selectively Inhibit Mutant Huntingtin Expression, Cell, 150: 895-908 (2012).

\* cited by examiner

NUCLEIC ACID PRODRUGS AND METHODS OF USE THEREOF

CROSS REFERENCE

This application is a US National Phase entry of International Application No. PCT/US2010/041068, filed Jul. 6, 2010, which claims the benefit of U.S. Provisional Application No. 61/223,369, filed Jul. 6, 2009, and U.S. Provisional Application No. 61/242,722, filed Sep. 15, 2009, each of which is incorporated herein by reference in its entirety.

FIELD OF THE INVENTION

Described herein are nucleic acid prodrugs and nucleic acid prodrugs comprising chiral phosphorous moieties and methods of making and using the same.

BACKGROUND OF THE INVENTION

Oligonucleotides are useful in therapeutic, diagnostic, research, and new and nanomaterials applications. The use of natural sequences of DNA or RNA is limited, for example, by their stability to nucleases. Additionally, in vitro studies have shown that the properties of antisense nucleotides such as binding affinity, sequence specific binding to the complementary RNA, stability to nucleases are affected by the configurations of the phosphorous atoms. Therefore, there is a need for prodrugs of stereodefined oligonucleotides to impart additional stability to oligonucleotide molecules in a number of in-vitro and in-vivo applications Prodrugs of stereodefined oligonucleotides which comprise phosphorus atom-modified nucleic acids and methods of use thereof are described herein.

SUMMARY OF THE INVENTION

One embodiment provides for a chiral nucleic acid prodrug.

One embodiment provides a nucleic acid prodrug having the following structure:

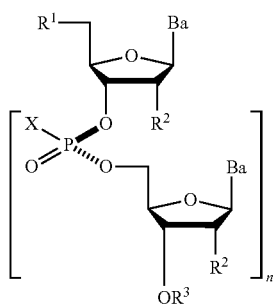

Formula 1 wherein $R^1$ is —OH, —SH, —NR$^d$R$^d$, —N$_3$, halogen, hydrogen, alkyl, alkenyl, alkynyl, alkyl-Y$^1$—, alkenyl-Y$^1$—, alkynyl-Y$^1$—, aryl-Y$^1$—, heteroaryl-Y$^1$—, —P(O)(R$^e$)$_2$, —HP(O)(R$^e$), —OR$^a$ or —SR$^c$;
$Y^1$ is O, NR$^d$, S, or Se;
$R^a$ is a blocking group;
$R^c$ is a blocking group;
each instance of R$^d$ is independently hydrogen, alkyl, alkenyl, alkynyl, aryl, acyl, substituted silyl, carbamate, —P(O)(R$^e$)$_2$, or —HP(O)(R$^e$);

each instance of R$^e$ is independently hydrogen, alkyl, aryl, alkenyl, alkynyl, alkyl-Y$^2$—, alkenyl-Y$^2$—, alkynyl-Y$^2$—, aryl-Y$^2$—, or heteroaryl-Y$^2$—, or a cation which is Na$^{+1}$, Li$^{+1}$, or K$^{+1}$;
$Y^2$ is O, NR$^d$, or S;
each instance of R$^2$ is independently hydrogen, —OH, —SH, —NR$^d$R$^d$, —N$_3$, halogen, alkyl, alkenyl, alkynyl, alkyl-Y$^1$—, alkenyl-Y$^1$—, alkynyl-Y$^1$—, aryl-Y$^1$—, heteroaryl-Y$^1$—, —OR$^b$, or —SR$^c$, wherein R$^b$ is a blocking group;
each instance of Ba is independently a blocked or unblocked adenine, cytosine, guanine, thymine, uracil or modified nucleobase;
at least one instance of X is —OCH$_2$CH$_2$S—S(O)$_2$R$_{10}$, —OCH$_2$CH$_2$S—SCH$_2$CH$_2$OH, —OCH$_2$CH$_2$CO$_2$H,

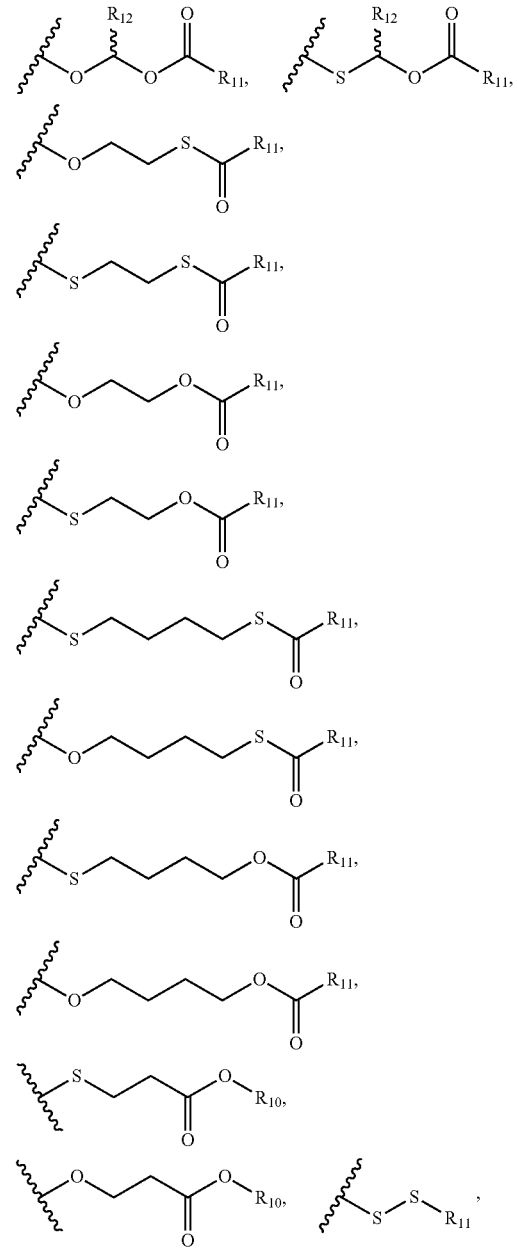

-continued

[chemical structures]

R³ is hydrogen, a blocking group, a linking moiety connected to a solid support or a linking moiety connected to a nucleic acid;
$R_{10}$ is an alkyl group having 1 to 4 carbon atoms;
$R_{11}$ is alkyl, aryl, heteroaryl, heterocyclyl, or cycloalkyl;
$R_{12}$ is hydrogen or alkyl;
Z is S or O;
q is 0, 1, or 3;
w is 1, 2, 3, 4, 5, or 6;
$R_{15}$ and $R_{16}$ are independently hydrogen or methyl;
$R_{17}$ is selected from alkyl, aryl or a $CH_2CH=CH_2$;
$R_{18}$ is selected from $N(CH_3)_2$,

[chemical structures]

and
n is an integer of 1 to about 200.
Another embodiment provides for a nucleic acid prodrug having the following structure:

Formula 1

[chemical structure]

wherein $R^1$ is —OH, —SH, —NR$^d$R$^d$, —N$_3$, halogen, hydrogen, alkyl, alkenyl, alkynyl, alkyl-Y$^1$—, alkenyl-Y$^1$—, alkynyl-Y$^1$—, aryl-Y$^1$—, heteroaryl-Y$^1$—, —P(O)(R$^e$)$_2$, —HP(O)(R$^e$), —OR$^a$ or —SR$^c$;
$Y^1$ is O, NR$^d$, S, or Se;
$R^a$ is a blocking group;
$R^c$ is a blocking group;
each instance of $R^d$ is independently hydrogen, alkyl, alkenyl, alkynyl, aryl, acyl, substituted silyl, carbamate, —P(O)(R$^e$)$_2$, or —HP(O)(R$^e$);
each instance of $R^e$ is independently hydrogen, alkyl, aryl, alkenyl, alkynyl, alkyl-Y$^2$—, alkenyl-Y$^2$—, alkynyl-Y$^2$—, aryl-Y$^2$—, or heteroaryl-Y$^2$—, or a cation which is Na$^{+1}$, Li$^{+1}$, or K$^{+1}$;
$Y^2$ is O, NR$^d$, or S;
each instance of $R^2$ is independently hydrogen, —OH, —SH, —NR$^d$R$^d$, —N$_3$, halogen, alkyl, alkenyl, alkynyl, alkyl-Y$^1$—, alkenyl-Y$^1$—, alkynyl-Y$^1$—, aryl-Y$^1$—, heteroaryl-Y$^1$—, —OR$^b$, or —SR$^c$, wherein $R^b$ is a blocking group;
each instance of B$^a$ is independently a blocked or unblocked adenine, cytosine, guanine, thymine, uracil or modified nucleobase;
at least one instance of X is

[chemical structures]

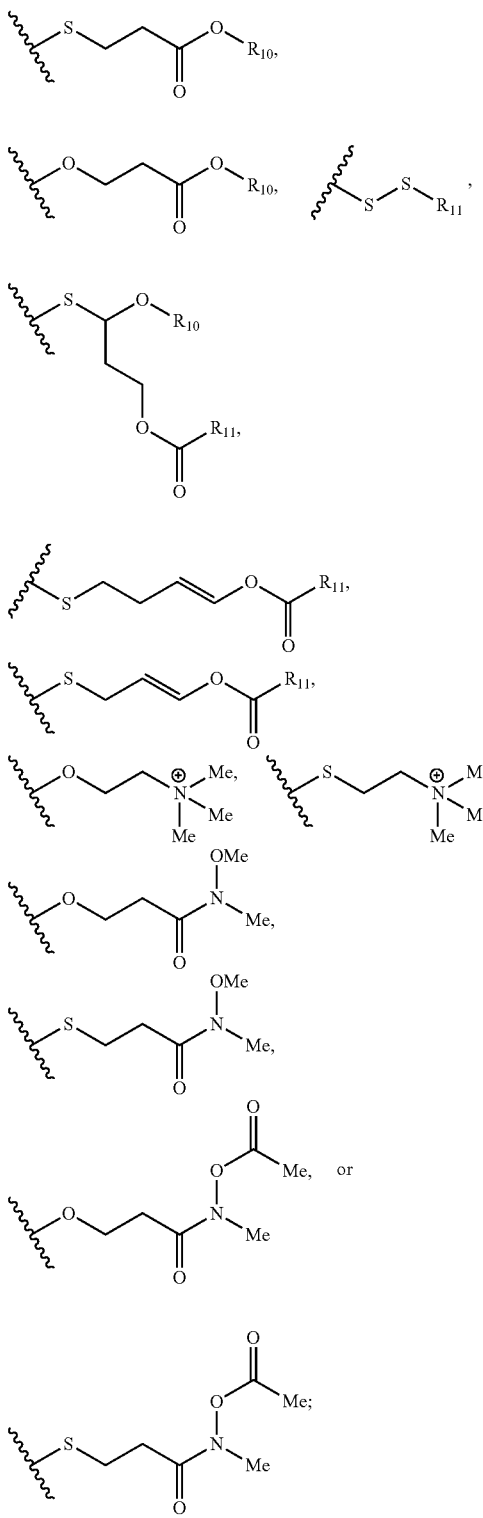

R³ is hydrogen, a blocking group, a linking moiety connected to a solid support or a linking moiety connected to a nucleic acid;
R₁₀ is an alkyl group having 1 to 4 carbon atoms;
R₁₁ is alkyl, aryl, heteroaryl, heterocyclyl, or cycloalkyl;
R₁₂ is hydrogen or alkyl; and
n is an integer of 1 to about 200.

A further embodiment provides the nucleic acid prodrug wherein each X-phosphonate moiety of the compound of Formula 1 is more than 98% diastereomerically pure as determined by $^{31}$P NMR spectroscopy or reverse-phase HPLC.

A further embodiment provides the nucleic acid prodrug wherein each X-phosphonate moiety has a $R_P$ configuration.

A further embodiment provides the nucleic acid prodrug wherein each X-phosphonate moiety has a SP configuration. A further embodiment provides the nucleic acid prodrug wherein each X-phosphonate independently has a RP configuration or a $S_P$ configuration.

A further embodiment provides the nucleic acid prodrug wherein $R_{10}$ is methyl. A further embodiment provides the nucleic acid prodrug wherein $R_{11}$ is methyl. A further embodiment provides the nucleic acid prodrug wherein $R_{12}$ is methyl.

A further embodiment provides the nucleic acid prodrug, wherein at least 25% of the X moieties of the nucleic acid prodrug are independently selected from

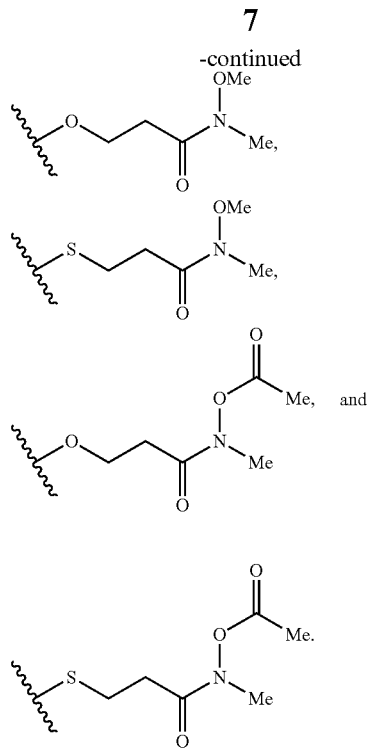
A further embodiment provides the nucleic acid prodrug, wherein at least 50% of the X moieties of the nucleic acid prodrug are independently selected from
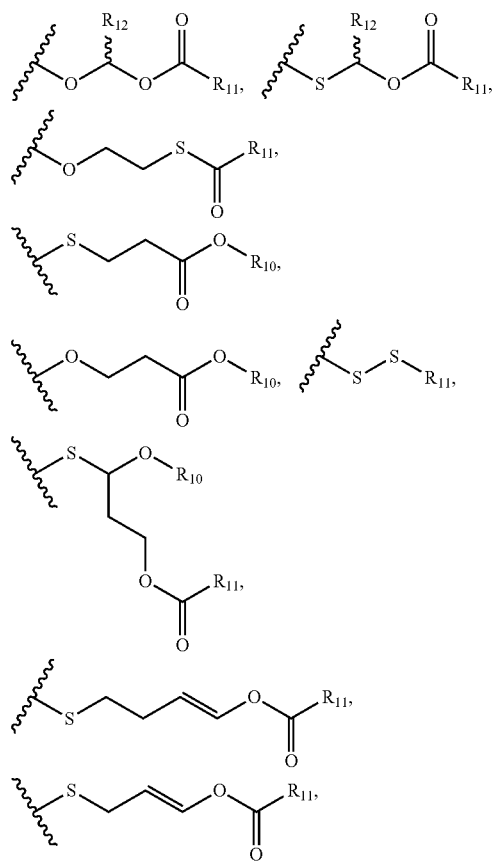
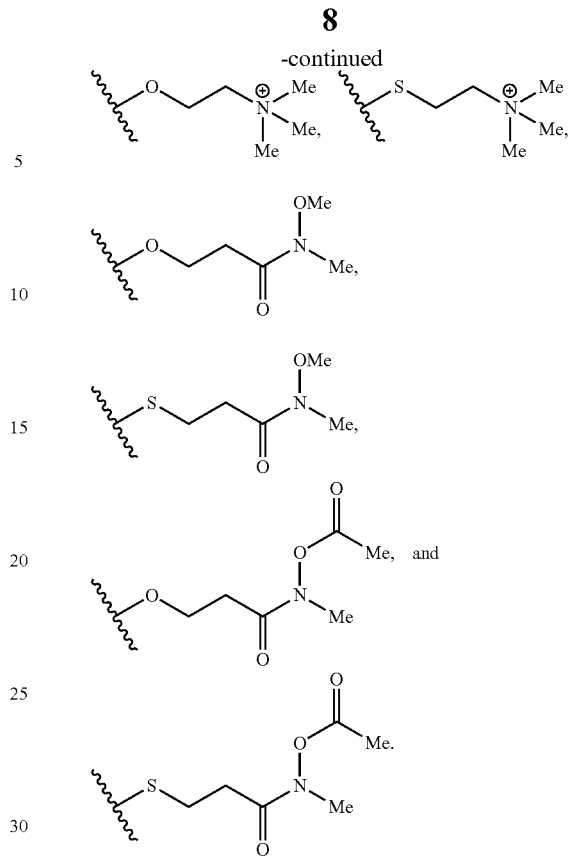
A further embodiment provides the nucleic acid prodrug, wherein at least 90% of the X moieties of the nucleic acid prodrug are independently selected from
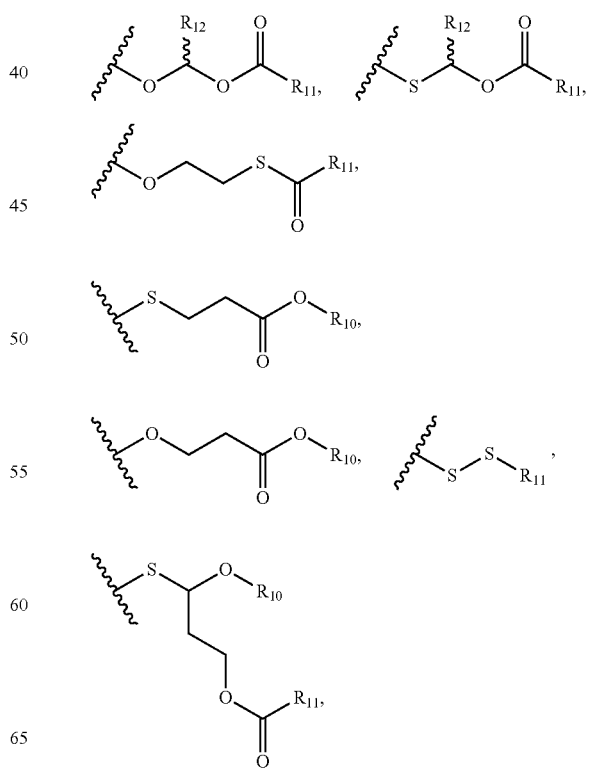

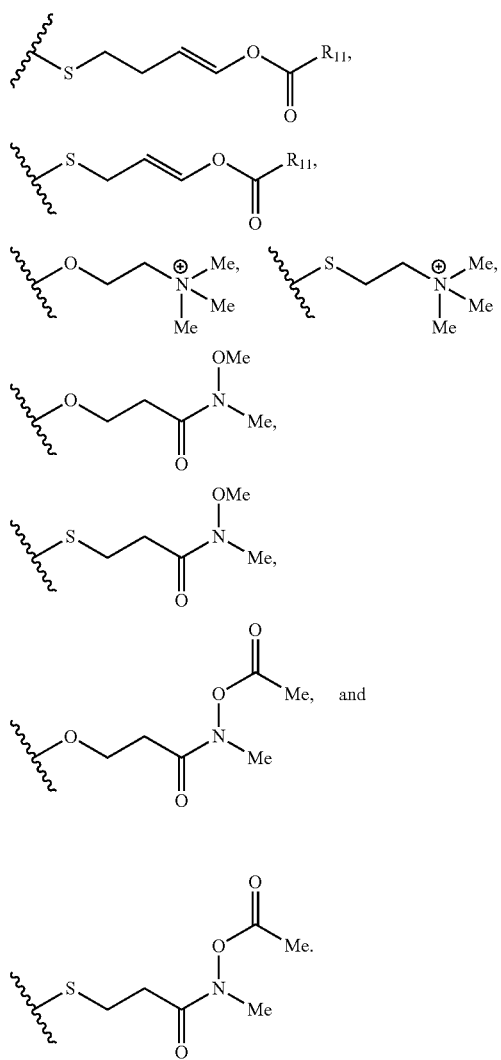
A further embodiment provides the nucleic acid prodrug, wherein each X moiety of the nucleic acid prodrug is independently selected from
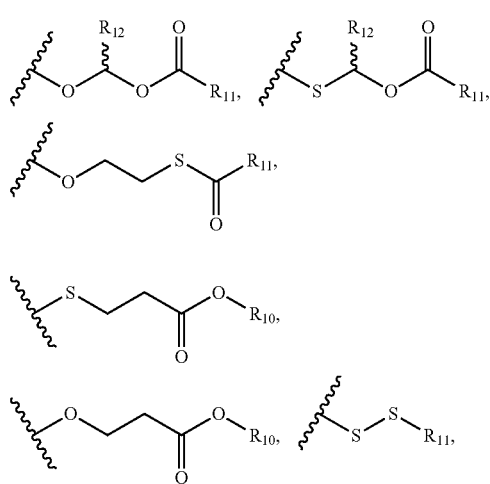
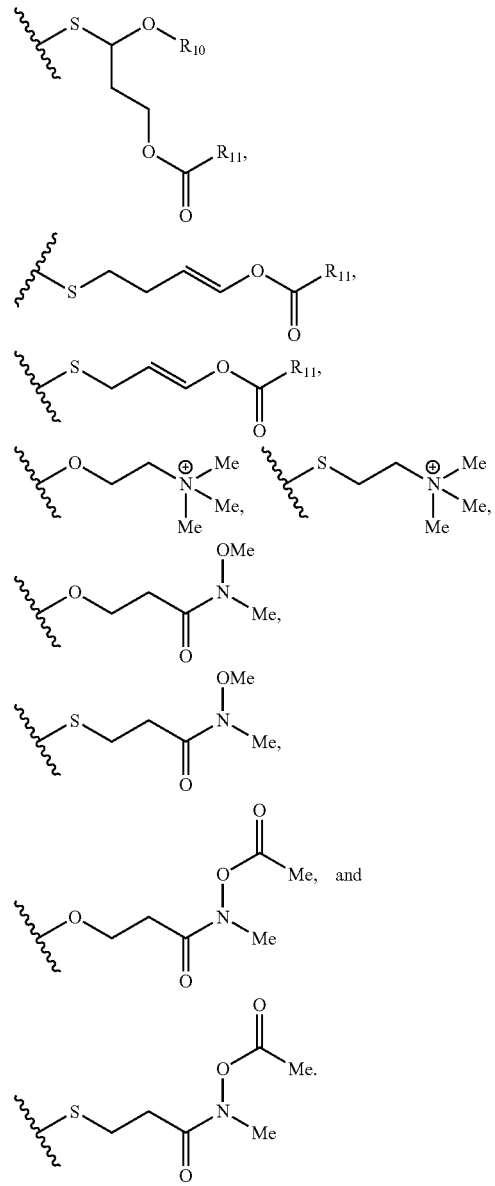
A further embodiment provides the nucleic acid prodrug, wherein each X moiety of the nucleic acid prodrug is independently selected from —OCH$_2$CH$_2$S—S(O)$_2$R$_{10}$, —OCH$_2$CH$_2$S—SCH$_2$CH$_2$OH, —OCH$_2$CH$_2$CO$_2$H,
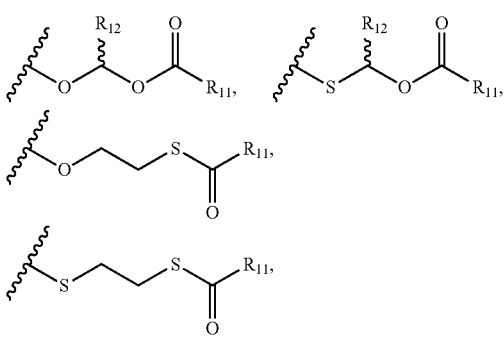

-continued

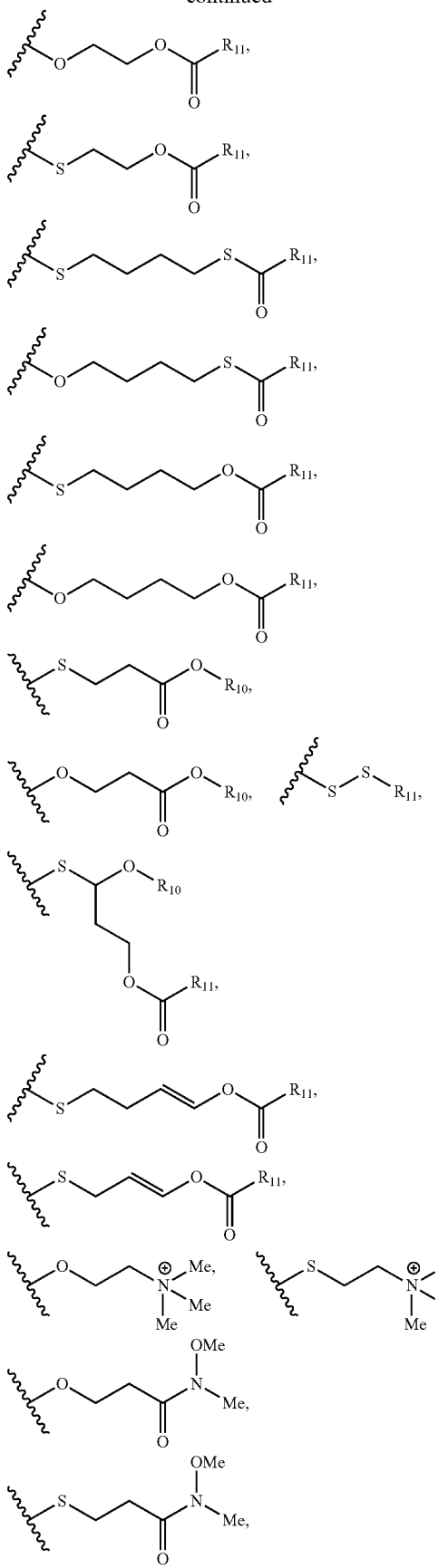

-continued

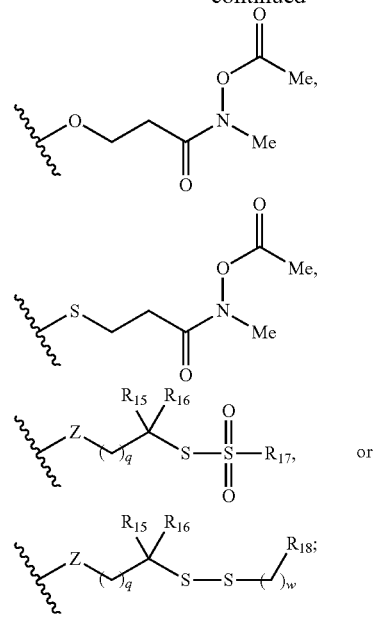

R³ is hydrogen, a blocking group, a linking moiety connected to a solid support or a linking moiety connected to a nucleic acid;
R₁₀ is an alkyl group having 1 to 4 carbon atoms;
R₁₁ is alkyl, aryl, heteroaryl, heterocyclyl, or cycloalkyl;
R₁₂ is hydrogen or alkyl;
Z is S or O;
q is 0, 1, or 3;
w is 1, 2, 3, 4, 5, or 6;
R₁₅ and R₁₆ are independently hydrogen or methyl;
R₁₇ is selected from alkyl, aryl or a CH₂CH=CH₂; and
R₁₈ is selected from N(CH₃)₂,

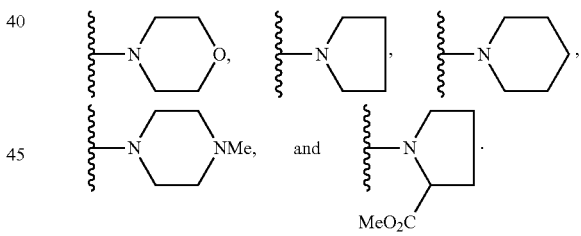

One embodiment provides a nucleic acid prodrug having the following structure:

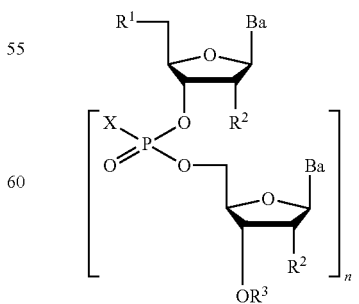

wherein R¹ is —OH, —SH, —NR^d R^d, —N₃, halogen, hydrogen, alkyl, alkenyl, alkynyl, alkyl-Y¹—, alkenyl- $Y^1$—, alkynyl-$Y^1$—, aryl-$Y^1$—, heteroaryl-$Y^1$—, —P(O)($R^e$)$_2$, —HP(O)($R^e$), —O$R^a$ or —S$R^c$;

$Y^1$ is O, N$R^d$, S, or Se;

$R^a$ is a blocking group;

$R^c$ is a blocking group;

each instance of $R^d$ is independently hydrogen, alkyl, alkenyl, alkynyl, aryl, acyl, substituted silyl, carbamate, —P(O)($R^e$)$_2$, or —HP(O)($R^e$);

each instance of $R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$—, or a cation which is Na$^{+1}$, Li$^{+1}$, or K$^{+1}$;

$Y^2$ is O, N$R^d$, or S;

each instance of $R^2$ is independently hydrogen, —OH, —SH, —N$R^dR^d$, —N$_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —O$R^b$, or —S$R^c$, wherein $R^b$ is a blocking group; each instance of Ba is independently a blocked or unblocked adenine, cytosine, guanine, thymine, uracil or modified nucleobase;

at least one X is,

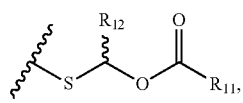

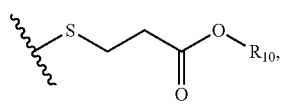

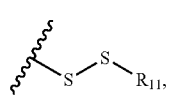

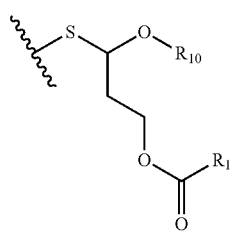

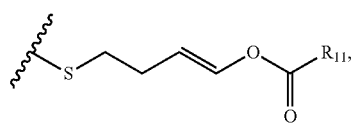

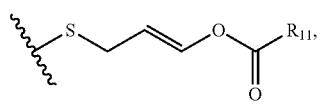

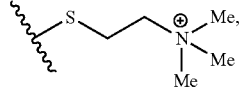

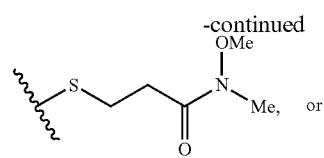

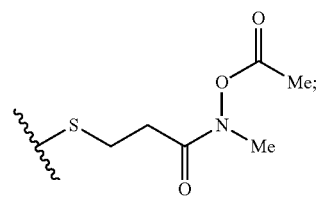

wherein $R_{10}$ is an alkyl group having 1 to 4 carbon atoms; $R_{11}$ is alkyl, aryl, heteroaryl, heterocyclyl, or cycloalkyl; and $R_{12}$ is hydrogen or alkyl.

$R^3$ is hydrogen, a blocking group, a linking moiety connected to a solid support or a linking moiety connected to a nucleic acid; and n is an integer of 1 to about 200.

A further embodiment provides a nucleic acid prodrug wherein $R_{10}$ is methyl. A further embodiment provides a nucleic acid prodrug wherein $R_{11}$ is methyl. A further embodiment provides a nucleic acid prodrug wherein $R_{12}$ is methyl A further embodiment provides a nucleic acid prodrug, wherein at least 25% of the X moieties of the nucleic acid prodrug are independently selected from

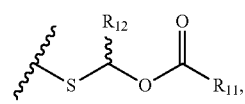

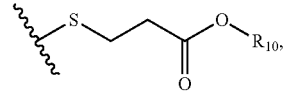

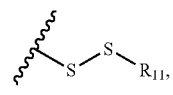

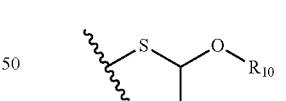

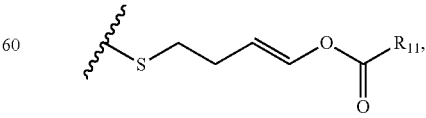

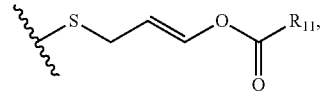

-continued

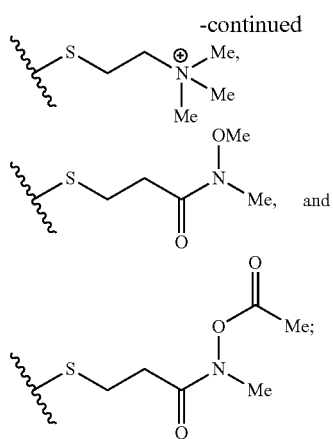

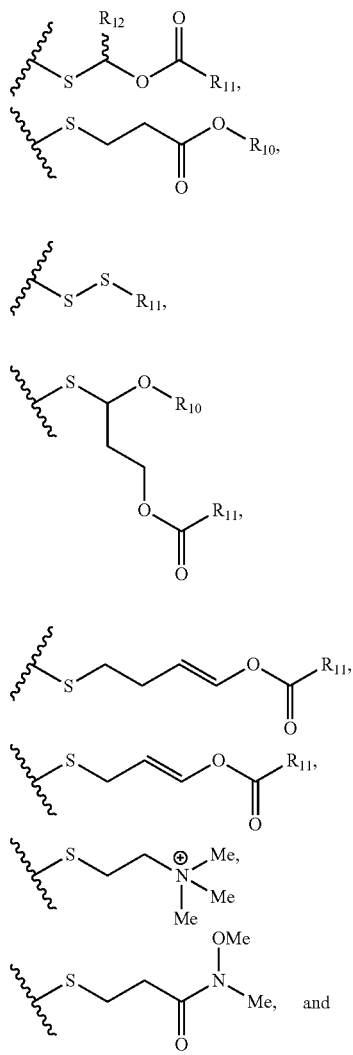

wherein R10 is an alkyl group having 1 to 4 carbon atoms; R11 is alkyl, aryl, heteroaryl, heterocyclyl, or cycloalkyl; and R12 is hydrogen or alkyl. A further embodiment provides a nucleic acid prodrug, wherein at least 50% of the X moieties of the nucleic acid prodrug are independently selected from -continued

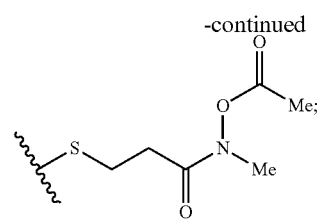

wherein R10 is an alkyl group having 1 to 4 carbon atoms; R11 is alkyl, aryl, heteroaryl, heterocyclyl, or cycloalkyl; and R12 is hydrogen or alkyl. A further embodiment provides a nucleic acid prodrug, wherein at least 90% of the X moieties of the nucleic acid prodrug are independently selected from

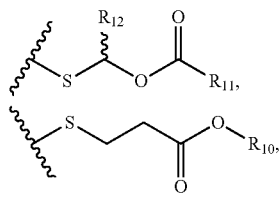

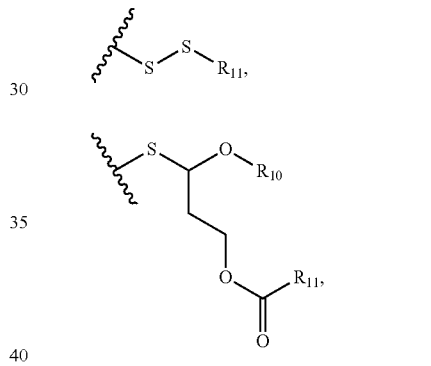

wherein R10 is an alkyl group having 1 to 4 carbon atoms; R11 is alkyl, aryl, heteroaryl, heterocyclyl, or cycloalkyl;

and R12 is hydrogen or alkyl. A further embodiment provides a nucleic acid prodrug, wherein at each X moiety of the nucleic acid prodrug is independently selected from

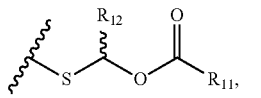

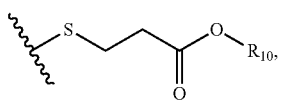

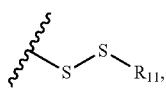

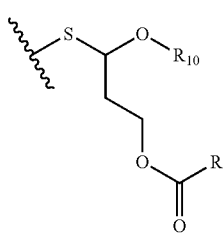

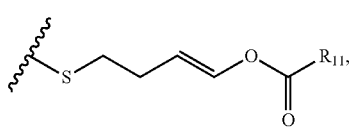

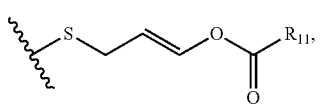

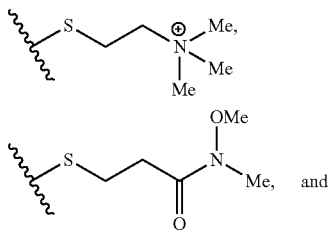

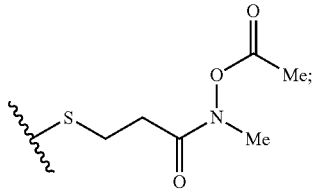

wherein $R_{10}$ is an alkyl group having 1 to 4 carbon atoms; $R_{11}$ is alkyl, aryl, heteroaryl, heterocyclyl, or cycloalkyl; and $R_{12}$ is hydrogen or alkyl.

One embodiment provides a pharmaceutical composition comprising a nucleic acid prodrug having the following structure:

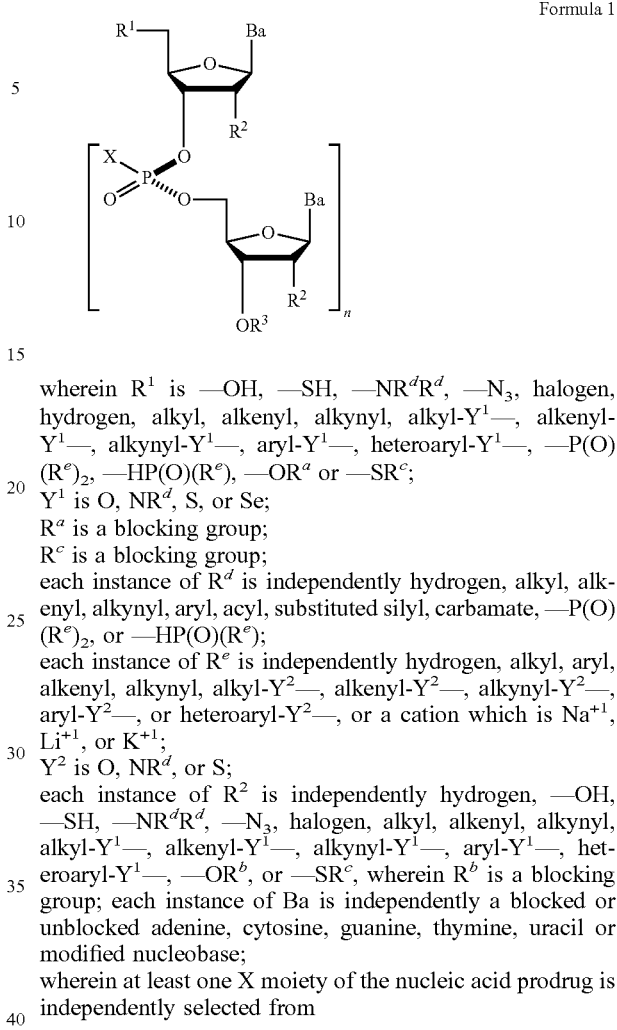

Formula 1 wherein $R^1$ is —OH, —SH, —NR$^d$R$^d$, —N$_3$, halogen, hydrogen, alkyl, alkenyl, alkynyl, alkyl-Y$^1$—, alkenyl-Y$^1$—, alkynyl-Y$^1$—, aryl-Y$^1$—, heteroaryl-Y$^1$—, —P(O)(R$^e$)$_2$, —HP(O)(R$^e$), —OR$^a$ or —SR$^c$;
$Y^1$ is O, NR$^d$, S, or Se;
$R^a$ is a blocking group;
$R^c$ is a blocking group;
each instance of $R^d$ is independently hydrogen, alkyl, alkenyl, alkynyl, aryl, acyl, substituted silyl, carbamate, —P(O)(R$^e$)$_2$, or —HP(O)(R$^e$);
each instance of $R^e$ is independently hydrogen, alkyl, aryl, alkenyl, alkynyl, alkyl-Y$^2$—, alkenyl-Y$^2$—, alkynyl-Y$^2$—, aryl-Y$^2$—, or heteroaryl-Y$^2$—, or a cation which is Na$^{+1}$, Li$^{+1}$, or K$^{+1}$;
$Y^2$ is O, NR$^d$, or S;
each instance of $R^2$ is independently hydrogen, —OH, —SH, —NR$^d$R$^d$, —N$_3$, halogen, alkyl, alkenyl, alkynyl, alkyl-Y$^1$—, alkenyl-Y$^1$—, alkynyl-Y$^1$—, aryl-Y$^1$—, heteroaryl-Y$^1$—, —OR$^b$, or —SR$^c$, wherein R$^b$ is a blocking group; each instance of Ba is independently a blocked or unblocked adenine, cytosine, guanine, thymine, uracil or modified nucleobase;
wherein at least one X moiety of the nucleic acid prodrug is independently selected from

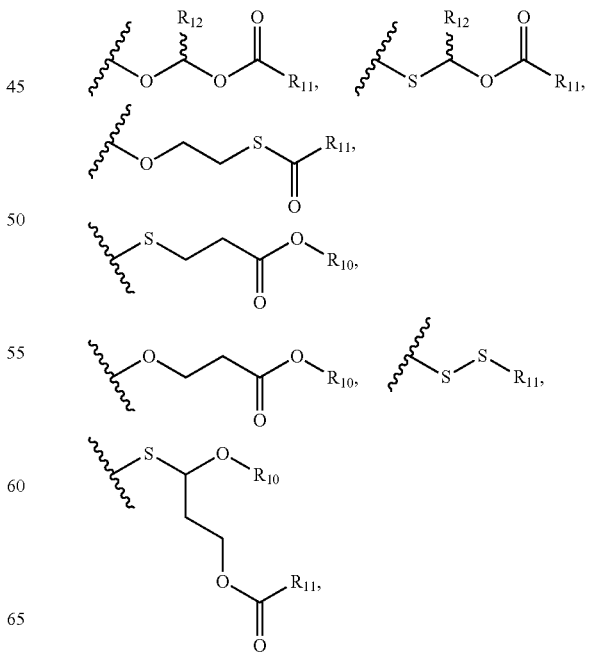

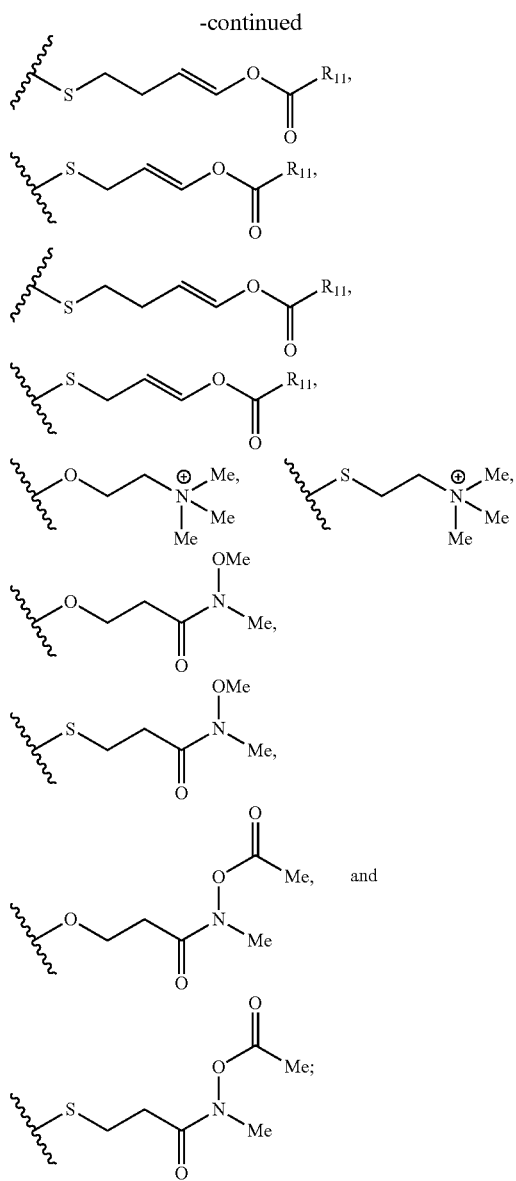

wherein R₁₀ is an alkyl group having 1 to 4 carbon atoms; R₁₁ is alkyl, aryl, heteroaryl, heterocyclyl, or cycloalkyl; and R₁₂ is hydrogen or alkyl;
R³ is hydrogen, a blocking group, a linking moiety connected to a solid support or a linking moiety connected to a nucleic acid; and
n is an integer of 1 to about 200;
wherein the method used to synthesize the nucleic acid prodrug comprises the steps of: (1) reacting a molecule comprising an achiral H-phosphonate moiety and a nucleoside comprising a 5'-OH moiety to form a condensed intermediate; and (2) converting the condensed intermediate to the nucleic acid prodrug comprising a chiral X-phosphonate moiety.

Another embodiment provides a pharmaceutical composition comprising a nucleic acid prodrug having the structure of Formula 1, wherein each X-phosphonate moiety of the compound of Formula 1 is more than 98% diastereomerically pure as determined by 31P NMR spectroscopy or reverse-phase HPLC. Another embodiment provides a pharmaceutical composition comprising a nucleic acid prodrug having the structure of Formula 1 wherein each X-phosphonate moiety has a RP configuration. Another embodiment provides a pharmaceutical composition comprising a nucleic acid prodrug having the structure of Formula 1, wherein each X-phosphonate moiety has a SP configuration. Another embodiment provides a pharmaceutical composition comprising a nucleic acid prodrug having the structure of Formula 1 wherein each X-phosphonate independently has a RP configuration or a S$_P$ configuration.

Another embodiment provides a pharmaceutical composition comprising a nucleic acid prodrug having the structure of Formula 1, wherein at least 25% of the X moieties of the nucleic acid prodrug are independently selected from

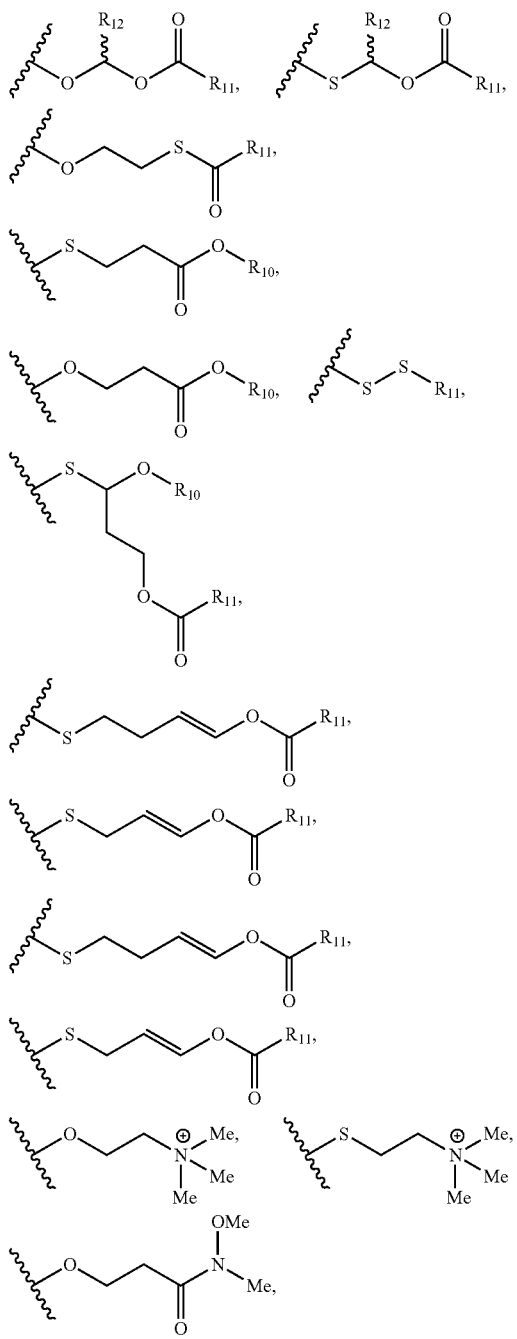

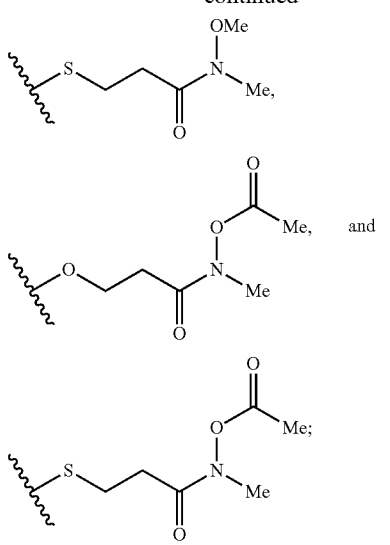

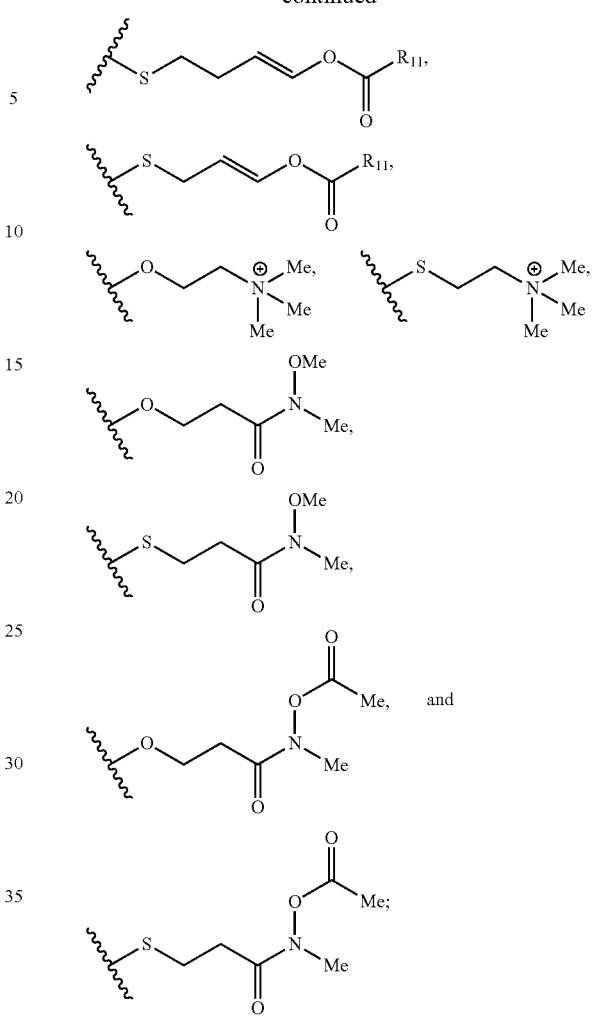

wherein R10 is an alkyl group having 1 to 4 carbon atoms; R11 is alkyl, aryl, heteroaryl, heterocyclyl, or cycloalkyl; and R12 is hydrogen or alkyl. Another embodiment provides a pharmaceutical composition comprising a nucleic acid prodrug having the structure of Formula 1, wherein at least 50% of the X moieties of the nucleic acid prodrug are independently selected from

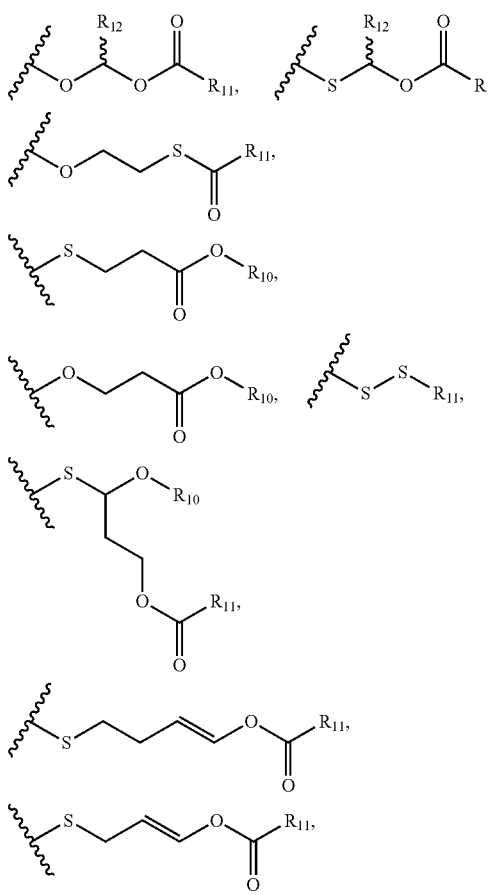

wherein R10 is an alkyl group having 1 to 4 carbon atoms; R11 is alkyl, aryl, heteroaryl, heterocyclyl, or cycloalkyl; and R12 is hydrogen or alkyl. Another embodiment provides a pharmaceutical composition comprising a nucleic acid prodrug having the structure of Formula 1, wherein at least 90% of the X moieties of the nucleic acid prodrug are independently selected from

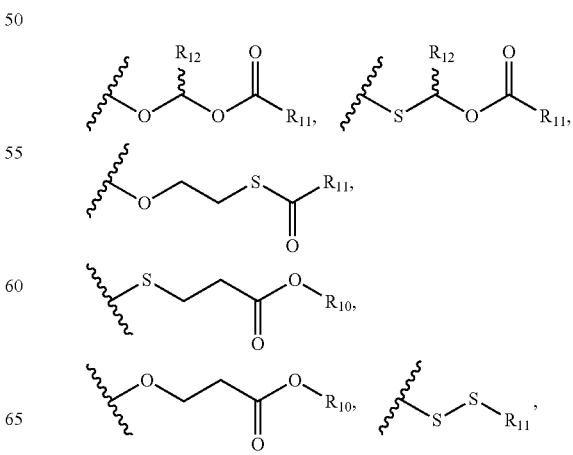

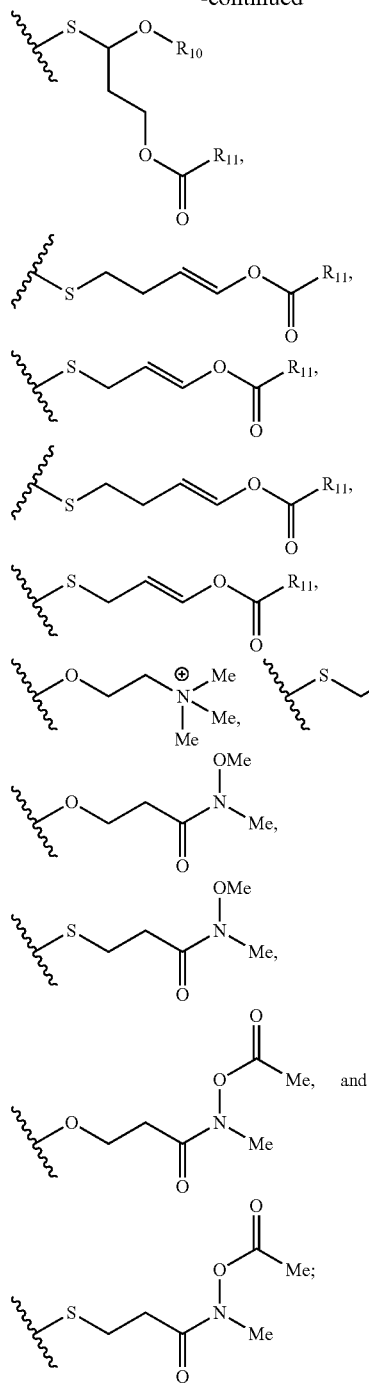
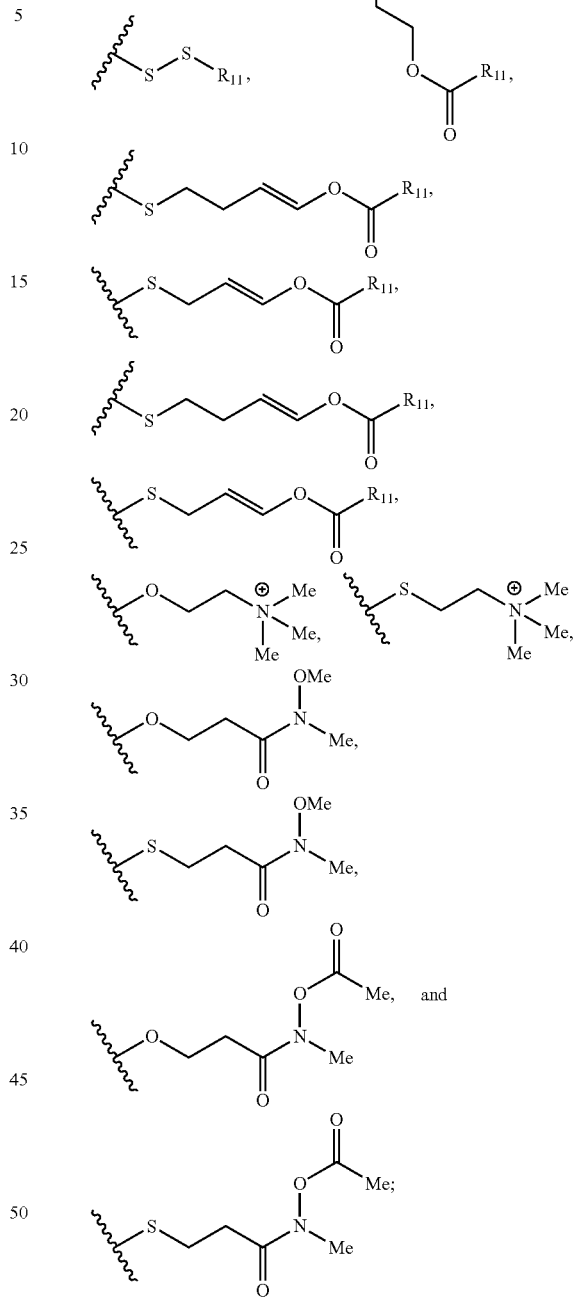

wherein R10 is an alkyl group having 1 to 4 carbon atoms; R11 is alkyl, aryl, heteroaryl, heterocyclyl, or cycloalkyl; and R12 is hydrogen or alkyl. Another embodiment provides a pharmaceutical composition comprising a nucleic acid prodrug having the structure of Formula 1, wherein each instance of X is independently selected from

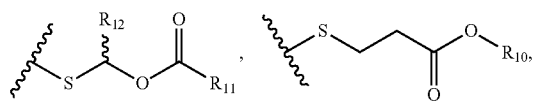

wherein $R_{10}$ is an alkyl group having 1 to 4 carbon atoms; $R_{11}$ is alkyl, aryl, heteroaryl, heterocyclyl, or cycloalkyl; and $R_{12}$ is hydrogen or alkyl.

Another embodiment provides a pharmaceutical composition comprising a nucleic acid prodrug having the structure of Formula 1 wherein $R_{10}$ is methyl. Another embodiment provides a pharmaceutical composition comprising a nucleic acid prodrug having the structure of Formula 1 wherein $R_{11}$ is methyl. Another embodiment provides a pharmaceutical composition comprising a nucleic acid prodrug having the structure of Formula 1 wherein $R_{12}$ is methyl.

One embodiment provides a method of treating a disease associated with upregulated RNase L by administering a therapeutic amount of a chiral nucleic acid prodrug. Another embodiment provides a method of treating a disease associated with upregulated RNase L, wherein the disease is chronic fatigue syndrome. Another embodiment provides a method of treating a disease associated with downregulated RNase L by administering a therapeutic amount of a chiral nucleic acid prodrug. Another embodiment provides a method of treating a disease with downregulated RNase L, wherein the disease is cancer. IN another embodiment, the cancer is selected from prostate, colorectal, and pancreatic cancer. In one embodiment, the cancer with downregulated RNase L is pancreatic cancer. In another embodiment the cancer with downregulated RNase L is prostate cancer. In yet another embodiment, the cancer with downregulated RNase L is colorectal cancer.

One embodiment provides a method of treating cancer comprising administering a therapeutic amount of a nucleic acid prodrug having the following structure:

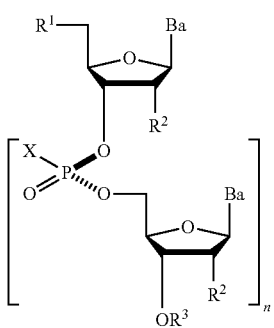

Formula 1 wherein $R^1$ is —OH, —SH, —NR$^d$R$^d$, —N$_3$, halogen, hydrogen, alkyl, alkenyl, alkynyl, alkyl-Y$^1$—, alkenyl-Y$^1$—, alkynyl-Y$^1$—, aryl-Y$^1$—, heteroaryl-Y$^1$—, —P(O)(R$^e$)$_2$, —HP(O)(R$^e$), —OR$^a$ or —SR$^c$;
$Y^1$ is O, NR$^d$, S, or Se;
$R^a$ is a blocking group;
$R^c$ is a blocking group;
each instance of $R^d$ is independently hydrogen, alkyl, alkenyl, alkynyl, aryl, acyl, substituted silyl, carbamate, —P(O)(R$^e$)$_2$, or —HP(O)(R$^e$);
each instance of $R^e$ is independently hydrogen, alkyl, aryl, alkenyl, alkynyl, alkyl-Y$^2$—, alkenyl-Y$^2$—, alkynyl-Y$^2$—, aryl-Y$^2$—, or heteroaryl-Y$^2$—, or a cation which is Na$^{+1}$, Li$^{+1}$, or K$^{+1}$;
$Y^2$ is O, NR$^d$, or S;
each instance of $R^2$ is independently hydrogen, —OH, —SH, —NR$^d$R$^d$, —N$_3$, halogen, alkyl, alkenyl, alkynyl, alkyl-Y$^1$—, alkenyl-Y$^1$—, alkynyl-Y$^1$—, aryl-Y$^1$—, heteroaryl-Y$^1$—, —OR$^b$, or —SR$^c$, wherein $R^b$ is a blocking group;
each instance of Ba is independently a blocked or unblocked adenine, cytosine, guanine, thymine, uracil or modified nucleobase;
at least one X moiety of the nucleic acid prodrug is independently selected from

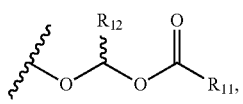 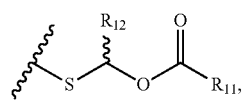

-continued

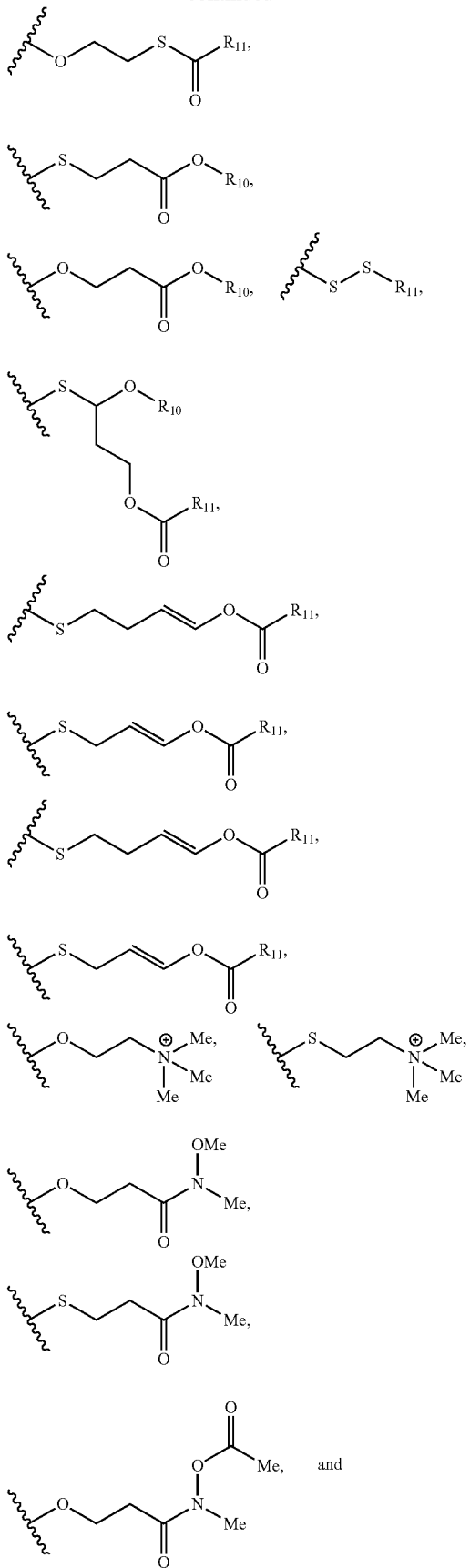

-continued

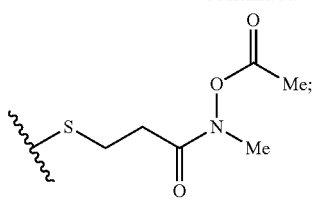

wherein $R_{10}$ is an alkyl group having 1 to 4 carbon atoms; $R_{11}$ is alkyl, aryl, heteroaryl, heterocyclyl, or cycloalkyl; and $R_{12}$ is hydrogen or alkyl;

$R^3$ is hydrogen, a blocking group, a linking moiety connected to a solid support or a linking moiety connected to a nucleic acid; and n is an integer of 1 to about 200;

$R^{10}$ is an alkyl group having 1 to 4 carbon atoms;

wherein the method used to synthesize the nucleic acid prodrug comprises the steps of: (1) reacting a molecule comprising an achiral H-phosphonate moiety and a nucleoside comprising a 5'-OH moiety to form a condensed intermediate; and (2) converting the condensed intermediate to the nucleic acid prodrug comprising a chiral X-phosphonate moiety.

Another embodiment provides a method of treating cancer comprising administering a therapeutic amount of a compound of Formula 1, wherein at least 25% of the X moieties of the nucleic acid prodrug are independently selected from

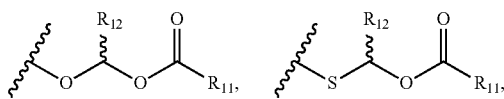

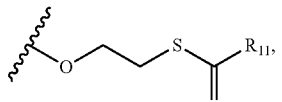

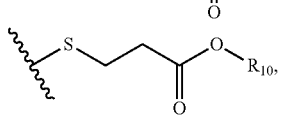

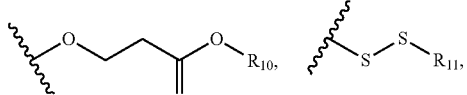

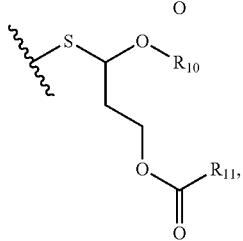

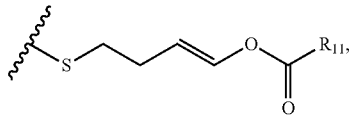

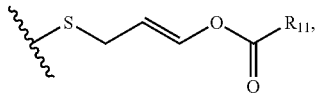

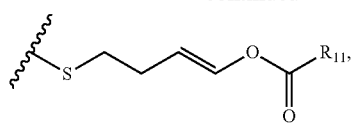

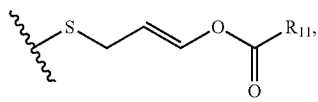

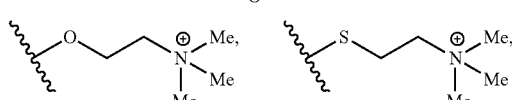

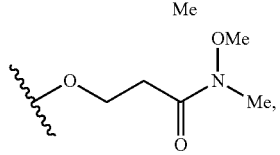

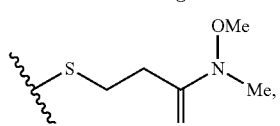

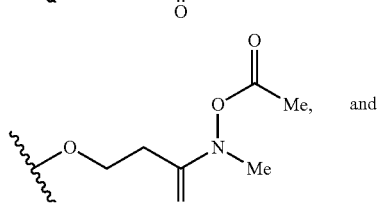   and

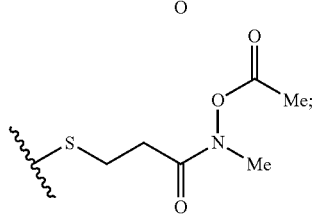

wherein R10 is an alkyl group having 1 to 4 carbon atoms; R11 is alkyl, aryl, heteroaryl, heterocyclyl, or cycloalkyl; and R12 is hydrogen or alkyl. Another embodiment provides a method of treating cancer comprising administering a therapeutic amount of a compound of Formula 1, wherein at least 50% of the X moieties of the nucleic acid prodrug are independently selected from

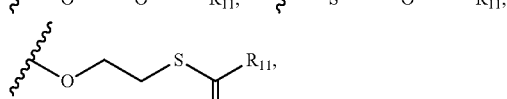

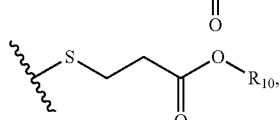

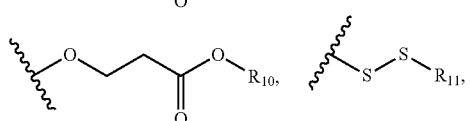

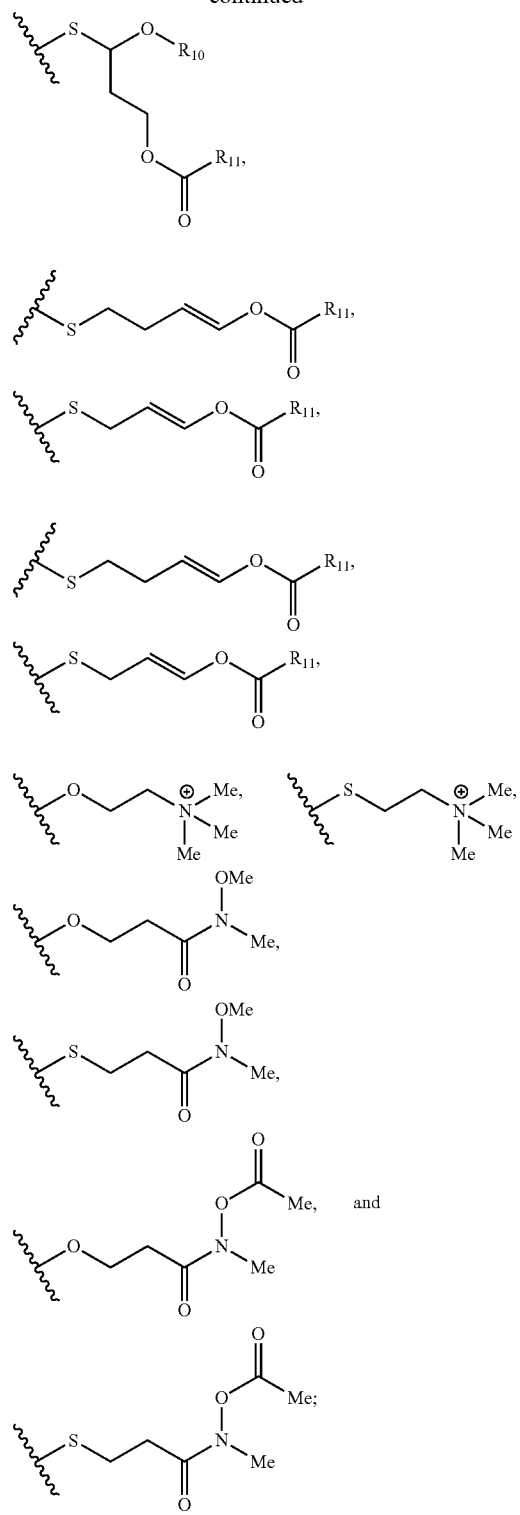
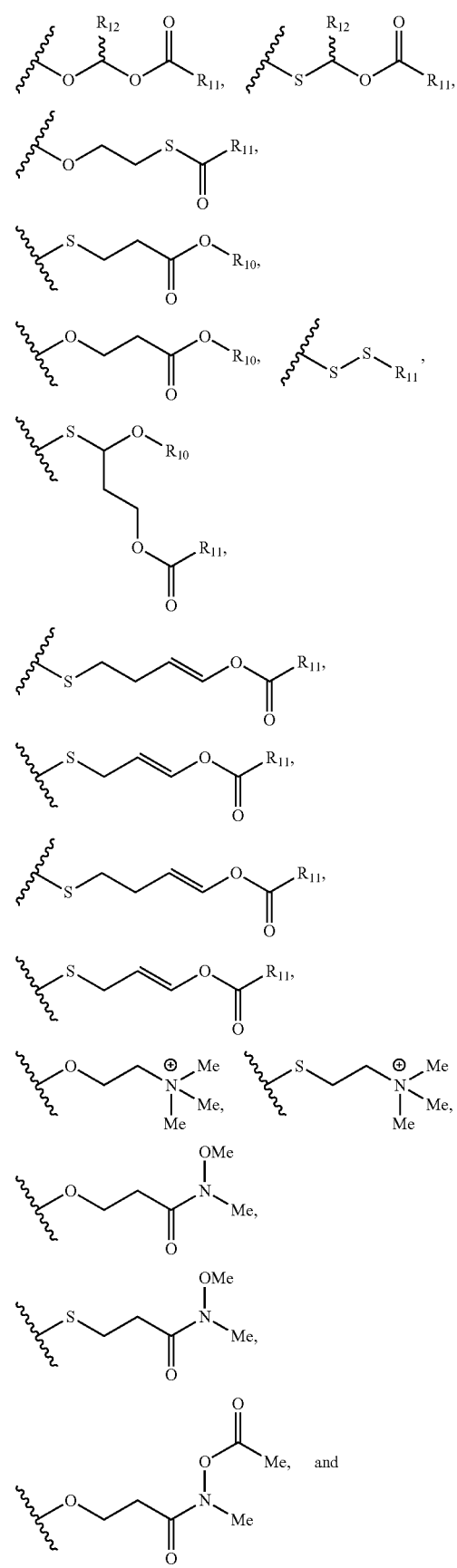
wherein R10 is an alkyl group having 1 to 4 carbon atoms; R11 is alkyl, aryl, heteroaryl, heterocyclyl, or cycloalkyl; and R12 is hydrogen or alkyl. Another embodiment provides a method of treating cancer comprising administering a therapeutic amount of a compound of Formula 1, wherein at least 90% of the X moieties of the nucleic acid prodrug are independently selected from

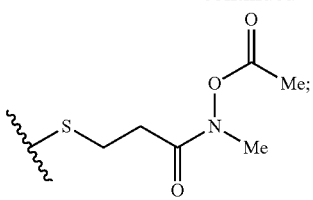

wherein R10 is an alkyl group having 1 to 4 carbon atoms; R11 is alkyl, aryl, heteroaryl, heterocyclyl, or cycloalkyl; and R12 is hydrogen or alkyl. Another embodiment provides a method of treating cancer comprising administering a therapeutic amount of a compound of Formula 1, wherein each instance of X is independently selected from

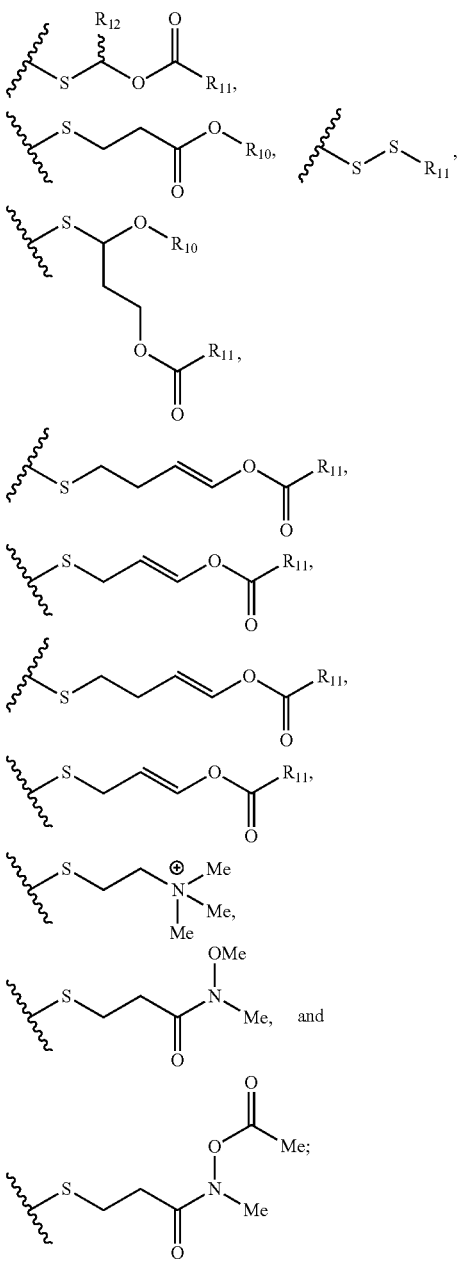

wherein $R_{10}$ is an alkyl group having 1 to 4 carbon atoms; $R_{11}$ is alkyl, aryl, heteroaryl, heterocyclyl, or cycloalkyl; and $R_{12}$ is hydrogen or alkyl.

Another embodiment provides a method of treating cancer comprising administering a therapeutic amount of a compound of Formula 1, wherein $R_{10}$ is methyl. Another embodiment provides a method of treating cancer comprising administering a therapeutic amount of a compound of Formula 1, wherein $R_{11}$ is methyl. Another embodiment provides a method of treating cancer comprising administering a therapeutic amount of a compound of Formula 1, wherein $R_{12}$ is methyl.

Another embodiment provides a method of treating cancer comprising administering a therapeutic amount of a compound of Formula 1, wherein each X-phosphonate moiety of the compound of Formula 1 is more than 98% diastereomerically pure as determined by $^{31}$P NMR spectroscopy or reverse-phase HPLC. Another embodiment provides a method of treating cancer comprising administering a therapeutic amount of a compound of Formula 1, wherein each X-phosphonate moiety has a RP configuration. Another embodiment provides a method of treating cancer comprising administering a therapeutic amount of a compound of Formula 1, wherein each X-phosphonate moiety has a SP configuration. Another embodiment provides a method of treating cancer comprising administering a therapeutic amount of a compound of Formula 1, wherein each X-phosphonate independently has a RP configuration or a $S_P$ configuration.

Another embodiment provides a method of treating cancer comprising administering a therapeutic amount of a compound of Formula 1, wherein the cancer is pancreatic cancer.

One embodiment provides a nucleic acid prodrug having the following structure:

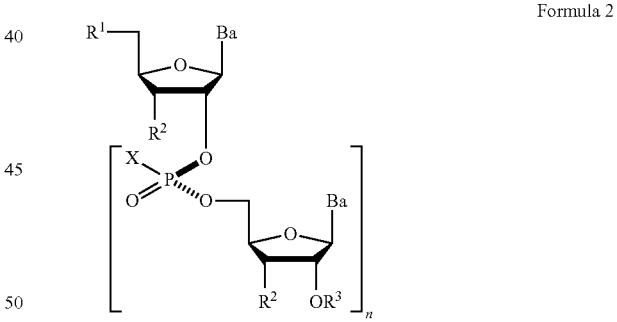

Formula 2 wherein $R^1$ is —OH, —SH, —NR$^d$R$^d$, —N$_3$, halogen, hydrogen, alkyl, alkenyl, alkynyl, alkyl-Y$^1$—, alkenyl-Y$^1$—, alkynyl-Y$^1$—, aryl-Y$^1$—, heteroaryl-Y$^1$—, —P(O)(R$^e$)$_2$, —HP(O)(R$^e$), —OR$^a$ or —SR$^c$;

$Y^1$ is O, NR$^d$, S, or Se;

$R^a$ is a blocking group;

$R^c$ is a blocking group;

each instance of R$^d$ is independently hydrogen, alkyl, alkenyl, alkynyl, aryl, acyl, substituted silyl, carbamate, —P(O)(R$^e$)$_2$, or —HP(O)(R$^e$);

each instance of R$^e$ is independently hydrogen, alkyl, aryl, alkenyl, alkynyl, alkyl-Y$^2$—, alkenyl-Y$^2$—, alkynyl-Y$^2$—, aryl-Y$^2$—, or heteroaryl-Y$^2$—, or a cation which is Na$^{+1}$, Li$^{+1}$, or K$^{+1}$;

$Y^2$ is O, NR$^d$, or S;

each instance of $R^2$ is independently hydrogen, —OH, —SH, —NR$^d$R$^d$, —N$_3$, halogen, alkyl, alkenyl, alkynyl, alkyl-Y$^1$—, alkenyl-Y$^1$—, alkynyl-Y$^1$—, aryl-Y$^1$—, heteroaryl-Y$^1$—, —OR$^b$, or —SR$^c$, wherein R$^b$ is a blocking group;

each instance of Ba is independently a blocked or unblocked adenine, cytosine, guanine, thymine, uracil or modified nucleobase;

at least one instance of X is

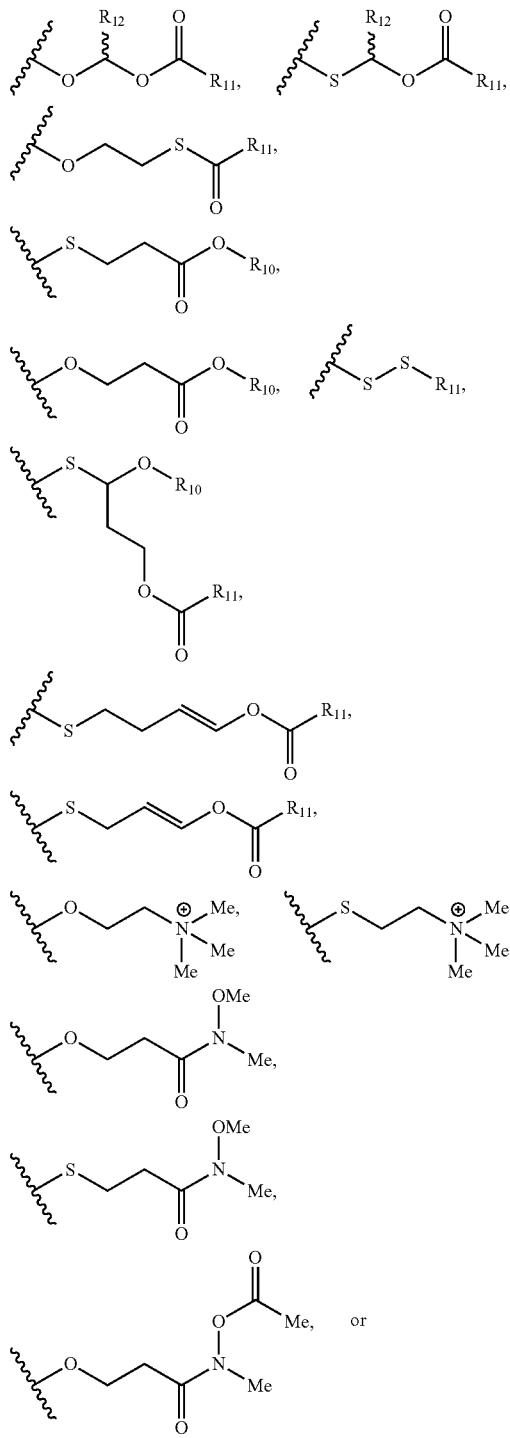

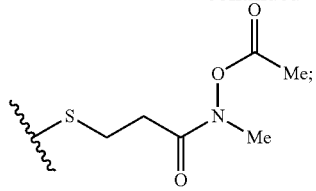

$R^3$ is hydrogen, a blocking group, a linking moiety connected to a solid support or a linking moiety connected to a nucleic acid;

$R_{10}$ is an alkyl group having 1 to 4 carbon atoms;

$R_{11}$ is alkyl, aryl, heteroaryl, heterocyclyl, or cycloalkyl;

$R_{12}$ is hydrogen or alkyl; and n is an integer of 1 to about 200.

One embodiment provides a nucleic acid prodrug of Formula 2, wherein each X-phosphonate moiety of the compound of Formula 2 is more than 98% diastereomerically pure as determined by 31P NMR spectroscopy or reverse-phase HPLC. Another embodiment provides a nucleic acid prodrug of Formula 2, wherein each X-phosphonate moiety has a RP configuration. Another embodiment provides a nucleic acid prodrug of Formula 2, wherein each X-phosphonate moiety has a SP configuration. Another embodiment provides a nucleic acid prodrug of Formula 2, wherein each X-phosphonate independently has a RP configuration or a S$_P$ configuration.

Another embodiment provides a nucleic acid prodrug of Formula 2 wherein $R_{10}$ is methyl. Another embodiment provides a nucleic acid prodrug of Formula 2 wherein $R_{11}$ is methyl. Another embodiment provides a nucleic acid prodrug of Formula 2 wherein $R_{12}$ is methyl Another embodiment provides a nucleic acid prodrug of Formula 2, wherein at least 25% of the X moieties of the nucleic acid prodrug are independently selected from

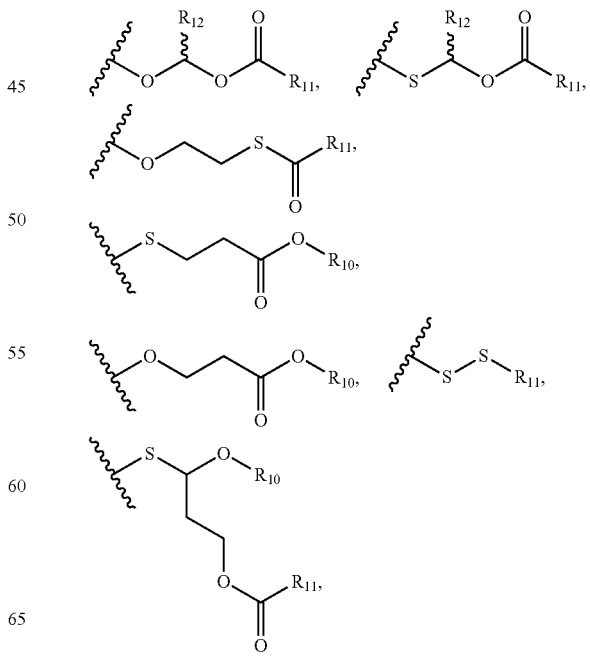

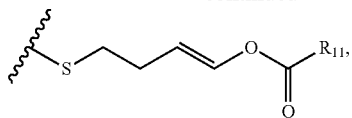
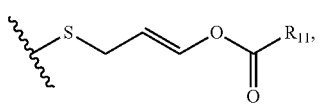
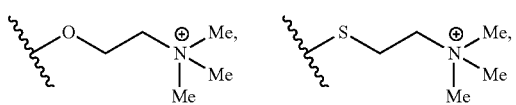
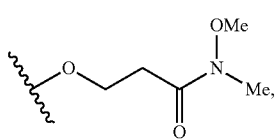
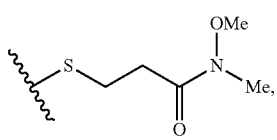
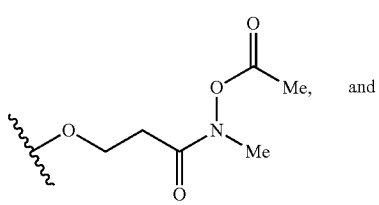
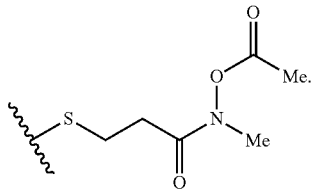
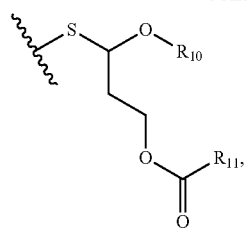
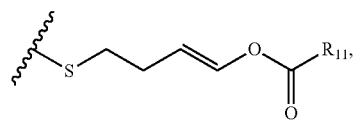
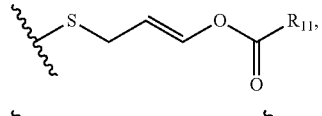
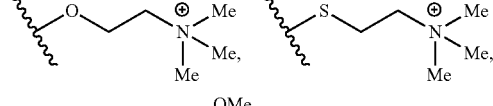
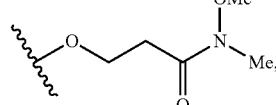
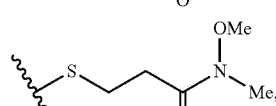
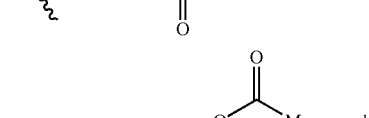
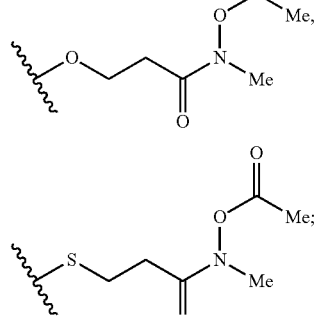
Another embodiment provides a nucleic acid prodrug of Formula 2, wherein at least 50% of the X moieties of the nucleic acid prodrug are independently selected from
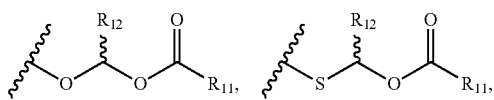
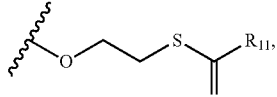
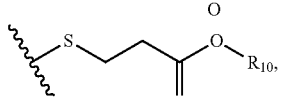
Another embodiment provides a nucleic acid prodrug of Formula 2, wherein at least 90% of the X moieties of the nucleic acid prodrug are independently selected from
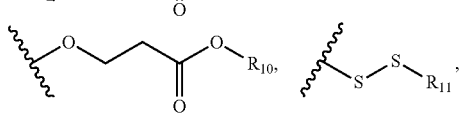

-continued
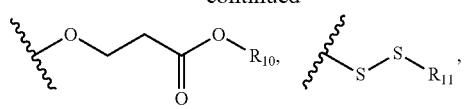
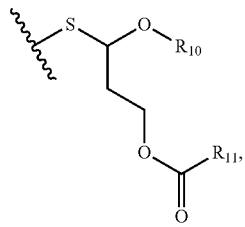
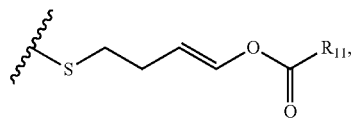
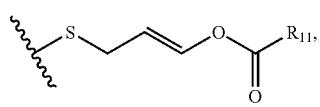
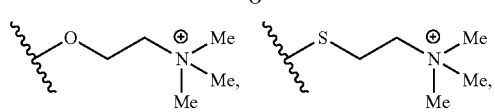
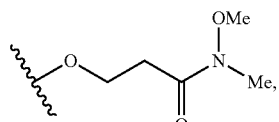
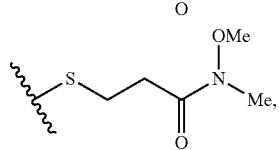
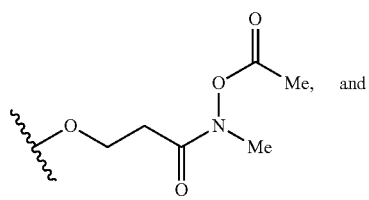
and
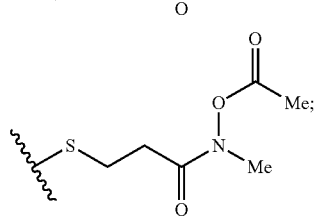
Another embodiment provides a nucleic acid prodrug of Formula 2, wherein each X moiety of the nucleic acid prodrug is independently selected from
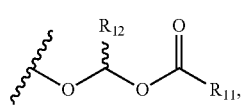 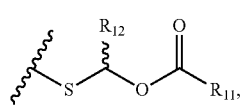
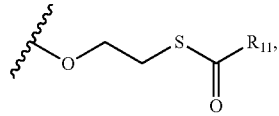
-continued
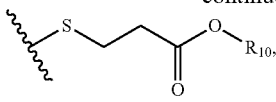
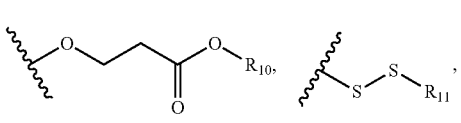
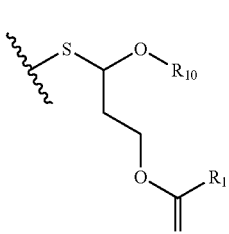
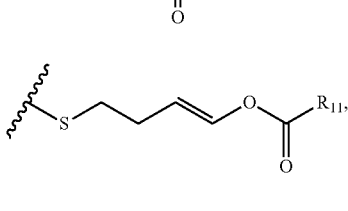
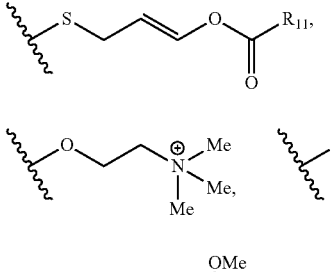
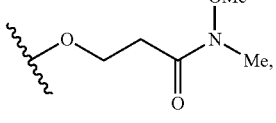
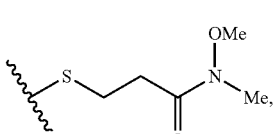
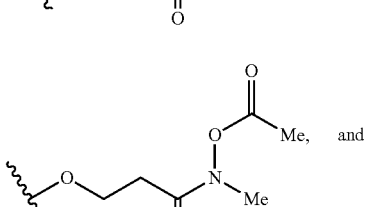
and
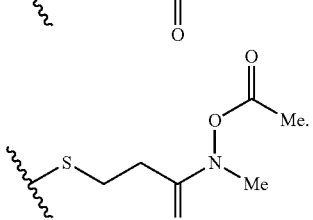
One embodiment provides a pharmaceutical composition comprising a nucleic acid prodrug having the following structure:

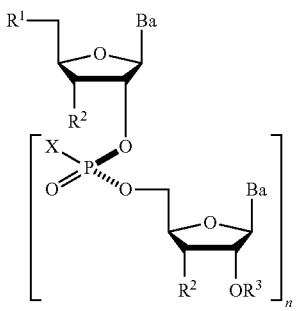

Formula 2 wherein R¹ is —OH, —SH, —NR$^d$R$^d$, —N₃, halogen, hydrogen, alkyl, alkenyl, alkynyl, alkyl-Y¹—, alkenyl-Y¹—, alkynyl-Y¹—, aryl-Y¹—, heteroaryl-Y¹—, —P(O)(R$^e$)₂, —HP(O)(R$^e$), —OR$^a$ or —SR$^c$;
Y¹ is O, NR$^d$, S, or Se;
R$^a$ is a blocking group;
R$^c$ is a blocking group;
each instance of R$^d$ is independently hydrogen, alkyl, alkenyl, alkynyl, aryl, acyl, substituted silyl, carbamate, —P(O)(R$^e$)₂, or —HP(O)(R$^e$);
each instance of R$^e$ is independently hydrogen, alkyl, aryl, alkenyl, alkynyl, alkyl-Y²—, alkenyl-Y²—, alkynyl-Y²—, aryl-Y²—, or heteroaryl-Y²—, or a cation which is Na$^{+1}$, Li$^{+1}$, or K$^{+1}$;
Y² is O, NR$^d$, or S;
each instance of R² is independently hydrogen, —OH, —SH, —NR$^d$R$^d$, —N₃, halogen, alkyl, alkenyl, alkynyl, alkyl-Y¹—, alkenyl-Y¹—, alkynyl-Y¹—, aryl-Y¹—, heteroaryl-Y¹—, —OR$^b$, or —SR$^c$, wherein R$^b$ is a blocking group;
each instance of Ba is independently a blocked or unblocked adenine, cytosine, guanine, thymine, uracil or modified nucleobase;
wherein at least one X moiety of the nucleic acid prodrug is independently selected from

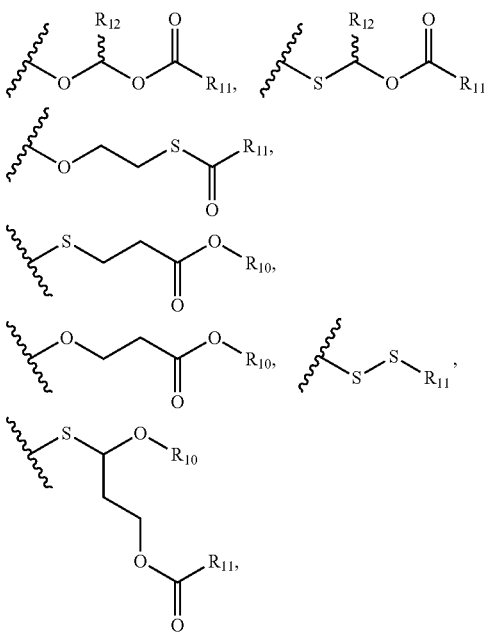

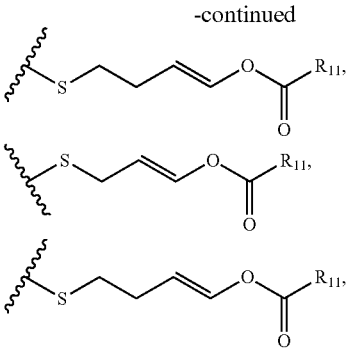

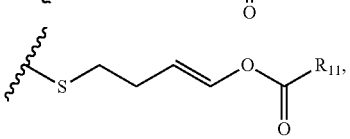

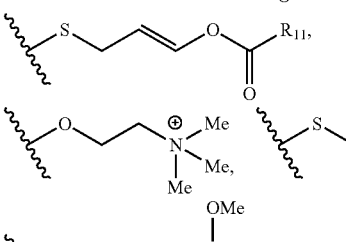

wherein R₁₀ is an alkyl group having 1 to 4 carbon atoms;
R₁₁ is alkyl, aryl, heteroaryl, heterocyclyl, or cycloalkyl; and
R₁₂ is hydrogen or alkyl;
R³ is hydrogen, a blocking group, a linking moiety connected to a solid support or a linking moiety connected to a nucleic acid; and
n is an integer of 1 to about 200;
wherein the method used to synthesize the nucleic acid prodrug comprises the steps of: (1) reacting a molecule comprising an achiral H-phosphonate moiety and a nucleoside comprising a 5'-OH moiety to form a condensed intermediate; and (2) converting the condensed intermediate to the nucleic acid prodrug comprising a chiral X-phosphonate moiety.

Another embodiment provides a pharmaceutical composition comprising a compound of Formula 2 wherein each X-phosphonate moiety of the compound of Formula 2 is more than 98% diastereomerically pure as determined by 31P NMR spectroscopy or reverse-phase HPLC. Another embodiment provides a pharmaceutical composition comprising a compound of Formula 2 wherein each X-phosphonate moiety has a RP configuration. Another embodiment provides a pharmaceutical composition comprising a compound of Formula 2 wherein each X-phosphonate moiety has a SP configuration. Another embodiment provides a pharmaceutical composition comprising a compound of Formula 2 wherein each X-phosphonate independently has a RP configuration or a $S_P$ configuration.

Another embodiment provides a pharmaceutical composition comprising a compound of Formula 2, wherein at least 25% of the X moieties of the nucleic acid prodrug are independently selected from

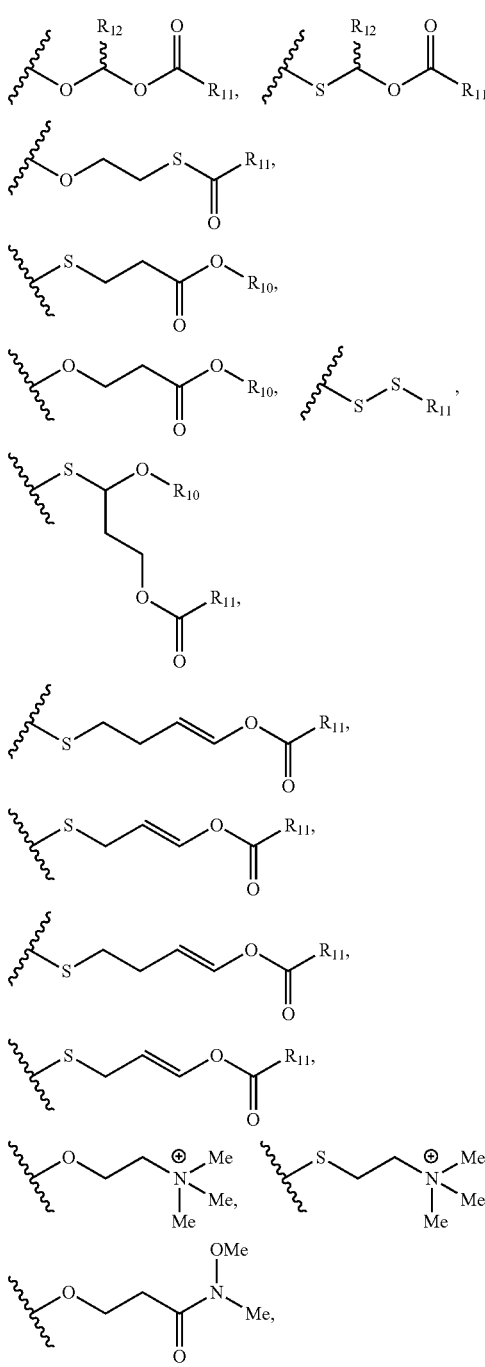

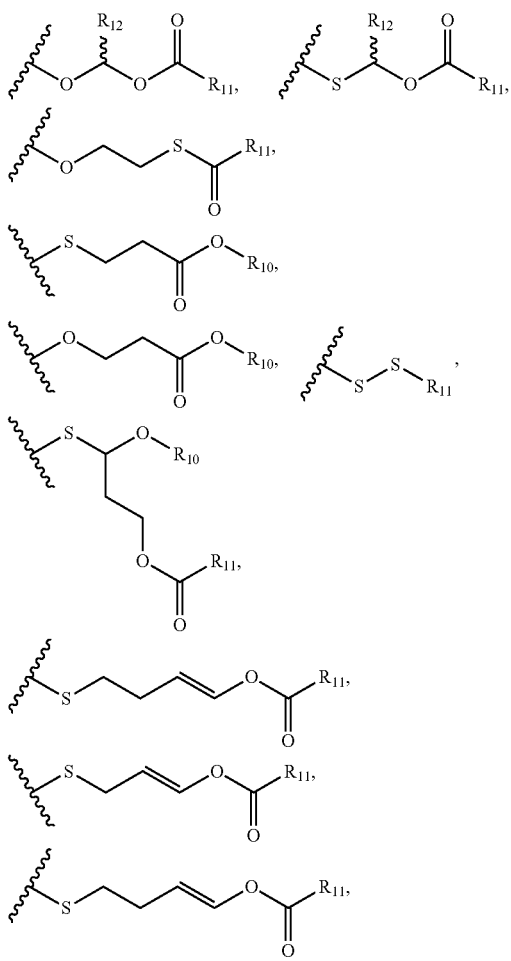

wherein R10 is an alkyl group having 1 to 4 carbon atoms; R11 is alkyl, aryl, heteroaryl, heterocyclyl, or cycloalkyl; and R12 is hydrogen or alkyl. Another embodiment provides a pharmaceutical composition comprising a compound of Formula 2, wherein at least 50% of the X moieties of the nucleic acid prodrug are independently selected from -continued

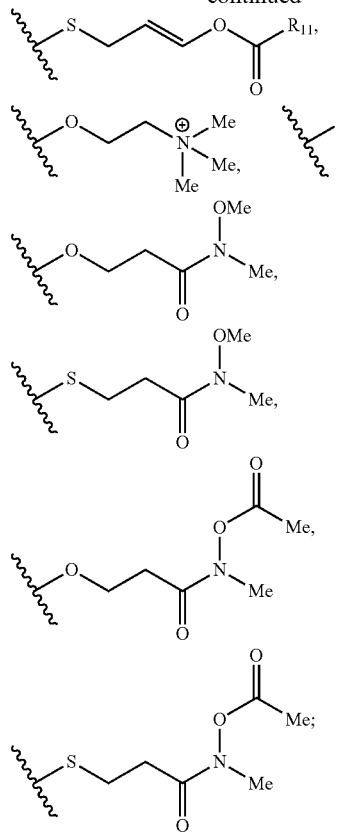

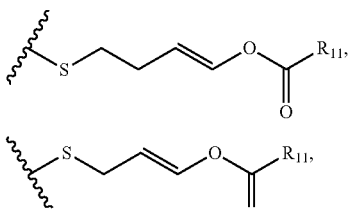

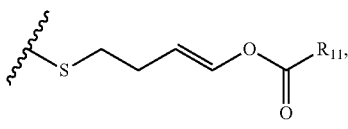

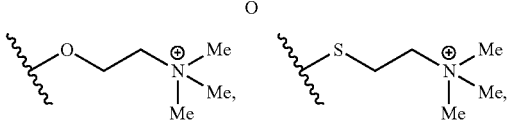

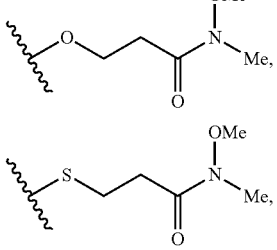

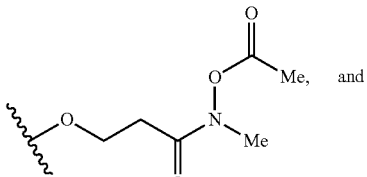

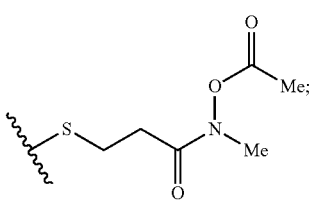

wherein R10 is an alkyl group having 1 to 4 carbon atoms; R11 is alkyl, aryl, heteroaryl, heterocyclyl, or cycloalkyl; and R12 is hydrogen or alkyl. Another embodiment provides a pharmaceutical composition comprising a compound of Formula 2, wherein at least 90% of the X moieties of the nucleic acid prodrug are independently selected from

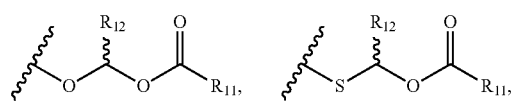

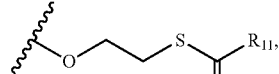

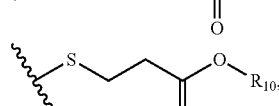

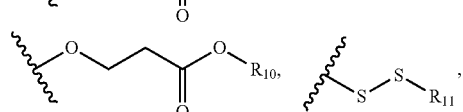

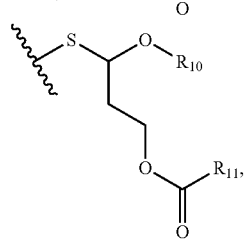

-continued wherein R10 is an alkyl group having 1 to 4 carbon atoms; R11 is alkyl, aryl, heteroaryl, heterocyclyl, or cycloalkyl; and R12 is hydrogen or alkyl. Another embodiment provides a pharmaceutical composition comprising a compound of Formula 2, wherein each instance of X is independently selected from

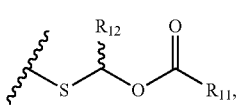

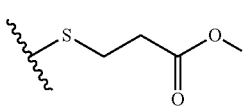 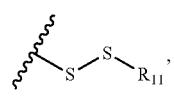

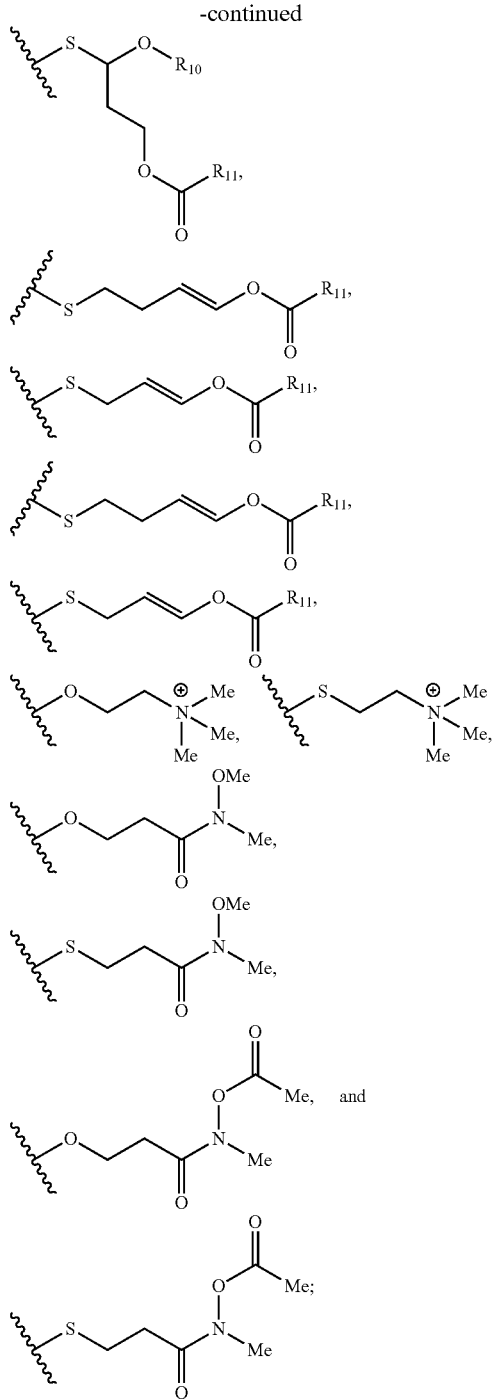

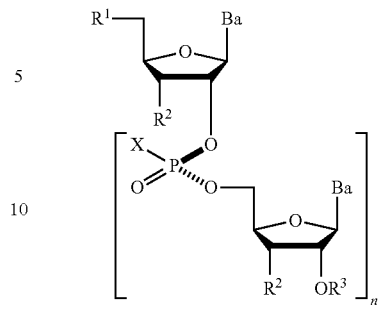

Formula 2 wherein $R^1$ is —OH, —SH, —NR$^d$R$^d$, —N$_3$, halogen, hydrogen, alkyl, alkenyl, alkynyl, alkyl-Y$^1$—, alkenyl-Y$^1$—, alkynyl-Y$^1$—, aryl-Y$^1$—, heteroaryl-Y$^1$—, —P(O)(R$^e$)$_2$, —HP(O)(R$^e$), —OR$^a$ or —SR$^c$;

$Y^1$ is O, NR$^d$, S, or Se;

$R^a$ is a blocking group;

$R^c$ is a blocking group;

each instance of $R^d$ is independently hydrogen, alkyl, alkenyl, alkynyl, aryl, acyl, substituted silyl, carbamate, —P(O)(R$^e$)$_2$, or —HP(O)(R$^e$);

each instance of $R^e$ is independently hydrogen, alkyl, aryl, alkenyl, alkynyl, alkyl-Y$^2$—, alkenyl-Y$^2$—, alkynyl-Y$^2$—, aryl-Y$^2$—, or heteroaryl-Y$^2$—, or a cation which is Na$^{+1}$, Li$^{+1}$, or K$^{+1}$;

$Y^2$ is O, NR$^d$, or S;

each instance of $R^2$ is independently hydrogen, —OH, —SH, —NR$^d$R$^d$, —N$_3$, halogen, alkyl, alkenyl, alkynyl, alkyl-Y$^1$—, alkenyl-Y$^1$—, alkynyl-Y$^1$—, aryl-Y$^1$—, heteroaryl-Y$^1$—, —OR$^b$, or —SR$^c$, wherein R$^b$ is a blocking group;

each instance of Ba is independently a blocked or unblocked adenine, cytosine, guanine, thymine, uracil or modified nucleobase;

at least one X moiety of the nucleic acid prodrug is independently selected from

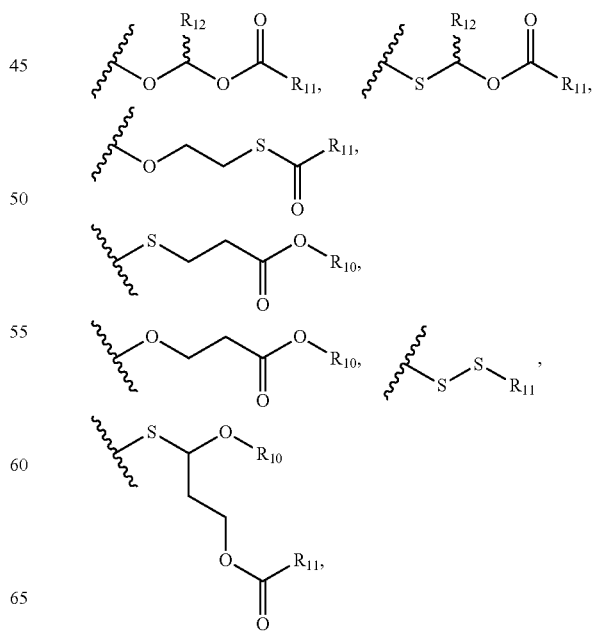

wherein $R_{10}$ is an alkyl group having 1 to 4 carbon atoms; $R_{11}$ is alkyl, aryl, heteroaryl, heterocyclyl, or cycloalkyl; and $R_{12}$ is hydrogen or alkyl.

Another embodiment provides a pharmaceutical composition comprising a compound of Formula 2 wherein $R_{10}$ is methyl. Another embodiment provides a pharmaceutical composition comprising a compound of Formula 2 wherein $R_{11}$ is methyl. Another embodiment provides a pharmaceutical composition comprising a compound of Formula 2 wherein $R_{12}$ is methyl.

One embodiment provides a method of treating cancer comprising administering a therapeutic amount of a nucleic acid prodrug having the following structure:

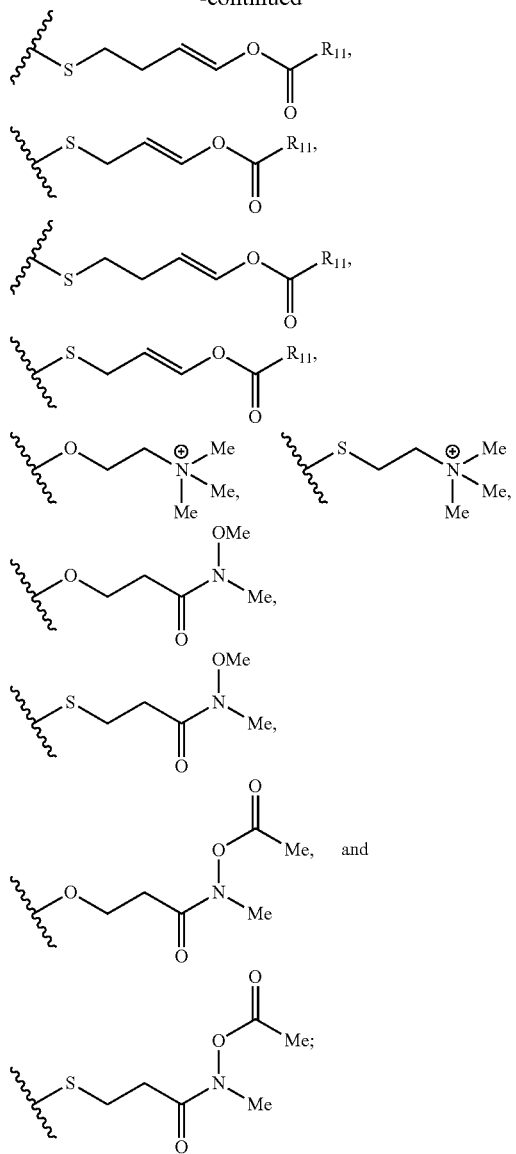

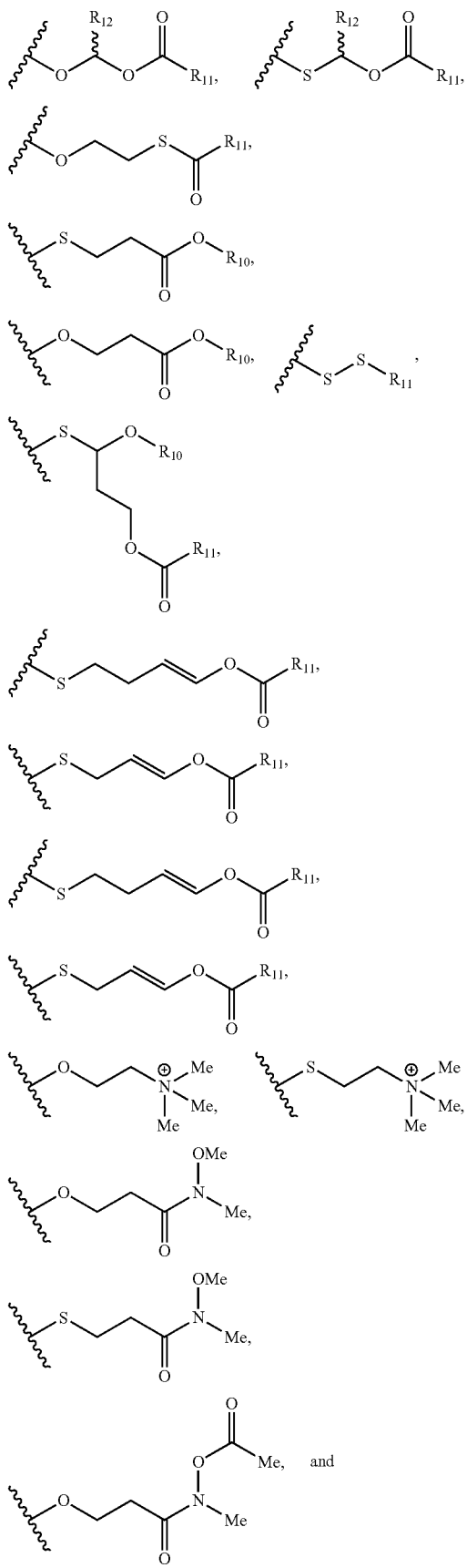

wherein $R_{10}$ is an alkyl group having 1 to 4 carbon atoms; $R_{11}$ is alkyl, aryl, heteroaryl, heterocyclyl, or cycloalkyl; and $R_{12}$ is hydrogen or alkyl;

$R^3$ is hydrogen, a blocking group, a linking moiety connected to a solid support or a linking moiety connected to a nucleic acid; and n is an integer of 1 to about 200;

$R^{10}$ is an alkyl group having 1 to 4 carbon atoms;

wherein the method used to synthesize the nucleic acid prodrug comprises the steps of: (1) reacting a molecule comprising an achiral H-phosphonate moiety and a nucleoside comprising a 5'-OH moiety to form a condensed intermediate; and (2) converting the condensed intermediate to the nucleic acid prodrug comprising a chiral X-phosphonate moiety.

Another embodiment provides a method of treating cancer comprising administering a therapeutic amount of a compound having the structure of Formula 2, wherein at least 25% of the X moieties of the nucleic acid prodrug are independently selected from -continued

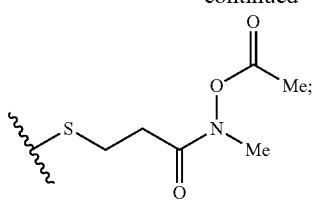

wherein R10 is an alkyl group having 1 to 4 carbon atoms; R11 is alkyl, aryl, heteroaryl, heterocyclyl, or cycloalkyl; and R12 is hydrogen or alkyl. Another embodiment provides a method of treating cancer comprising administering a therapeutic amount of a compound having the structure of Formula 2, wherein at least 50% of the X moieties of the nucleic acid prodrug are independently selected from

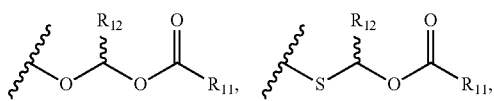

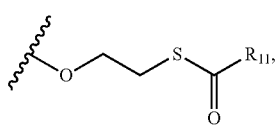

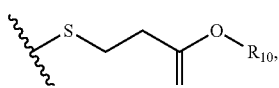

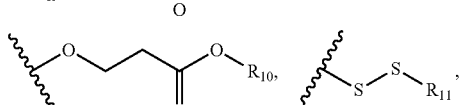

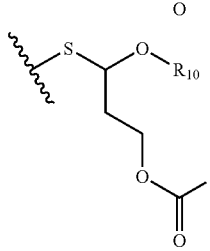

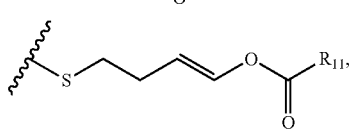

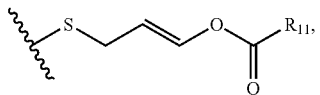

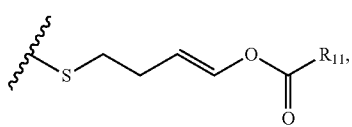

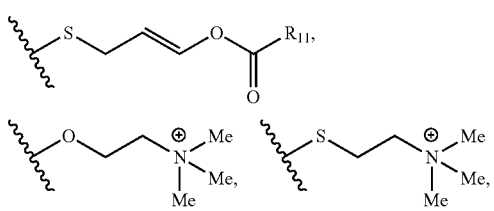

-continued

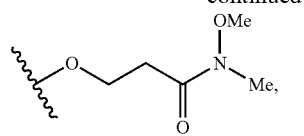

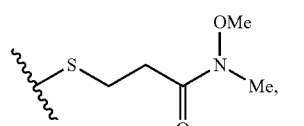

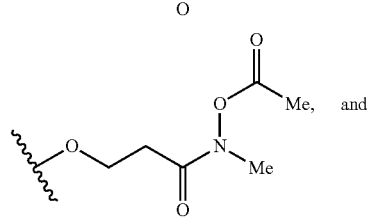 and

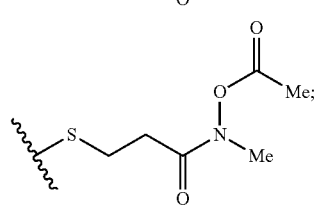

wherein R10 is an alkyl group having 1 to 4 carbon atoms; R11 is alkyl, aryl, heteroaryl, heterocyclyl, or cycloalkyl; and R12 is hydrogen or alkyl. Another embodiment provides a method of treating cancer comprising administering a therapeutic amount of a compound having the structure of Formula 2, wherein at least 90% of the X moieties of the nucleic acid prodrug are independently selected from

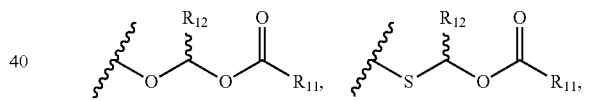

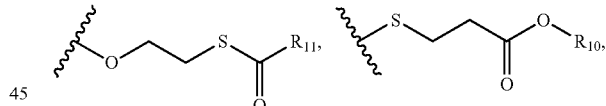

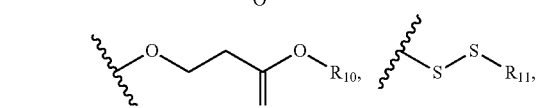

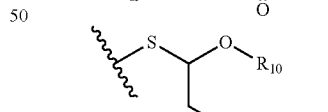

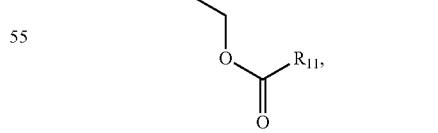

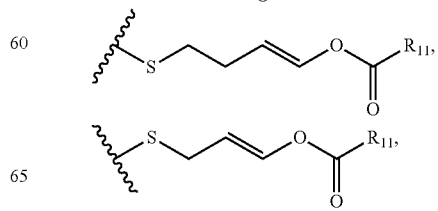

-continued

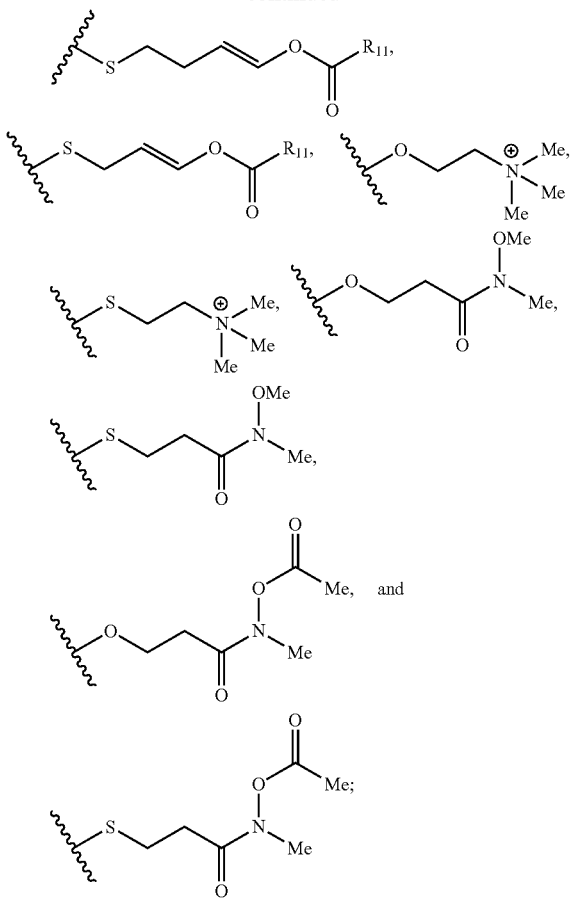

wherein R10 is an alkyl group having 1 to 4 carbon atoms; R11 is alkyl, aryl, heteroaryl, heterocyclyl, or cycloalkyl; and R12 is hydrogen or alkyl. Another embodiment provides a method of treating cancer comprising administering a therapeutic amount of a compound having the structure of Formula 2, wherein each instance of X is independently selected from

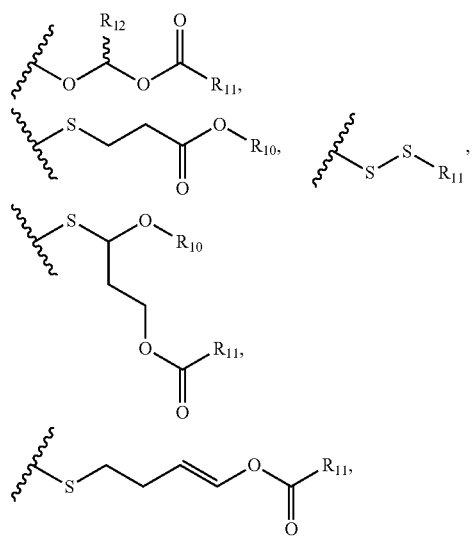

-continued

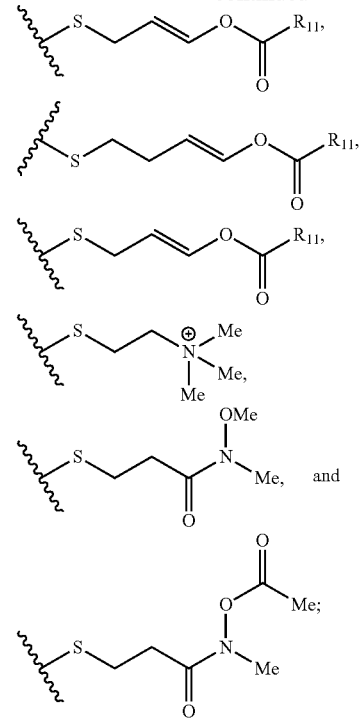

wherein $R_{10}$ is an alkyl group having 1 to 4 carbon atoms; $R_{11}$ is alkyl, aryl, heteroaryl, heterocyclyl, or cycloalkyl; and $R_{12}$ is hydrogen or alkyl.

Another embodiment provides a method of treating cancer comprising administering a therapeutic amount of a compound having the structure of Formula 2, wherein $R_{10}$ is methyl. Another embodiment provides a method of treating cancer comprising administering a therapeutic amount of a compound having the structure of Formula 2, wherein $R_{11}$ is methyl. Another embodiment provides a method of treating cancer comprising administering a therapeutic amount of a compound having the structure of Formula 2, wherein $R_{12}$ is methyl Another embodiment provides a method of treating cancer comprising administering a therapeutic amount of a compound having the structure of Formula 2, wherein each X-phosphonate moiety of the compound of Formula 2 is more than 98% diastereomerically pure as determined by $^{31}P$ NMR spectroscopy or reverse-phase HPLC.

Another embodiment provides a method of treating cancer comprising administering a therapeutic amount of a compound having the structure of Formula 2, wherein each X-phosphonate moiety has a RP configuration. Another embodiment provides a method of treating cancer comprising administering a therapeutic amount of a compound having the structure of Formula 2, wherein each X-phosphonate moiety has a SP configuration. Another embodiment provides a method of treating cancer comprising administering a therapeutic amount of a compound having the structure of Formula 2, wherein each X-phosphonate independently has a RP configuration or a $S_P$ configuration.

One embodiment provides a method of treating cancer comprising administering a therapeutic amount of a compound having the structure of Formula 2, wherein the cancer is pancreatic cancer.

One embodiment provides a method of treating cancer comprising administering a therapeutic amount of a compound having the structure of Formula 2, wherein the compound has the following formula:

Formula A₃-2

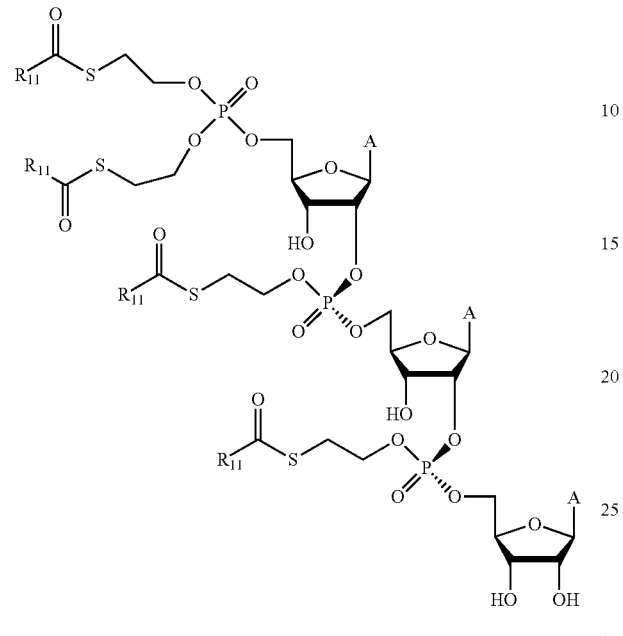

wherein each A is adenine and each $R_{11}$ is independently selected from alkyl, aryl, heteroaryl, heterocyclyl, and cycloalkyl. A further embodiment provides a method of treating pancreatic cancer comprising administering a therapeutic amount of a compound of Formula $A_3$-2.

One embodiment provides a method of treating cancer comprising administering a therapeutic amount of a compound having the structure of Formula 2, wherein the compound has the following formula:

Formula A₃-3

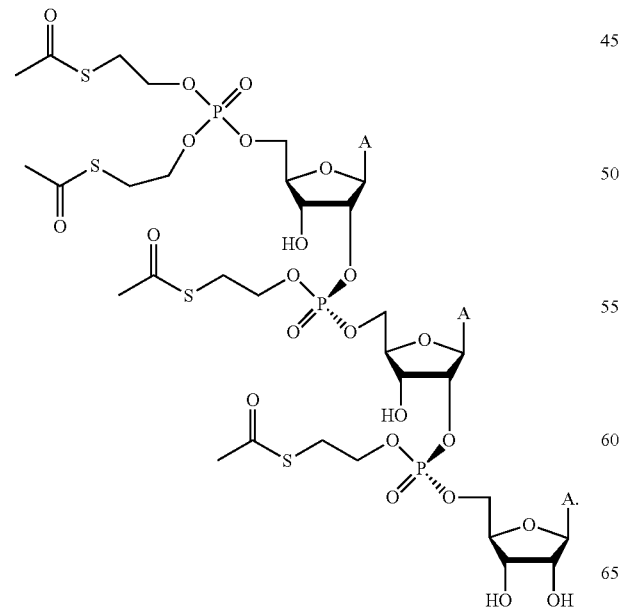

A further embodiment provides a method of treating pancreatic cancer comprising administering a therapeutic amount of a compound of Formula $A_3$-3.

One embodiment provides a compound or its pharmaceutically acceptable salt having the following formula:

Formula A₃-1

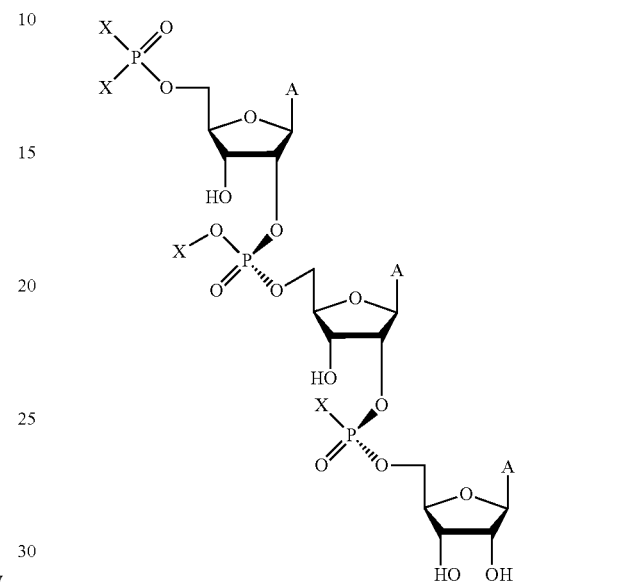

wherein each A is adenine; and at least one X moiety is

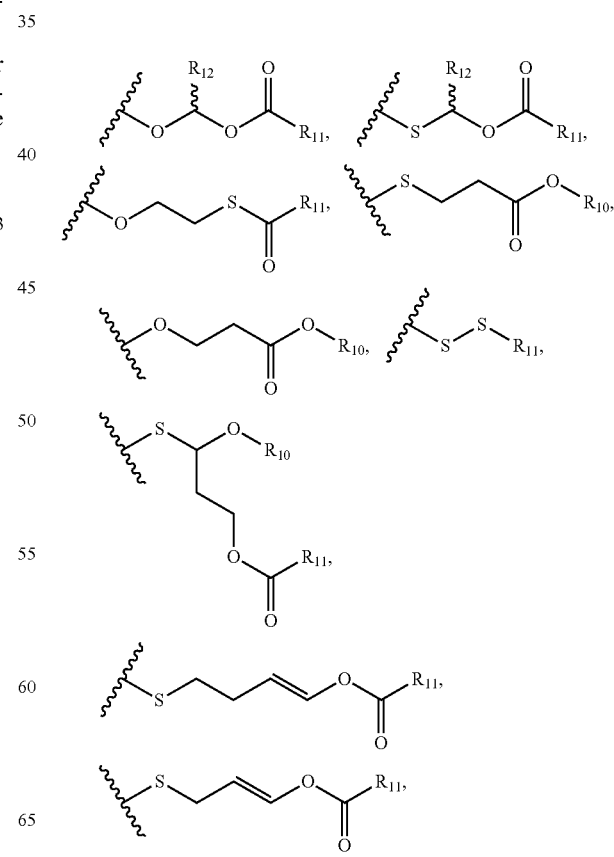

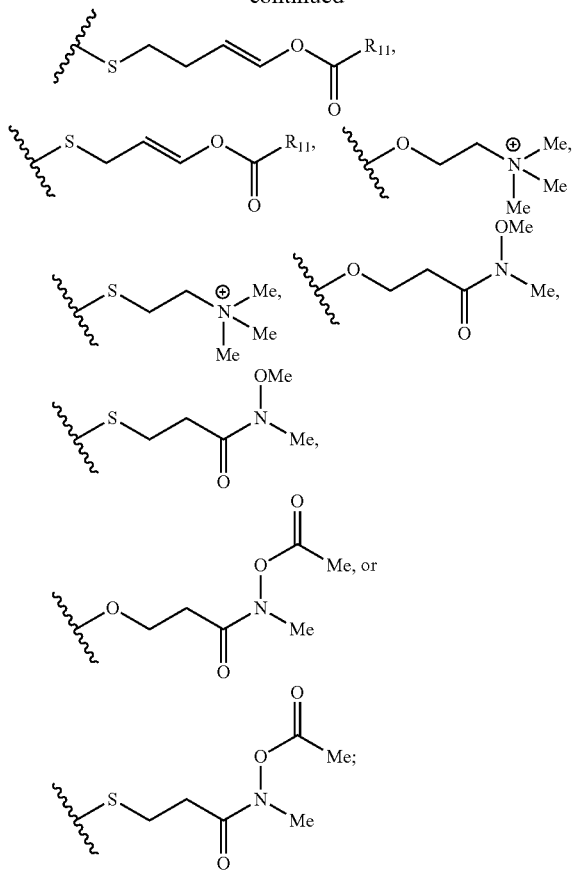

wherein $R_{10}$ is an alkyl group having 1 to 4 carbon atoms; $R_{11}$ is alkyl, aryl, heteroaryl, heterocyclyl, or cycloalkyl; and $R_{12}$ is hydrogen or alkyl.

Another embodiment provides a compound or its pharmaceutically acceptable salt having the structure of Formula A3-1, wherein at least two of the X moieties of the nucleic acid prodrug are independently selected from

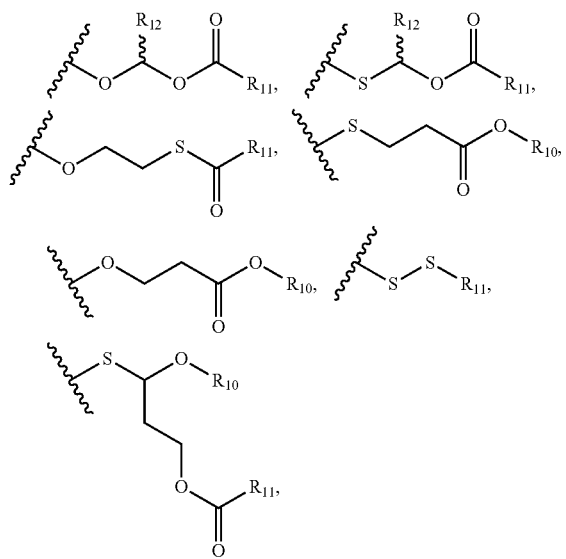

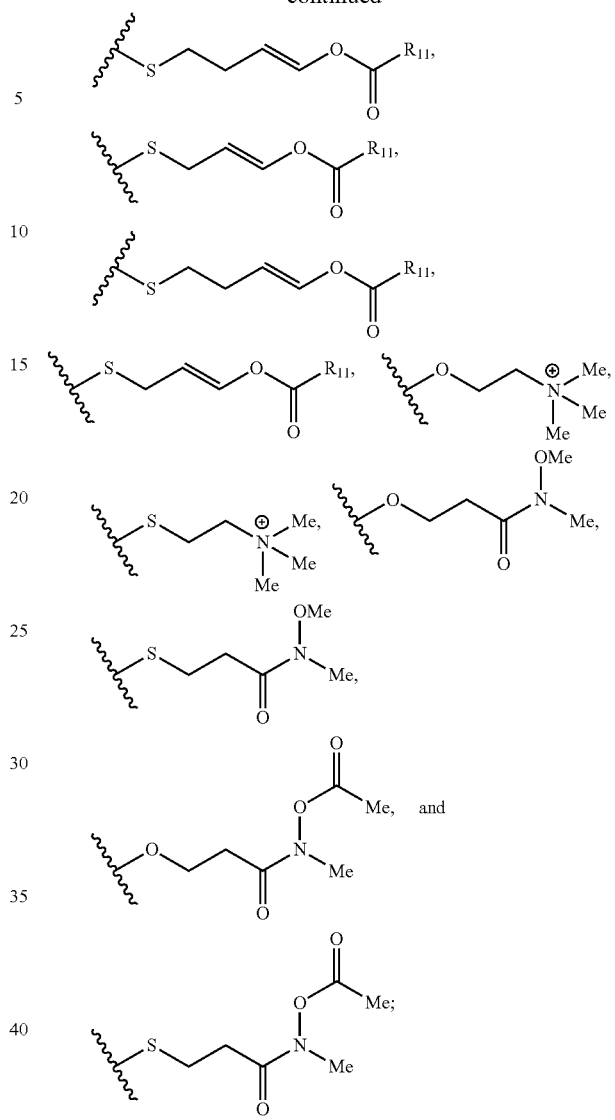

wherein $R_{10}$ is an alkyl group having 1 to 4 carbon atoms; $R_{11}$ is alkyl, aryl, heteroaryl, heterocyclyl, or cycloalkyl; and $R_{12}$ is hydrogen or alkyl.

Another embodiment provides a compound or its pharmaceutically acceptable salt having the structure of Formula $A_3$-1, wherein at least three of the X moieties of the nucleic acid prodrug are independently selected from

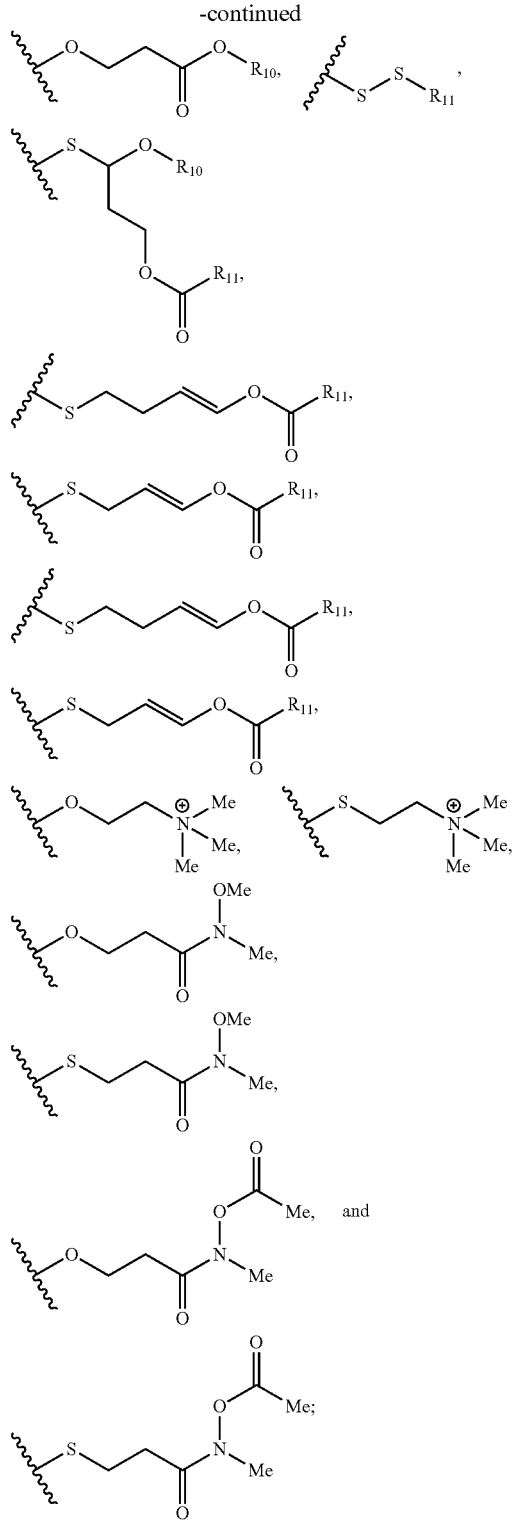
wherein $R_{10}$ is an alkyl group having 1 to 4 carbon atoms; $R_{11}$ is alkyl, aryl, heteroaryl, heterocyclyl, or cycloalkyl; and $R_{12}$ is hydrogen or alkyl.
Another embodiment provides a compound or its pharmaceutically acceptable salt having the structure of Formula $A_3$-1, wherein each X moiety of the nucleic acid prodrug is independently selected from
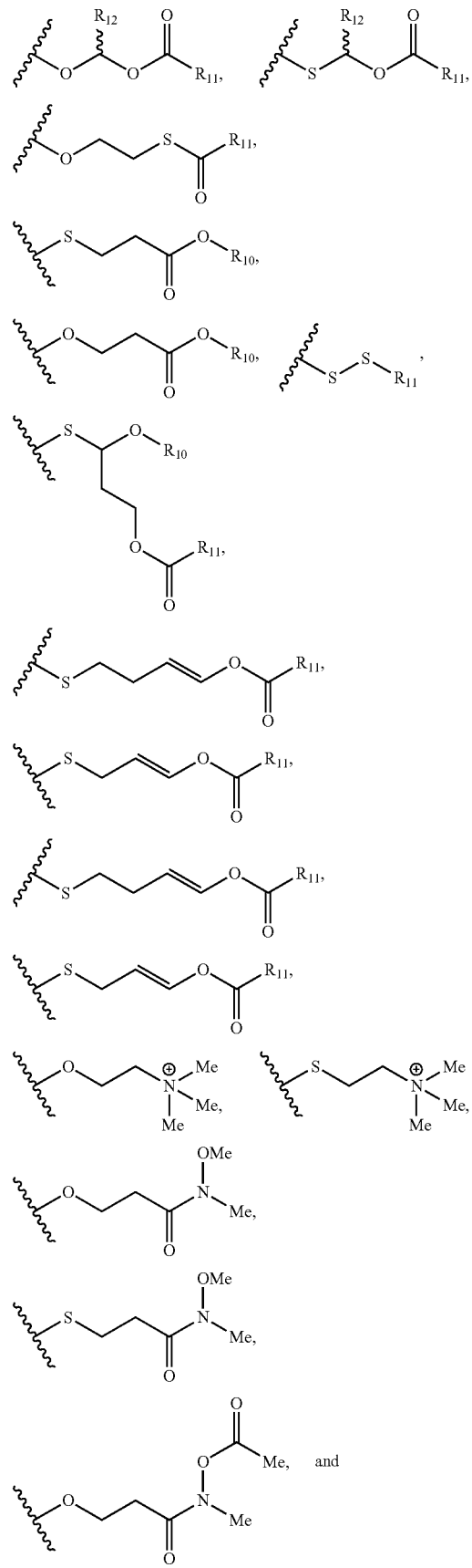

-continued

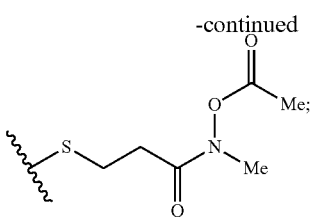

wherein $R_{10}$ is an alkyl group having 1 to 4 carbon atoms; $R_{11}$ is alkyl, aryl, heteroaryl, heterocyclyl, or cycloalkyl; and $R_{12}$ is hydrogen or alkyl.

Another embodiment provides a compound or its pharmaceutically acceptable salt having the structure of Formula $A_3$-1, wherein the compound has the following formula:

Formula $A_3$-3

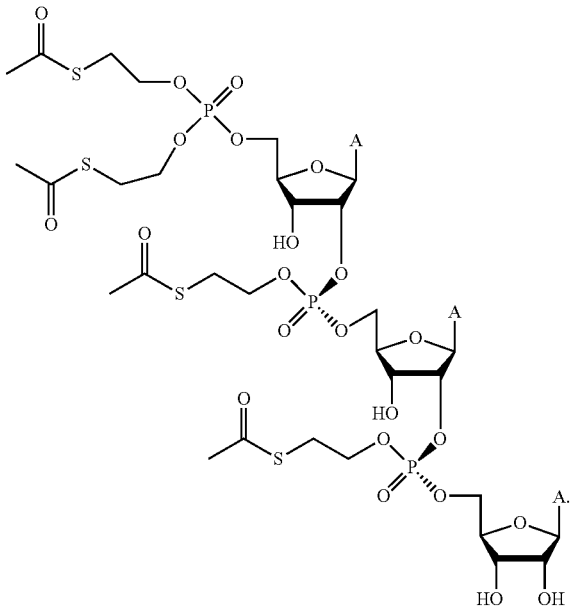

INCORPORATION BY REFERENCE

All publications and patent applications disclosed herein in this specification are herein incorporated by reference in their entirety to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

FIG. 4 provides a reaction timecourse as determined by LC-MS for the glutathione assisted prodrug release of compound 64a.

DETAILED DESCRIPTION OF THE INVENTION

Figure 1:
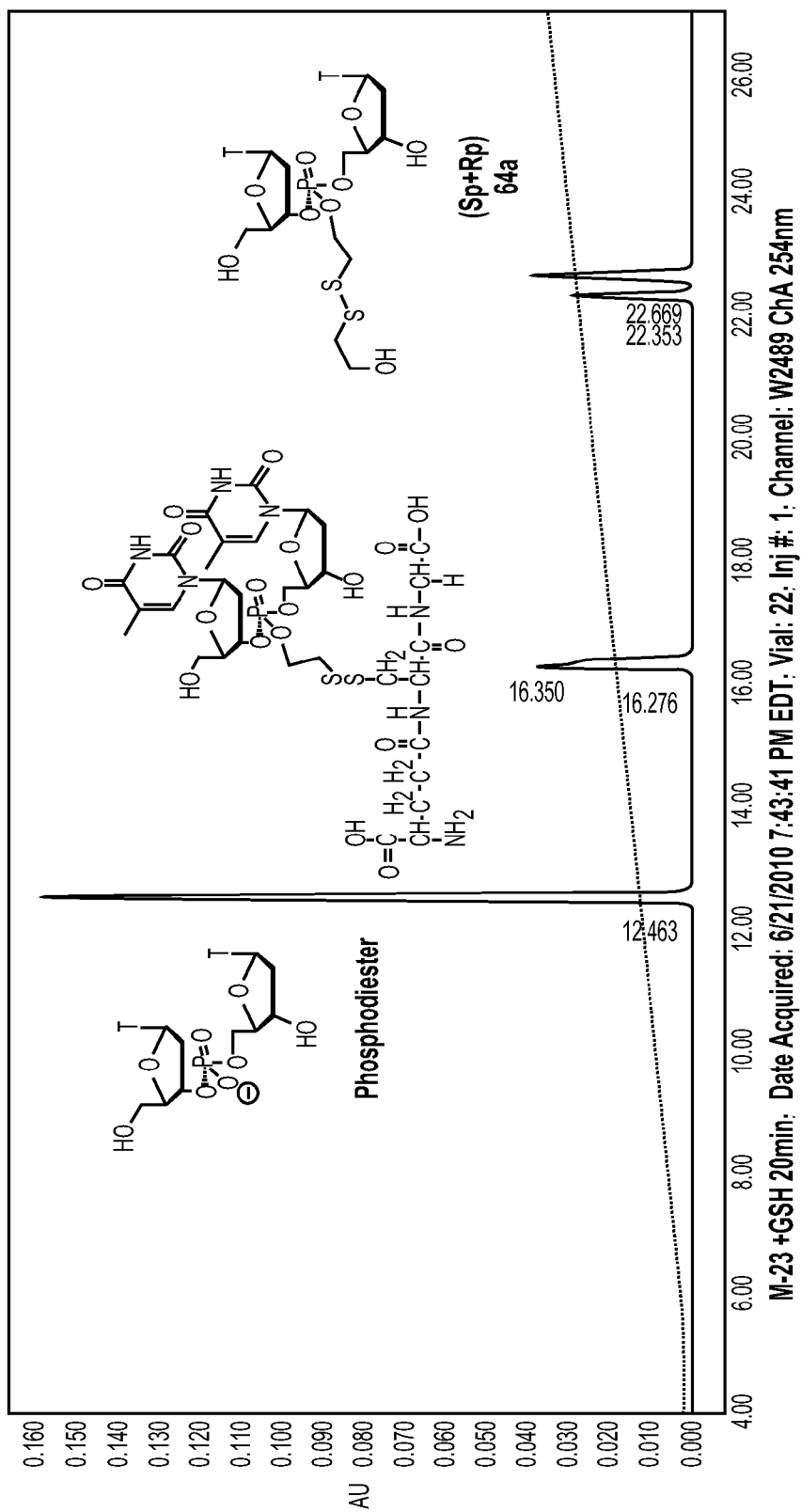
FIG. 1 provides a representative analytical HPLC profile for compound 64 and GSH.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless otherwise stated, the following terms used in this application, including the specification and claims, have the definitions given below. It must be noted that, as used in the specification and the appended claims, the singular forms "a" "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes" and "included" is not limiting.

Certain Chemical Terminology

Unless otherwise noted, the use of general chemical terms, such as though not limited to "alkyl," "amine," "aryl," are unsubstituted.

As used herein, $C_1$-$C_x$ includes $C_1$-$C_2$, $C_1$-$C_3$ .... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The terms "heteroatom" or "hetero" as used herein, alone or in combination, refer to an atom other than carbon or hydrogen. Heteroatoms are may be independently selected from among oxygen, nitrogen, sulfur, phosphorous, silicon, selenium and tin but are not limited to these atoms. In embodiments in which two or more heteroatoms are present, the two or more heteroatoms can be the same as each another, or some or all of the two or more heteroatoms can each be different from the others.

The term "alkyl" as used herein, alone or in combination, refers to a straight-chain or branched-chain saturated hydrocarbon monoradical having from one to about ten carbon atoms, or one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl- 1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms. In one embodiment, the "alkyl" is substituted. Unless otherwise indicated, the "alkyl" is unsubstituted.

The term "alkenyl" as used herein, alone or in combination, refers to a straight-chain or branched-chain hydrocarbon monoradical having one or more carbon-carbon double-bonds and having from two to about ten carbon atoms, or two to about six carbon atoms. The group may be in either the cis or trans conformation about the double bond(s), and should be understood to include both isomers. Examples include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" or "$C_{2-6}$ alkenyl", means that the alkenyl group may consist of 2 carbon atoms, 3 carbon atoms, 4 carbon atoms, 5 carbon atoms or 6 carbon atoms. In one embodiment, the "alkenyl" is substituted. Unless otherwise indicated, the "alkenyl" is unsubstituted.

The term "alkynyl" as used herein, alone or in combination, refers to a straight-chain or branched-chain hydrocarbon monoradical having one or more carbon-carbon triple-bonds and having from two to about ten carbon atoms, or from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$ alkynyl", means that the alkynyl group may consist of 2 carbon atoms, 3 carbon atoms, 4 carbon atoms, 5 carbon atoms or 6 carbon atoms. In one embodiment, the "alkynyl" is substituted. Unless otherwise indicated, the "alkynyl" is unsubstituted.

The terms "heteroalkyl", "heteroalkenyl" and "heteroalkynyl" as used herein, alone or in combination, refer to alkyl, alkenyl and alkynyl structures respectively, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof), or heteroatomic group such as though not limited to —O—O—, —S—S—, —O—S—, —S—O—, =N—N=, —N=N—, —N=N—NH—, —P(O)$_2$—, —O—P(O)$_2$—, —P(O)$_2$—O—, —S(O)—, —S(O)$_2$—, —SnH$_2$— and the like.

The terms "haloalkyl", "haloalkenyl" and "haloalkynyl" as used herein, alone or in combination, refer to alkyl, alkenyl and alkynyl groups respectively, as defined above, in which one or more hydrogen atoms is replaced by fluorine, chlorine, bromine or iodine atoms, or combinations thereof. In some embodiments two or more hydrogen atoms may be replaced with halogen atoms that are the same as each another (e.g. difluoromethyl); in other embodiments two or more hydrogen atoms may be replaced with halogen atoms that are not all the same as each other (e.g. 1-chloro-1-fluoro-1-iodoethyl). Non-limiting examples of haloalkyl groups are fluoromethyl, chloromethyl and bromoethyl. A non-limiting example of a haloalkenyl group is bromoethenyl. A non-limiting example of a haloalkynyl group is chloroethynyl.

The term "carbon chain" as used herein, alone or in combination, refers to any alkyl, alkenyl, alkynyl, heteroalkyl, heteroalkenyl or heteroalkynyl group, which is linear, cyclic, or any combination thereof. If the chain is part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining the chain length. If the chain contains heteroatoms as part of the backbone, those atoms are not calculated as part of the carbon chain length.

The term "cycloalkyl" as used herein, alone or in combination, refers to a saturated, hydrocarbon monoradical ring, containing from three to about fifteen ring carbon atoms or from three to about ten ring carbon atoms, though may include additional, non-ring carbon atoms as substituents (e.g. methylcyclopropyl). Whenever it appears herein, a numerical range such as "$C_3$-$C_6$ cycloalkyl" or "$C_{3-6}$ cycloalkyl", means that the cycloalkyl group may consist of 3 carbon atoms, 4 carbon atoms, 5 carbon atoms or 6 carbon atoms, i.e., is cyclopropyl, cyclobutyl, cyclopentyl or cyclohepty, although the present definition also covers the occurrence of the term "cycloalkyl" where no numerical range is designated. The term includes fused, non-fused, bridged and spiro radicals. A fused cycloalkyl may contain from two to four fused rings where the ring of attachment is a cycloalkyl ring, and the other individual rings may be alicyclic, heterocyclic, aromatic, heteroaromatic or any combination thereof. Examples include, but are not limited to cyclopropyl, cyclopentyl, cyclohexyl, decalinyl, and bicyclo[2.2.1]heptyl and adamantyl ring systems. Illustrative examples include, but are not limited to the following moieties:

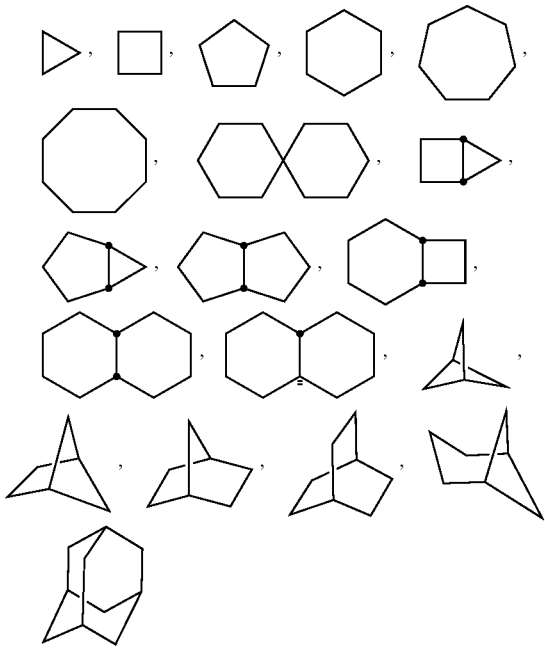

and the like.

In one embodiment, the "cycloalkyl" is substituted. Unless otherwise indicated, the "cycloalkyl" is unsubstituted.

The terms "non-aromatic heterocyclyl" and "heteroalicyclyl" as used herein, alone or in combination, refer to a saturated, partially unsaturated, or fully unsaturated nonaromatic ring monoradicals containing from three to about twenty ring atoms, where one or more of the ring atoms are an atom other than carbon, independently selected from among oxygen, nitrogen, sulfur, phosphorous, silicon, selenium and tin but are not limited to these atoms. In embodiments in which two or more heteroatoms are present in the ring, the two or more heteroatoms can be the same as each another, or some or all of the two or more heteroatoms can each be different from the others. The terms include fused, non-fused, bridged and spiro radicals. A fused non-aromatic heterocyclic radical may contain from two to four fused rings where the attaching ring is a non-aromatic heterocycle, and the other individual rings may be alicyclic, heterocyclic, aromatic, heteroaromatic or any combination thereof. Fused ring systems may be fused across a single bond or a double bond, as well as across bonds that are carbon-carbon, carbon-hetero atom or hetero atom-hetero atom. The terms also include radicals having from three to about twelve skeletal ring atoms, as well as those having from three to about ten skeletal ring atoms. Attachment of a non-aromatic heterocyclic subunit to its parent molecule can be via a heteroatom or a carbon atom. Likewise, additional substitution can be via a heteroatom or a carbon atom. As a non-limiting example, an imidazolidine non-aromatic heterocycle may be attached to a parent molecule via either of its N atoms (imidazolidin-1-yl or imidazolidin-3-yl) or any of its carbon atoms (imidazolidin-2-yl, imidazolidin-4-yl or imidazolidin-5-yl). In certain embodiments, non-aromatic heterocycles contain one or more carbonyl or thiocarbonyl groups such as, for example, oxo- and thio-containing groups. Examples include, but are not limited to pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Illustrative examples of heterocycloalkyl groups, also referred to as non-aromatic heterocycles, include:

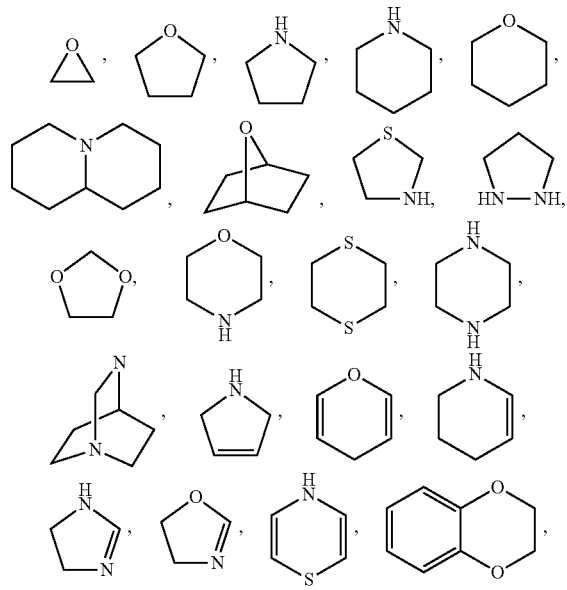

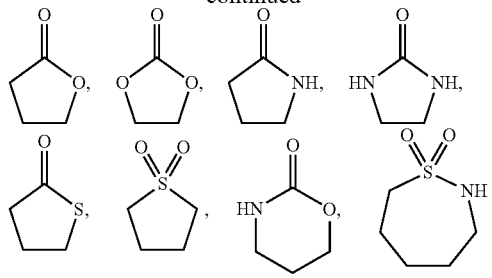

and the like.

The terms also include all ring forms of the carbohydrates, including but not limited to the monosaccharides, the disaccharides and the oligosaccharides. In one embodiment, the "non-aromatic heterocyclyl" or "heteroalicyclyl" is substituted. Unless otherwise indicated, the "non-aromatic heterocyclyl" or "heteroalicyclyl" is unsubstituted.

The term "aryl" as used herein, alone or in combination, refers to an aromatic hydrocarbon radical of six to about twenty ring carbon atoms, and includes fused and non-fused aryl rings. A fused aryl ring radical contains from two to four fused rings where the ring of attachment is an aryl ring, and the other individual rings may be alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl. In one embodiment, the "aryl" is substituted. Unless otherwise indicated, the "aryl" is unsubstituted.

The term "heteroaryl" as used herein, alone or in combination, refers to an aromatic monoradicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazinyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide. Illustrative examples of heteroaryl groups include the following moieties:

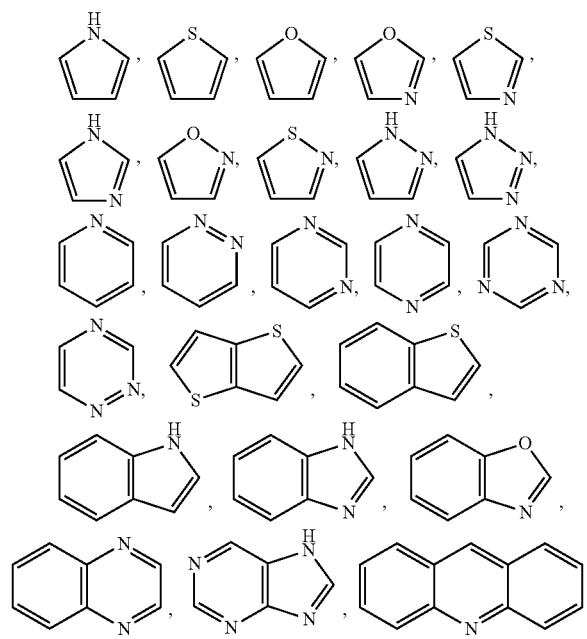

and the like.

In one embodiment, the "heteroaryl" is substituted. Unless otherwise indicated, the "heteroaryl" is unsubstituted.

The term "heterocyclyl" as used herein, alone or in combination, refers collectively to heteroalicyclyl and heteroaryl groups. Herein, whenever the number of carbon atoms in a heterocycle is indicated (e.g., $C_1$-$C_6$ heterocycle), at least one non-carbon atom (the heteroatom) must be present in the ring. Designations such as "$C_1$-$C_6$ heterocycle" refer only to the number of carbon atoms in the ring and do not refer to the total number of atoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). For heterocycles having two or more heteroatoms, those two or more heteroatoms can be the same or different from one another. Non-aromatic heterocyclic groups include groups having only three atoms in the ring, while aromatic heterocyclic groups must have at least five atoms in the ring. Bonding (i.e. attachment to a parent molecule or further substitution) to a heterocycle can be via a heteroatom or a carbon atom. In one embodiment, the "heterocyclyl" is substituted. Unless otherwise indicated, the "heterocycyl" is unsubstituted.

The terms "halogen", "halo" or "halide" as used herein, alone or in combination refer to fluoro, chloro, bromo and/or iodo.

Certain Pharmaceutical Terminology

The term "subject", "patient" or "individual" as used herein in reference to individuals suffering from a disorder, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "effective amount", "therapeutically effective amount" or "pharmaceutically effective amount" as used herein, refer to an amount of at least one agent or compound being administered that is sufficient to treat or prevent the particular disease or condition. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively nontoxic chemical compounds or agents that facilitate the incorporation of a compound into cells or tissues.

The term "prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to acyloxy, thioacyloxy, 2-carboalkoxyethyl, disulfide, thiaminal, and enol ester derivatives of a phosphorus atom-modified nucleic acid.

The term "pro-oligonucleotide" or "pronucleotide" or "nucleic acid prodrug" refers to an oligonucleotide which has been modified to be a prodrug of the oligonucleotide.

Certain Nucleic Acid Terminology

Natural nucleic acids have a phosphate backbone; artificial nucleic acids may contain other types of backbones, but contain the same bases.

The term "nucleotide" as used herein refers to a monomeric unit of a polynucleotide that consists of a heterocyclic base, a sugar, and one or more phosphate groups. The naturally occurring bases, (guanine, (G), adenine, (A), cytosine, (C), thymine, (T), and uracil (U)) are derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are linked via phosphate bonds to form nucleic acids, or polynucleotides, though many other linkages are known in the art (such as, though not limited to phosphorothioates, boranophosphates and the like). Artificial nucleic acids include PNAs (peptide nucleic acids), phosphothionates, and other variants of the phosphate backbone of native nucleic acids.

The term "nucleoside" refers to a moiety wherein a nucleobase or a modified nucleobase is covalently bound to a sugar or modified sugar.

The term "sugar" refers to a monosaccharide in closed and/or open form. Sugars include, but are not limited to, ribose, deoxyribose, pentofuranose, pentopyranose, and hexopyranose moieties.

The term "modified sugar" refers to a moiety that can replace a sugar. The modified sugar mimics the spatial arrangement, electronic properties, or some other physicochemical property of a sugar.

The terms "nucleic acid" and "polynucleotide" as used herein refer to a polymeric form of nucleotides of any length, either ribonucleotides (RNA) or deoxyribonucleotides (DNA). These terms refer to the primary structure of the molecules and, thus, include double- and single-stranded DNA, and double- and single-stranded RNA. These terms include, as equivalents, analogs of either RNA or DNA made from nucleotide analogs and modified polynucleotides such as, though not limited to, methylated and/or capped polynucleotides. The terms encompass poly- or oligo-ribonucleotides (RNA) and poly- or oligo-deoxyribonucleotides (DNA); RNA or DNA derived from N-glycosides or C-glycosides of nucleobases and/or modified nucleobases; nucleic acids derived from sugars and/or modified sugars; and nucleic acids derived from phosphate bridges and/or modified phosphorous-atom bridges. The term encompasses nucleic acids containing any combinations of nucleobases, modified nucleobases, sugars, modified sugars, phosphate bridges or modified phosphorous atom bridges. Examples include, and are not limited to, nucleic acids containing ribose moieties, the nucleic acids containing deoxy-ribose moieties, nucleic acids containing both ribose and deoxyribose moieties, nucleic acids containing ribose and modified ribose moieties. The prefix poly- refers to a nucleic acid containing about 1 to about 10,000 nucleotide monomer units and wherein the prefix oligo- refers to a nucleic acid containing about 1 to about 200 nucleotide monomer units.

The term "nucleobase" refers to the parts of nucleic acids that are involved in the hydrogen-bonding that binds one nucleic acid strand to another complementary strand in a sequence specific manner. The most common naturally-occurring nucleobases are adenine (A), guanine (G), uracil (U), cytosine (C), and thymine (T).

The term "modified nucleobase" refers to a moiety that can replace a nucleobase. The modified nucleobase mimics the spatial arrangement, electronic properties, or some other physicochemical property of the nucleobase and retains the property of hydrogen-bonding that binds one nucleic acid strand to another in a sequence specific manner. A modified nucleobase can pair with all of the five naturally occurring bases (uracil, thymine, adenine, cytosine, or guanine) without substantially affecting the melting behavior, recognition by intracellular enzymes or activity of the oligonucleotide duplex.

The term "chiral reagent" refers to a compound that is chiral or enantiopure and can be used for asymmetric induction in nucleic acid synthesis.

The term "chiral ligand" or "chiral auxiliary" refers to a moiety that is chiral or enantiopure and controls the stereochemical outcome of a reaction.

In a condensation reaction, the term "condensing reagent" refers to a reagent that activates a less reactive site and renders it more susceptible to attack by a nucleophile.

The term "blocking group" refers to a group that transiently masks the reactivity of a functional group. The functional group can be subsequently unmasked by removal of the blocking group.

The terms "boronating agents", "sulfur electrophiles", "selenium electrophiles" refer to compounds that are useful in the modifying step used to introduce BH$_3$, S, and Se groups, respectively, for modification at the phosphorus atom.

The term "moiety" refers to a specific segment or functional group of a molecule. Chemical moieties are often recognized chemical entities embedded in or appended to a molecule.

The term "solid support" refers to any support which enables synthetic mass production of nucleic acids and can be reutilized at need. As used herein, the term refers to a polymer, that is insoluble in the media employed in the reaction steps performed to synthesize nucleic acids, and is derivatized to comprise reactive groups.

The term "linking moiety" refers to any moiety optionally positioned between the terminal nucleoside and the solid support or between the terminal nucleoside and another nucleoside, nucleotide, or nucleic acid.

A "DNA molecule" refers to the polymeric form of deoxyribonucleotides (adenine, guanine, thymine, or cytosine) in its either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA).

A DNA "coding sequence" or "coding region" is a double-stranded DNA sequence which is transcribed and translated into a polypeptide in vivo when placed under the control of appropriate expression control sequences. The boundaries of the coding sequence (the "open reading frame" or "ORF") are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence is, usually, be located 3' to the coding sequence. The term "non-coding sequence" or "non-coding region" refers to regions of a polynucleotide sequence that are not translated into amino acids (e.g. 5' and 3' un-translated regions).

The term "reading frame" refers to one of the six possible reading frames, three in each direction, of the double stranded DNA molecule. The reading frame that is used determines which codons are used to encode amino acids within the coding sequence of a DNA molecule.

As used herein, an "antisense" nucleic acid molecule comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid molecule can hydrogen bond to a sense nucleic acid molecule.

The term "base pair" or ("bp"): a partnership of adenine (A) with thymine (T), or of cytosine (C) with guanine (G) in a double stranded DNA molecule. In RNA, uracil (U) is substituted for thymine.

As used herein a "codon" refers to the three nucleotides which, when transcribed and translated, encode a single amino acid residue; or in the case of UUA, UGA or UAG encode a termination signal. Codons encoding amino acids are well known in the art and are provided for convenience herein in Table 1.

TABLE 1

Codon Usage Table

| Codon | Amino acid | AA | Abbr. | Codon | Amino acid | AA | Abbr. |
|---|---|---|---|---|---|---|---|
| UUU | Phenylalanine | Phe | F | UCU | Serine | Ser | S |
| UUC | Phenylalanine | Phe | F | UCC | Serine | Ser | S |
| UUA | Leucine | Leu | L | UCA | Serine | Ser | S |
| UUG | Leucine | Leu | L | UCG | Serine | Ser | S |
| CUU | Leucine | Leu | L | CCU | Proline | Pro | P |
| CUC | Leucine | Leu | L | CCC | Proline | Pro | P |
| CUA | Leucine | Leu | L | CCA | Proline | Pro | P |
| CUG | Leucine | Leu | L | CCG | Proline | Pro | P |
| AUU | Isoleucine | Ile | I | ACU | Threonine | Thr | T |
| AUC | Isoleucine | Ile | I | ACC | Threonine | Thr | T |
| AUA | Isoleucine | Ile | I | ACA | Threonine | Thr | T |
| AUG | Methionine | Met | M | ACH | Threonine | Thr | T |
| GUU | Valine | Val | V | GCU | Alanine | Ala | A |
| GUC | Valine | Val | V | GCC | Alanine | Ala | A |
| GUA | Valine | Val | V | GCA | Alanine | Ala | A |
| GUG | Valine | Val | V | GCG | Alanine | Ala | A |
| UAU | Tyrosine | Tyr | Y | UGU | Cysteine | Cys | C |
| UAC | Tyrosine | Tyr | Y | UGC | Cysteine | Cys | C |
| UUA | | Stop | | UGA | | Stop | |
| UAG | | Stop | | UGG | Tryptophan | Trp | W |
| CAU | Histidine | His | H | CGU | Arginine | Arg | R |
| CAC | Histidine | His | H | CGC | Arginine | Arg | R |
| CAA | Glutamine | Gln | Q | CGA | Arginine | Arg | R |
| CAG | Glutamine | Gln | Q | CGG | Arginine | Arg | R |
| AAU | Asparagine | Asn | N | AGU | Serine | Ser | S |
| AAC | Asparagine | Asn | N | AGC | Serine | Ser | S |
| AAA | Lysine | Lys | K | AGA | Arginine | Arg | R |
| AAG | Lysine | Lys | K | AGG | Arginine | Arg | R |
| GAU | Aspartate | Asp | D | GGU | Glycine | Gly | G |
| GAC | Aspartate | Asp | D | GGC | Glycine | Gly | G |
| GAA | Glutamate | Glu | E | GGA | Glycine | Gly | G |
| GAG | Glutamate | Glu | E | GGG | Glycine | Gly | G |

As used herein, a "wobble position" refers to the third position of a codon. Mutations in a DNA molecule within the wobble position of a codon, in some embodiments, result in silent or conservative mutations at the amino acid level. For example, there are four codons that encode Glycine, i.e., GGU, GGC, GGA and GGG, thus mutation of any wobble position nucleotide, to any other nucleotide, does not result in a change at the amino acid level of the encoded protein and, therefore, is a silent substitution.

Accordingly a "silent substitution" or "silent mutation" is one in which a nucleotide within a codon is modified, but does not result in a change in the amino acid residue encoded by the codon. Examples include mutations in the third position of a codon, as well in the first position of certain codons such as in the codon "CGG" which, when mutated to AGG, still encodes Arg.

The terms "gene," "recombinant gene" and "gene construct" as used herein, refer to a DNA molecule, or portion of a DNA molecule, that encodes a protein or a portion thereof. The DNA molecule can contain an open reading frame encoding the protein (as exon sequences) and can further include intron sequences. The term "intron" as used herein, refers to a DNA sequence present in a given gene which is not translated into protein and is found in some, but not all cases, between exons. It can be desirable for the gene to be operably linked to, (or it can comprise), one or more promoters, enhancers, repressors and/or other regulatory sequences to modulate the activity or expression of the gene, as is well known in the art.

As used herein, a "complementary DNA" or "cDNA" includes recombinant polynucleotides synthesized by reverse transcription of mRNA and from which intervening sequences (introns) have been removed.

"Homology" or "identity" or "similarity" refers to sequence similarity between two nucleic acid molecules. Homology and identity can each be determined by comparing a position in each sequence which can be aligned for purposes of comparison. When an equivalent position in the compared sequences is occupied by the same base, then the molecules are identical at that position; when the equivalent site occupied by the same or a similar nucleic acid residue (e.g., similar in steric and/or electronic nature), then the molecules can be referred to as homologous (similar) at that position. Expression as a percentage of homology/similarity or identity refers to a function of the number of identical or similar nucleic acids at positions shared by the compared sequences. A sequence which is "unrelated" or "non-homologous" shares less than 40% identity, less than 35% identity, less than 30% identity, or less than 25% identity with a sequence described herein. In comparing two sequences, the absence of residues (amino acids or nucleic acids) or presence of extra residues also decreases the identity and homology/similarity.

The term "homology" describes a mathematically based comparison of sequence similarities which is used to identify genes with similar functions or motifs. The nucleic acid sequences described herein can be used as a "query sequence" to perform a search against public databases, for example, to identify other family members, related sequences or homologs. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used (See www.ncbi.nlm.nih.gov).

As used herein, "identity" means the percentage of identical nucleotide residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well-known Smith Waterman algorithm can also be used to determine identity.

A "heterologous" region of a DNA sequence is an identifiable segment of DNA within a larger DNA sequence that is not found in association with the larger sequence in nature. Thus, when the heterologous region encodes a mammalian gene, the gene can usually be flanked by DNA that does not flank the mammalian genomic DNA in the genome of the source organism. Another example of a heterologous coding sequence is a sequence where the coding sequence itself is not found in nature (e.g., a cDNA where the genomic coding sequence contains introns or synthetic sequences having codons or motifs different than the unmodified gene). Allelic variations or naturally-occurring mutational events do not give rise to a heterologous region of DNA as defined herein.

The term "transition mutations" refers to base changes in a DNA sequence in which a pyrimidine (cytidine (C) or thymidine (T) is replaced by another pyrimidine, or a purine (adenosine (A) or guanosine (G) is replaced by another purine.

The term "transversion mutations" refers to base changes in a DNA sequence in which a pyrimidine (cytidine (C) or thymidine (T) is replaced by a purine (adenosine (A) or guanosine (G), or a purine is replaced by a pyrimidine.

Nucleic Acid Prodrugs Comprising a Chiral X-Phosphonate Moiety

The general principles of prodrug design are outlined by Bundgard (*Design and Application of Prodrugs. In a Textbook of Drug Design and Development*; Krogsgaard-Larsen, P., Bundgard, H., Eds.; Harwood: Reading, UK, 1991).

One strategy to improve the pharmaceutical properties of molecules with desirable biological activity but poor pharmaceutical properties is to administer the molecule of interest as a prodrug derivative. These prodrugs can exhibit one or more of the properties of increased oral bioavailability, increased cell permeability, increased water solubility, reduced first-pass effect, increased stability, active transport by intestinal transporters, or avoidance of efflux transporters, when compared to the parent molecule.

Oligonucleotides have several pharmaceutical properties which can be improved through the application of prodrug strategies. In particular, oligonucleotides are rapidly degraded by nucleases and exhibit poor cellular uptake through the cytoplasmic cell membrane (Poijarvi-Virta et al., Curr. Med. Chem. (2006), 13(28); 3441-65; Wagner et al., Med. Res. Rev. (2000), 20(6):417-51; Peyrottes et al., Mini Rev. Med. Chem. (2004), 4(4):395-408; Gosselin et al., (1996), 43(1):196-208; Bologna et al., (2002), Antisense & Nucleic Acid Drug Development 12:33-41). In one example, Vives et al., (Nucleic Acids Research (1999), 27(20):4071-76) found that tert-butyl SATE pro-oligonucleotides displayed markedly increased cellular penetration compared to the parent oligonucleotide.

In some embodiments, the prodrug moiety is removed selectively by esterases, nucleases or a cytochrome P450 enzyme, including but not limited to those listed below.

| Family | Gene |
|---|---|
| CYP1 | CYP1A1, CYP1A2, CYP1B1 |
| CYP2 | CYP2A6, CYP2A7, CYP2A13, CYP2B6, CYP2C8, CYP2C9, CYP2C18, CYP2C19, CYP2D6, CYP2E1, CYP2F1, CYP2J2, CYP2R1, CYP2S1, CYP2U1, CYP2W1 |

| Family | Gene |
|---|---|
| CYP3 | CYP3A4, CYP3A5, CYP3A7, CYP3A43 |
| CYP4 | CYP4A11, CYP4A22, CYP4B1, CYP4F2, CYP4F3, CYP4F8, CYP4F11, CYP4F12, CYP4F22, CYP4V2, CYP4X1, CYP4Z1 |
| CYP5 | CYP5A1 |
| CYP7 | CYP7A1, CYP7B1 |
| CYP8 | CYP8A1 (prostacyclin synthase), CYP8B1 (bile acid biosynthesis) |
| CYP11 | CYP11A1, CYP11B1, CYP11B2 |
| CYP17 | CYP17A1 |
| CYP19 | CYP19A1 |
| CYP20 | CYP20A1 |
| CYP21 | CYP21A2 |
| CYP24 | CYP24A1 |
| CYP26 | CYP26A1, CYP26B1, CYP26C1 |
| CYP27 | CYP27A1 (bile acid biosynthesis), CYP27B1 (vitamin D3 1-alpha hydroxylase, activates vitamin D3), CYP27C1 (unknown function) |
| CYP39 | CYP39A1 |
| CYP46 | CYP46A1 |
| CYP51 | CYP51A1 (lanosterol 14-alpha demethylase) |

In some embodiments, the prodrug is removed when the prooligonucleotide has not yet been transported through the cell membrane. In other embodiments, the prodrug is removed from the pro-oligonucleotide only after it is transported through the cell membrane. Alternatively, the prodrug is removed only after it is transported into an organelle within the cell. In some embodiments, the prodrug moiety is removed through a non-enzymatic removal including but not limited to the spontaneous reduction inside the cell.

Described herein are prodrugs of a nucleic acid comprising a modification of a chiral X-phosphonate, wherein the modification improves one or more physicochemical, pharmacokinetic or pharmacodynamic property of the nucleic acid. A prodrug moiety is connected to an oxygen or sulfur atom which is connected to the phosphorus atom of a phosphonate or phosphothiorate group of the nucleotide. The prodrug moiety includes but is not limited to S-acyl-2-thioethyl, acyloxy, thioacyloxy, 2-carboalkoxyethyl, disulfide, thiaminal, and enol ester derivatives.

In one embodiment, the prodrug moiety is an S-acyl-2-thioethyl moiety having the following structure:

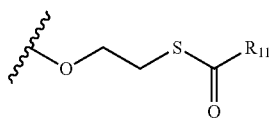

wherein $R_{11}$ is alkyl, aryl, heteroaryl, heterocyclyl, or cycloalkyl. In some embodiments, $R_{11}$ is methyl, ethyl or cyclopropyl.

In other embodiments, the prodrug moiety is an acyloxy moiety having following structure:

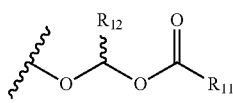

wherein $R_{11}$ is alkyl, aryl, heteroaryl, heterocyclyl, or cycloalkyl, and $R_{12}$ is hydrogen or alkyl. In some embodiments, $R_{11}$ is methyl and $R_{12}$ is hydrogen.

Alternatively, the prodrug moiety is a thioacyloxy moiety having the following structure:

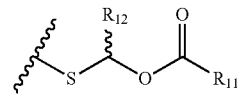

wherein $R_{11}$ is alkyl, aryl, heteroaryl, heterocyclyl, or cycloalkyl, and $R_{12}$ is hydrogen or alkyl. In some embodiments, $R_{11}$ is methyl and $R_{12}$ is hydrogen.

The invention also provides a prodrug 2-carboalkoxyethyl moeity having one of the following structures:

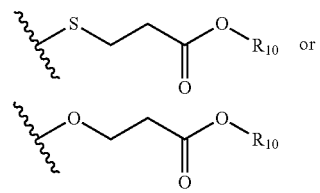

wherein $R^{10}$ is an alkyl group having 1 to 4 carbon atoms. In some embodiments, $R^{10}$ is methyl or ethyl.

In yet other embodiments, the prodrug moiety is a disulfide moiety having the following structure:

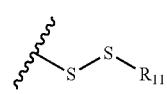

wherein $R_{11}$ is alkyl, aryl, heteroaryl, heterocyclyl, or cycloalkyl. In some embodiments, $R_{11}$ is methyl, ethyl or benzyl.

In further embodiments, the prodrug moiety is a thioacetal moiety having the following structure:

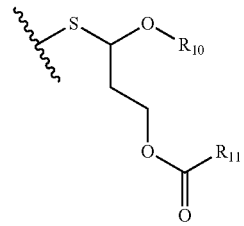

wherein $R^{10}$ is an alkyl group having 1 to 4 carbon atoms and $R_{11}$ is alkyl, aryl, heteroaryl, heterocyclyl, or cycloalkyl. In some embodiments, $R^{10}$ is methyl and $R_{11}$ is methyl or phenyl.

The invention also provides enol ester prodrug moieties having one of the following structures:

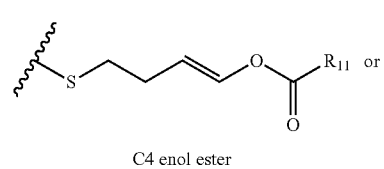

C4 enol ester

-continued

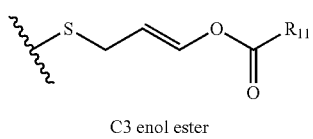

C3 enol ester wherein $R_{11}$ is alkyl, aryl, heteroaryl, heterocyclyl, or cycloalkyl. In some embodiments, the C3-enol ester prodrug moiety or the C4 enol ester prodrug moiety is in the cis form. In some embodiments of the C3-enol ester prodrug moiety or the C4 enol ester prodrug moiety, $R_{11}$ is methyl, ethyl or phenyl.

In one embodiment, the prodrug moiety is a trialkylammoniumethyl moiety having one of the following structures:

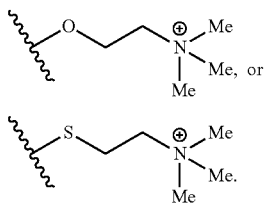

In one embodiment, the prodrug moiety is a alkylhydroxamate moiety having one of the following structures:

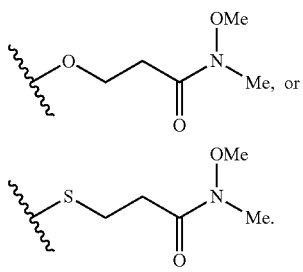

In one embodiment, the prodrug moiety is a acylhydroxamate moiety having one of the following structures:

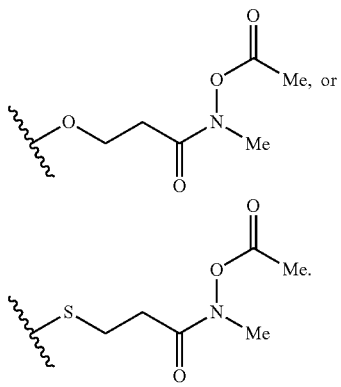

One embodiment provides a nucleic acid prodrug having the following structure:

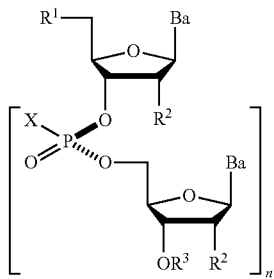

Formula 1 wherein $R^1$ is —OH, —SH, —NR$^d$R$^d$, —N$_3$, halogen, hydrogen, alkyl, alkenyl, alkynyl, alkyl-Y$^1$—, alkenyl-Y$^1$—, alkynyl-Y$^1$—, aryl-Y$^1$—, heteroaryl-Y$^1$—, —P(O)(R$^e$)$_2$, —HP(O)(R$^e$), —OR$^a$ or —SR$^c$;

$Y^1$ is O, NR$^d$, S, or Se;

$R^a$ is a blocking group;

$R^c$ is a blocking group;

each instance of R$^d$ is independently hydrogen, alkyl, alkenyl, alkynyl, aryl, acyl, substituted silyl, carbamate, —P(O)(R$^e$)$_2$, or —HP(O)(R$^e$);

each instance of R$^e$ is independently hydrogen, alkyl, aryl, alkenyl, alkynyl, alkyl-Y$^2$—, alkenyl-Y$^2$—, alkynyl-Y$^2$—, aryl-Y$^2$—, or heteroaryl-Y$^2$—, or a cation which is Na$^{+1}$, Li$^{+1}$, or K$^{+1}$;

$Y^2$ is O, NR$^d$, or S;

each instance of $R^2$ is independently hydrogen, —OH, —SH, —NR$^d$R$^d$, —N$_3$, halogen, alkyl, alkenyl, alkynyl, alkyl-Y$^1$—, alkenyl-Y$^1$—, alkynyl-Y$^1$—, aryl-Y$^1$—, heteroaryl-Y$^1$—, —OR$^b$, or —SR$^c$, wherein R$^b$ is a blocking group;

each instance of Ba is independently a blocked or unblocked adenine, cytosine, guanine, thymine, uracil or modified nucleobase;

at least one instance of X is —OCH$_2$CH$_2$S—S(O)$_2$R$_{10}$, —OCH$_2$CH$_2$S—SCH$_2$CH$_2$OH, —OCH$_2$CH$_2$CO$_2$H,

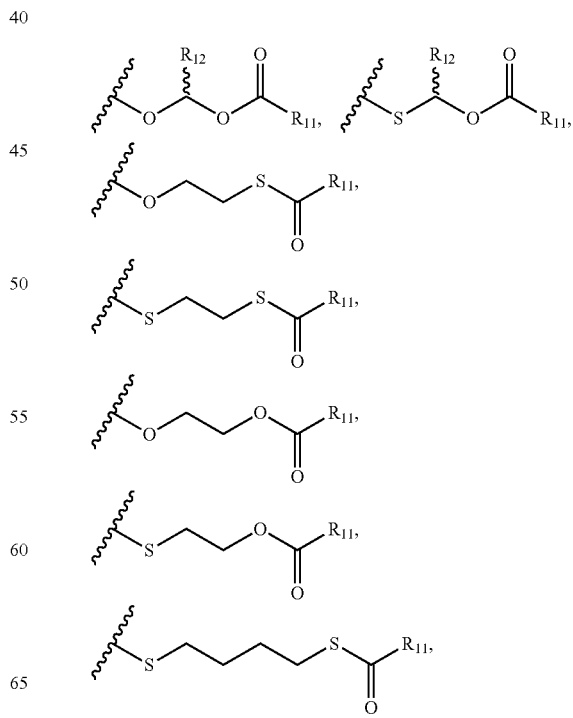

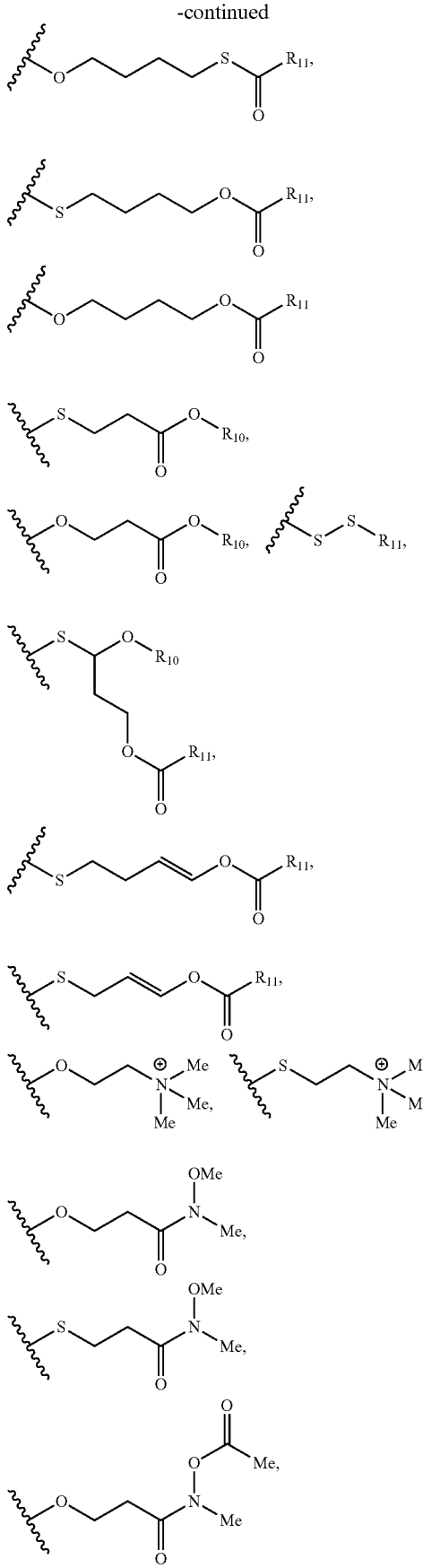
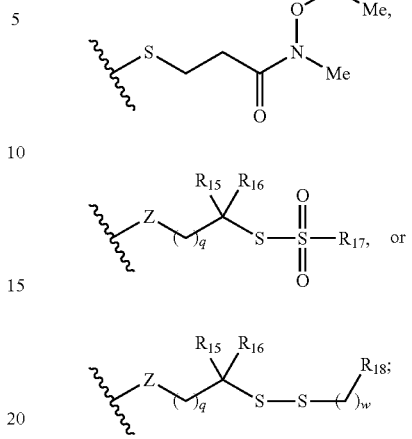
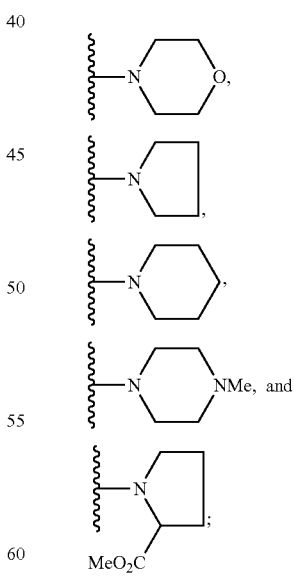

$R^3$ is hydrogen, a blocking group, a linking moiety connected to a solid support or a linking moiety connected to a nucleic acid;

$R_{10}$ is an alkyl group having 1 to 4 carbon atoms;

$R_{11}$ is alkyl, aryl, heteroaryl, heterocyclyl, or cycloalkyl;

$R_{12}$ is hydrogen or alkyl;

Z is S or O;

q is 0, 1, or 3;

w is 1, 2, 3, 4, 5, or 6;

$R_{15}$ and $R_{16}$ are independently hydrogen or methyl;

$R_{17}$ is selected from alkyl, aryl or a $CH_2CH=CH_2$;

$R_{18}$ is selected from $N(CH_3)_2$, and n is an integer of 1 to about 200.

In one aspect the invention provides a nucleic acid prodrug having the following structure:

Formula 1

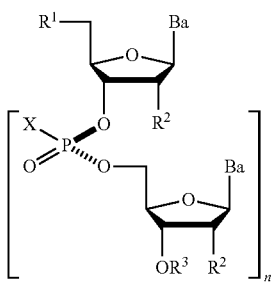

wherein $R^1$ is —OH, —SH, —NR$^d$R$^d$, —N$_3$, halogen, hydrogen, alkyl, alkenyl, alkynyl, alkyl-Y$^1$—, alkenyl-Y$^1$—, alkynyl-Y$^1$—, aryl-Y$^1$—, heteroaryl-Y$^1$—, —OP(O)(R$^e$)$_2$, —HP(O)(R$^e$), —OR$^a$ or —SR$^c$;

$Y^1$ is O, NR$^d$, S, or Se;

$R^a$ is a blocking group;

$R^c$ is a blocking group;

each instance of $R^d$ is independently hydrogen, alkyl, alkenyl, alkynyl, aryl, acyl, substituted silyl, carbamate, —P(O)(R$^e$)$_2$, or —HP(O)(R$^e$);

each instance of $R^e$ is independently hydrogen, alkyl, aryl, alkenyl, alkynyl, alkyl-Y$^2$—, alkenyl-Y$^2$—, alkynyl-Y$^2$—, aryl-Y$^2$—, or heteroaryl-Y$^2$—, or a cation which is Na$^{+1}$, Li$^{+1}$, or K$^{+1}$;

$Y^2$ is O, NR$^d$, or S;

each instance of $R^2$ is independently hydrogen, —OH, —SH, —NR$^d$R$^d$, —N$_3$, halogen, alkyl, alkenyl, alkynyl, alkyl-Y$^1$—, alkenyl-Y$^1$—, alkynyl-Y$^1$—, aryl-Y$^1$—, heteroaryl-Y$^1$—, —OR$^b$, or —SR$^c$, wherein R$^b$ is a blocking group;

each instance of Ba is independently a blocked or unblocked adenine, cytosine, guanine, thymine, uracil or modified nucleobase;

each instance of X is

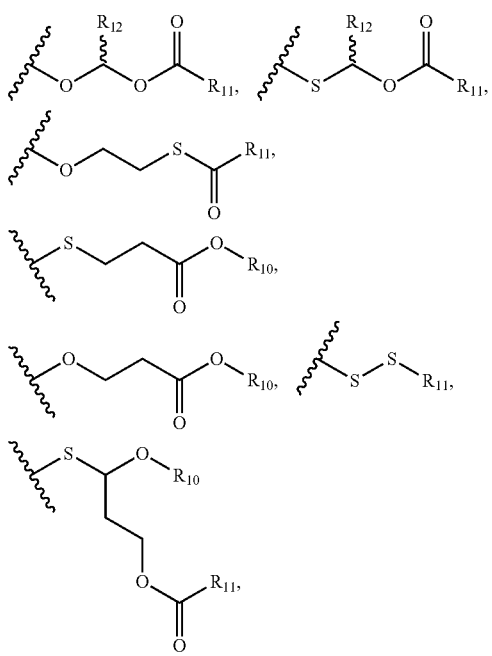

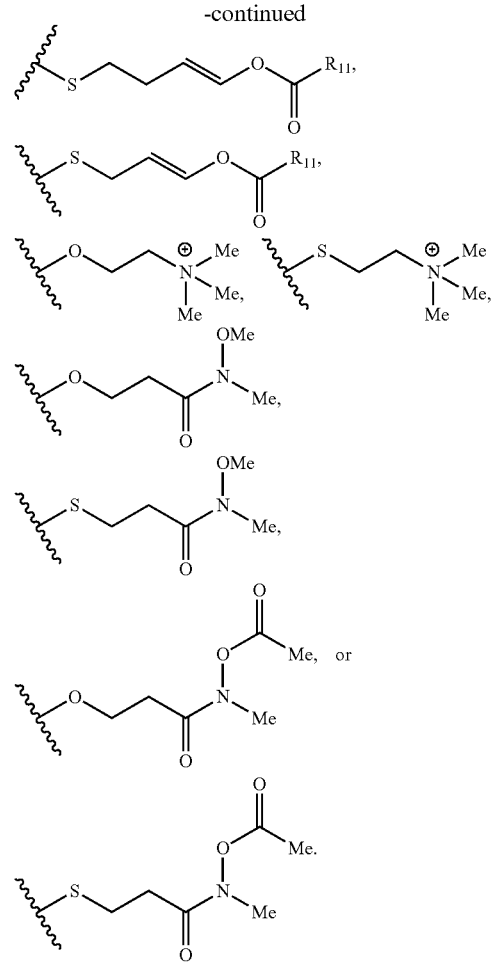

$R^3$ is hydrogen, a blocking group, a linking moiety connected to a solid support or a linking moiety connected to a nucleic acid;

$R^{10}$ is an alkyl group having 1 to 4 carbon atoms;

$R^{11}$ is alkyl, aryl, heteroaryl, heterocyclyl, or cycloalkyl;

$R^{12}$ is hydrogen or alkyl; and n is an integer of 1 to about 200.

In one aspect the invention provides a nucleic acid prodrug having the following structure:

Formula 2

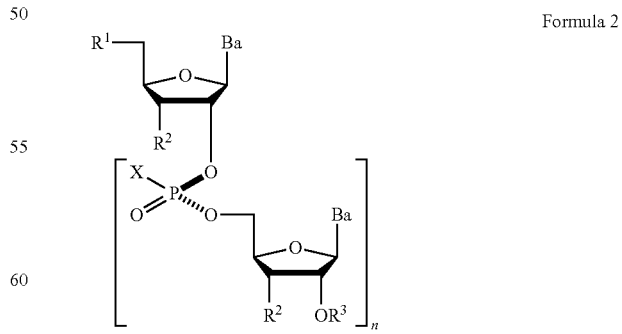

wherein $R^1$ is —OH, —SH, —NR$^d$R$^d$, —N$_3$, halogen, hydrogen, alkyl, alkenyl, alkynyl, alkyl-Y$^1$—, alkenyl-Y$^1$—, alkynyl-Y$^1$—, aryl-Y$^1$—, heteroaryl-Y$^1$—, —OP(O)(R$^e$)$_2$, —HP(O)(R$^e$), —OR$^a$ or —SR$^c$;

$Y^1$ is O, $NR^d$, S, or Se;

$R^a$ is a blocking group;

$R^c$ is a blocking group;

each instance of $R^d$ is independently hydrogen, alkyl, alkenyl, alkynyl, aryl, acyl, substituted silyl, carbamate, —P(O)$(R^e)_2$, or —HP(O)$(R^e)$;

each instance of $R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$—, or a cation which is $Na^{+1}$, $Li^{+1}$, or $K^{+1}$;

$Y^2$ is O, $NR^d$, or S;

each instance of $R^2$ is independently hydrogen, —OH, —SH, $—NR^d R^d$, $—N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, $—OR^b$, or $—SR^c$, wherein $R^b$ is a blocking group;

each instance of Ba is independently a blocked or unblocked adenine, cytosine, guanine, thymine, uracil or modified nucleobase;

each instance of X is

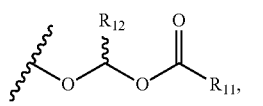

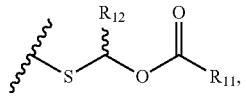

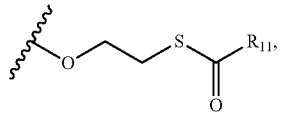

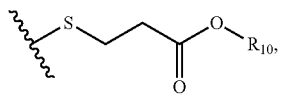

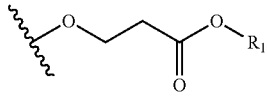

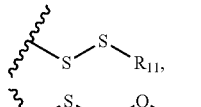

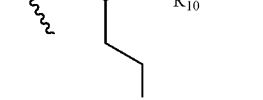

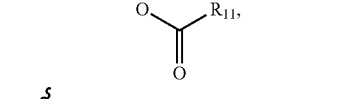

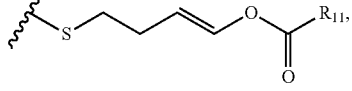

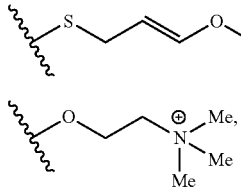

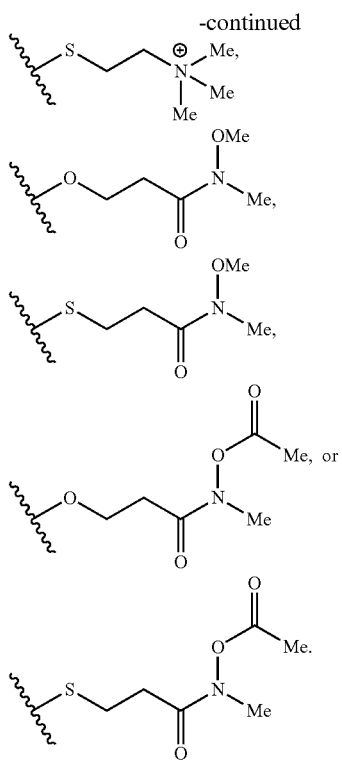

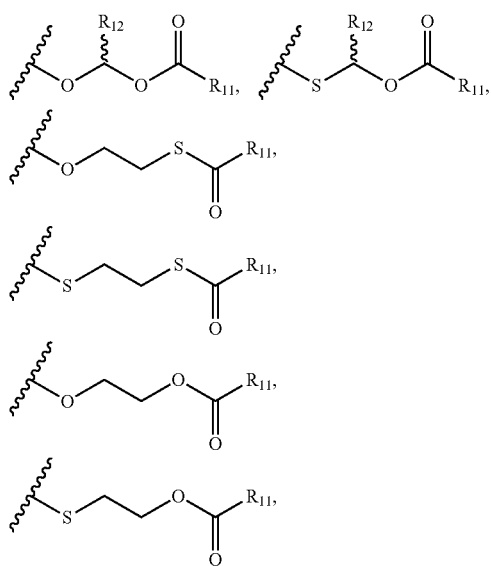

$R^3$ is hydrogen, a blocking group, a linking moiety connected to a solid support or a linking moiety connected to a nucleic acid;

$R^{10}$ is an alkyl group having 1 to 4 carbon atoms;

$R_{11}$ is alkyl, aryl, heteroaryl, heterocyclyl, or cycloalkyl;

$R_{12}$ is hydrogen or alkyl; and n is an integer of 1 to about 200.

A further embodiment provides the nucleic acid prodrug of Formula 1 or Formula 2, wherein each X moiety of the nucleic acid prodrug is independently selected from —OCH2CH2S—S(O)$_2$R10, —OCH2CH2S—SCH2CH2OH, —OCH2CH2CO2H, -continued

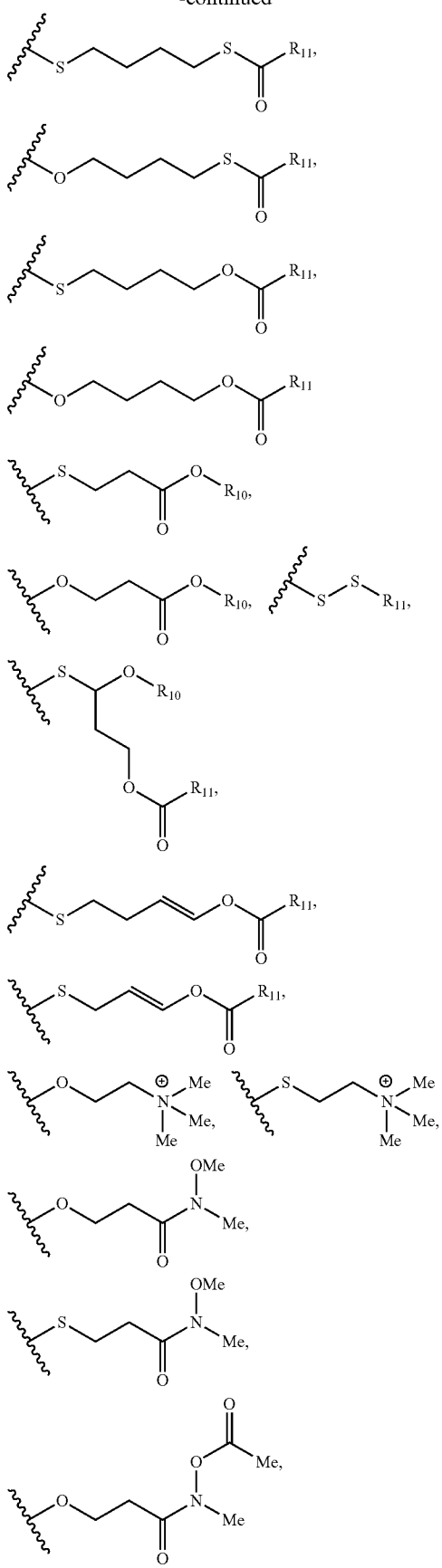

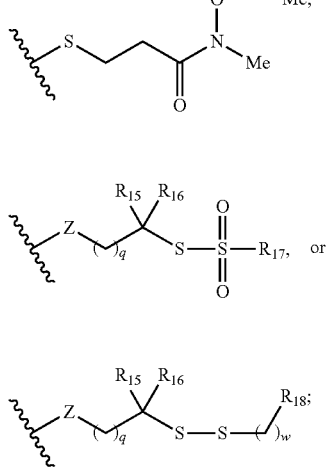

$R^3$ is hydrogen, a blocking group, a linking moiety connected to a solid support or a linking moiety connected to a nucleic acid;

$R_{10}$ is an alkyl group having 1 to 4 carbon atoms;

$R_{11}$ is alkyl, aryl, heteroaryl, heterocyclyl, or cycloalkyl;

$R_{12}$ is hydrogen or alkyl;

Z is S or O;

q is 0, 1, or 3;

w is 1, 2, 3, 4, 5, or 6;

$R_{15}$ and $R_{16}$ are independently hydrogen or methyl;

$R_{17}$ is selected from alkyl, aryl or a $CH_2CH\!=\!CH_2$; and $R_{18}$ is selected from $N(CH_3)_2$,

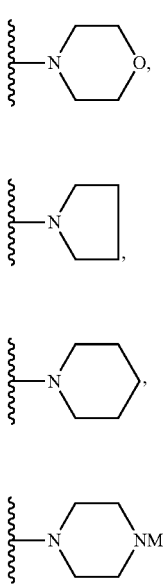

-continued

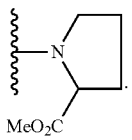

In some embodiments, n is an integer of 1 to about 50; 1 to about 40; 1 to about 30; 1 to about 25; 1 to about 20; 1 to about 15; or 1 to about 10.

One embodiment provides a non-racemic pro-oligonucleotide wherein the pro-oligonucleotide is an analog of 2-5A, having a structure of the following formula:

Formula A$_3$-1

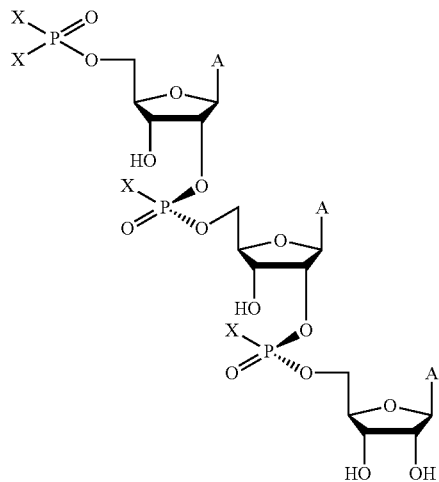

wherein X is any of the prodrug moieties described herein.

In some embodiments, the non-racemic pro-oligonucleotide is a 2-5A analog having the following structure:

Formula A$_3$-2

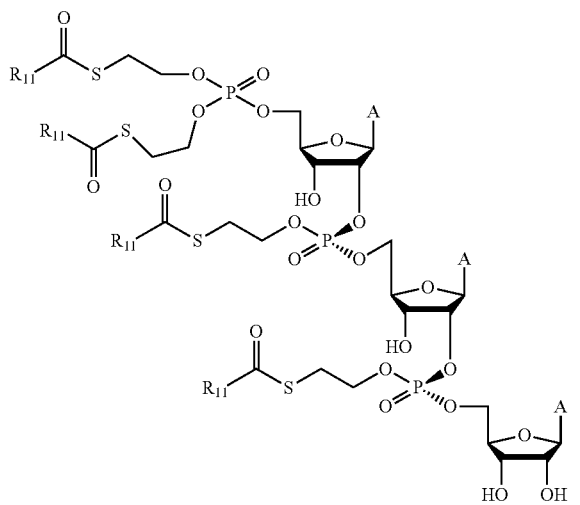

wherein R$_{11}$ is alkyl, aryl, heteroaryl, heterocyclyl, or cycloalkyl.

In one embodiment, non-racemic pro-oligonucleotide is a 2-5A analog having the following structure:

Formula A$_3$-3

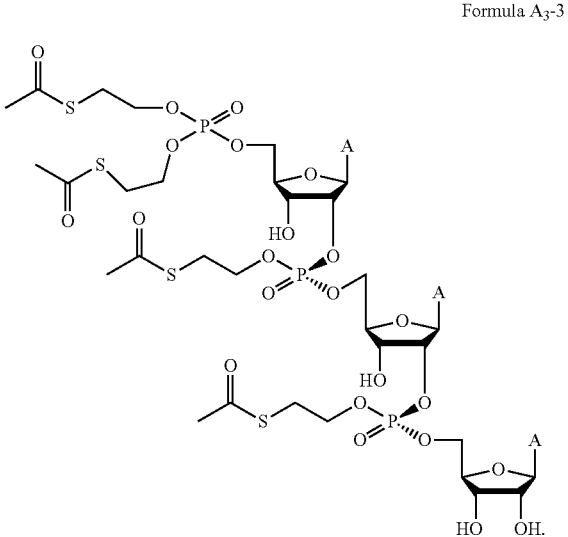

EXEMPLARY METHODS OF SYNTHESIS

General Discussion of the Methods of Synthesis of Nucleic Acid Prodrugs Comprising a Chiral X-Phosphonate Moiety The methods described herein provide for an efficient synthesis of phosphorus atom-modified nucleic acid prodrugs wherein the stereochemical configuration at a phosphorus atom is controlled, thus producing a stereodefined oligonucleotide. While the exemplary methods of synthesis described herein provide for a 3'-5' nucleotide linkage, the 2'-5' nucleotide linkage is also contemplated.

The pro-oligonucleotides of the invention may be synthesized by modifying either a chiral phosphorothioate or chiral H-phosphonate of a nucleotide or nucleic acid.

A S-acyl-2-thioethyl pronucleotide may be synthesized from a nucleic acid or nucleotide comprising a chiral H-phosphonate as shown in the following scheme:

Scheme 1

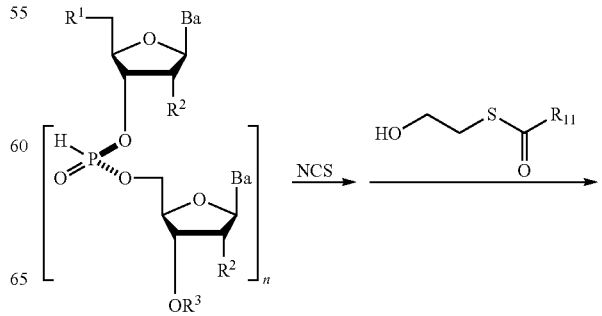

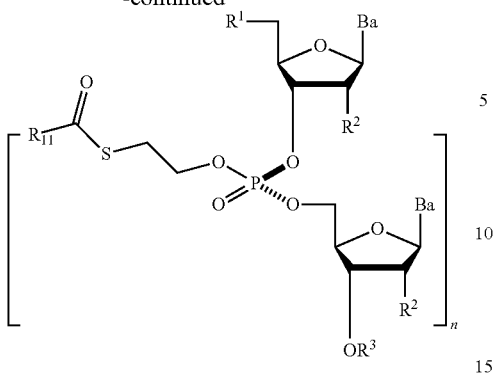

In some embodiments, R1 is —OP(O)(Re)2, wherein Re is

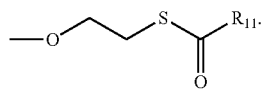

The chiral H-phosphonate is treated with N-chlorosuccinimide and then reacted with S-acyl-2-thioethyl alcohol to produce a S-acyl-2-thioethyl prodrug. Protecting groups present at $R^1$, $R^2$, and/or $R^3$ may be subsequently removed.

An acyloxy nucleic acid prodrug may be synthesized from a nucleic acid or nucleotide comprising a chiral H-phosphonate as shown in the following scheme:

Scheme 2

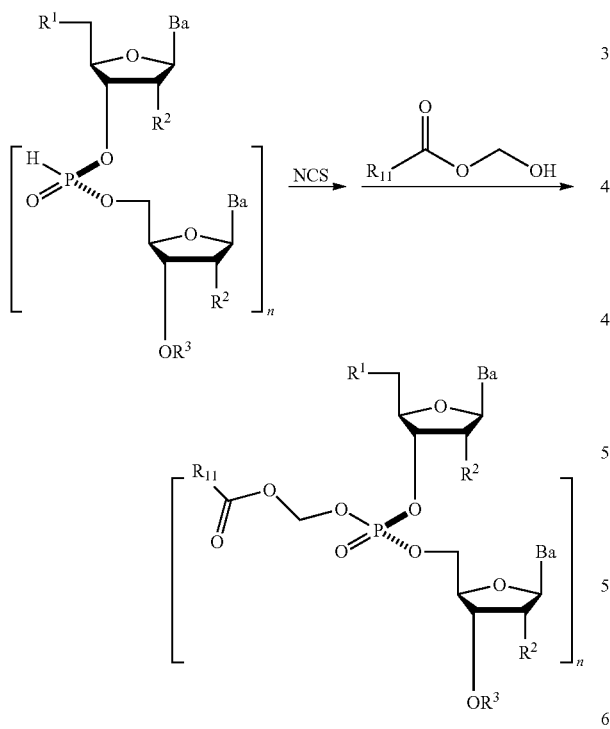

The chiral H-phosphonate is treated with N-chlorosuccinimide and then reacted with a hydroxymethyl acetate compound to produce an acyloxy prodrug. Protecting groups present at $R^1$, $R^2$, and/or $R^3$ may be subsequently removed.

A thioacyloxy nucleic acid prodrug may be synthesized from a nucleic acid or nucleotide comprising a chiral phosphorothioate as shown in the following scheme:

Scheme 3

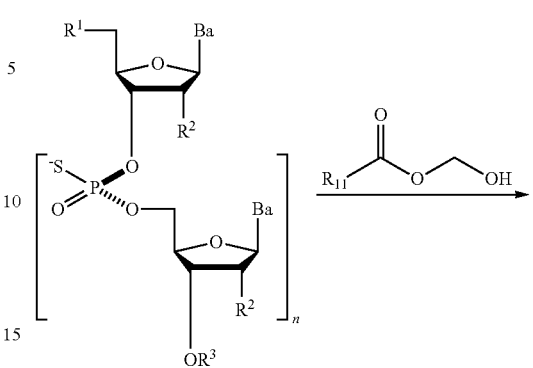

The chiral phosphorothioate is treated with a chloromethyl acyloxy compound to produce an acyloxy prodrug. Protecting groups present at $R^1$, $R^2$, and/or $R^3$ may be subsequently removed.

A 2-carboalkoxyethyl nucleic acid prodrug may be synthesized from a nucleic acid or nucleotide comprising a chiral phosphorothioate as shown in the following scheme:

Scheme 4

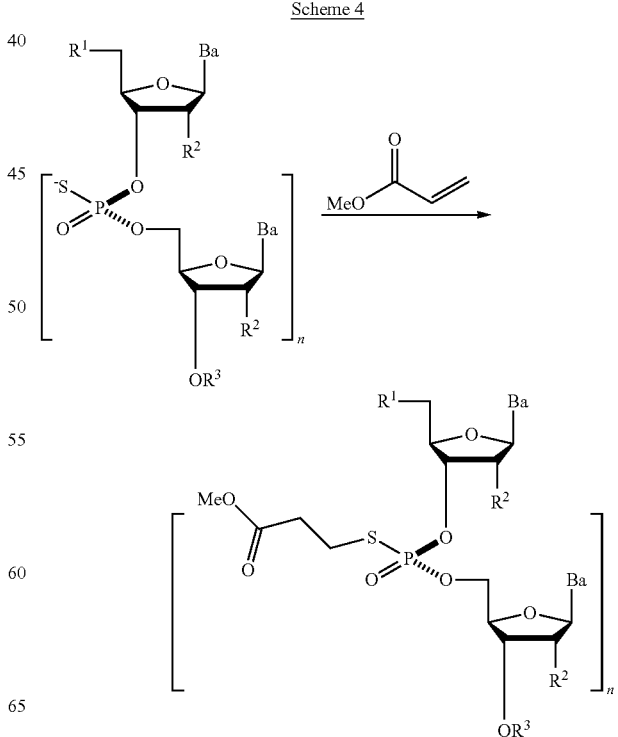

The deprotonated chiral phosphorothioate is reacted with an alkyl acrylate to produce a 2-carboalkoxyethyl pronucleotide. Protecting groups present at $R^1$, $R^2$, and/or $R^3$ may be subsequently removed.

A disulfide nucleic acid prodrug may be synthesized from a nucleic acid or nucleotide comprising a chiral phosphorothioate as shown in the following scheme:

Scheme 5

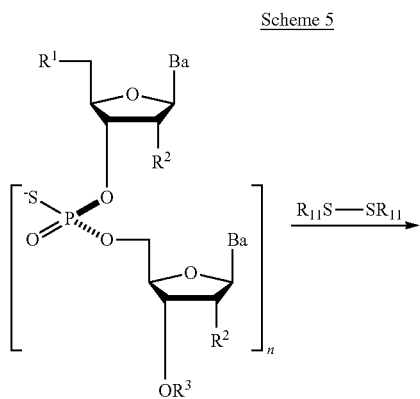

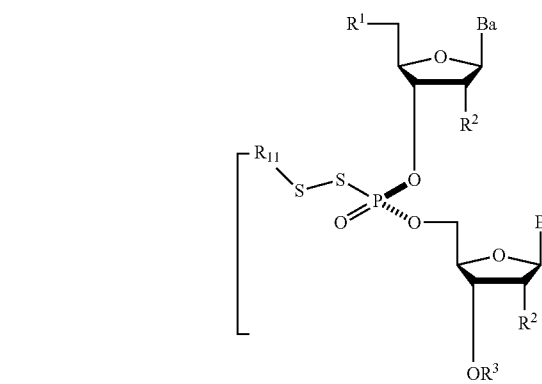

The deprotonated chiral phosphorothioate is reacted with a dialkyl sulfide to produce an alkyl disulfide pronucleotide. Protecting groups present at $R^1$, $R^2$, and/or $R^3$ may be subsequently removed.

A thioacetal nucleic acid prodrug may be synthesized from a nucleic acid or nucleotide comprising a chiral phosphorothioate as shown in the following scheme:

Scheme 6

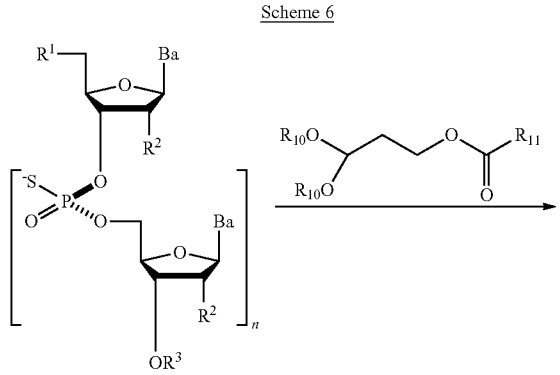

-continued

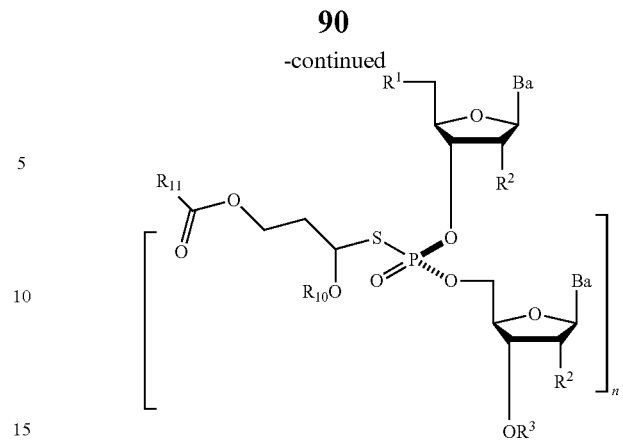

A 1,1,-dialkyoxy 3-acyloxy propane is reacted with trimethylsilyltriflate and the deprotonated chiral phosphorothioate is then added to the reaction mixture to produce an thioacetal pronucleotide. Protecting groups present at $R^1$, $R^2$, and/or $R^3$ may be subsequently removed.

A C3 enol ester nucleic acid prodrug may be synthesized from a nucleic acid or nucleotide comprising a chiral phosphorothioate as shown in the following scheme:

Scheme 7

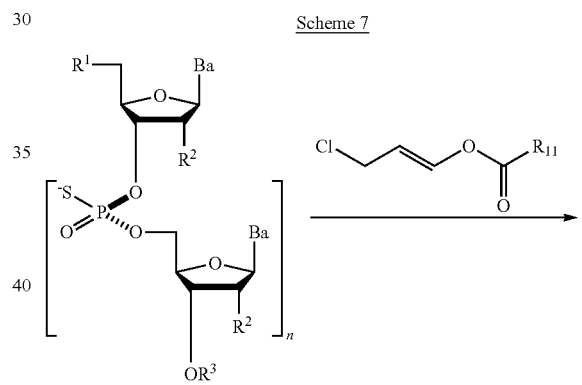

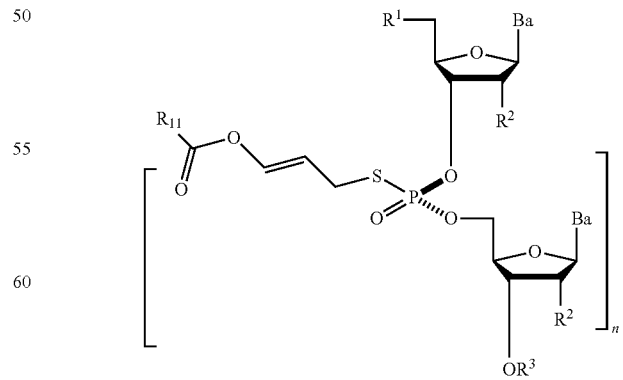

The deprotonated chiral phosphorothioate is reacted with an (E)-3-chloro-1-acyloxy-prop-1-ene compound to produce the C3 enol ester nucleic acid prodrug. Protecting groups present at $R^1$, $R^2$, and/or $R^3$ may be subsequently removed.

A C4 enol ester nucleic acid prodrug may be synthesized from a nucleic acid or nucleotide comprising a chiral phosphorothioate as shown in the following scheme:

Scheme 8

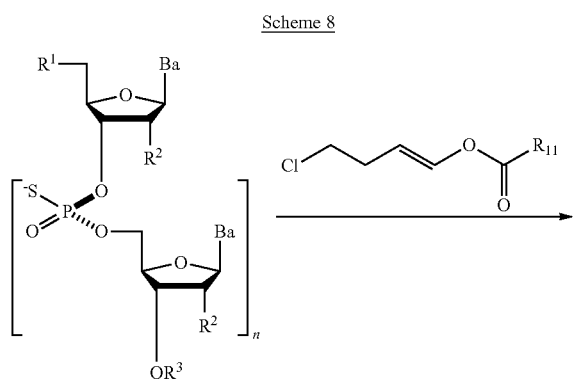

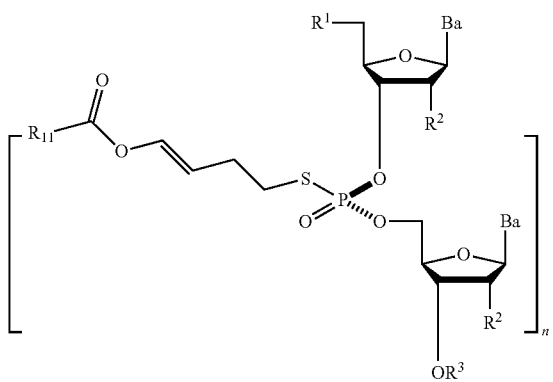

-continued

The deprotonated chiral phosphorothioate is reacted with an (E)-3-chloro-1-acyloxy-but-1-ene compound to produce the C3 enol ester nucleic acid prodrug. Protecting groups present at $R^1$, $R^2$, and/or $R^3$ may be subsequently removed.

In some embodiments the nucleic acid comprising a chiral phosphorothioate or chiral H-phosphonate is synthesized as described herein. In other embodiments, other methods of synthesis may be used to provide the nucleic acid comprising a chiral phosphorothioate or chiral H-phosphonate.

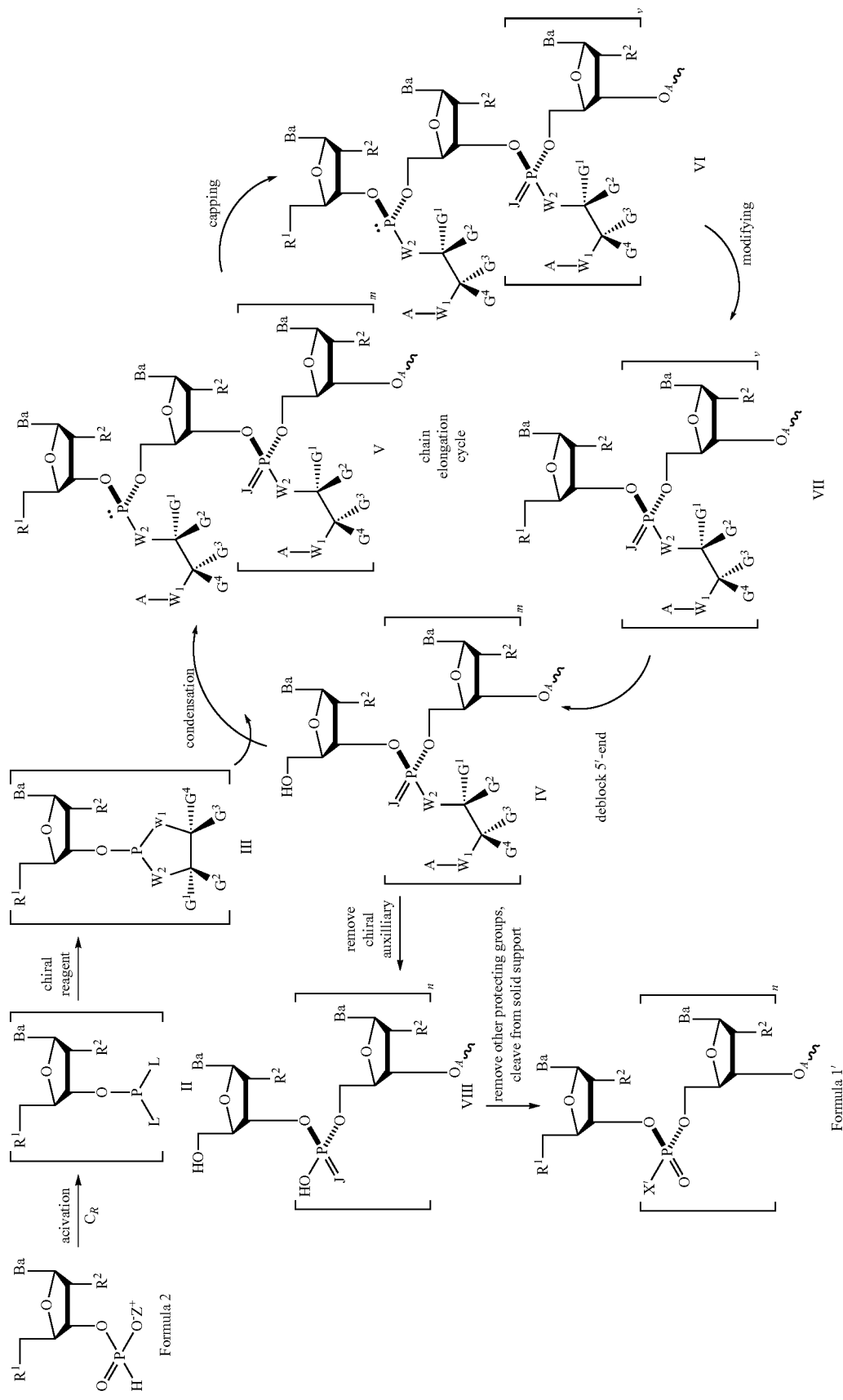

The reaction of a molecule comprising an achiral H-phosphonate moiety of Formula 2 with a nucleoside comprising nucleophilic moiety of Formula IV results in the formation of a condensed intermediate (V); which is converted to a nucleic acid comprising a chiral X'-phosphonate moiety which can be further modified to produce the prodrug oligonucleotide of Formula I comprising a chiral X-phosphonate moiety. The synthesis of the condensed intermediate comprises the steps of (a) activation of the compound of Formula 2 with a condensing agent to form intermediate II, (b) reaction with a chiral reagent to form intermediate III, followed by (c) reaction with the compound of Formula IV.

The condensed intermediate may be converted to a nucleic acid comprising a chiral X' phosphonate moiety of Formula 1' by capping the chiral auxiliary with a moiety A, which is an acyl, aryl, alkyl, aralkyl, or silyl moiety, and modifying the phosphorus to introduce J, which is S, Se, or $BH_3$, thus producing a compound of Formula VII.

The compound of Formula VII may be converted to the compound of Formula 1', where X' is S, Se, or $BH_3$, and n is 1, by cleaving the chiral reagent, and deblocking blocking groups and cleaving from solid support if desired. Alternatively the compound of Formula VII is subjected to chain elongation by deblocking the 5' terminus, and repeating coupling steps to produce a condensed intermediate as before. The steps of capping, modifying, deblocking, and chain elongation are repeated until the desired n is achieved. At that point, the chiral reagents at each phosphonate are cleaved, the remaining blocking groups are cleaved, including cleaving from a solid support, if desired, to produce the compound of Formula 1', where X' is S, Se, or $BH_3$, and n is greater than or equal to 2 and less than about 200. The compound of Formula 1', where X' is S is then converted by the methods described herein to form the pro-oligonucleotide compound of Formula 1.

Modifying Agents Used to Introduce S, Se, or $BH_2$ at Chiral Phosphorus of the Condensed Intermediate V in Route A.

In some embodiments, the modifying agent is a sulfur electrophile, selenium electrophile, or boronating agent. In some embodiments, the sulfur electrophile is a compound having one of the following formulas:

$S_8$(Formula B), $Z^{10}$—S—S—$Z^{11}$, or $Z^{10}$—S—X—$Z^{11}$, wherein $Z^{10}$ and $Z^{11}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{10}$ and $Z^{11}$ are taken together to form a 3 to 8 membered alicyclic or heterocyclic ring, which may be substituted or unsubstituted; X is $SO_2$, S, O, or $NR^f$; and $R^f$ is hydrogen, alkyl, alkenyl, alkynyl, or aryl. In other embodiments, the sulfur electrophile is a compound of Formula B, C, D, E, or F:

$S_8$                        Formula B

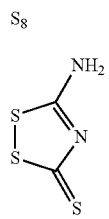

Formula C

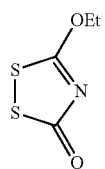

Formula D

Formula E

Formula F

In other embodiments, the sulfur electrophile is Formula F, Formula E or Formula B.

In some embodiments, the selenium electrophile is a compound having one of the following formulas:

Se(Formula G), $Z^{10}$—Se—Se—$Z^{11}$, or $Z^{10}$—Se—X—$Z^{11}$, wherein $Z^{10}$ and $Z^{11}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{10}$ and $Z^{11}$ are taken together to form a 3 to 8 membered alicyclic or heterocyclic ring, which may be substituted or unsubstituted; X is $SO_2$, S, O, or $NR^f$; and $R^f$ is hydrogen, alkyl, alkenyl, alkynyl, or aryl.

In other embodiments, the selenium electrophile is a compound of Formula G, H, I, J, K, or L.

Se           Formula G

KSeCN      Formula H

Formula I

Formula J

Formula K

Formula L

In some embodiments, the selenium electrophile is Formula G or Formula L.

In some embodiments, the boronating agent is borane-N,N-diisopropylethylamine ($BH_3$.DIPEA), borane-pyridine ($BH_3$.Py), borane-2-chloropyridine ($BH_3$.CPy), borane-aniline ($BH_3$.An), borane-tetrahydrofuran ($BH_3$.THF), or borane-dimethylsulfide ($BH_3$.$Me_2$S), aniline-cyanoborane, triphenylphosphine-carboalkoxyboranes.

In other embodiments, the boronating agent is borane-N,N-diisopropylethylamine (BH3.DIPEA), borane-2-chloropyridine (BH3.CPy), borane-tetrahydrofuran (BH3.THF), or borane-dimethylsulfide (BH3.Me2S).

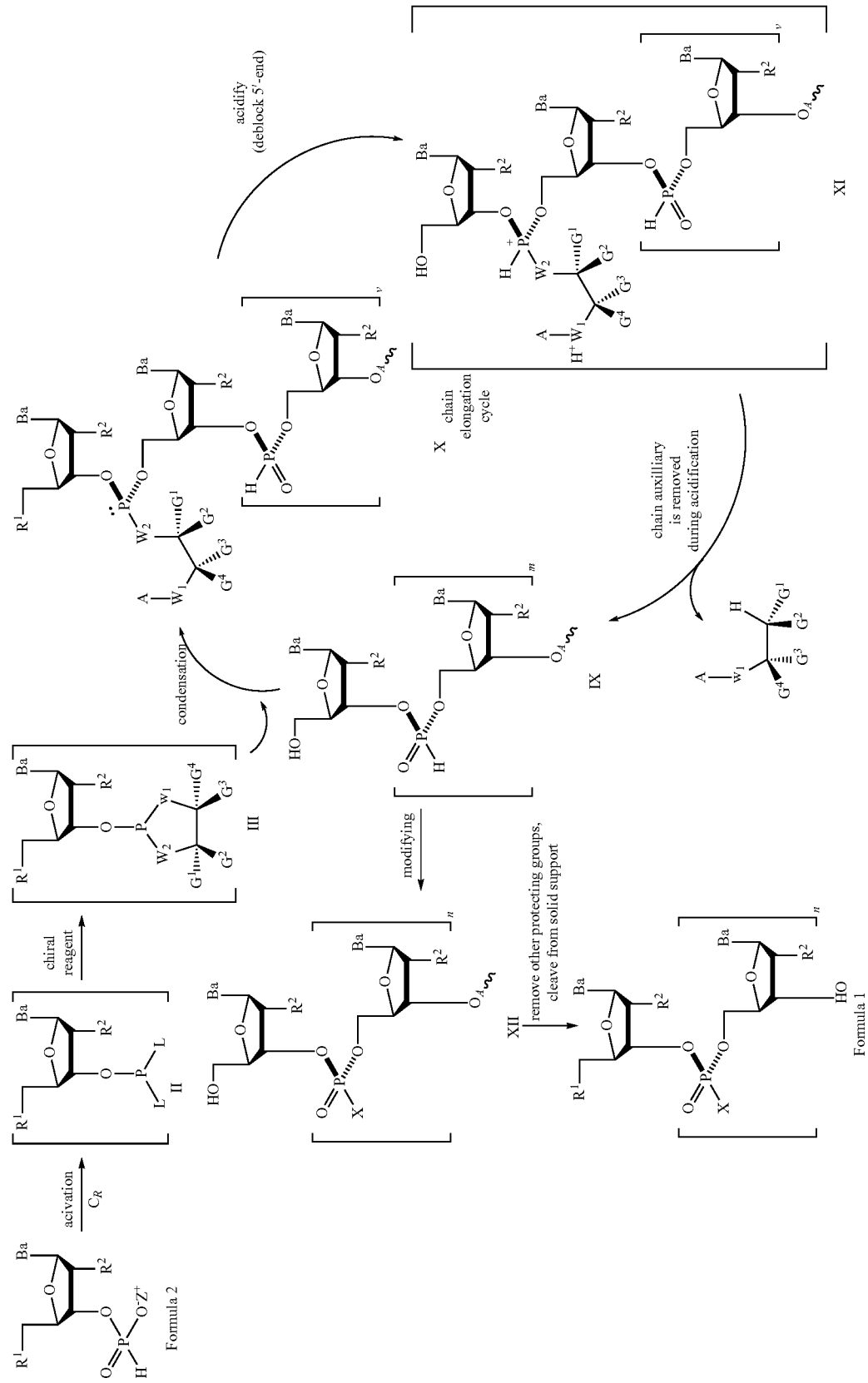
Scheme 10. Synthesis of a precursor of a prodrug oligonucleotide via chiral H-phosphonates (Route B).

In another embodiment, described in Scheme 10, an achiral H-phosphonate of Formula 2 is treated with a condensing reagent to form an intermediate of structure II. The intermediate of structure II is not isolated and is treated in the same pot with a chiral reagent to form a chiral intermediate of structure III. The intermediate of structure III is not isolated and undergoes a reaction in the same pot with a nucleoside or modified nucleoside of structure IX to provide a chiral phosphite compound of structure X. In some embodiments, structure X is extracted into a solvent to separate it from side products, impurities, and/or reagents. In other embodiments, when the method is performed via solid phase synthesis, the solid support comprising the compound of structure X is filtered away from side products, impurities, and/or reagents. The compound of structure X is treated with an acid to remove the blocking group at the 5'-end of the growing nucleic acid chain (structure XI). The acidification step also removes the chiral auxiliary ligand to provide a chiral H-phosphonate IX. The 5'-deblocked intermediate is optionally allowed to re-enter the chain elongation cycle to form a condensed intermediate containing a blocked 5'-end, which is then acidified to remove the 5'-end blocking group and chiral auxiliary ligand.

When the desired chain length has been reached, the 5'-deprotected intermediate undergoes a modifying step to introduce a moiety X bonded to each of the phosphorus atoms to provide a compound of structure XII. The modified intermediate is deblocked by removal of remaining protecting groups, e.g., nucleobase, modified nucleobase, sugar or modified sugar protecting groups are removed, to provide a nucleic acid of Formula 1. In embodiments where a solid support is used, the phosphorus-atom modified nucleic acid is then cleaved from the solid support. In certain embodiments, the nucleic acids is left attached on the solid support for purification purposes and then cleaved from the solid support following purification. In one embodiment, the synthesis described in Scheme 10 is useful when the G1 and G2 positions of the chiral auxiliary ligand of Formula A are not hydrogen.

Modification of the Compound of Formula IX Obtained Via Route B to Introduce an X— or X'—Phosphonate Moiety.

Other methods used to modify the compound of Formula IX obtained via Route B are illustrated in Reaction Schemes 10a and 10b. Phosphonate and phosphite are known to tautomerize and exist in equilibrium. The phosphite tautomer is less stable than the phosphonate tautomer. Equilibrium lies toward the phosphonate tautomer under neutral conditions due to the very strong P=O bond. Under acidic conditions, the phosphoryl group of the phosphonate becomes reversibly protonated. Cleavage of the P—H bond in the intermediate occurs slowly to produce the phosphite intermediate. Structure IX is then modified to form structure XII, using reagents shown in Reaction Schemes 10a and 10b.

Reaction Scheme 10a.
Modification of phosphorus center of intermediates synthesized via Route B, using an initial halogenation phosphorus.

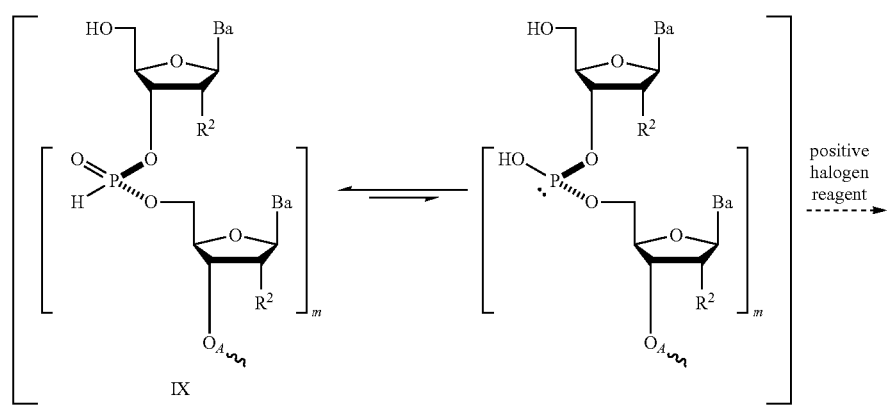

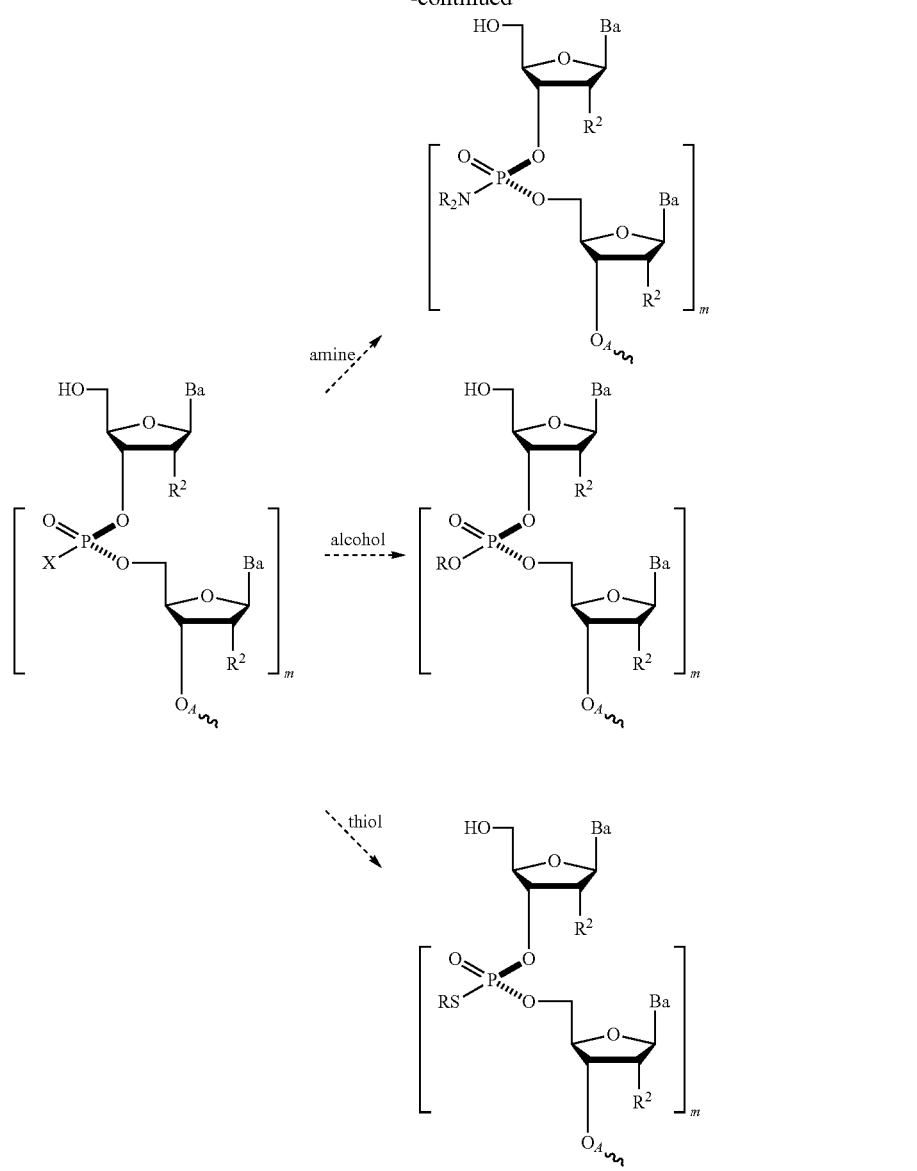
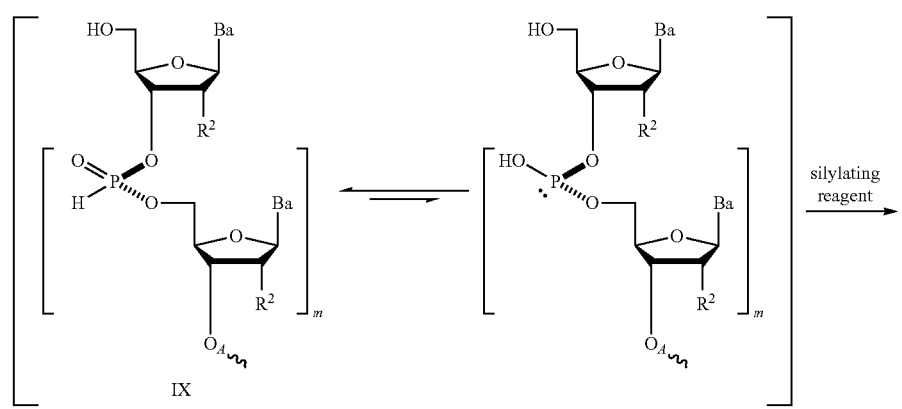
Reaction Scheme 10b.
Modification of phosphorus in intermediates synthesized via Route B, using an initial silylation.

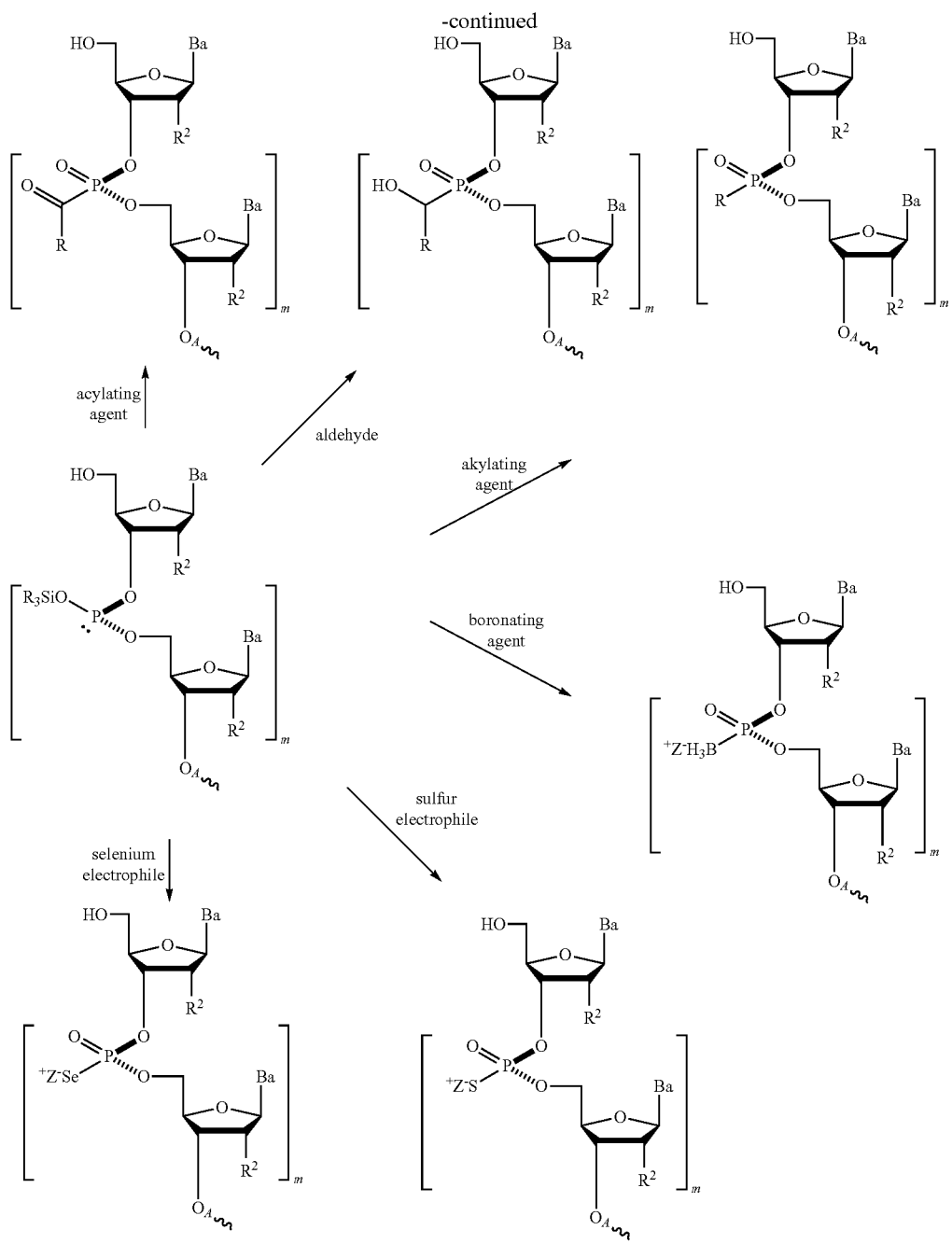

In some embodiments, the modifying step is performed by reacting structure IX with a halogenating reagent followed by reacting with a nucleophile. In specific embodiments, the halogenating reagent is CCl4, CBr4, CI4, Cl2, Br2, I2, sulfuryl chloride (SO2Cl2), phosgene, triphosgene, sulfur monochloride, sulfur dichloride, chloramine, CuCl2, N-chlorosuccinimide (NCS), N-bromosuccinimide (NBS), or N-iodosuccinimide (NIS). In other specific embodiments, the halogenating reagent is CCl4, CBr4, Cl2, sulfuryl chloride (SO2Cl2), or N-chlorosuccinimide (NCS). In some embodiments, the nucleophile is primary or secondary amines, alcohols, or thiols. In other embodiments, the nucleophile is $NR^{f}R^{f}H$, $R^{f}OH$, or $R^{f}SH$, wherein $R^{f}$ is hydrogen, alkyl, alkenyl, alkynyl, or aryl, and at least one of $R^{f}$ of $NR^{f}R^{f}H$ is not hydrogen.

The modifying step can also be performed by reacting structure IX with a silylating reagent followed by reaction with a sulfur electrophile, a selenium electrophile, a boronating agent, an alkylating agent, an aldehyde, or an acylating agent.

In specific embodiments, the silylating reagent is chlorotrimethylsilane (TMS-Cl), triisopropylsilylchloride (TIPS-Cl), t-butyldimethylsilylchloride (TBDMS-Cl), t-butyldiphenylsilylchloride (TBDPS-Cl), 1,1,1,3,3,3-hexamethyldisilazane (HMDS), N-trimethylsilyldimethylamine (TMSDMA), N-trimethylsilyldiethylamine (TMSDEA), N-trimethylsilylacetamide (TMSA), N,O-bis(trimethylsilyl)acetamide (BSA), or N,O-bis(trimethylsilyl)trifluoroacetamide (BSTFA).

In other specific embodiments, the sulfur electrophile is a compound having one of the following formulas:

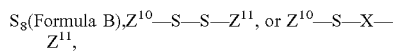

wherein $Z^{10}$ and $Z^{11}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{10}$ and $Z^{11}$ are taken together to form a 3 to 8 membered alicyclic or heterocyclic ring, which may be substituted or unsubstituted; X is $SO_2$, O, or $NR^f$; and $R^f$ is hydrogen, alkyl, alkenyl, alkynyl, or aryl. In other embodiments, the sulfur electrophile is a compound of Formula B, C, D, E, or F:

$S_8$          Formula B

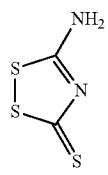 Formula C

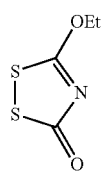 Formula D

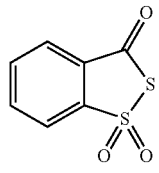 Formula E

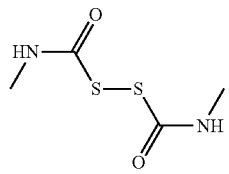 Formula F

In other embodiments, the sulfur electrophile is Formula F, Formula E or Formula B.

In some embodiments, selenium electrophile is a compound having one of the following formulas:

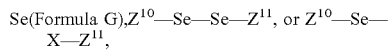

wherein $Z^{10}$ and $Z^{11}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{10}$ and $Z^{11}$ are taken together to form a 3 to 8 membered alicyclic or heterocyclic ring, which may be substituted or unsubstituted; X is $SO_2$, S, O, or $NR^f$; and $R^f$ is hydrogen, alkyl, alkenyl, alkynyl, or aryl.

In other embodiments, the selenium electrophile is a compound of Formula G, H, I, J, K, or L.

Se          Formula G

KSeCN          Formula H

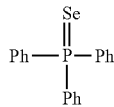 Formula I

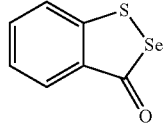 Formula J

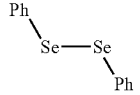 Formula K

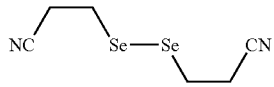 Formula L

In some embodiments, the selenium electrophile is Formula G or Formula L.

In some embodiments, the boronating agent is borane-N,N-diisopropylethylamine (BH3.DIPEA), borane-pyridine (BH3.Py), borane-2-chloropyridine (BH3.CPy), borane-aniline (BH3.An), borane-tetrahydrofuran (BH3.THF), or borane-dimethylsulfide (BH3.Me2S), aniline-cyanoborane, triphenylphosphine-carboalkoxyboranes. In other embodiments, the boronating agent is borane-N,N-diisopropylethylamine ($BH_3$.DIPEA), borane-2-chloropyridine ($BH_3$.CPy), borane-tetrahydrofuran ($BH_3$.THF), or borane-dimethylsulfide ($BH_3$.Me$_2$S).

In other embodiments, the alkylating agent is an alkyl halide, alkenyl halide, alkynyl halide, alkyl sulfonate, alkenyl sulfonate, or alkynyl sulfonate.

In other embodiments, the aldehyde is (para)-formaldehyde, alkyl aldehyde, alkenyl aldehyde, alkynyl aldehyde, or aryl aldehyde.

In yet other embodiments, the acylating agent is a compound of Formula M or N:

 Formula M

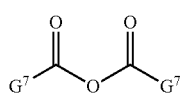 Formula N wherein $G^7$ is alkyl, cycloalkyl, heterocyclic, cycloalkylalkyl, heterocycloalkyl, aryl, heteroaryl, alkyloxy, aryloxy, or heteroaryloxy; and M is F, Cl, Br, I, 3-nitro-1,2,4-triazole, imidazole, alkyltriazole, tetrazole, pentafluorobenzene, or 1-hydroxybenzotriazole.

Scheme 11. Synthesis of a chiral dinucleoside phosphorothioate by stereoselective synthesis.

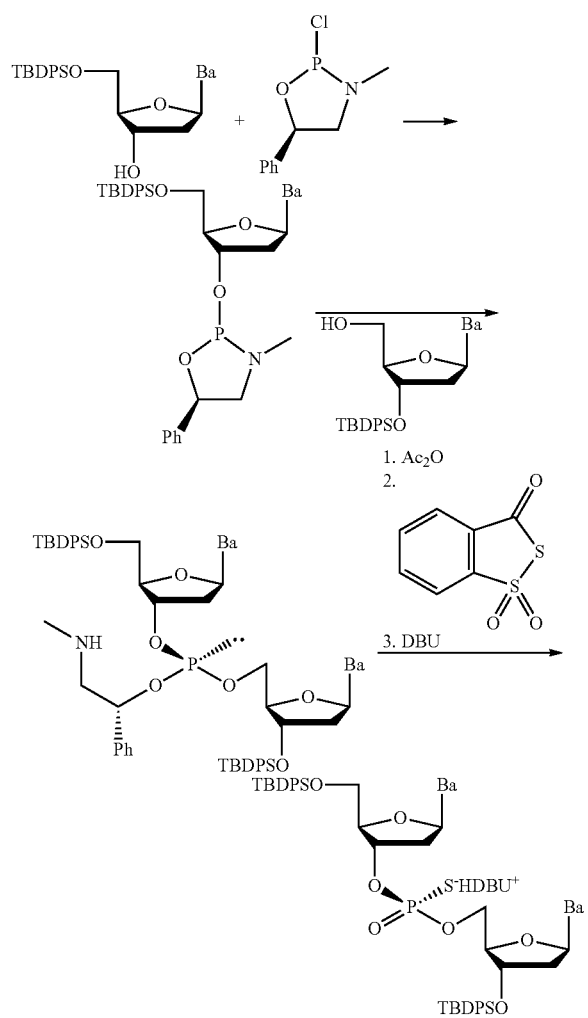

One method of stereoselective dinucleoside phosphorothioate synthesis involves the use of stereochemically pure 3'-phosphoramidites as described by Oka et al, (*J. Am. Chem. Soc.* (2003), 125:8307-17). As shown in the Scheme 6a (above), 2-chlorooxazaphospholidine derivatives are allowed to react with a 5'-O-(TBDPS)nucleoside to afford the 3'-O-oxazaphospholidine derivative. Reaction of a 3'-O-(TBDPS)nucleoside with the 3'-O-oxazaphospholidine derivative in the presence of an activator such as N-(cyanomethyl)pyrrolidine gives the dinucleoside phosphite as a single diastereomer. The dinucleoside phosphite can be converted to the phosphorothioate by a three-step process involving acetylation with acetic anhydride, sulfurization with the Beaucage reagent (3H-1,2-benzodithiol-3-one-1,1-dioxide; Iyer et al, *J. Am. Chem. Soc.* (1990), 112:1253-4), and cleavage of the chiral auxiliary with excess DBU. The protected dinucleoside phosphorthioate is then converted to the prodrug by the methods disclosed herein.

Other methods useful for the synthesis of dinucleoside phosphorthioates include enzymatic methods (Hacia et al. *Biochemistry* (1994), 33:5367-9; Tang et al. *Nucleosides Nucleotides* (1995), 14:985-990), methods involving separation of diasteromeric phosphorthioate mixtures prepared by non-stereoselective methods (Zon et al *Oligonucleotides and Analogues: A Practical Approach*; IRL Press: London, 1991, pp 87-108) and methods involving stereoselective synthesis of phosphorthioates (Wilk et al. *J. Am. Chem. Soc.* 2000, 122, 2149-2156; Lu et al, *Angew. Chem., Int. Ed.* 2000, 39, 4521-4524; Iyer et al *Tetrahedron:Asymmetry* 1995, 6, 1051-1054. Iyer et al *Tetrahedron Lett.* 1998, 39, 2491-2494; Lu et al *Tetrahedron* 2001, 57, 1677-1687. Stec et al *Nucleic Acids Res.* 1991, 19, 5883-5888; Stec et al *J. Am. Chem. Soc.* 1995, 117, 12019-12029; Uznań ski et al *J. Am. Chem. Soc.* 1992, 114, 10197-10202.

Reverse 5' to 3' Nucleic Acid Synthesis

A nucleic acid of Formula 1 comprising a chiral X-phosphonate moiety alternatively is synthesized from the 5' to 3' direction. In embodiments where a solid support is used, the nucleic acid is attached to the solid support through its 5' end of the growing nucleic acid, thereby presenting its 3' group for reaction, including enzymatic reaction (e.g. ligation and polymerization). In some embodiments, this orientation is engineered by preparing nucleoside monomers comprising an achiral H-phosphonate moiety at the 5' position and protected hydroxyl group at the 3' position. In an embodiment, the nucleic acid is synthesized according to Scheme 12. In Scheme 12, —$R^4$ is —ORb as defined above or, in the last cycle of synthesis, is $R^4$, which is equivalent to $R^1$ as defined herein.

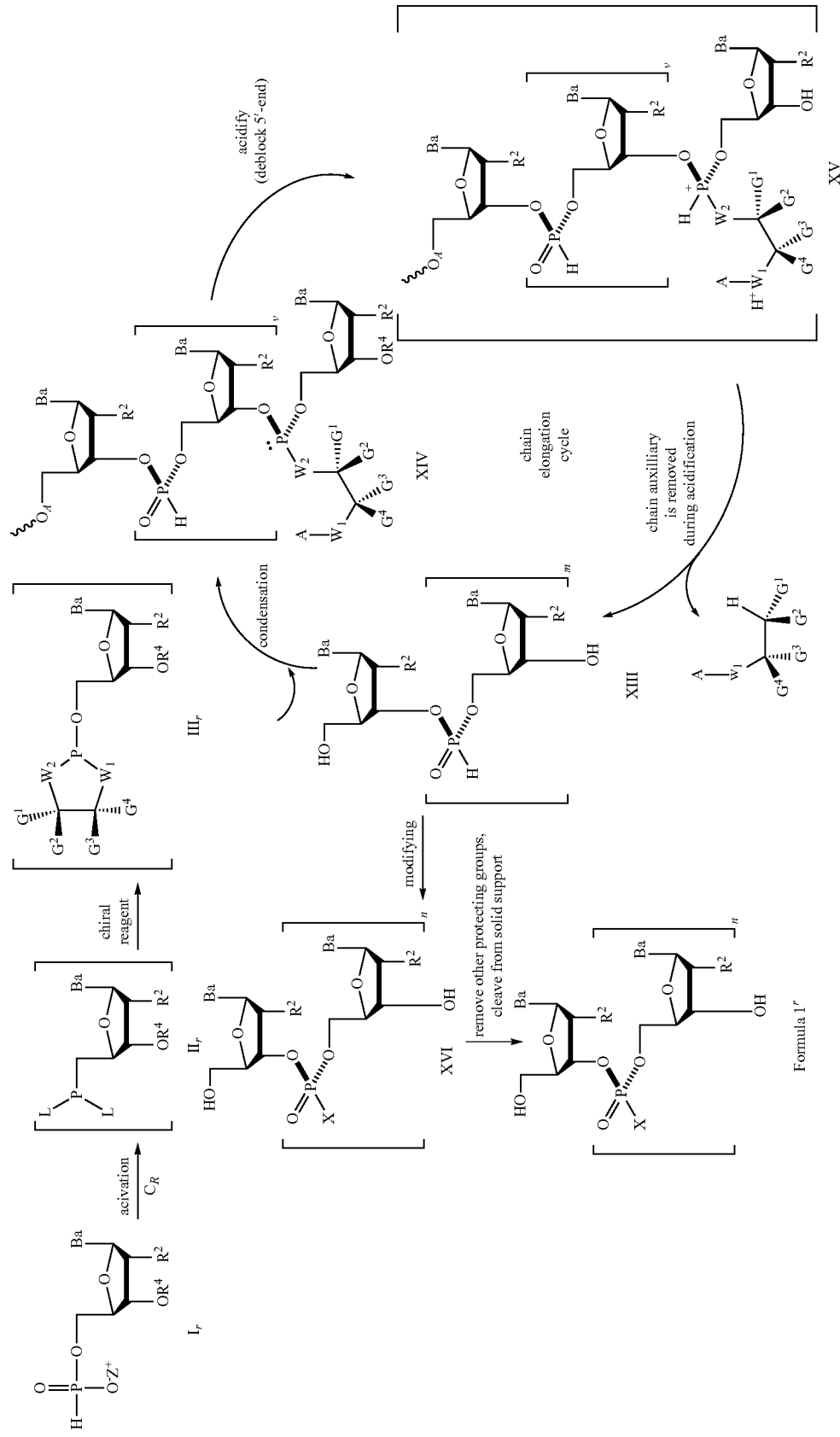

In the embodiment described in Scheme 12, an achiral H-phosphonate of structure Ir is treated with a condensing reagent to form an intermediate of structure IIr. The intermediate of structure IIr is not isolated and is treated in the same pot with a chiral reagent to form an intermediate of structure IIIr. The intermediate of structure IIIr is not isolated and undergoes a reaction in the same pot with a nucleoside or modified nucleoside of structure XIII to provide a chiral phosphite compound of structure XIV. In some embodiments, structure XIV is extracted into a solvent to separate it from side products, impurities, and/or reagents. In other embodiments, when the method is performed via solid phase synthesis, the solid support comprising the compound of structure XIV is filtered away from side products, impurities, and/or reagents. The compound of structure XIV is treated with an acid to remove the blocking group at the 3'-end of the growing nucleic acid chain (structure XV). The acidification step also removes the chiral auxiliary ligand to provide a compound of structure XIII. The 3'-deblocked intermediate is optionally allowed to re-enter the chain elongation cycle to form a condensed intermediate containing a blocked 3'-end, which is then acidified to remove the 3'-end blocking group and chiral auxillary ligand. Following at least one round of chain elongation cycle, the 3'-deprotected intermediate undergoes a modifying step to introduce a moiety X bonded to each of the phosphorus atoms to provide a compound of structure XVI. The modified intermediate is deblocked by removal of remaining protecting groups, e.g., nucleobase, modified nucleobase, sugar or modified sugar protecting groups are removed, to provide a nucleic acid of Formula 1. In other embodiments, the nucleoside comprising a 3'-OH moiety is an intermediate from a previous chain elongation cycle as described herein. In yet other embodiments, the nucleoside comprising a 3'-OH moiety is an intermediate obtained from another known nucleic acid synthetic method. After a cycle of synthesis with the first nucleoside, nucleosides, nucleotides, or nucleic acids that contain an unprotected —OH moiety can be used for subsequent elongation cycles. In embodiments where a solid support is used, the phosphorus-atom modified nucleic acid can then be cleaved from the solid support, located at the 5' end. In certain embodiments, the nucleic acids can optionally be left attached on the solid support for purification purposes and then cleaved from the solid support following purification. In one aspect, the synthesis described in Scheme 12 is useful when both of the G1 and G2 position of the chiral auxiliary ligand of Formula A are not hydrogen. The reverse 5' to 3' synthesis can be accomplished using the same starting materials in Scheme 12 in a mechanism analogous to steps in Route A.

Generation of Phosphothiotriesters with Reversible Protecting Groups from H-Phosphonate Phosphorothioates can be synthesized in a stereospecific manner from H-phosphonates with retention of configuration at phosphorus atom (*J. Org. Chem.* 1991, 3861-3869). Also contemplated is the use of this reaction to synthesize phosphorothiotriesters using thiol-containing moiety that also carries bioreversible protecting group, see Scheme 13. Additionally, stereocontrolled solid-phase synthesis of oligonucleoside H-phosphonates has also been reported (*Angew. Chem. Int. Ed.* 2009, 48, 496-499) and it is contemplated that this method, combined with alkylation during solid support synthesis, to prepare phosphothiotriesters on support.

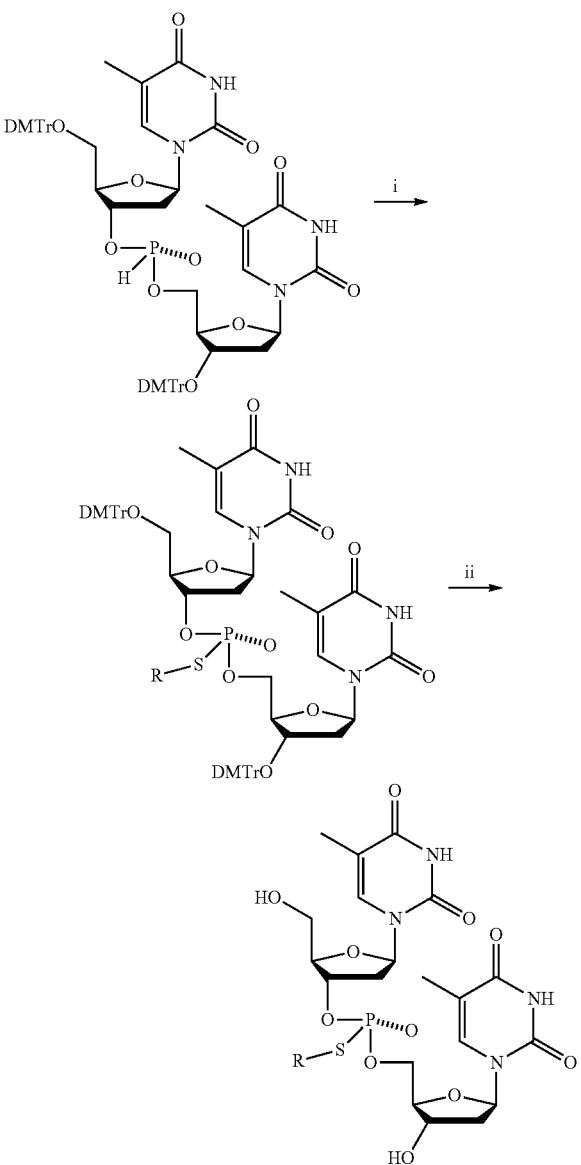

Scheme 13 i) I$_2$, ACN: Py (3:2), TBDPSCl and the respective thiol
ii) 3% DCA/DCM

Reaction Conditions and Reagents Used in the Methods of the Invention.

Conditions

The steps of reacting a molecule comprising an achiral H-phosphonate moiety and a nucleoside comprising a 5'-OH moiety to form a condensed intermediate can occur without isolating any intermediates. In some embodiments, the steps of reacting a molecule comprising an achiral H-phosphonate moiety and a nucleoside comprising a 5'-OH moiety to form a condensed intermediate occurs is a one-pot reaction. In an embodiment, a molecule comprising an achiral H-phosphonate moiety, condensing reagent, chiral reagent, and compound comprising a free nucleophilic moiety are added to the reaction mixture at different times. In another embodiment, a molecule comprising an achiral H-phosphonate moiety, condensing reagent, and chiral reagent are present in the same reaction vessel or same pot. In another embodiment, a molecule comprising an achiral H-phosphonate moiety, condensing reagent, chiral reagent, and compound comprising a free nucleophilic moiety are present in the same reaction or same pot. This allows the reaction to be performed without isolation of intermediates and eliminates time-consuming steps, resulting in an economical and efficient synthesis. In specific embodiments, the achiral H-phosphonate, condensing reagent, chiral amino alcohol, 5'-OH nucleoside are present at the same time in a reaction. In a further embodiment, the formation of the chiral intermediate for condensation is formed in situ and is not isolated prior to the condensation reaction. In another embodiment, a molecule comprising an achiral H-phosphonate moiety has been activated by reaction with a condensing reagent, chiral reagent in a different reaction vessel from that used when reacting the chiral intermediate with the compound comprising a free 5'-OH moiety.

Synthesis on Solid Support

In some embodiments, the synthesis of the nucleic acid is performed in solution. In other embodiments, the synthesis of the nucleic acid is performed on solid phase. The reactive groups of a solid support may be unprotected or protected. During oligonucleotide synthesis a solid support is treated with various reagents in several synthesis cycles to achieve the stepwise elongation of a growing oligonucleotide chain with individual nucleotide units. The nucleoside unit at the end of the chain which is directly linked to the solid support is termed "the first nucleoside" as used herein. The first nucleoside is bound to the solid support via a linker moiety, i.e. a diradical with covalent bonds to both the polymer of the solid support and the nucleoside. The linker stays intact during the synthesis cycles performed to assemble the oligonucleotide chain and is cleaved after the chain assembly to liberate the oligonucleotide from the support.

Solid supports for solid-phase nucleic acid synthesis include the supports described in, e.g., U.S. Pat. Nos. 4,659,774, 5,141,813, 4,458,066; Caruthers U.S. Pat. Nos. 4,415,732, 4,458,066, 4,500,707, 4,668,777, 4,973,679, and 5,132,418; Andrus et al. U.S. Pat. Nos. 5,047,524, 5,262,530; and Koster U.S. Pat. Nos. 4,725,677 (reissued as Re34,069). In Some Embodiments, the Solid Phase is an Organic Polymer support. In other embodiments, the solid phase is an inorganic polymer support. In some embodiments, the organic polymer support is polystyrene, aminomethyl polystyrene, a polyethylene glycol-polystyrene graft copolymer, polyacrylamide, polymethacrylate, polyvinylalcohol, highly cross-linked polymer (HCP), or other synthetic polymers, carbohydrates such as cellulose and starch or other polymeric carbohydrates, or other organic polymers and any copolymers, composite materials or combination of the above inorganic or organic materials. In other embodiments, the inorganic polymer support is silica, alumina, controlled polyglass (CPG), which is a silica-gel support, or aminopropyl CPG. Other useful solid supports include fluorous solid supports (see e.g., WO/2005/070859), long chain alkylamine (LCAA) controlled pore glass (CPG) solid supports (see e.g., S. P. Adams, K. S. Kavka, E. J. Wykes, S. B. Holder and G. R. Galluppi, *J. Am. Chem. Soc.*, 1983, 105, 661-663; G. R. Gough, M. J. Bruden and P. T. Gilham, *Tetrahedron Lett.*, 1981, 22, 4177-4180). Membrane supports and polymeric membranes (see e.g. Innovation and Perspectives in Solid Phase Synthesis, Peptides, Proteins and Nucleic Acids, ch 21 pp 157-162, 1994, Ed. Roger Epton and U.S. Pat. No. 4,923,901) are also useful for the synthesis of nucleic acids. Once formed, a membrane can be chemically functionalized for use in nucleic acid synthesis. In addition to the attachment of a functional group to the membrane, the use of a linker or spacer group attached to the membrane may be used to minimize steric hindrance between the membrane and the synthesized chain.

Other suitable solid supports include those generally known in the art to be suitable for use in solid phase methodologies, including, for example, glass sold as Primer™ 200 support, controlled pore glass (CPG), oxalyl-controlled pore glass (see, e.g., Alul, et al., *Nucleic Acids Research*, 1991, 19, 1527), TentaGel Support-an aminopolyethyleneglycol derivatized support (see, e.g., Wright, et al., *Tetrahedron Lett.*, 1993, 34, 3373), and Poros-a copolymer of polystyrene/divinylbenzene.

Surface activated polymers have been demonstrated for use in synthesis of natural and modified nucleic acids and proteins on several solid supports mediums. The solid support material can be any polymer suitably uniform in porosity, has sufficient amine content, and sufficiently flexible to undergo any attendant manipulations without losing integrity. Examples of suitable selected materials include nylon, polypropylene, polyester, polytetrafluoroethylene, polystyrene, polycarbonate, and nitrocellulose. Other materials can serve as the solid support, depending on the design of the investigator. In consideration of some designs, for example, a coated metal, in particular gold or platinum can be selected (see e.g., US publication No. 20010055761). In one embodiment of oligonucleotide synthesis, for example, a nucleoside is anchored to a solid support which is functionalized with hydroxyl or amino residues. Alternatively, the solid support is derivatized to provide an acid labile trialkoxytrityl group, such as a trimethoxytrityl group (TMT). Without being bound by theory, it is expected that the presence of the trialkoxytrityl protecting group will permit initial detritylation under conditions commonly used on DNA synthesizers. For a faster release of oligonucleotide material in solution with aqueous ammonia, a diglycoate linker is optionally introduced onto the support.

Linking Moiety

A linking moiety or linker is optionally used to connect the solid support to the compound comprising a free nucleophilic moiety. Suitable linkers are known such as short molecules which serve to connect a solid support to functional groups (e.g., hydroxyl groups) of initial nucleosides molecules in solid phase synthetic techniques. In some embodiments, the linking moiety is a succinamic acid linker, or a succinate linker (—CO—$CH_2$—$CH_2$—CO—), or an oxalyl linker (—CO—CO—). In other embodiments, the linking moiety and the nucleoside are bonded together through an ester bond. In other embodiments, the linking moiety and the nucleoside are bonded together through an amide bond. In further embodiments, the linking moiety connects the nucleoside to another nucleotide or nucleic acid. Suitable linkers are disclosed in, for example, Oligonucleotides And Analogues A Practical Approach, Ekstein, F. Ed., IRL Press, N.Y., 1991, Chapter 1.

A linker moiety is used to connect the compound comprising a free nucleophilic moiety to another nucleoside, nucleotide, or nucleic acid. In some embodiments, the linking moiety is a phosphodiester linkage. In other embodiments, the linking moiety is an H-phosphonate moiety. In yet other embodiments, the linking moiety is an X-phosphonate moiety.

Solvents for Synthesis

Synthesis of the nucleic acids is performed in an aprotic organic solvent. In some embodiments, the solvent is acetonitrile, pyridine, tetrahydrofuran, or dichloromethane.

In some embodiments, when the aprotic organic solvent is not basic, a base is present in the reacting step. In some embodiments where a base is present, the base is pyridine, quinoline, or N,N-dimethylaniline. Other examples of bases include pyrrolidine, piperidine, N-methylpyrrolidine, pyridine, quinoline, N,N-dimethylaminopyridine (DMAP), or N,N-dimethylaniline. In some embodiments, the aprotic organic solvent is anhydrous. In other embodiments, the anhydrous aprotic organic solvent is freshly distilled. In some embodiments, the freshly distilled anhydrous aprotic organic solvent is pyridine. In other embodiments, the freshly distilled anhydrous aprotic organic solvent is tetrahydrofuran. In other embodiments, the freshly distilled anhydrous aprotic organic solvent is acetonitrile.

Acidification Conditions to Remove Blocking Groups.

Acidification to remove blocking groups is accomplished by a Brønsted acid or Lewis acid. In some embodiments, acidification is used to remove $R^1$ blocking groups. Useful Brønsted acids are carboxylic acids, alkylsulfonic acids, arylsulfonic acids, phosphoric acid and its derivatives, phosphonic acid and its derivatives, alkylphosphonic acids and their derivatives, arylphosphonic acids and their derivatives, phosphinic acid, dialkylphosphinic acids, and diarylphosphinic acids which have a pKa (25° C. in water) value of −0.6 (trifluoroacetic acid) to 4.76 (acetic acid) in an organic solvent or water (in the case of 80% acetic acid). The concentration of the acid (1 to 80%) used in the acidification step depends on the acidity of the acid. Consideration to the acid strength must be taken into account as strong acid conditions will result in depurination/depyrimidination, wherein purinyl or pyrimidinyl bases are cleaved from ribose ring.

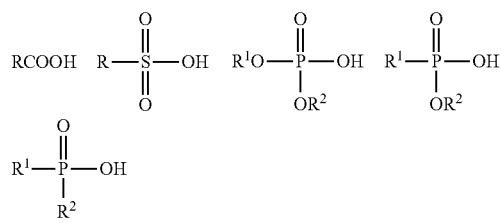

R=H, alkyl, aryl R=alkyl, aryl $R^1$, $R^2$=H, alkyl, aryl $R^1$, $R^2$=H, alkyl, aryl $R^1$, $R^2$=H, alkyl, aryl In some embodiments, acidification is accomplished by a Lewis acid in an organic solvent. Useful Lewis acids are $ZnX_2$ wherein X is Cl, Br, I, or $CF_3SO_3$.

In some embodiments, the acidifying comprises adding an amount of a Brønsted or Lewis acid effective to convert the condensed intermediate into the compound of Formula 4 without removing purine moieties from the condensed intermediate.

Acids that are useful in the acidifying step also include, but are not limited to 10% phosphoric acid in an organic solvent, 10% hydrochloric acid in an organic solvent, 1% trifluoroacetic acid in an organic solvent, 3% dichloroacetic acid in an organic solvent or 80% acetic acid in water. The concentration of any Brønsted or Lewis acid used in the process is selected such that the concentration of the acid does not exceed a concentration that causes cleavage of the nucleobase from the sugar moiety.

In some embodiments, acidification comprises adding 1% trifluoroacetic acid in an organic solvent. In some embodiments, acidification comprises adding about 0.1% to about 8% trifluoroacetic acid in an organic solvent. In other embodiments, acidification comprises adding 3% dichloroacetic acid in an organic solvent. In other embodiments, acidification comprises adding about 0.1% to about 10% dichloroacetic acid in an organic solvent. In yet other embodiments, acidification comprises adding 3% trichloroacetic acid in an organic solvent. In yet other embodiments, acidification comprises adding about 0.1% to about 10% trichloroacetic acid in an organic solvent. In some embodiments, acidification comprises adding 80% acetic acid in water. In some embodiments, acidification comprises adding about 50% to about 90%, or about 50% to about 80%, about 50% to about 70%, about 50% to about 60%, about 70% to about 90% acetic acid in water. In some embodiments, the acidification comprises the further addition of cation scavengers to the acidic solvent. In specific embodiments, the cation scavengers can be triethylsilane or triisopropylsilane. In some embodiments, $R^1$ is deblocked prior to the step of acidifying the condensed intermediate. In some embodiments, $R^1$ is deblocked by acidification, which comprises adding 1% trifluoroacetic acid in an organic solvent. In some embodiments, $R^1$ is deblocked by acidification, which comprises adding 3% dichloroacetic acid in an organic solvent. In some embodiments, $R^1$ is deblocked by acidification, which comprises adding 3% trichloroacetic acid in an organic solvent.

Removal of Blocking Moieties or Groups

Functional groups such as hydroxyl or amino moieties which are located on nucleobases or sugar moieties are routinely blocked with blocking (protecting) groups (moieties) during synthesis and subsequently deblocked. In general, a blocking group renders a chemical functionality of a molecule inert to specific reaction conditions and can later be removed from such functionality in a molecule without substantially damaging the remainder of the molecule (see e.g., Green and Wuts, Protective Groups in Organic Synthesis, 2nd Ed., John Wiley & Sons, New York, 1991). For example, amino groups can be blocked with nitrogen blocking groups such as phthalimido, 9-fludrenylmethoxycarbonyl (FMOC), triphenylmethylsulfenyl, t-BOC, 4,4'-dimethoxytrityl (DMTr), 4-methoxytrityl (MMTr), 9-phenylxanthin-9-yl (Pixyl), trityl (Tr), or 9-(p-methoxyphenyl)xanthin-9-yl (MOX). Carboxyl groups can be protected as acetyl groups. Hydroxy groups can be protected such as tetrahydropyranyl (THP), t-butyldimethylsilyl (TBDMS), 1-[(2-chloro-4-methyl)phenyl]-4-methoxypiperidin-4-yl (Ctmp), 1-(2-fluorophenyl)-4-methoxypiperidin-4-yl (Fpmp), 1-(2-chloroethoxy)ethyl, 3-methoxy-1,5-dicarbomethoxypentan-3-yl (MDP), bis(2-acetoxyethoxy)methyl (ACE), triisopropylsilyloxymethyl (TOM), 1-(2-cyanoethoxy)ethyl (CEE), 2-cyanoethoxymethyl (CEM), [4-(N-dichloroacetyl-N-methylamino)benzyloxy]methyl, 2-cyanoethyl (CN), pivaloyloxymethyl (PivOM), levunyloxymethyl (ALE). Other representative hydroxyl blocking groups have been described (see e.g., Beaucage et al., Tetrahedron, 1992, 46, 2223). In some embodiments, hydroxyl blocking groups are acid-labile groups, such as the trityl, monomethoxytrityl, dimethoxytrityl, trimethoxytrityl, 9-phenylxanthin-9-yl (Pixyl) and 9-(p-methoxyphenyl)xanthin-9-yl (MOX). Chemical functional groups can also be blocked by including them in a precursor form. Thus an azido group can be considered a blocked form of an amine as the azido group is easily converted to the amine. Further representative protecting groups utilized in nucleic acid synthesis are known (see e.g. Agrawal et al., Protocols for Oligonucleotide Conjugates, Eds., Humana Press, New Jersey, 1994, Vol. 26, pp. 1-72).

Various methods are known and used for removal of blocking groups from the nucleic acids. In some embodiments, all blocking groups are removed. In other embodiments, the blocking groups are partially removed. In yet other embodiments, reaction conditions can be adjusted to remove blocking groups on certain moieties. In certain embodiments where $R^2$ is a blocking group, removal of the blocking group at $R^2$ is orthogonal to the removal of the blocking group at $R^1$. The blocking groups at $R^1$ and $R^2$ remain intact during the synthesis steps and are collectively removed after the chain assembly. In some embodiments, the $R^2$ blocking group are removed simultaneously with the cleavage of the nucleic acids from the solid support and with the removal of the nucleobase blocking groups. In specific embodiments, the blocking group at $R^1$ is removed while the blocking groups at $R^2$ and nucleobases remain intact. Blocking groups at $R^1$ are cleavable on solid supports with an organic base such as a primary amine, a secondary amine, or a mixture thereof. Deblocking of the $R^1$ position is commonly referred to as front end deprotection.

In an embodiment, the nucleobase blocking groups, if present, are cleavable after the assembly of the respective nucleic acid with an acidic reagent. In another embodiment, one or more of the nucleobase blocking groups is cleavable under neither acidic nor basic conditions, e.g. cleavable with fluoride salts or hydrofluoric acid complexes. In yet another embodiment, one or more of the nucleobase blocking groups are cleavable after the assembly of the respective nucleic acid in the presence of base or a basic solvent, and wherein the nucleobase blocking group is stable to the conditions of the front end deprotection step with amines.

In some embodiments, blocking groups for nucleobases are not required. In other embodiments, blocking groups for nucleobases are required. In yet other embodiments, certain nucleobases require blocking group while other nucleobases do not require blocking groups. In embodiments where the nucleobases are blocked, the blocking groups are either completely or partially removed under conditions appropriate to remove the blocking group at the front end. For example, $R^1$ can denote $OR^a$, wherein $R^a$ is acyl, and Ba denotes guanine blocked with an acyl group including, but not limited to isobutyryl, acetyl or 4-(tert-butylphenoxy) acetyl. The acyl groups at R1 and Ba will be removed or partially removed during the same deblocking step.

Reagents
Condensing Reagent

The condensing reagent ($C_R$) useful in the methods of the invention has one of the following general formulae:

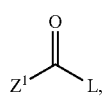

$C_R1$

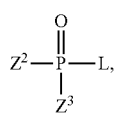

$C_R2$

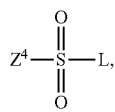

$C_R3$

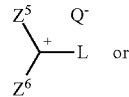

$C_R4$

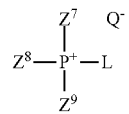

$C_R5$ wherein $Z^1$, $Z^2$, $Z^3$, $Z^4$, $Z^5$, $Z^6$, $Z^7$, $Z^8$, and $Z^9$ are independently selected from alkyl, aminoalkyl, cycloalkyl, heterocyclic, cycloalkylalkyl, heterocycloalkyl, aryl, heteroaryl, alkyloxy, aryloxy, or heteroaryloxy, or wherein any of $Z^2$ and $Z^3$, $Z^5$ and $Z^6$, $Z^7$ and $Z^8$, $Z^8$ and $Z^9$, $Z^9$ and $Z^7$, or $Z^7$ and $Z^8$ and $Z^9$ are taken together to form a 3 to 20 membered alicyclic or heterocyclic ring; $Q^-$ is a counter anion; and L is a leaving group.

In some embodiments, the counter ion of the condensing reagent $C_R$ is $Cl^-$, $Br^-$, $BF_4^-$, $PF_6^-$, $TfO^-$, $Tf_2N^-$, $AsF_6^-$, $ClO_4^-$, or $SbF_6^-$, wherein Tf is $CF_3SO_2$. In some embodiments, the leaving group of the condensing reagent $C_R$ is F, Cl, Br, I, 3-nitro-1,2,4-triazole, imidazole, alkyltriazole, tetrazole, pentafluorobenzene, or 1-hydroxybenzotriazole.

Examples of condensing agents that can be used in the process include, and are not limited to, pentafluorobenzoyl chloride, carbonyldiimidazole (CDI), 1-mesitylenesulfonyl-3-nitrotriazole (MSNT), 1-ethyl-3-(3'-dimethylaminopropyl)carbodiimide hydrochloride (EDCI-HCl), benzotriazole-1-yloxytris(dimethylamino)phosphonium hexafluorophosphate (PyBOP), N,N'-bis(2-oxo-3-oxazolidinyl)phosphinic chloride (BopCl), 2-(1H-7-azabenzotriazol-1-yl)-1,1,3,3-tetramethyluronium hexafluorophosphate (HATU), and O-benzotriazole-N,N,N',N'-tetramethyluronium hexafluorophosphate (HBTU), DIPCDI; N,N'-bis(2-oxo-3-oxazolidinyl)phosphinic bromide (BopBr), 1,3-dimethyl-2-(3-nitro-1,2,4-triazol-1-yl)-2-pyrrolidin-1-yl-1,3,2-diazaphospholidinium hexafluorophosphate (MNTP), 3-nitro-1,2,4-triazol-1-yl-tris(pyrrolidin-1-yl)phosphonium hexafluorophosphate (PyNTP), bromotripyrrolidinophosphonium hexafluorophosphate (PyBrOP); O-(benzotriazol-1-yl)-N,N,N',N'-tetramethyluronium tetrafluoroborate (TBTU); and tetramethylfluoroformamidinium hexafluorophosphate (TFFH). In certain embodiments, the counter ion of the condensing reagent $C_R$ is $Cl^-$, $Br^-$, $BF_4^-$, $PF_6^-$, $TfO^-$, $Tf_2N^-$, $AsF_6^-$, $ClO_4^-$, or $SbF_6^-$, wherein Tf is $CF_3SO_2$.

In other embodiments of the invention, the condensing reagent is 1-(2,4,6-triisopropylbenzenesulfonyl)-5-(pyridin-2-yl)tetrazolide, pivaloyl chloride, bromotrispyrrolidinophosphonium hexafluorophosphate, N,N'-bis(2-oxo-3-oxazolidinyl)phosphinic chloride (BopCl), or 2-chloro-5,5-dimethyl-2-oxo-1,3,2-dioxaphosphinane. In one embodiment, the condensing reagent is N,N'-bis(2-oxo-3-oxazolidinyl)phosphinic chloride (BopCl). Other known condensing reagents have been described (see e.g., WO/2006/066260).

In other embodiments, the condensing reagent is 1,3-dimethyl-2-(3-nitro-1,2,4-triazol-1-yl)-2-pyrrolidin-1-yl-1,3,2-diazaphospholidinium hexafluorophosphate (MNTP), or 3-nitro-1,2,4-triazol-1-yl-tris(pyrrolidin-1-yl)phosphonium hexafluorophosphate (PyNTP).

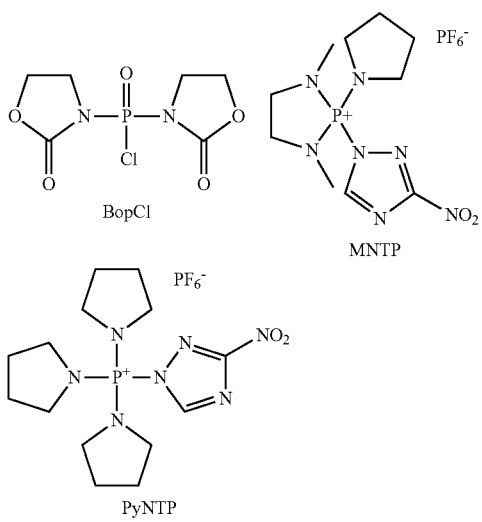

BopCl

MNTP

PyNTP

Chiral Reagent

In the methods of the present invention, chiral reagents are used to confer stereoselectivity in the production of X-phosphonate linkages. Many different chiral auxiliaries may be used in this process which are compounds of Formula 3-I where W1 and W2 are any of —O—, —S—, or —NG5-, which are capable of reacting with the H-phosphonate starting material, a compound of Formula 2 to form the chiral intermediate, as shown in structure III of Schemes 5 and 6.

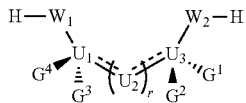

Formula 3-I $U_1$ and $U_3$ are carbon atoms which are bonded to $U_2$ if present, or to each other if r is 0, via a single, double or triple bond. $U_2$ is —C—, —CG$^8$-, —CG$^8$G$^8$-, —NG$^8$-, —N—, —O—, or —S— where r is an integer of 0 to 5 and no more than two heteroatoms are adjacent. When any one of $U_2$ is C, a triple bond must be formed between a second instance of $U_2$, which is C, or to one of $U_1$ or $U_3$. Similarly, when any one of $U_2$ is CG$^8$, a double bond is formed between a second instance of $U_2$ which is —CG$^8$- or —N—, or to one of $U_1$ or $U_3$.

For example, in some embodiments, —$U_1$—($U_2$)$_r$—$U_3$— is —CG$^3$G$^4$-CG'G$^2$-. In some embodiments, —$U_1$—($U_2$)$_r$—$U_3$— is —CG$^3$=CG$^1$-. In some embodiments, —$U_1$—($U_2$)$_r$—$U_3$— is —C≡C—. In some embodiments, —$U_1$—($U_2$)$_r$—$U_3$— is —CG$^3$=CG$^8$-CG$^1$G$^2$-. In some embodiments, —$U_1$—($U_2$)$_r$—$U_3$— is —CG$^3$G$^4$-O-CG$^1$G$^2$-. In some embodiments, —$U_1$—($U_2$)$_r$—$U_3$— is —CG$^3$G$^4$-NG$^8$-CG$^1$G$^2$-. In some embodiments, —$U_1$—($U_2$)$_r$—$U_3$— is —CG$^3$G$^4$-N-CG$^2$-. In some embodiments, —$U_1$—($U_2$)$_r$—$U_3$— is —CG$^3$G$^4$-N=C G$^8$-CG$^1$G$^2$-.

$G^1$, $G^2$, $G^3$, $G^4$, $G^5$, and $G^8$ are independently hydrogen, alkyl, aralkyl, cycloalkyl, cycloalkylalkyl, heterocyclyl, hetaryl, or aryl, or two of $G^1$, $G^2$, $G^3$, $G^4$, and $G^5$ are $G^6$ taken together form a saturated, partially unsaturated or unsaturated carbocyclic or heteroatom-containing ring of up to about 20 ring atoms which is monocyclic or polycyclic, and is fused or unfused. In some embodiments, the ring so formed is substituted by oxo, thioxo, alkyl, alkenyl, alkynyl, heteroaryl, or aryl moieties. In some embodiments, when the ring formed by taking two G$^6$ together is substituted, it is substituted by a moiety which is bulky enough to confer stereoselectivity during the reaction.

For example, in some embodiments, the ring formed by taking two of G$^6$ together is cyclopentyl, pyrrolyl, cyclopropyl, cyclohexenyl, cyclopentenyl, tetrahydropyranyl, or piperazinyl.

In some embodiments of the invention, the chiral reagent is a compound of Formula 3.

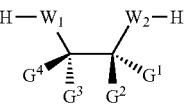
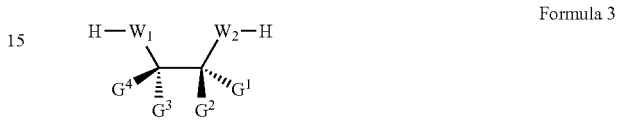

Formula 3

In some embodiments of Formula 3, $W_1$ and $W_2$ are independently —NG$^5$-, —O—, or —S—; G$^1$, G$^2$, G$^3$, G$^4$, and G$^5$ are independently hydrogen, alkyl, aralkyl, cycloalkyl, cycloalkylalkyl, heterocyclyl, hetaryl, or aryl, or two of G$^1$, G$^2$, G$^3$, G$^4$, and G$^5$ are G$^6$ taken together form a saturated, partially unsaturated or unsaturated carbocyclic or heteroatom-containing ring of up to about 20 ring atoms which is monocyclic or polycyclic, fused or unfused, and no more than four of G$^1$, G$^2$, G$^3$, G$^4$, and G$^5$ are G$^6$. Similarly to the compounds of Formula 3', any of G$^1$, G$^2$, G$^3$, G$^4$, or G$^5$ are substituted by oxo, thioxo, alkyl, alkenyl, alkynyl, heteroaryl, or aryl moieties. In some embodiments, such substitution induces stereoselectivity in X-phosphonate production.

In some embodiments of the invention, the chiral reagent has one of the following Formulae:

Formulae 3-A

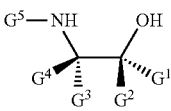

3-B

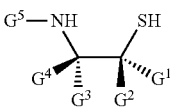

3-C

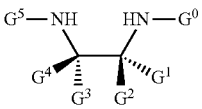

3-D

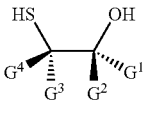

3-E

3-F

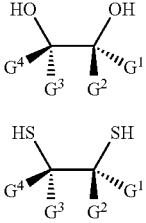

In some embodiments, the chiral reagent is an aminoalcohol. In some other embodiments, the chiral reagent is an aminothiol. In yet other embodiments, the chiral reagent is an aminophenol. In some embodiments, the chiral reagent is (S)— and (R)-2-methylamino-1-phenylethanol, (1R,2S)-ephedrine, or (1R,2S)-2-methylamino-1,2-diphenylethanol.

In other embodiments of the invention the chiral reagent is a compound of one of the following formulae:

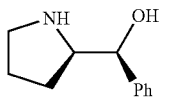

Formula O

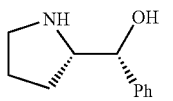

Formula P

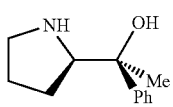

Formula Q

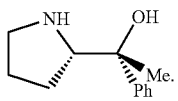

Formula R

The choice of chiral reagent, for example, the isomer represented by Formula O or its stereoisomer, Formula P, permits the specific control of the chirality at phosphorus. Thus either a RP or SP configuration can be selected in each synthesis cycle, permitting control of the overall three dimensional structure of the nucleic acid product. In some embodiments of the invention, a nucleic acid product has all RP stereocenters. In some embodiments of the invention, a nucleic acid product has all SP stereocenters. In some embodiments, the selection of RP and SP centers is made to confer a specific three dimensional superstructure to the nucleic acid chain.

Stereochemistry of Oligonucleoside Phosphorothioate Linkages

Oligonucleoside phosphorothioates have shown therapeutic potential (Stein et al., Science (1993), 261:1004-12; Agrawal et al., Antisence Res. and Dev. (1992), 2:261-66; Bayever et al., Antisense Res. and Dev. (1993), 3:383-390). Oligonucleoside phosphorothioates prepared without regard to the sterochemistry of the phosphorothioate exist as a mixture of 2n diastereomers, where n is the number of internucleotide phosphorothioates linkages. The chemical and biological properties of these diastereomeric phosphorothioates can be distinct. For example, Wada et al (Nucleic Acids Symposium Series No. 51 p. 119-120; doi:10.1093/nass/nrm060) found that stereodefined-(Rp)-(Ups)$_9$U/(Ap)$_9$A duplex showed a higher Tm value than that of natural-(Up)$_9$U/(Ap)$_9$A and stereodefined-(Sp)-(Ups)$_9$U did not form a duplex. In another example, in a study by Tang et al., (Nucleosides Nucleotides (1995), 14:985-990) stereopure Rp-oligodeoxyribonucleoside phosphorothioates were found to possess lower stability to nucleases endogenous to human serum that the parent oligodeoxyribonucleoside phosphorothioates with undefined phosphorous chirality.

Nucleobases and Modified Nucleobases

The nucleobase Ba in Formula 1 is a natural nucleobase or a modified nucleobase derived from natural nucleobases. Examples include, but are not limited to, uracil, thymine, adenine, cytosine, and guanine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, RNA, 2003, 9, 1034-1048, Limbach et al. *Nucleic Acids Research*, 1994, 22, 2183-2196 and Revankar and Rao, *Comprehensive Natural Products Chemistry*, vol. 7, 313, are also contemplated as Ba moieties of Formula 1.

Compounds represented by the following general formulae are also contemplated as modified nucleobases:

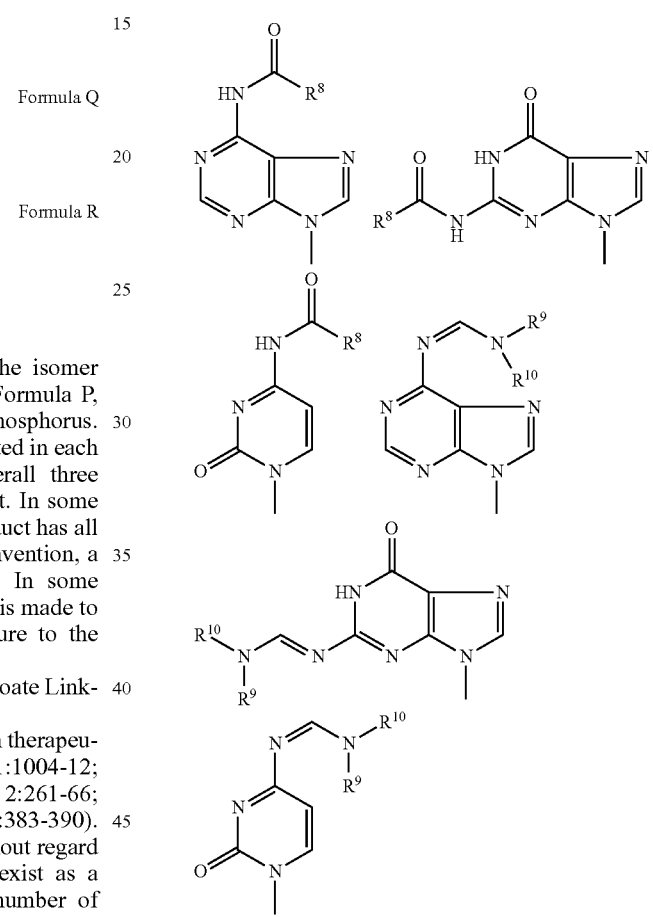

In the formulae above, $R^8$ is a linear or branched alkyl, aryl, aralkyl, or aryloxylalkyl group having 1 to 15 carbon atoms, including, by way of example only, a methyl, isopropyl, phenyl, benzyl, or phenoxymethyl group; and each of $R^9$ and $R^{10}$ represents a linear or branched alkyl group having 1 to 4 carbon atoms.

Modified nucleobases also include expanded-size nucleobases in which one or more benzene rings has been added. Nucleic base replacements described in the Glen Research catalog (www.glenresearch.com); Krueger A T et al, *Acc. Chem. Res.*, 2007, 40, 141-150; Kool, ET, *Acc. Chem. Res.*, 2002, 35, 936-943; Benner S. A., et al., *Nat. Rev. Genet.*, 2005, 6, 553-543; Romesberg, F. E., et al., *Curr. Opin. Chem. Biol.*, 2003, 7, 723-733; Hirao, I., *Curr. Opin. Chem. Biol.*, 2006, 10, 622-627, are contemplated as useful for the synthesis of the nucleic acids described herein. Some examples of these expanded-size nucleobases are shown below:

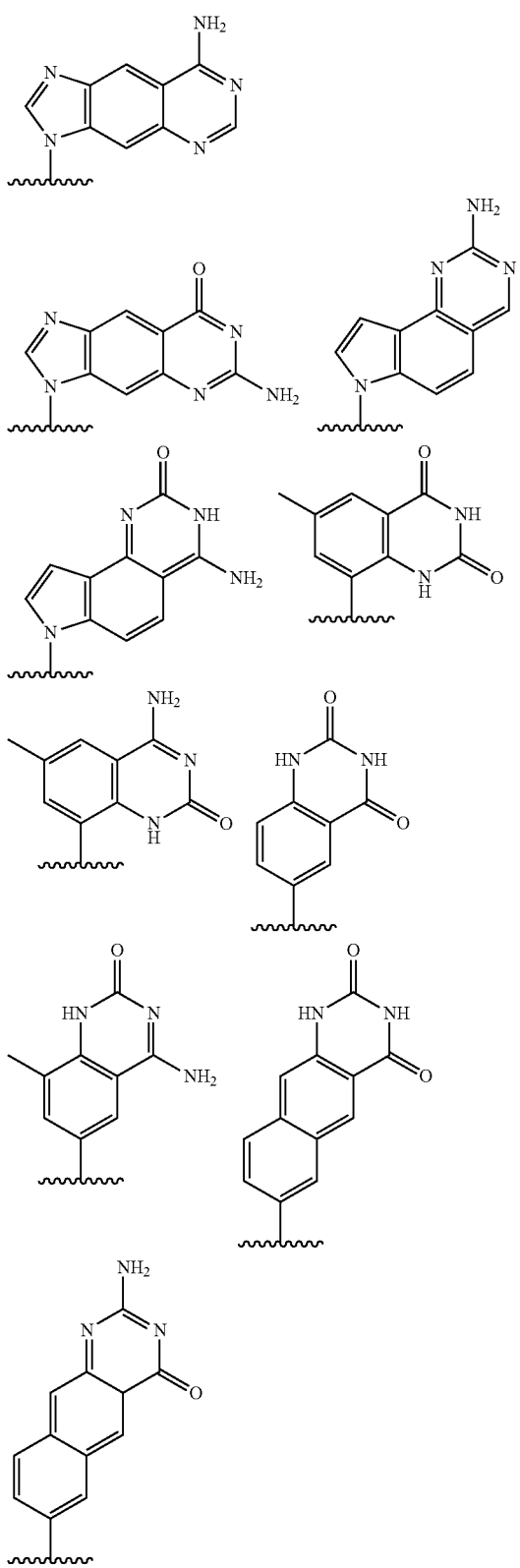

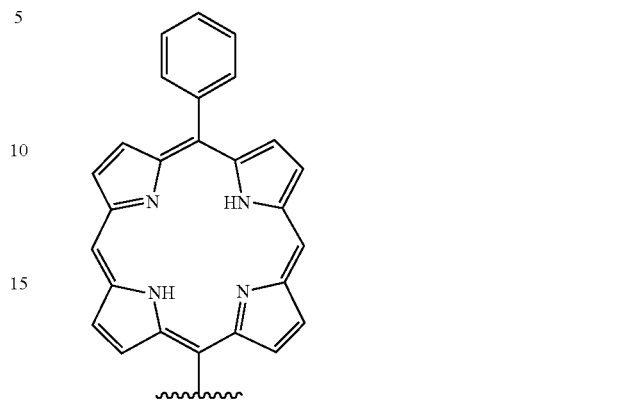

2002, 4, 4377-4380. Shown below is an example of a porphyrin-derived ring which can be used as a base replacement:

Other modified nucleobases also include base replacements such as those shown below:

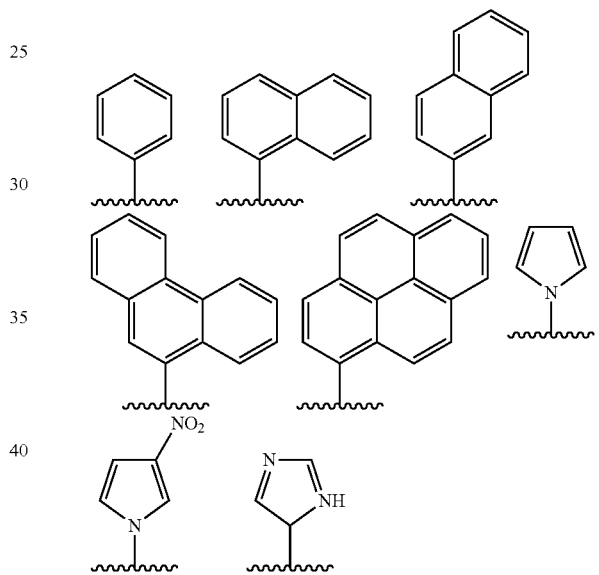

Modified nucleobases which are fluorescent are also contemplated. Non-limiting examples of these base replacements include phenanthrene, pyrene, stillbene, isoxanthine, isozanthopterin, terphenyl, terthiophene, benzoterthiophene, coumarin, lumazine, tethered stillbene, benzo-uracil, and naphtho-uracil, as shown below:

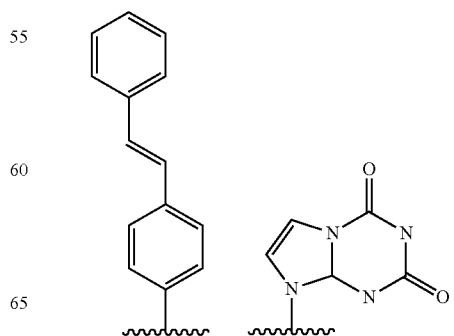

Herein, modified nucleobases also encompass structures that are not considered nucleobases but are other moieties such as, but not limited to, corrin- or porphyrin-derived rings. Porphyrin-derived base replacements have been described in Morales-Rojas, H and Kool, ET, *Org. Lett.*, -continued

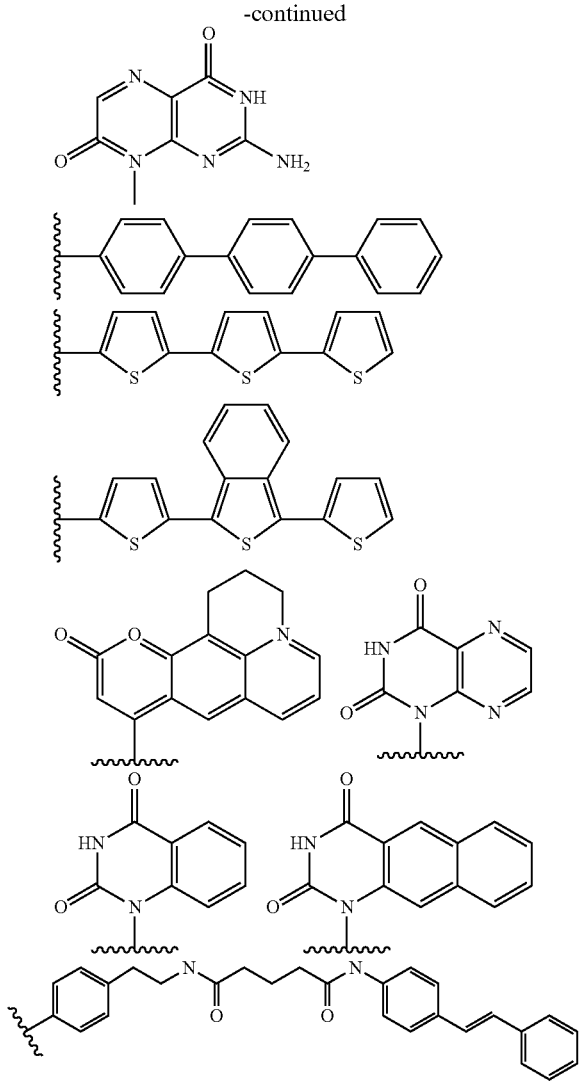

The modified nucleobases can be unsubstituted or contain further substitutions such as heteroatoms, alkyl groups, or linking moieties connected to fluorescent moieties, biotin or avidin moieties, or other protein or peptides. Modified nucleobases also include certain 'universal bases' that are not nucleobases in the most classical sense, but function similarly to nucleobases. One representative example of such a universal base is 3-nitropyrrole.

In addition to nucleosides of structure IV or IX, other nucleosides can also be used in the process disclosed herein and include nucleosides that incorporate modified nucleobases, or nucleobases covalently bound to modified sugars. Some examples of nucleosides that incorporate modified nucleobases include 4-acetylcytidine; 5-(carboxyhydroxylmethyl)uridine; 2'-O-methylcytidine; 5-carboxymethylaminomethyl-2-thiouridine; 5-carboxymethylaminomethyluridine; dihydrouridine; 2'-O-methylpseudouridine; beta,D-galactosylqueosine; 2'-O-methylguanosine; N6-isopentenyladenosine; 1-methyladenosine; 1-methylpseudouridine; 1-methylguanosine; 1-methylinosine; 2,2-dimethylguanosine; 2-methyladenosine; 2-methylguanosine; N7-methylguanosine; 3-methyl-cytidine; 5-methylcytidine; N6-methyladenosine; 7-methylguanosine; 5-methylaminoethyluridine; 5-methoxyaminomethyl-2-thiouridine; beta,D-mannosylqueosine; 5-methoxycarbonylmethyluridine; 5-methoxyuridine; 2-methylthio-N6-isopentenyladenosine; N-((9-beta,D-ribofuranosyl-2-methylthiopurine-6-yl)carbamoyl)threonine; N-((9-beta,D-ribofuranosylpurine-6-yl)-N-methylcarbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; and 2'-O-methyluridine.

In some embodiments, nucleosides include 6'-modified bicyclic nucleoside analogs that have either (R) or (S)-chirality at the 6'-position and include the analogs described in U.S. Pat. No. 7,399,845. In other embodiments, nucleosides include 5'-modified bicyclic nucleoside analogs that have either (R) or (S)-chirality at the 5'-position and include the analogs described in US Patent Application Publication No. 20070287831.

In some embodiments, the nucleobases or modified nucleobases comprises biomolecule binding moieties such as antibodies, antibody fragments, biotin, avidin, streptavidin, receptor ligands, or chelating moieties. In other embodiments, Ba is 5-bromouracil, 5-iodouracil, or 2,6-diaminopurine. In yet other embodiments, Ba is modified by substitution with a fluorescent or biomolecule binding moiety. In some embodiments, the substituent on Ba is a fluorescent moiety. In other embodiments, the substituent on Ba is biotin or avidin.

Modified Sugars of the Nucleotide/Nucleoside.

The most common naturally occurring nucleotides are ribose sugars linked to the nucleobases adenosine (A), cytosine (C), guanine (G), and thymine (T) or uracil (U). Also contemplated are modified nucleotides wherein the phosphate group or the modified phosphorous atom moieties in the nucleotides can be linked to various positions of the sugar or modified sugar. As non-limiting examples, the phosphate group or the modified phosphorous-atom moiety can be linked to the 2', 3', 4' or 5' hydroxyl moiety of a sugar or modified sugar. Nucleotides that incorporate the modified nucleobases described above can also be used in the process disclosed herein. In some embodiments, nucleotides or modified nucleotides comprising an unprotected —OH moiety are used in the process disclosed herein.

In addition to the ribose moiety described in Schemes 1-4-b, other modified sugars can also be incorporated in the nucleic acids disclosed herein. In some embodiments, the modified sugars contain one or more substituents at the 2' position including one of the following: F; $CF_3$, CN, $N_3$, NO, $NO_2$, O—, S—, or N-alkyl; O—, S—, or N-alkenyl; O—, S- or N-alkynyl; or O-alkyl-O-alkyl, O-alkyl-N-alkyl or N-alkyl-O-alkyl wherein the alkyl, alkenyl and alkynyl may be substituted or unsubstituted $C_1$-$C_{10}$ alkyl or $C_2$-$C_{10}$ alkenyl and alkynyl. Examples of substituents include, and are not limited to, $O(CH_2)_nOCH_3$, and $O(CH_2)_nNH_2$, wherein n is from 1 to about 10, MOE, DMAOE, DMAEOE. Also contemplated herein are modified sugars described in WO 2001/088198; and Martin et al., Helv. Chim. Acta, 1995, 78, 486-504. In some embodiments, modified sugars comprise substituted silyl groups, an RNA cleaving group, a reporter group, a fluorescent label, an intercalator, a group for improving the pharmacokinetic properties of a nucleic acid, or a group for improving the pharmacodynamic properties of a nucleic acid, and other substituents having similar properties. The modifications may be made at the at the 2', 3', 4', 5', or 6' positions of the sugar or modified sugar, including the 3' position of the sugar on the 3'-terminal nucleotide or in the 5' position of the 5'-terminal nucleotide.

Modified sugars also include sugar mimetics such as cyclobutyl or cyclopentyl moieties in place of the pentofuranosyl sugar. Representative United States patents that teach the preparation of such modified sugar structures include, but are not limited to, U.S. Pat. Nos. 4,981,957;

5,118,800; 5,319,080; and 5,359,044. Some modified sugars that are contemplated include:

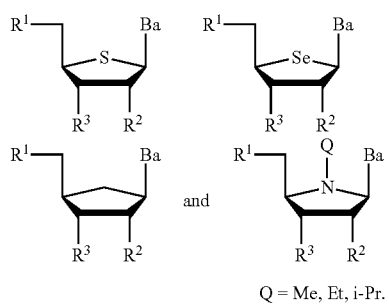

Q = Me, Et, i-Pr.

Other non-limiting examples of modified sugars include glycerol, which form glycerol nucleic acid (GNA) analogues. One example of a GNA analogue is shown below and is described in Zhang, R et al., *J. Am. Chem. Soc.,* 2008, 130, 5846-5847; Zhang L, et al., *J. Am. Chem. Soc.,* 2005, 127, 4174-4175 and Tsai C H et al., *PNAS,* 2007, 14598-14603:

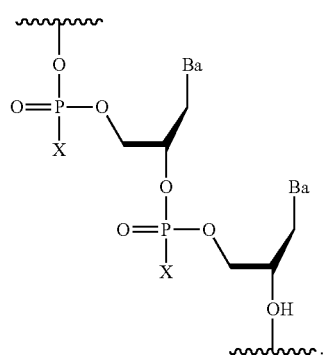

wherein X is as defined herein. Another example of a GNA derived analogue, flexible nucleic acid (FNA) based on the mixed acetal aminal of formyl glycerol, is described in Joyce G F et al., *PNAS,* 1987, 84, 4398-4402 and Heuberger B D and Switzer C, *J. Am. Chem. Soc.,* 2008, 130, 412-413, and is shown below:

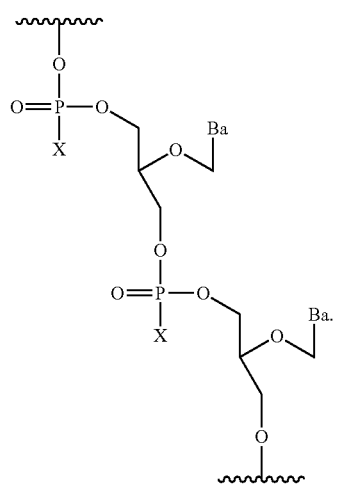

Other non-limiting examples of modified sugars include hexopyranosyl (6' to 4'), pentopyranosyl (4' to 2'), pentopyranosyl (4' to 3'), or tetrofuranosyl (3' to 2') sugars. Hexopyranosyl (6' to 4') sugars contemplated include:

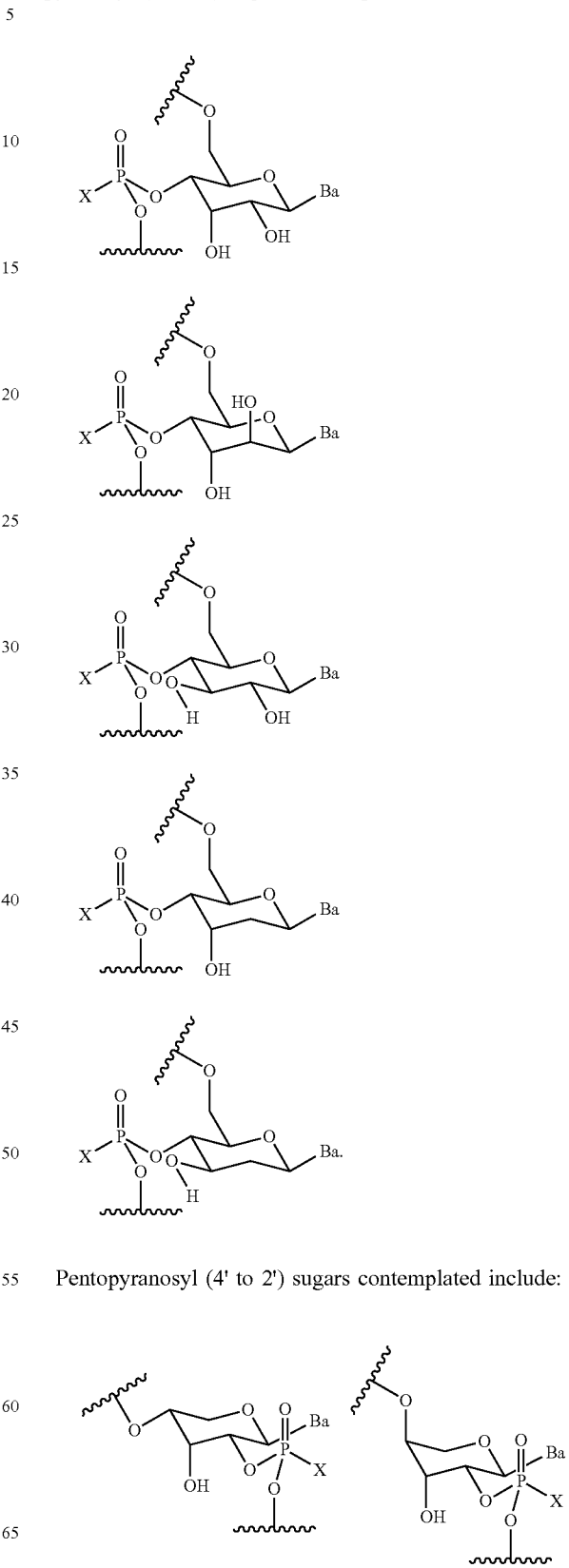

Pentopyranosyl (4' to 2') sugars contemplated include:

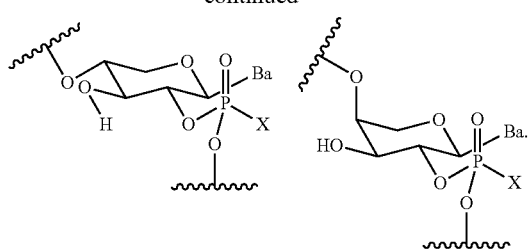
Pentopyranosyl (4' to 3') sugars contemplated include:
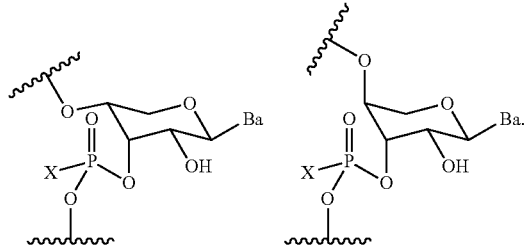
Tetrofuranosyl (3' to 2') sugars contemplated include:
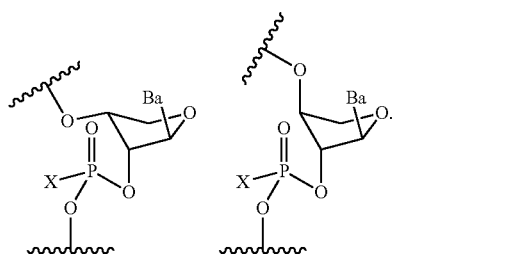
Other modified sugars contemplated include:
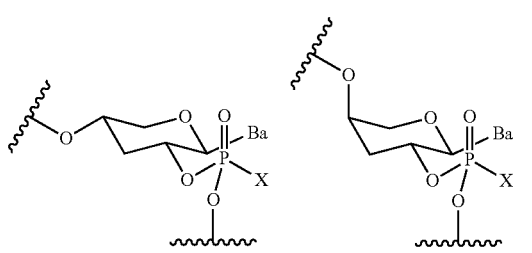
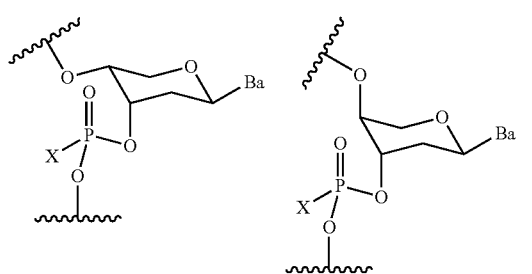
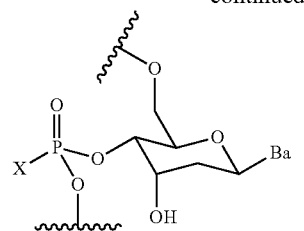
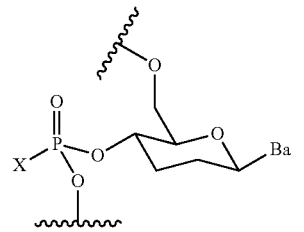
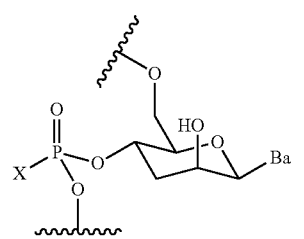
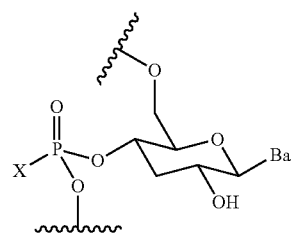
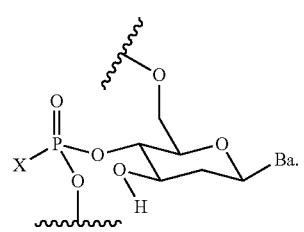
Further contemplated are the sugar mimetics illustrated below wherein X is selected from S, Se, $CH_2$, N-Me, N-Et or N-iPr.
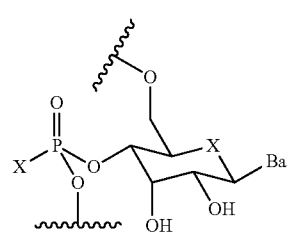

131
-continued
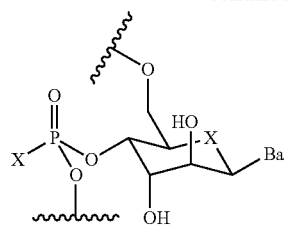
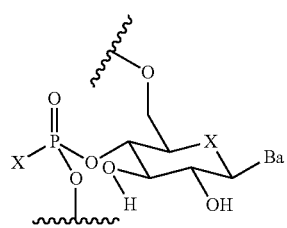
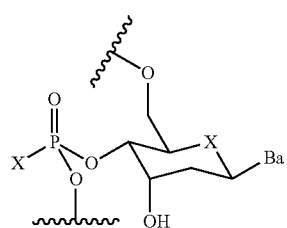
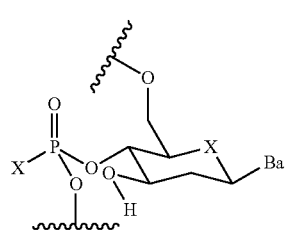
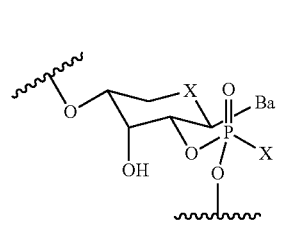
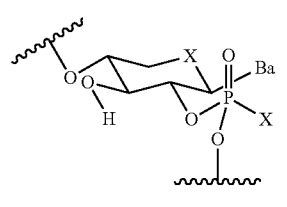
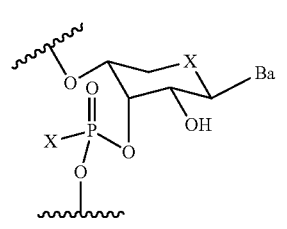
132
-continued
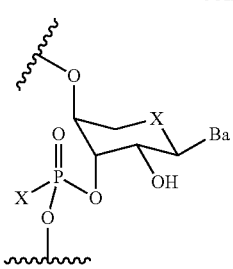
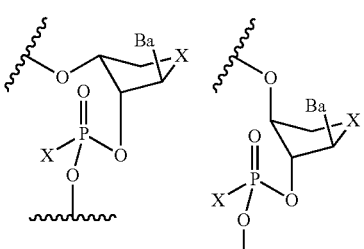
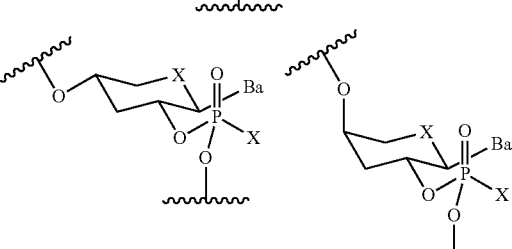
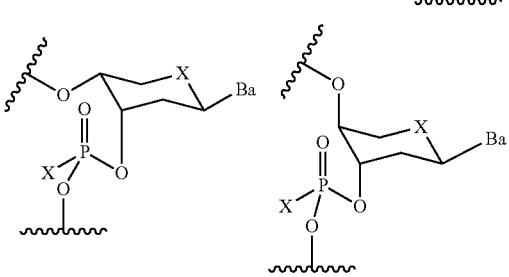
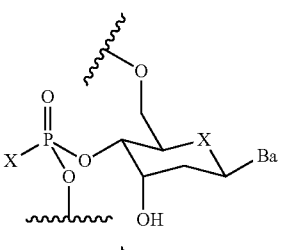
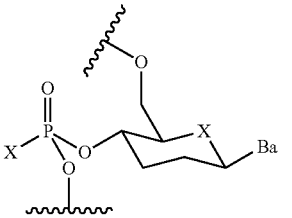
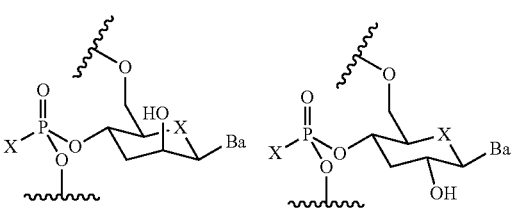

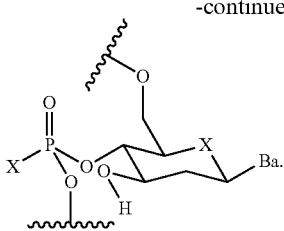

The modified sugars and sugar mimetics can be prepared by methods known in the art, including, but not limited to: A. Eschenmoser, Science (1999), 284:2118; M. Bohringer et al, Helv. Chim. Acta (1992), 75:1416-1477; M. Egli et al, J. Am. Chem. Soc. (2006), 128(33):10847-56; A. Eschenmoser in *Chemical Synthesis: Gnosis to Prognosis*, C. Chatgilialoglu and V. Sniekus, Ed., (Kluwer Academic, Netherlands, 1996), p. 293; K.-U. Schoning et al, Science (2000), 290:1347-1351; A. Eschenmoser et al, Helv. Chim. Acta (1992), 75:218; J. Hunziker et al, Helv. Chim. Acta (1993), 76:259; G. Otting et al, Helv. Chim. Acta (1993), 76:2701; K. Groebke et al, Helv. Chim. Acta (1998), 81:375; and A. Eschenmoser, Science (1999), 284:2118.

Blocking Groups

In the reactions described, it is necessary in certain embodiments to protect reactive functional groups, for example hydroxy, amino, thiol or carboxy groups, where these are desired in the final product, to avoid their unwanted participation in the reactions. Protecting groups are used to block some or all reactive moieties and prevent such groups from participating in chemical reactions until the protective group is removed. In one embodiment, each protective group is removable by a different means. Protective groups that are cleaved under totally disparate reaction conditions fulfill the requirement of differential removal. In some embodiments, protective groups are removed by acid, base, and/or hydrogenolysis. Groups such as trityl, dimethoxytrityl, acetal and t-butyldimethylsilyl are acid labile and are used in certain embodiments to protect carboxy and hydroxy reactive moieties in the presence of amino groups protected with Cbz groups, which are removable by hydrogenolysis, and/or Fmoc groups, which are base labile. In other embodiments, carboxylic acid and hydroxy reactive moieties are blocked with base labile groups such as, but not limited to, methyl, ethyl, and acetyl in the presence of amines blocked with acid labile groups such as t-butylcarbamate or with carbamates that are both acid and base stable but hydrolytically removable.

In another embodiment, hydroxy reactive moieties are blocked with hydrolytically removable protective groups such as the benzyl group, while amine groups capable of hydrogen bonding with acids are blocked with base labile groups such as Fmoc. In another embodiment, carboxylic acid reactive moieties are protected by conversion to simple ester compounds, or they are, in yet another embodiment, blocked with oxidatively-removable protective groups such as 2,4-dimethoxybenzyl, while co-existing amino groups are blocked with fluoride labile silyl or carbamate blocking groups.

Allyl blocking groups are useful in the presence of acid- and base-protecting groups since the former are stable and can be subsequently removed by metal or pi-acid catalysts. For example, an allyl-blocked hydroxy groups can be deprotected with a Pd(0)-catalyzed reaction in the presence of acid labile t-butylcarbamate or base-labile acetate amine protecting groups. Yet another form of protecting group is a resin to which a compound or intermediate is attached. As long as the residue is attached to the resin, that functional group is blocked and cannot react. Once released from the resin, the functional group is available to react.

Typically blocking/protecting groups useful in the synthesis of the compounds described herein are, by way of example only:

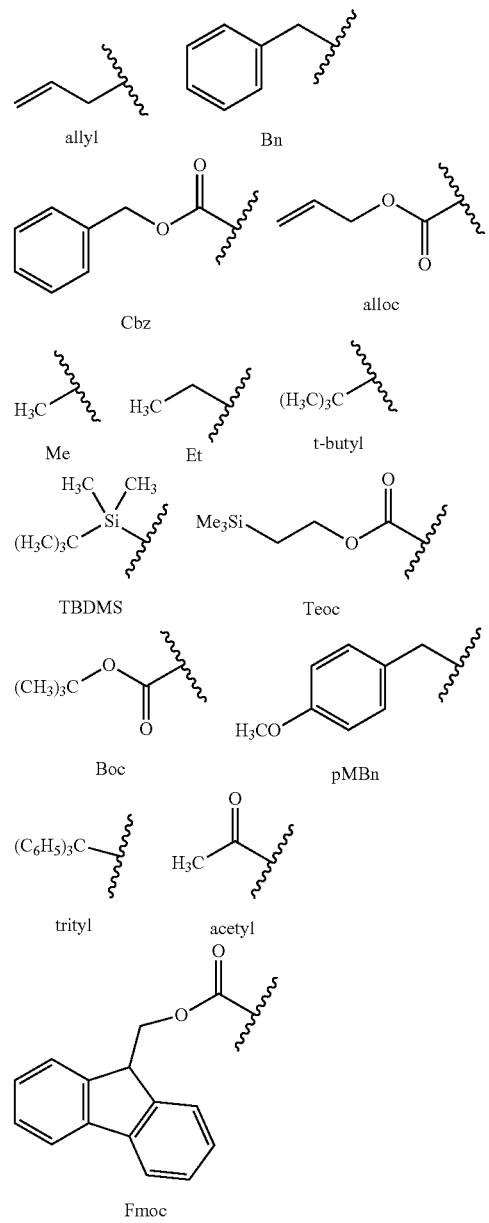

Representative protecting groups useful to protect nucleotides during synthesis include base labile protecting groups and acid labile protecting groups. Base labile protecting groups are used to protect the exocyclic amino groups of the heterocyclic nucleobases. This type of protection is generally achieved by acylation. Three commonly used acylating groups for this purpose are benzoyl chloride, phenoxyacetic anhydride, and isobutyryl chloride. These protecting groups are stable to the reaction conditions used during nucleic acid synthesis and are cleaved at approximately equal rates during the base treatment at the end of synthesis.

In some embodiments, the 5'-protecting group is trityl, monomethoxy trityl, dimethoxytrityl, trimethoxytrityl, 2-chlorotrityl, DATE, TBTr, 9-phenylxanthine-9-yl (Pixyl), or 9-(p-methoxyphenyl)xanthine-9-yl (MOX).

In some embodiments, thiol moieties are incorporated in the compounds of Formula 1, 2, 4, or 5 and are protected. In some embodiments, the protecting groups include, but are not limited to, pixyl, trityl, benzyl, p-methoxybenzyl (PMB), or tert-butyl (t-Bu).

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Methods of Use of the Nucleic Acid Prodrugs Comprising a Chiral X-Phosphonate Moiety The stereodefined oligonucleotide prodrug comprising a chiral phosphorous or phosphorothioate moiety which are obtained by the methods of the invention are useful in a number of areas for applications due to a combination of stability, defined chirality and ease of synthesis. Broadly, the compounds synthesized by this method are useful as therapeutics, diagnostic probes and reagents, synthetic tools for producing other oligonucleotide products, and nanostructure materials suitable for a variety of new materials and computing applications.

The stereodefined oligonucleotide prodrug of the invention have improved serum stability over that of natural DNA/RNA equivalents, and in particular, stereodefined oligonucleotide prodrug of the class of phosphorothioates. Further, the SP isomer is more stable than the RP isomer. In some embodiments, the level of serum stability is modulated by the introduction of either all SP centers or SP centers at selected positions to confer resistance to degradation. In other embodiments, introduction of selectable RP and/or $S_P$ stereocenters can provide for specific base pairing association with an endogenous or exogenous target thus protecting the target from metabolism or enhancing a particular biological reaction.

RNase H activation is also modulated by the presence of the stereocontrolled phosphorothioate nucleic acid analogs, with natural DNA/RNA being more susceptible than the RP stereoisomer which in turn is more susceptible than the corresponding $S_P$ isomer.

Improved duplex stability towards RNA is seen with RP phosphorothioate oligonucleotides having greater duplex stability than corresponding SP oligonucleotides which in turn demonstrates higher stability than that of natural DNA/RNA. Improved duplex stability towards DNA is seen with SP having greater duplex stability than RP which has more stability than that of natural DNA/RNA. (P. Guga, Curr. Top. Med. Chem., 2007, 7, 695-713).

These molecules may be useful as therapeutic agents, in a number of particular applications. They can be incorporated into oligonucleotides which also contain the standard DNA/RNA nucleosides, or they may be synthesized as entire sequences of the stereocontrolled oligonucleotides of the invention. Some categories of therapeutic agents include but are not limited to antisense oligonucleotides, antigene oligonucleotides which form triple helix with targeted sequences to repress transcription of undesired genes and modulate protein expression and/or activity, decoy oligonucleotides, DNA vaccines, aptamers, ribozymes, deoxyribozymes (DNAzymes or DNA enzymes), siRNAs, microRNAs, ncRNAs (non-coding RNAs), and P-modified prodrugs. Modulation encompasses indirectly or directly increasing or decreasing the activity of a protein or inhibition or promotion of the expression of a protein. These nucleic acid compounds can be used to control cell proliferation, viral replication, or any other cell signaling process.

In one example, the field of siRNA therapeutics has a need for oligonucleotide species that can afford increased stability against RNase activity, in order to improve the duration of action over that seen with siRNA composed of natural nucleosides. Additionally, A-form helix formation appears to be more indicative of success at entering RNAi than the presence of specific native elements on the oligonucleotide. Both of these requirements can be afforded by the use of the stereocontrolled oligonucleotides of the invention may provide enhanced stability (Y-L Chiu, T. M. Rana *RNA*, 2003, 9, 1034-1048).

Methods of Treatment

The nucleic acids described herein are useful as therapeutic agents against various disease states, including use as antiviral agents. The nucleic acids can be used as agents for treatment of diseases through modulation of DNA and/or RNA activity. In some embodiments, the nucleic acids can be used for inhibiting specific gene expression. For example, the nucleic acids can be complementary to a specific target messenger RNA (mRNA) sequence. They can be used to inhibit viral replication of myriad viruses. Exemplary virus families include orthomyxoviruses, pox viruses, herpes viruses, papilloma viruses, picornaviruses, flaviviruses, retroviruses, hepatitis viruses, paramyxoviruses, reoviruses, parvoviruses, filoviruses, coronaviruses, arenaviruses, rhabdoviruses and adenoviruses. Additional virus families are known and are also contemplated herein. Other examples include uses as antisense compounds against HIV RNA or other retroviral RNA or for hybridizing to HIV mRNA encoding the tat protein, or to the TAR region of HIV mRNA. In some embodiments, the nucleic acids mimic the secondary structure of the TAR region of HIV mRNA, and by doing so bind the tat protein. In an embodiment, the nucleic acids is used to inhibit expression of a target protein by contacting a cell with a compound of Formula 1 wherein the expression of other proteins in the cell are not inhibited or are minimally inhibited. In some embodiment, target protein inhibition occurs in vivo in a mammal. In other embodiments, a therapeutically effective amount of a compound of Formula 1 is administered for inhibiting the expression of a target protein.

Other examples of proteins where expression can be modulated include Jun N-terminal kinase (JNK) proteins, diacylglycerol acyltransferase I, apolipoprotein B, glucagon receptor, Aurora B, acyl CoA cholesterol acyltransferase-2, c-reactive protein, STAT (signal transducers and activators of transcription) family of proteins, and MDR P-glycoprotein. The nucleic acids can be used to inhibit protein phosphatase 1B (PTP1B) expression, RNA-dependent RNA viral polymerase. The nucleic acids can be used to induce events such as apoptosis in cancer cells or to make a cell more susceptible to apoptosis. The nucleic acids can be used to modulate activities of proteins. For example, it can help modulate RNase H activity targeting multidrug resistance (MDR) RNA molecules.

In another aspect, the present invention provides methods of treating a disease mediated by undesired gene expression in a subject (e.g., mammals, such as humans) in need of such treatment. By "diseases" is meant diseases, or disease symptoms. The method includes administering to the subject an effective amount of a non-racemic pro-oligonucleotide of the present invention.

Examples of diseases mediated by undesired gene expression include cancer (e.g., leukemia, tumors, and metastases), allergy, asthma, obesity, inflammation (e.g., inflammatory diseases such as inflammatory airways disease), hypercholesterolemia, hematological disorders, severe acute respiratory syndrome (SARS), obstructive airways disease, asthma, autoimmune diseases, retroviral diseases such as AIDS or HIV, other viral infections, intrauterine infections, metabolic diseases, infection (e.g., bacterial, viral, yeast, fungal), CNS diseases, brain tumors, degenerative neural diseases, cardiovascular diseases, and diseases associated with angiogenesis, neovascularization, and vasculogenesis.

In an exemplary embodiment, the compounds are useful for treating cancer, including pancreatic cancer, and other diseases or disorders involving abnormal cell proliferation.

Located in the upper abdomen (in the retroperitoneum), the pancreas is a dual-function gland of the digestive and endocrine system. In certain instances, the pancreas functions as an endocrine gland (e.g., producing several important hormones). In certain instances, the pancreas functions as an exocrine gland (e.g., secreting fluids containing digestive enzymes that pass to the small intestine).

Pancreatic cancer is the fourth most common cause of cancer death in the US (after lung, colon and breast), comprising 6% of all cancer-related deaths. In 2008, an estimated 37,680 new cases of pancreatic cancer will have been diagnosed in the US, with 34,290 deaths. Incidence of the disease, rises linearly after age 50, with the only definitive risk factor being cigarette smoking (smokers are four times more likely to develop the disease than non-smokers). Invasive pancreatic cancer is almost always fatal. The collective median survival time of all patients is 4-6 months. Relative 1-year survival is 24%; the overall 5-year survival rate <5%.

Pancreatic cancer is asymptomatic in its early stage and often remains undiagnosed for several months (less than one third of patients being diagnosed within 2 months of the onset symptoms). In certain instances, the delayed diagnosis results in (either partially or fully) metastasis of the cancerous cells to the liver or lymph nodes.

Currently, surgery (resectioning of the pancreas) is the primary and only curative therapy for pancreatic cancer. However, only 15-25% of tumors are resectable at the time of diagnosis and only 10-20% of patients undergoing surgery survive more than two years. Once tumor infiltration occurs and other tissues have been affected, surgery is no longer possible.

In certain instances, diabetes mellitus or pancreatitis predisposes an individual to develop a proliferative disorder of a plurality of pancreatic cells. In certain instances, individuals are at an increased risk of developing a proliferative disorder of a plurality of pancreatic cells due to a hereditary syndrome selected from the group consisting of hereditary nonpolyposis colorectal cancer (HNPCC) and familial adenomatous polyposis (FAP). In certain instances, individuals are at an increased risk of developing a proliferative disorder of a plurality of pancreatic cells due to a mutation in a gene selected from the group consisting of MSH2, MSH6, MLH1, and APC.

Ideally, effective treatment of pancreatic cancer should (i) control the primary tumor mass, both initially and subsequently, and (ii) treat the metastatic tumor cells. Chemoprevention (the administration of agents such as drugs, biologics, nutrients and the like) slows the progression of, reverses, or inhibits carcinogenesis, thereby lowering the risk of developing invasive or clinically significant disease.

Disclosed herein, in certain embodiments, is a method of treating pancreatic cancer. As used herein, "pancreatic cancer" includes forms of cancer of the pancreas. In some embodiments, the pancreatic cancer is metastatic pancreatic cancer. In some embodiments, the pancreatic cancer is a carcinoma, sarcoma, cancer, or combinations thereof. In some embodiments, a pancreatic cancer to be treated includes sporadic and hereditary pancreatic cancers. In some embodiments, the pancreatic cancer is duct cell carcinoma, acinar cell carcinoma, papillary mucinous carcinoma, signet ring carcinoma, adenosquamous carcinoma, undifferentiated carcinoma, mucinous carcinoma, giant cell carcinoma, small cell carcinoma, cystcancer, serous cystcancer, mucinous cystcancer, unclassified pancreatic cancer, pancreatoblastoma, or combinations thereof.

In some embodiments, an individual in need of treatment for pancreatic cancer presents with a localized tumor of the pancreas. In some embodiments, an individual in need of treatment for pancreatic cancer presents with a negative regional lymph node biopsy. In some embodiments, an individual in need of treatment for pancreatic cancer presents with a positive regional lymph node biopsy. In some embodiments, an individual in need of treatment for pancreatic cancer presents with a nodal negative pancreatic tumor (e.g., node-negative). In some embodiments, an individual in need of treatment for pancreatic cancer presents with a nodal positive tumor (e.g., node-positive).

In some embodiments, the pancreatic cancer in an individual in need of treatment for pancreatic cancer has metastasized to other locations in the body. In some embodiments, the pancreatic cancer has metastasized to a location selected from the group consisting of lymph node, stomach, bile duct, liver, bone, ovary, peritoneum and brain.

In some embodiments, cancer cells or precancerous cells are identified by histological typing or grading of a tissue sample (e.g., a biopsy sample). In some embodiments, cancer cells or precancerous cells are identified through the use of appropriate molecular markers.

In some embodiments, the pancreatic cancer in an individual in need of treatment for pancreatic cancer is staged according to the American Joint Committee on Cancer (AJCC) TNM classification system, where the tumor (T) has been assigned a stage of Tx, T1, T2, T3, T4; and where the regional lymph nodes (N) have been assigned a stage of NX, N0, N1; and where distant metastasis (M) has been assigned a stage of MX, M0, or M1. In some embodiments, the pancreatic cancer in an individual in need of treatment for pancreatic cancer is staged as Stage 0, I, IA, IB, II, IIA, IIB, III, and IV pancreatic cancer. In some embodiments, the pancreatic cancer in an individual in need of treatment for pancreatic cancer is staged as Grade GX (e.g., grade cannot be assessed), Grade 1, Grade 2, Grade 3 or Grade 4.

More specific examples of cancers treated with the compounds of the present invention include breast cancer, lung cancer, melanoma, colorectal cancer, bladder cancer, ovarian cancer, prostate cancer, renal cancer, squamous cell cancer, glioblastoma, Kaposi's sarcoma, multiple myeloma, and leukemia.

Evaluation and Treatment of Cancer

The term "tumor cell antigen" is defined herein as an antigen that is present in higher quantities on a tumor cell or in body fluids than unrelated tumor cells, normal cells, or in normal body fluid. The antigen presence may be tested by any number of assays known to those skilled in the art and include without limitation negative and/or positive selection with antibodies, such as an ELISA assay, a radioimmunoassay, or by Western Blot.

"Apoptosis inducing agent" is defined herein to induce apoptosis/programmed cell death, and include, for example, anticancer agents and treatments wherein cells (e.g., tumor cells) are induced to undergo programmed cell death. Exemplary apoptosis inducing agents are described in more detail below.

The terms "apoptosis" or "programmed cell death," refers to the physiological process by which unwanted or useless cells are eliminated during development and other normal biological processes. Apoptosis is a mode of cell death that occurs under normal physiological conditions and the cell is an active participant in its own demise ("cellular suicide"). It is most often found during normal cell turnover and tissue homeostasis, embryogenesis, induction and maintenance of immune tolerance, development of the nervous system and endocrine-dependent tissue atrophy. Cells undergoing apoptosis show characteristic morphological and biochemical features. These features include chromatin aggregation, nuclear and cytoplasmic condensation, partition of cytoplasm and nucleus into membrane bound vesicles (apoptotic bodies), which contain ribosomes, morphologically intact mitochondria and nuclear material. In vivo, these apoptotic bodies are rapidly recognized and phagocytized by macrophages, dendritic cells or adjacent epithelial cells. Due to this efficient mechanism for the removal of apoptotic cells in vivo no inflammatory response is elicited. In vitro, the apoptotic bodies as well as the remaining cell fragments ultimately swell and finally lyse. This terminal phase of in vitro cell death has been termed "secondary necrosis." Apoptosis can be measured by methods known to those skilled in the art like DNA fragmentation, exposure of Annexin V, activation of caspases, release of cytochrome c, etc. A cell that has been induced to die is termed herein as an "apoptotic cell."

Apoptosis can also be tested using a standard Annexin V Apoptosis Assay: NIH:OVCAR-3 cells are grown in 6-well plates (NUNC) and irradiated or treated with an antagonist (or in combination with another anti-cancer drug) for 4-48 hours, washed and stained with Annexin V-FITC (BD-Pharmingen) for 1 hour. Cells are analyzed by flow cytometry (Becton-Dickinson, CellQuest), counterstained with Propidium Iodide and analyzed again in the flow cytometer.

Patients can be assessed with respect to symptoms at one or more multiple time points including prior to, during, and after treatment regimens. Treatment can result in improving the subject's condition and can be assessed by determining if one or more of the following factors has occurred: decreased tumor size, decreased cell proliferation, decreased numbers of cells, decreased neovascularization, increased apoptosis, or decreased survival of at least a portion of the tumor cells. One or more of these occurrences may, in some cases, result in partial or total elimination of the cancer and prolongation of survival of the patient. Alternatively, for terminal stage cancers, treatment may result in stasis of disease, better quality of life and/or prolongation of survival.

Methods of Assaying Cell Migration

Assays for cell migration have been described in the literature, e.g., by Brooks, et al., J. Clin. Invest 1997, 99:1390-1398 and methods for measuring cell migration are known to those of skill in the art. In one method for measuring cell migration described herein, membranes from transwell migration chambers are coated with substrate, the transwells washed, and non-specific binding sites blocked with BSA. Tumor cells from sub-confluent cultures are harvested, washed, and resuspended in migration buffer in the presence or absence of assay antibodies. After the tumor cells are allowed to migrate to the underside of the coated transwell membranes, the cells remaining on the top-side of the membrane are removed and cells that migrate to the under-side are stained with crystal violet. Cell migration is then quantified by direct cell counts per microscopic field.

Methods of Assaying Tumor Growth

Tumor growth can be assayed by methods known to those of skill in the art, e.g., the SCID mouse model, the nude mouse model, and BALB/c mice with syngeneic tumors. SCID mouse models for tumor growth are carried out as follows: subconfluent human M21 melanoma cells (or any desired tumor cell type) are harvested, washed, and resuspended in sterile PBS ($20\times10^6$ per mL). SCID mice are injected subcutaneously with 100 µL of M21 human melanoma cell ($2\times10^6$) suspension. Three days after tumor cell injection, mice are either untreated or treated intraperitoneally with an antagonist in the desired dose ranges. The mice are treated daily for 24 days. Tumor size is measured with calipers and the volume estimated using the formula $V=(L\times W^2)/2$, where V is equal to the volume, L is equal to the length, and W is equal to the width.

Alternatively, nude mouse models, SCID mouse models and/or BALB/c syngeneic mouse models can also be utilized to assess tumor growth and inhibition thereof by the humanized anti-endoglin antibodies or antigen-binding fragments described herein.

Methods of Assaying Cell Proliferation

Cell proliferation can be assayed by methods known to those of skill in the art. As described herein, subconfluent human endothelial cells (HUVECs) can be resuspended in proliferation buffer containing low (5.0%) serum in the presence or absence of CM (25 µL) from ECV or ECVL cells, and endothelial cells allowed to proliferate for 24 hours. Proliferation can be quantified by measuring mitochondrial dehydrogenase activity using a commercially available WST-1 assay kit (Chemicon). Also, as described herein, proliferation can be quantified by measuring $^3H$ incorporation using standard methods. (She et al., Int. J. Cancer, 108: 251-257 (2004)).

Other methods of assessing cell proliferation are known in the art and are contemplated herein. Further non-limiting examples are described in more detail in the examples.

One would understand that classification and staging systems described herein represent one means to assess treatment of cancers described herein; additionally, other staging schemes are known in the art and may be used in connection with the methods described herein. By way of example only, the TNM classification of malignant tumors may be used as a cancer staging system to describe the extent of cancer in a patient's body. T describes the size of the tumor and whether it has invaded nearby tissue, N describes regional lymph nodes that are involved, and M describes distant metastasis. TNM is maintained by the International Union Against Cancer (UICC) and is used by the American Joint Committee on Cancer (AJCC) and the International Federation of Gynecology and Obstetrics (FIGO). One would understand that not all tumors have TNM classifications such as, for example, brain tumors. Generally, T (a,is,(0), 1-4) is measured as the size or direct extent of the primary tumor. N (0-3) refers to the degree of spread to regional lymph nodes: N0 means that tumor cells are absent from regional lymph nodes, N1 means that tumor cells spread to the closest or small numbers of regional lymph nodes, N2 means that tumor cells spread to an extent between N1 and N3; N3 means that tumor cells spread to most distant or numerous regional lymph nodes. M (0/1) refers to the presence of metastasis: M0 means that no distant metastasis are present; M1 means that metastasis has occurred to distant organs (beyond regional lymph nodes). Other parameters may also be assessed. G (1-4) refers to the grade of cancer cells (i.e., they are low grade if they appear similar to normal cells, and high grade if they appear poorly differentiated). R (0/1/2) refers to the completeness of an operation (i.e., resection-boundaries free of cancer cells or not). L (0/1) refers to invasion into lymphatic vessels. V (0/1) refers to invasion into vein. C (1-4) refers to a modifier of the certainty (quality) of V.

Provided herein are methods for degrading, inhibiting the growth of or killing cancer cells comprising contacting the cells with an amount of a compound described herein effective to degrade, inhibit the growth of or kill cancer cells.

Provided herein are methods of inhibiting tumor size increase, reducing the size of a tumor, reducing tumor proliferation or preventing tumor proliferation in an individual comprising administering to said individual an effective amount of a compound described herein to inhibit tumor size increase, reduce the size of a tumor, reduce tumor proliferation or prevent tumor proliferation. Treatment of tumors in some cases includes stasis of symptoms, that is, by treating the patient, the cancer does not worsen and survival of the patient is prolonged.

Patients may be assessed with respect to symptoms at one or more multiple time points including prior to, during, and after treatment regimens. Treatment can result in improving the subject's condition and can be assessed by determining if one or more of the following events has occurred: decreased tumor size, decreased tumor cell proliferation, decreased numbers of cells, decreased neovascularization and/or increased apoptosis. One or more of these occurrences may, in some cases, result in partial or total elimination of the cancer and prolongation of survival of the patient. Alternatively, for terminal stage cancers, treatment may result in stasis of disease, better quality of life and/or prolongation of survival. Other methods of assessing treatment are known in the art and contemplated herein.

In an exemplary embodiment, the pro-oligonucleotide compounds of the invention are administered to a subject such as a mammal (e.g., a human), suffering from a medical disorder, e.g., a cancer, or non-malignant conditions characterized by the presence of a class of unwanted cells.

Primary outcome measures may be assessed for patients treated using the methods described herein and include, for example, progression-free survival. In one embodiment, an increase in progression free survival is observed in an amount of by about 2-fold, 5-fold, 10-fold, 20 fold, 50 fold or more compared to lack of treatment. In another embodiment, an increase in progression free survival is increased survival by about 3 months, about 6 months, about 9 months, about 12 months, about 18 months, about 2 years, about 3 years, about 4 years, about 5 years or more compared to lack of treatment.

Secondary outcome measures may also be assessed and include duration of response, time to tumor progression, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased neovascularization, reduced side effects, decreased adverse reactions, and/or increased patient compliance.

Other specific examples of diseases or disorders for which treatment by the compounds or compositions of the invention are useful for treatment or prevention include, but are not limited to transplant rejection (e.g., kidney, liver, heart, lung, islet cells, pancreas, bone marrow, cornea, small bowel, skin allografts or xenografts and other transplants), graft vs. host disease, osteoarthritis, rheumatoid arthritis, multiple sclerosis, diabetes, diabetic retinopathy, inflammatory bowel disease (e.g., Crohn's disease, ulcerative colitis, and other bowel diseases), renal disease, cachexia, septic shock, lupus, myasthenia gravis, psoriasis, dermatitis, eczema, seborrhea, Alzheimer's disease, Parkinson's disease, stem cell protection during chemotherapy, ex vivo selection or ex vivo purging for autologous or allogeneic bone marrow transplantation, ocular disease, retinopathies (e.g., macular degeneration, diabetic retinopathy, and other retinopathies), corneal disease, glaucoma, infections (e.g., bacterial, viral, or fungal), heart disease, including, but not limited to, restenosis.

Activation of RNAse L

The 2'-5' oligoadenylate (2-5A)/RNase L pathway is one of the enzymatic pathways induced by interferon. Rnase L is activated after binding to 5'-phosphoroylated fragments of 2'-5' adenylic acid. These fragments of 2'-5' adenylic acid (2-5A) are produced under the control of 2'-5' oligo(A) synthetase. This pathway is part of the innate immune system and has an important role in preventing viral infection. 2-5A-Induced cleavage of single-stranded RNA results in apoptosis. Biostable phosphorothioate analogs of 2-5A have been shown to be potent activators of Rnase L (Xianh et al., Cancer Research (2003), 63:6795-6801). In this study, the 2-5A analogs induced Rnase L activity and caused apoptosis in cultures of late-stage, metastatic human prostate cancer cell lines DU145, PC3 and LNCaP.

Sustained activation of RNase L triggers a mitochondrial pathway of apoptosis that eliminates virus-infected cells as well as cancerous/tumor cells. RNase L can inhibit fibrosarcoma growth, prostate cancer growth, colorectal cancer growth and pancreatic cancer growth. Given the common role of RNase L in different cancers, it is contemplated that the invention described herein can be use for the treatment of any type of cancer. Silverman, R H, Cytokine Growth Factor Rev, 18(5-6): 381-388 (2007); Bisbal, C. and Silverman, R H, *Biochimie*. 89(6-7): 789-798 (2007). By way of example, downregulation of RNase L refers to any reduction in expression levels of the gene or genes encoding RNase L, silencing of the gene or genes encoding RNase L, reduction in the levels of expression/translation of the proteins comprising RNase L, reduction in the amount of RNase L present within a cell, and/or any reduction in activity of RNase L as compared to a predetermined level of RNase L in an exemplary healthy population. Alternatively any reduction in RNase L levels as described herein can be indicative of downregulation of RNase L. In one exemplary embodiment, the compounds described herein are useful for the treatment of diseases having downregulated RNase L. In another embodiment, the disease associated with downregulated RNase L is cancer. In further embodiments, the cancer is pancreatic cancer, prostate cancer, or colorectal cancer. Alternatively, the compounds described herein are useful for the treatment of disease having upregulated RNase L. In one exemplary embodiment, the disease having upregulated RNase L is chronic fatigue syndrome. Additional diseases having upregulated RNase L are known in the art and contemplated herein.

When used as therapeutics, the nucleic acid described herein is administered as a pharmaceutical composition. In some embodiments, the pharmaceutical composition comprises a therapeutically effective amount of a nucleic acid comprising a chiral X-phosphonate moiety of Formula 1, or a pharmaceutically acceptable salt thereof, and at least one pharmaceutically acceptable inactive ingredient selected from pharmaceutically acceptable diluents, pharmaceutically acceptable excipients, and pharmaceutically acceptable carriers. In another embodiment, the pharmaceutical composition is formulated for intravenous injection, oral administration, buccal administration, inhalation, nasal administration, topical administration, ophthalmic administration or otic administration. In further embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

Pharmaceutical Compositions and Administration

In another aspect, the present invention provides a pharmaceutical composition comprising a non-racemic pro-oligonucleotide in admixture with a pharmaceutically acceptable excipient. One of skill in the art will recognize that the pharmaceutical compositions include the pharmaceutically acceptable salts of the non-racemic pro-oligonucleotides described above.

Compounds for Enhancing and Targeting Delivery

The pro-oligonucleotides described herein can be delivered using a variety of delivery strategies, including conjugates of oligonucleotides with various ligands, as well as use of nanocarrier approaches. Any nucleic acid delivery strategies are contemplated for use with the pro-oligonucleotides described herein. The choice between exemplary delivery strategies, including but not limited to, chemical conjugates, cationic lipid/liposomal transfer vessicles and supramolecular nanocarriers depends on the therapeutic context, and methods for determining the optimal delivery modality are known in the art and further contemplated herein.

Cell Penetrating Compounds ("CPCs")

Numerous compounds are known to act as carriers for cargo such as nucleic acids and facilitate entry of the nucleic acid in a cell in an in vivo setting. Exemplary carriers are described in Dietz et al., Molecular & Cellular Neuroscience, 27(2): 85-131 (2004) which is incorporated herein by reference. The prototypical CPCs derived from the Tat and antennepedia transcriptional regulators have been joined by a large number of new moieties. As an example, CPCs that are peptides can be relatively short (9-30 amino acids) polycationic peptides rich in argine and lysine, or membrane-interactive hydrophobic sequences. CPCs can be linked by recombinant DNA techniques or chemically coupled to peptides, oligonucleotides or nanocarriers, which then comprise the 'cargo' for the CPC.

Cell Targeting Ligands ("CTLs")

Another strategy is to deliver oligonucleotides by use of a CTL that binds with high affinity to a cell surface receptor that is capable of undergoing efficient internalization. Potential ligands include antibodies, polypeptides derived from phage display libraries, and small organic molecules. Additional cell-targeting ligands are known in the art, or will be developed, and are contemplated for use with the invention described herein. Because various receptors are often preferentially expressed on particular cell types, this approach offers the possibility of improved selectivity for the oligonucleotide reagents. Exemplary receptor targets include, but are not limited to, lipoprotein receptors (such as those in the liver), integrins, receptor tyrosine kinases, and the G-protein coupled receptor (GPCR) superfamily.

Nanocarriers

A variety of supramolecular nanocarriers can be used to deliver nucleic acids. Exemplary nanocarriers include, but are not limited to liposomes, cationic polymer complexes and various polymeric. Complexation of nucleic acids with various polycations is another approach for intracellular delivery; this includes use of PEGlyated polycations, polyethyleneamine (PEI) complexes, cationic block co-polymers, and dendrimers. Several cationic nanocarriers, including PEI and polyamidoamine dendrimers help to release contents from endosomes. Other approaches include use of polymeric nanoparticles, polymer micelles, quantum dots and lipoplexes.

Additional nucleic acid delivery strategies are known in addition to the exemplary delivery strategies described herein.

In therapeutic and/or diagnostic applications, the compounds of the invention can be formulated for a variety of modes of administration, including systemic and topical or localized administration. Techniques and formulations generally may be found in Remington, The Science and Practice of Pharmacy, (20th ed. 2000).

The compounds according to the invention are effective over a wide dosage range. For example, in the treatment of adult humans, dosages from 0.01 to 1000 mg, from 0.5 to 100 mg, from 1 to 50 mg per day, and from 5 to 100 mg per day are examples of dosages that may be used. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington, The Science and Practice of Pharmacy (20th ed. 2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington, The Science and Practice of Pharmacy (20th ed. 2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, the agents of the invention may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a subject (e.g., patient) to be treated.

For nasal or inhalation delivery, the agents of the invention may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this invention. For example, chemotherapeutic agents or other anti-proliferative agents may be combined with the inhibitors of this invention to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents the non-racemic pro-oligonucleotide of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the non-racemic pro-oligonucleotide-containing composition. Alternatively, these agents may be part of a single dosage form, mixed together with the non-racemic pro-oligonucleotide in a single composition.

The examples and preparations provided below further illustrate and exemplify the compounds of the present invention and methods of preparing such compounds. It is to be understood that the scope of the present invention is not limited in any way by the scope of the following examples and preparations.

EXAMPLES

Example 1

The synthesis of (SP)-1,8-Diazabicyclo[5.4.0]undec-7-enium 5'-O-(tert-butyldiphenylsilyl)thymidin-3'-yl 3'-O-(tert-butyldimethylsilyl)thymidin-5'-yl phosphorothioate [(SP)-4tt] is illustrated in Scheme A 8-Diazabicyclo[5.4.0]undec-7-enium 5'-O-(tert-butyldiphenylsilyl)thymidin-3'-yl phosphonate (1t) (100 μmol) is dried by repeated coevaporations with dry pyridine and then dissolved in dry pyridine (1 mL). N,N'-Bis(2-oxo-3-oxazolidinyl)phosphinic chloride (BopCl; 500 μmol) is added and the mixture is stirred for 5 min. A solution of amino alcohol (L-2) (100 μmol) is repeatedly coevaporated with dry pyridine and dissolved in dry pyridine (1 mL). The aminoalcohol solution is added to the reaction mixture dropwise via syringe, and the mixture is stirred for 5 min under argon. 3'-O-(tert-butyldimethylsilyl)thymidine 3t is dried using repeated coevaporations with dry pyridine and dissolved in

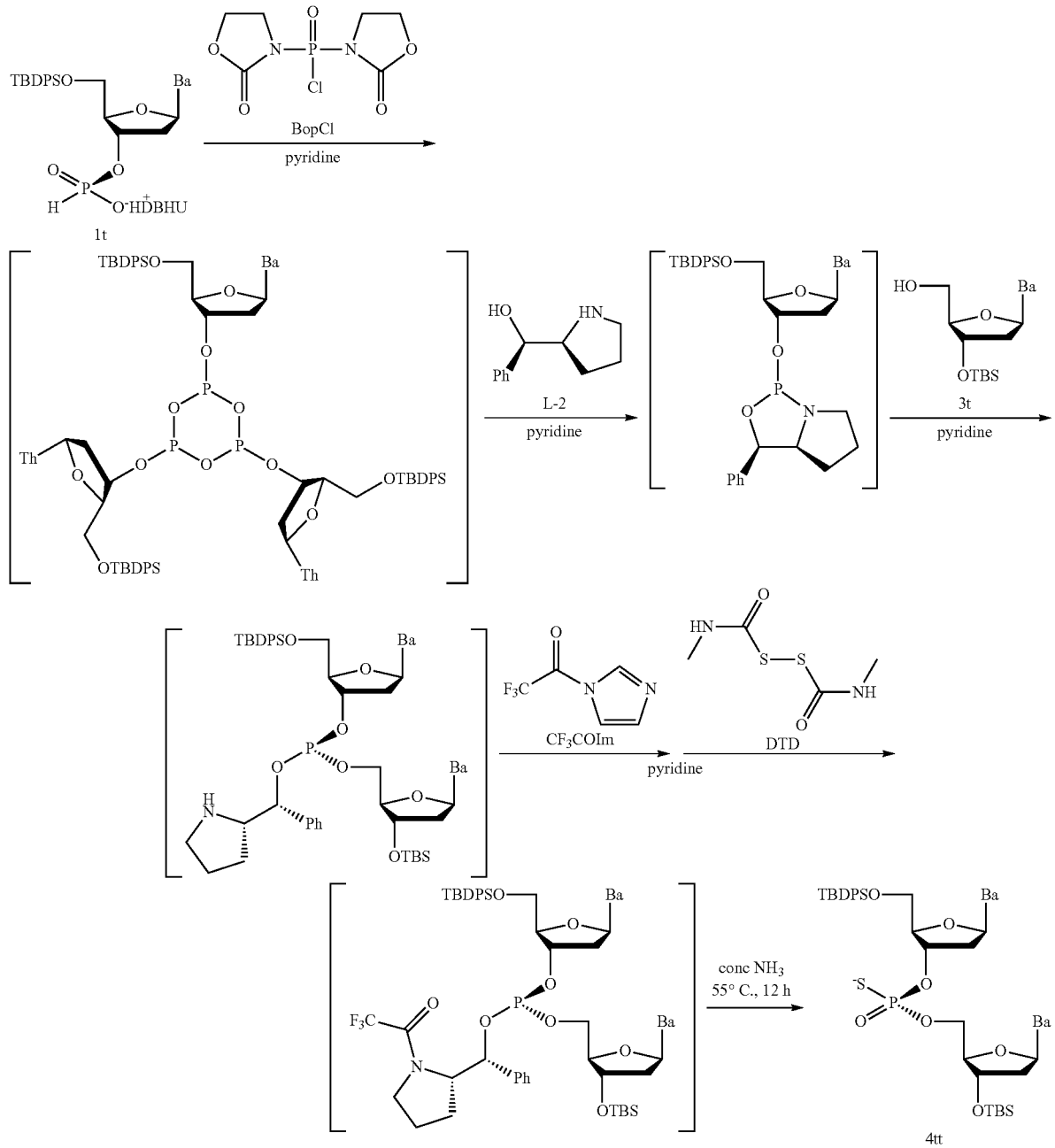

Scheme A

100 µmol pyridine. The above mixture is added via cannula to the solution of 3'-O-(tert-butyldimethylsilyl)thymidine 3t in dry (100 µmol) pyridine. After 5 min, N-trifluoroacetyl imidazole (CF3COIm; 200 µmol) is added. After an additional 30 s, N,N'-dimethylthiuram disulfide (DTD; 120 µmol) is added. Following an additional 3 min, the mixture is dried in vacuum. Concentrated NH3 (10 mL) is added to the residue, and the mixture is heated for 12 h at 55° C. The mixture is then allowed to cool to room temperature and then concentrated to dryness under reduced pressure. The mixture is diluted with CHCl3 (5 mL), and washed with 0.2 M phosphate buffer (pH 7.0, 5 mL). The aqueous layers are back-extracted with CHCl3 (2×5 mL). The combined organic layers are dried over Na2SO4, filtered, and concentrated to dryness under reduced pressure. The residue is purified by PTLC. The product is dissolved in CHCl3 (5 mL), washed with 0.2 M 1,8-diazabicyclo[5.4.0]undec-7-enium bicarbonate buffer (5 mL) and back-extracted with CHCl3 (2×5 mL). The combined organic layers are dried over Na2SO4, filtered, and concentrated to dryness to afford (SP)-4tt.

Example 2

The synthesis of $(S_P)$-1,8-Diazabicyclo[5.4.0]undec-7-enium 6-N-benzoyl-5'-O-(tert-butyldiphenylsilyl)-deoxyadenosin-3'-yl 3'-O-(tert-butyldimethylsilyl)thymidin-5'-yl phosphorothioate [$(S_P)$-4at]

(SP)-4 at is obtained from 1,8-diazabicyclo[5.4.0]undec-7-enium 6-N-benzoyl-5'-O-(tert-butyldiphenylsilyl)-deoxyadenosin-3'-yl phosphonate (1a) instead of 1t, using the reaction steps described in Example 1 and Scheme A for (SP)-4tt.

Example 3

The synthesis of $(S_P)$-1,8-Diazabicyclo[5.4.0]undec-7-enium 4-N-benzoyl-5'-O-(tert-butyldiphenylsilyl)-deoxycytidin-3'-yl 3'-O-(tert-butyldimethylsilyl)thymidin-5'-yl phosphorothioate [$(S_P)$-4ct]

(SP)-4ct is obtained from 1,8-diazabicyclo[5.4.0]undec-7-enium 4-N-benzoyl-5'-O-(tert-butyldiphenylsilyl)-deoxycytidin-3'-yl phosphonate (1c), instead of 1t, using the reaction steps described in Example 1 and Scheme A for (SP)-4tt.

Example 4

The synthesis of $(S_P)$-1,8-Diazabicyclo[5.4.0]undec-7-enium 2-N-phenoxyacetyl-5'-O-(tert-butyldiphenylsilyl)deoxyguanosin-3'-yl 3'-O-(tert-butyldimethylsilyl)thymidin-5'-yl phosphorothioate [$(S_P)$-4gt]

(SP)-4gt is obtained from 1,8-diazabicyclo[5.4.0]undec-7-enium 2-N-phenoxyacetyl-5'-O-(tert-butyldiphenylsilyl) deoxyguanosin-3'-yl phosphonate (1g) instead of 1t, using the reaction steps described in Example 1 and Scheme A for (SP)-4tt.

Example 5

The synthesis of $(R_P)$-1,8-Diazabicyclo[5.4.0]undec-7-enium 5'-O-(tert-butyldiphenylsilyl)thymidin-3'-yl 3'-O-(tert-butyldimethylsilyl)thymidin-5'-yl phosphorothioate [$(R_P)$-4tt]

(RP)-4tt is produced via the transformations described in Example 1 and Scheme A for the synthesis of (SP)-4tt using the amino alcohol D-2 as a chiral reagent, instead of L-2.

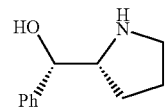

D-2

Example 6

The synthesis of $(R_P)$-1,8-Diazabicyclo[5.4.0]undec-7-enium 6-N-benzoyl-5'-O-(tert-butyldiphenylsilyl)deoxyadenosin-3'-yl 3'-O-(tert-butyldimethylsilyl)thymidin-5'-yl phosphorothioate [$(R_P)$-4at]

(RP)-4 at is produced via the transformations described in Example 2 using compound 1a and the amino alcohol D-2 as a chiral reagent, instead of L-2.

Example 7

The synthesis of $(R_P)$-1,8-Diazabicyclo[5.4.0]undec-7-enium 4-N-benzoyl-5'-O-(tert-butyldiphenylsilyl)deoxycytidin-3'-yl 3'-O-(tert-butyldimethylsilyl)thymidin-5'-yl phosphorothioate [$(R_P)$-4ct]

(RP)-4ct is produced via the transformations described above in Example 3 using compound 1c and the amino alcohol D-2 as a chiral reagent, instead of L-2.

Example 8

The synthesis of $(R_P)$-1,8-Diazabicyclo[5.4.0]undec-7-enium 2-N-phenoxyacetyl-5'-O-(tert-butyldiphenylsilyl)deoxyguanosin-3'-yl3'-O-(tert-butyldimethylsilyl)thymidin-5'-yl phosphorothioate [$(R_P)$-4gt]

(RP)-4gt is produced via the transformations described above in Example 4 using compound 1g and the amino alcohol D-2 as a chiral reagent, instead of L-2.

Scheme B

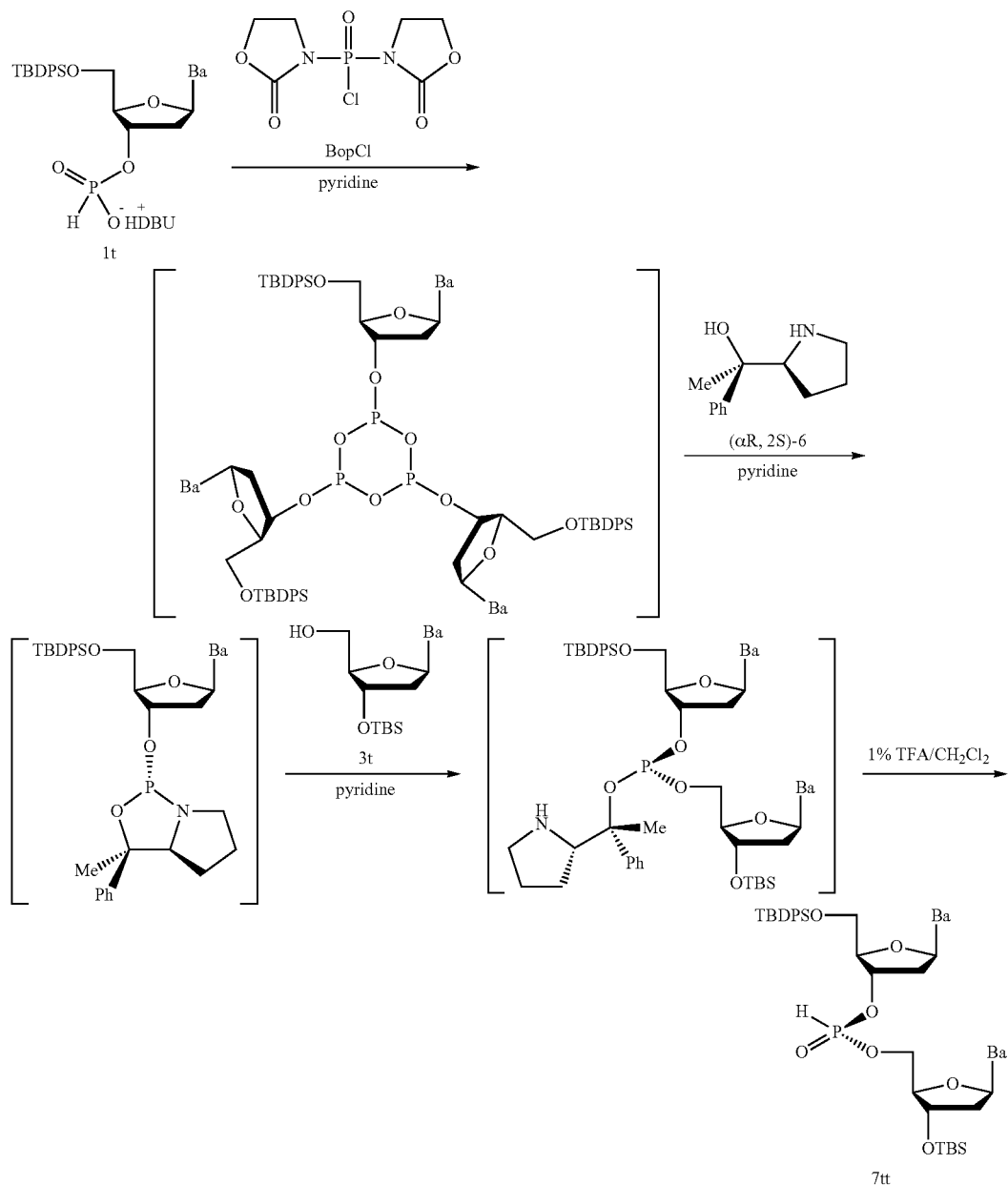

Example 9

Synthesis of (R$_P$)-5'-O-(tert-butyldiphenylsilyl)thymidin-3'-yl3'-O-(tert-butyldimethylsilyl)thymidin-5'-yl H-phosphonate [(R$_P$)-7tt] as described in Scheme B 1t (100 μmol) is dried by repeated coevaporations with dry pyridine and then dissolved in dry pyridine (1 mL). N,N'-Bis(2-oxo-3-oxazolidinyl)phosphinic chloride (BopCl; 500 μmol) is added, and the mixture is stirred for 5 min. To the mixture, a solution of amino alcohol ((αR,2S)-6) (100 μmol), which has been dried by coevaportions with dry pyridine and dissolved in dry pyridine (1 mL), is added dropwise via syringe, and the mixture is stirred for 5 min under argon. 3'-O-(tert-butyldimethylsilyl)thymidine is dried using repeated coevaporations with dry pyridine and dissolved in 100 μmol pyridine. The above mixture is added via cannula to the solution of 3'-O-(tert-butyldimethylsilyl)thymidine 3t in dry (100 μmol) pyridine. After 15 min, the mixture is concentrated under reduced pressure. The residue is diluted with CH$_2$Cl$_2$ (5 mL), and washed with saturated NaHCO3 (3×5 mL). The combined aqueous layers are back-extracted with CH$_2$Cl$_2$ (2×5 mL). The combined organic layers are dried over Na2SO4, filtered, and concentrated to ca. 1 mL under reduced pressure. The residue is added dropwise via a syringe to a stirred 1% trifluoroacetic acid (TFA) solution in dry CH2Cl2 (20 mL) at 0° C. After an additional 5 min, the mixture is diluted with dry CH2Cl2 (100 mL), and washed with saturated NaHCO3 aqueous solutions (2×100 mL). The combined aqueous layers are back-extracted with CH2Cl2 (2×100 mL). The combined organic layers are dried over Na2SO4, filtered, and concentrated to dryness under reduced pressure to afford crude (RP)-7tt.

Example 10

Synthesis of ($R_P$)-6-N-benzoyl-5'-O-(tert-butyldiphenylsilyl)deoxyadenosin-3'-yl 3'-O-(tert-butyldimethylsilyl)thymidin-5'-yl H-phosphonate [($R_P$)-7at]

Crude (RP)-7at is produced as described in Example 9 using 1a instead of 1t.

Example 11

Synthesis of ($R_P$)-4-N-benzoyl-5'-O-(tert-butyldiphenylsilyl)deoxycytidin-3'-yl 3'-O-(tert-butyldimethylsilyl)thymidin-5'-yl H-phosphonate [($R_P$)-7ct]

Crude (RP)-7ct is produced as described in Example 9 using 1c instead of 1t.

Example 12

Synthesis of ($R_P$)-2-N-phenoxyacetyl-5'-O-(tert-butyldiphenylsilyl)deoxyguanosin-3'-yl 3'-O-(tert-butyldimethylsilyl)thymidin-5'-yl H-phosphonate [($R_P$)-7gt]

Crude (RP)-7gt is produced as described in Example 9 using 1 g instead of 1t.

Example 13

Synthesis of ($S_P$)-5'-O-(tert-butyldiphenylsilyl)thymidin-3'-yl 3'-O-(tert-butyldimethylsilyl)thymidin-5'-yl H-phosphonate [($S_P$)-7tt]

Crude (SP)-7tt is produced as described in Example 9 using (αS,2R)-6 instead of (αR,2S)-6 as a chiral reagent.

Example 14

Synthesis of ($S_P$)-6-N-benzoyl-5'-O-(tert-butyldiphenylsilyl)deoxyadenosin-3'-yl 3'-O-(tert-butyldimethylsilyl)thymidin-5'-yl H-phosphonate [($S_P$)-7at]

Crude (SP)-7at is produced as described in Example 9 using compound 1a and (αS,2R)-6 instead of (αR,2S)-6 as a chiral reagent.

Example 15

Synthesis of ($S_P$)-4-N-benzoyl-5'-O-(tert-butyldiphenylsilyl)deoxycytidin-3'-yl 3'-O-(tert-butyldimethylsilyl)thymidin-5'-yl H-phosphonate [($S_P$)-7ct]

Crude (SP)-7ct is produced as described in Example 9 using compound 1c and (αS,2R)-6 instead of (αR,2S)-6 as a chiral reagent.

Example 16

Synthesis of ($S_P$)-2-N-phenoxyacetyl-5'-O-(tert-butyldiphenylsilyl)deoxyguanosin-3'-yl 3'-O-(tert-butyldimethylsilyl)thymidin-5'-yl H-phosphonate [($S_P$)-7gt]

Crude (SP)-7gt is produced as described in Example 9 using compound 1g instead of 1t and compound (αS,2R)-6 instead of compound (αR,2S)-6 as a chiral reagent.

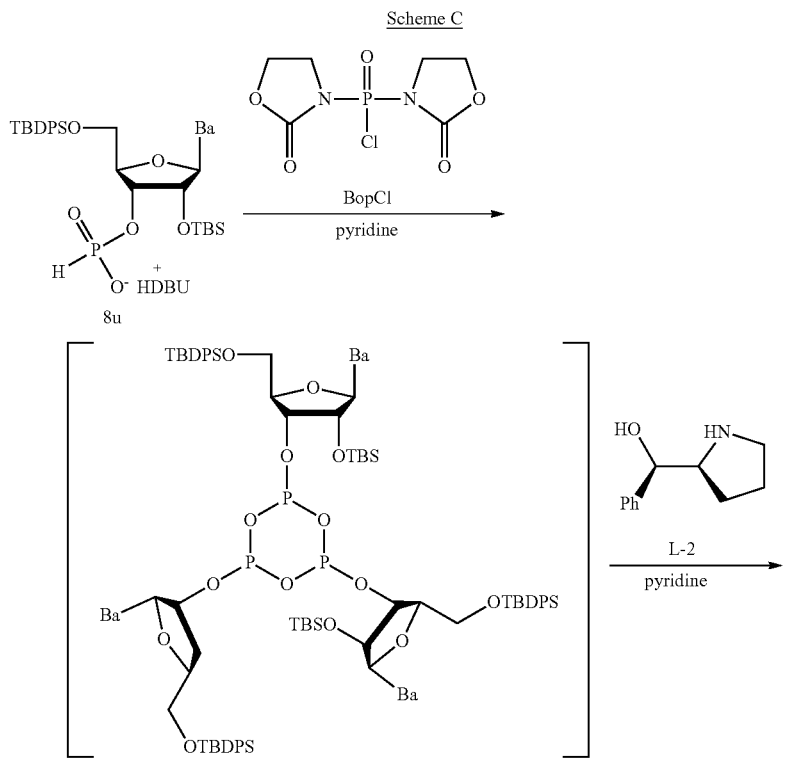

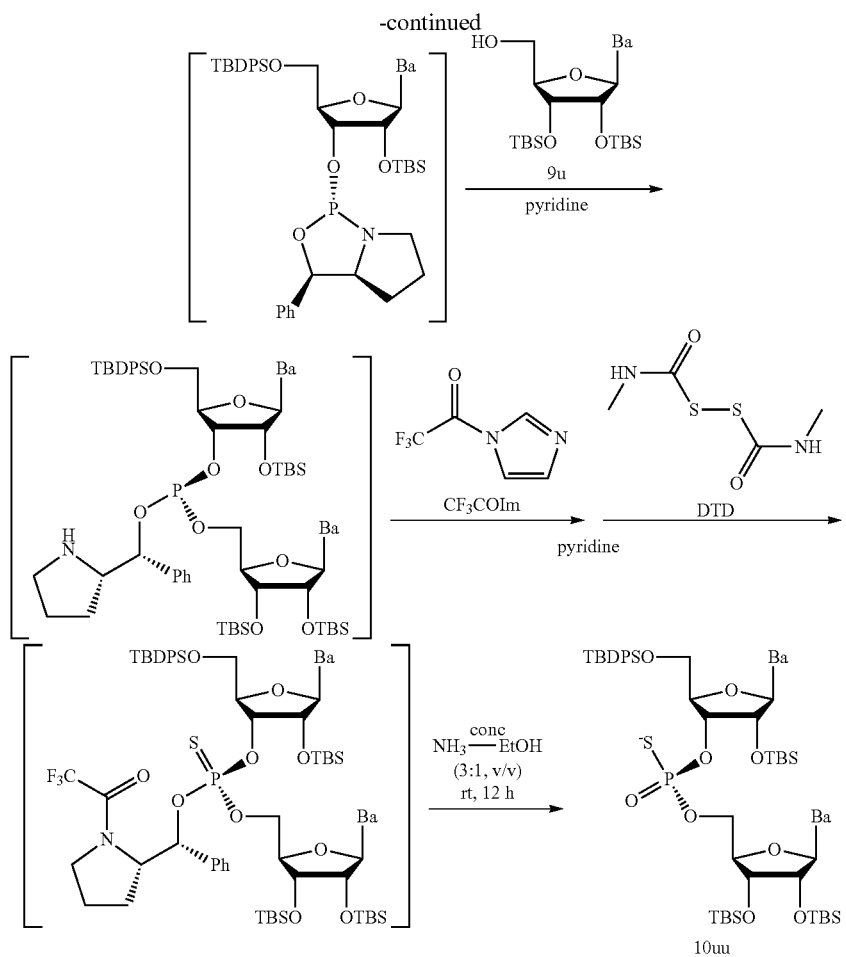

Example 17

Synthesis of (S$_P$)-1,8-Diazabicyclo[5.4.0]undec-7-enium 5'-O-(tert-butyldiphenylsilyl)-2'-O-(tert-butyldimethylsilyl)uridin-3'-yl 2',3'-O-bis(tert-butyldimethylsilyl)uridin-5'-yl phosphorothioate [(S$_P$)-10uu]

1,8-Diazabicyclo[5.4.0]undec-7-enium 5'-O-(tert-butyldiphenylsilyl)-2'-O-(tert-butyldimethylsilyl)uridin-3'-yl phosphonate (8u) (100 µmol) is dried by repeated coevaporations with dry pyridine and then dissolved in dry pyridine (1 mL). N,N'-Bis(2-oxo-3-oxazolidinyl)phosphinic chloride (BopCl; 500 µmol) is added, and the mixture is stirred for 5 min. To the mixture, a solution of amino alcohol (L-2) (100 µmol), which has been dried by repeated coevaportions with dry pyridine and dissolved in dry pyridine (1 mL), is added dropwise via syringe, and the mixture is stirred for 5 min under argon. 2',3'-O-bis(tert-butyldimethylsilyl)uridine 9u is dried by repeated coevaporations with dry pyridine and dissolved in 100 µmol pyridine. Then the above mixture is added via cannula into the solution of 2',3'-O-bis(tert-butyldimethylsilyl)uridine 9u (100 µmol). After 10 min, N-trifluoroacetyl imidazole (CF3COIm; 200 µmol) is added. After an additional 30 s, N,N'-dimethylthiuram disulfide (DTD; 120 µmol) is added. After an additional 3 min, the mixture is dried in vacuum. To the residue, conc NH3-EtOH (3:1, v/v, 10 mL) is added, and the mixture is stirred for 12 h, and then concentrated to dryness under reduced pressure. Then, the mixture is diluted with CHCl3 (5 mL), and washed with 0.2 M phosphate buffer (pH 7.0, 5 mL). The aqueous layers are back-extracted with CHCl3 (2×5 mL). The combined organic layers are dried over Na2SO4, filtered, and concentrated to dryness under reduced pressure. The residue is purified by PTLC. The product is dissolved in CHCl3 (5 mL), washed with 0.2 M 1,8-diazabicyclo[5.4.0]undec-7-enium bicarbonate buffer (5 mL) and back-extracted with CHCl3 (2×5 mL). The combined organic layers are dried over Na2SO4, filtered, and concentrated to dryness to afford (SP)-10uu.

Example 18

Synthesis of (S$_P$)-1,8-Diazabicyclo[5.4.0]undec-7-enium 6-N-benzoyl-5'-O-(tert-butyldiphenylsilyl)-2'-O-(tert-butyldimethylsilyl)adenosin-3'-yl 2',3'-O-bis(tert-butyldimethylsilyl)uridin-5'-yl phosphorothioate [(S$_P$)-10au]

(SP)-10au is produced as described in Example 17 using 1,8-diazabicyclo[5.4.0]undec-7-enium 6-N-benzoyl-5'-O-(tert-butyldiphenylsilyl)-2'-O-(tert-butyldimethylsilyl)adenosin-3'-yl phosphonate (8a) instead of 8u.

Example 19

Synthesis of (S$_P$)-1,8-Diazabicyclo[5.4.0]undec-7-enium 4-N-benzoyl-5'-O-(tert-butyldiphenylsilyl)-2'-O-(tert-butyldimethylsilyl)cytidin-3'-yl 2',3'-O-bis(tert-butyldimethylsilyl)uridin-5'-yl phosphorothioate [(S$_P$)-10cu]

(SP)-10cu is produced as described in Example 17 using 1,8-diazabicyclo[5.4.0]undec-7-enium 4-N-benzoyl-5'-O-(tert-butyldiphenylsilyl)-2'-O-(tert-butyldimethylsilyl)cytidin-3'-yl phosphonate (8c) instead of 8u.

Example 20

Synthesis of (S$_P$)-1,8-Diazabicyclo[5.4.0]undec-7-enium 2-N-phenoxyacetyl-5'-O-(tert-butyldiphenylsilyl)-2'-O-(tert-butyldimethylsilyl)guanosin-3'-yl 2',3'-O-bis(tert-butyldimethylsilyl)uridin-5'-yl phosphorothioate [(S$_P$)-10gu]

(SP)-10gu is produced as described in Example 17 using 1,8-diazabicyclo[5.4.0]undec-7-enium 2-N-phenoxyacetyl-5'-O-(tert-butyldiphenylsilyl)-2'-O-(tert-butyldimethylsilyl)guanosin-3'-yl phosphonate (8g) instead of 8u.

Example 21

Synthesis of (R$_P$)-1,8-Diazabicyclo[5.4.0]undec-7-enium 5'-O-(tert-butyldiphenylsilyl)-2'-O-(tert-butyldimethylsilyl)uridin-3'-yl 2',3'-O-bis(tert-butyldimethylsilyl)uridin-5'-yl phosphorothioate [(R$_P$)-10uu]

(R$_P$)-10uu is produced as described in Example 17 using chiral reagent D-2 instead of chiral reagent L-2.

Example 22

Synthesis of (R$_P$)-1,8-Diazabicyclo[5.4.0]undec-7-enium 6-N-benzoyl-5'-O-(tert-butyldiphenylsilyl)-2'-O-(tert-butyldimethylsilyl)adenosin-3'-yl 2',3'-O-bis(tert-butyldimethylsilyl)uridin-5'-yl phosphorothioate [(R$_P$)-10au]

(RP)-10au is produced as described in Example 17 using 8a instead of 8u and chiral reagent D-2 instead of chiral reagent L-2.

Example 23

Synthesis of (R$_P$)-1,8-Diazabicyclo[5.4.0]undec-7-enium 4-N-benzoyl-5'-O-(tert-butyldiphenylsilyl)-2'-O-(tert-butyldimethylsilyl)cytidin-3'-yl 2',3'-O-bis(tert-butyldimethylsilyl)uridin-5'-yl phosphorothioate [(R$_P$)-10cu]

(RP)-10cu is produced as described in Example 17 using 8c instead of 8u and chiral reagent D-2 instead of chiral reagent L-2.

Example 24

Synthesis of (R$_P$)-1,8-Diazabicyclo[5.4.0]undec-7-enium 2-N-phenoxyacetyl-5'-O-(tert-butyldiphenylsilyl)-2'-O-(tert-butyldimethylsilyl)guanosin-3'-yl 2',3'-O-bis(tert-butyldimethylsilyl)uridin-5'-yl phosphorothioate [(R$_P$)-10gu]

(RP)-10gu is produced as described in Example 17 using 8g instead of 8u and chiral reagent D-2 instead of chiral reagent L-2.

Scheme D

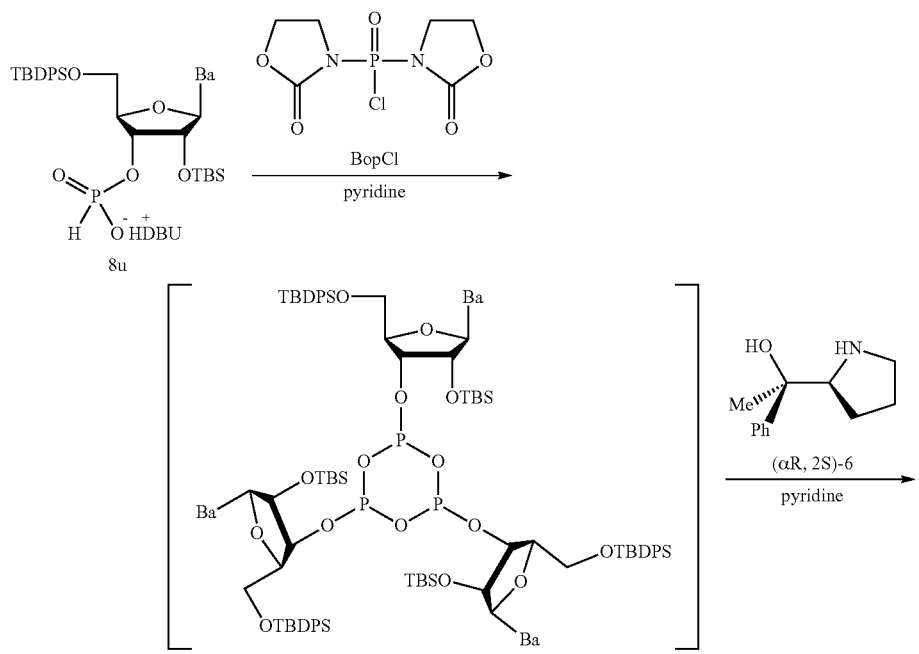

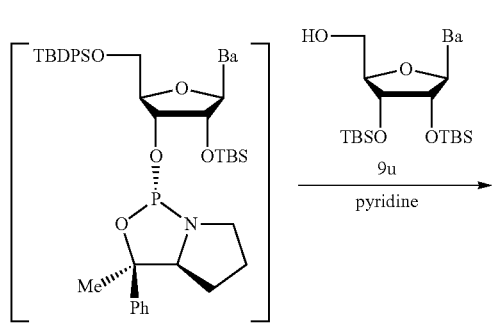
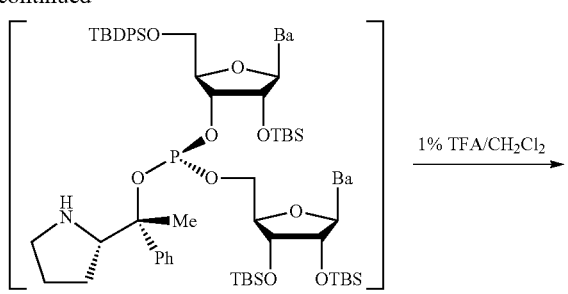
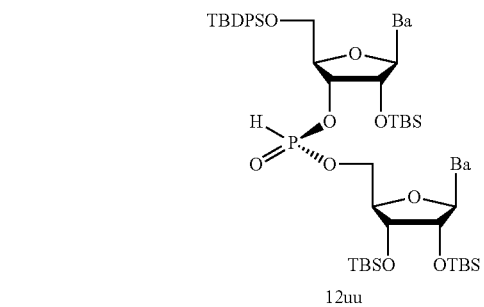

12uu

Example 25

Synthesis of (R$_P$)-5'-O-(tert-butyldiphenylsilyl)-2'-O-(tert-butyldimethylsilyl)uridin-3'-yl 2',3'-O-bis(tert-butyldimethylsilyl)uridin-5'-yl H-phosphonate [(R$_P$)-12uu]

8u (100 μmol) is dried by repeated coevaporations with dry pyridine and then dissolved in dry pyridine (1 mL). N,N'-Bis(2-oxo-3-oxazolidinyl)phosphinic chloride (BopCl; 500 μmol) is added, and the mixture is stirred for 5 min. To the mixture, a solution of amino alcohol ((αR,2S)-6) (100 μmol), which is dried by coevaportions with dry pyridine and dissolved in dry pyridine (1 mL), is added dropwise via syringe, and the mixture is stirred for 5 min under argon. Then the mixture is added via cannula into a solution of 9u (100 μmol), which is prepared by repeated coevaporations with dry pyridine and dissolution in pyridine. After 15 min, the mixture is concentrated under reduced pressure. The residue is diluted with CH2Cl2 (5 mL), and washed with saturated NaHCO3 (3×5 mL). The combined aqueous layers are back-extracted with CH2Cl2 (2×5 mL). The combined organic layers are dried over Na2SO4, filtered, and concentrated to ca. 1 mL under reduced pressure. The residue is added dropwise via a syringe to a stirred 1% trifluoroacetic acid (TFA) solution in dry CH2Cl2 (20 mL) at 0° C. After an additional 5 min, the mixture is diluted with dry CH2Cl2 (100 mL), and washed with saturated NaHCO3 aqueous solutions (2×100 mL). The combined aqueous layers are back-extracted with CH2Cl2 (2×100 mL). The combined organic layers are dried over Na2SO4, filtered, and concentrated to dryness under reduced pressure to afford crude (R$_P$)-12uu, which is analyzed by 31P NMR.

Example 26

Synthesis of (R$_P$)-6-N-Benzoyl-5'-O-(tert-butyldiphenylsilyl)-2'-O-(tert-butyldimethylsilyl)adenosin-3'-yl 2',3'-O-bis(tert-butyldimethylsilyl)uridin-5'-yl H-phosphonate [(R$_P$)-12 au]

Crude (RP)-12au is produced as described in Example 25 using 8a instead of 8u.

Example 27

Synthesis of (R$_P$)-4-N-Benzoyl-5'-O-(tert-butyldiphenylsilyl)-2'-O-(tert-butyldimethylsilyl)cytidin-3'-yl 2',3'-O-bis(tert-butyldimethylsilyl)uridin-5'-yl H-phosphonate [(R$_P$)-12cu]

Crude (RP)-12cu is produced as described in Example 25 using 8c instead of 8u.

Example 28

Synthesis of (R$_P$)-2-N-Phenoxyacetyl-5'-O-(tert-butyldiphenylsilyl)-2'-O-(tert-butyldimethylsilyl)guanosin-3'-yl 2',3'-O-bis(tert-butyldimethylsilyl)uridin-5'-yl H-phosphonate [(R$_P$)-12gu]

Crude (RP)-12gu is produced as described in Example 25 using 8g instead of 8u.

Example 29

Synthesis of (S$_P$)-5'-O-(tert-butyldiphenylsilyl)-2'-O-(tert-butyldimethylsilyl)uridin-3'-yl 2',3'-O-bis(tert-butyldimethylsilyl)uridin-5'-yl H-phosphonate [(S$_P$)-12uu]

Crude (SP)-12uu is produced as described in Example 25 using chiral reagent (αS,2R)-6 instead of chiral reagent (αR,2S)-6.

Example 30

Synthesis of (S$_P$)-6-N-Benzoyl-5'-O-(tert-butyldiphenylsilyl)-2'-O-(tert-butyldimethylsilyl)adenosin-3'-yl 2',3'-O-bis(tert-butyldimethylsilyl)uridin-5'-yl H-phosphonate [(S$_P$)-12au]

Crude (SP)-12au is produced as described in Example 25 using 8a instead of 8u and chiral reagent (αS,2R)-6 instead of chiral reagent (αR,2S)-6.

Example 31

Synthesis of $(S_P)$-4-N-Benzoyl-5'-O-(tert-butyldiphenylsilyl)-2'-O-(tert-butyldimethylsilyl)cytidin-3'-yl 2',3'-O-bis(tert-butyldimethylsilyl)uridin-5'-yl H-phosphonate [$(S_P)$-12cu]

Crude (SP)-12cu is produced as described in Example 25 using 8c instead of 8u and chiral reagent ($\alpha$S,2R)-6 instead of chiral reagent ($\alpha$R,2S)-6.

Example 32

Synthesis of $(S_P)$-2-N-Phenoxyacetyl-5'-O-(tert-butyldiphenylsilyl)-2'-O-(tert-butyldimethylsilyl)guanosin-3'-yl 2',3'-O-bis(tert-butyldimethylsilyl)uridin-5'-yl H-phosphonate [$(S_P)$-12gu]

Crude (SP)-12gu is produced as described in Example 25 using 8g instead of 8u and chiral reagent ($\alpha$S,2R)-6 instead of chiral reagent ($\alpha$R,2S)-6.

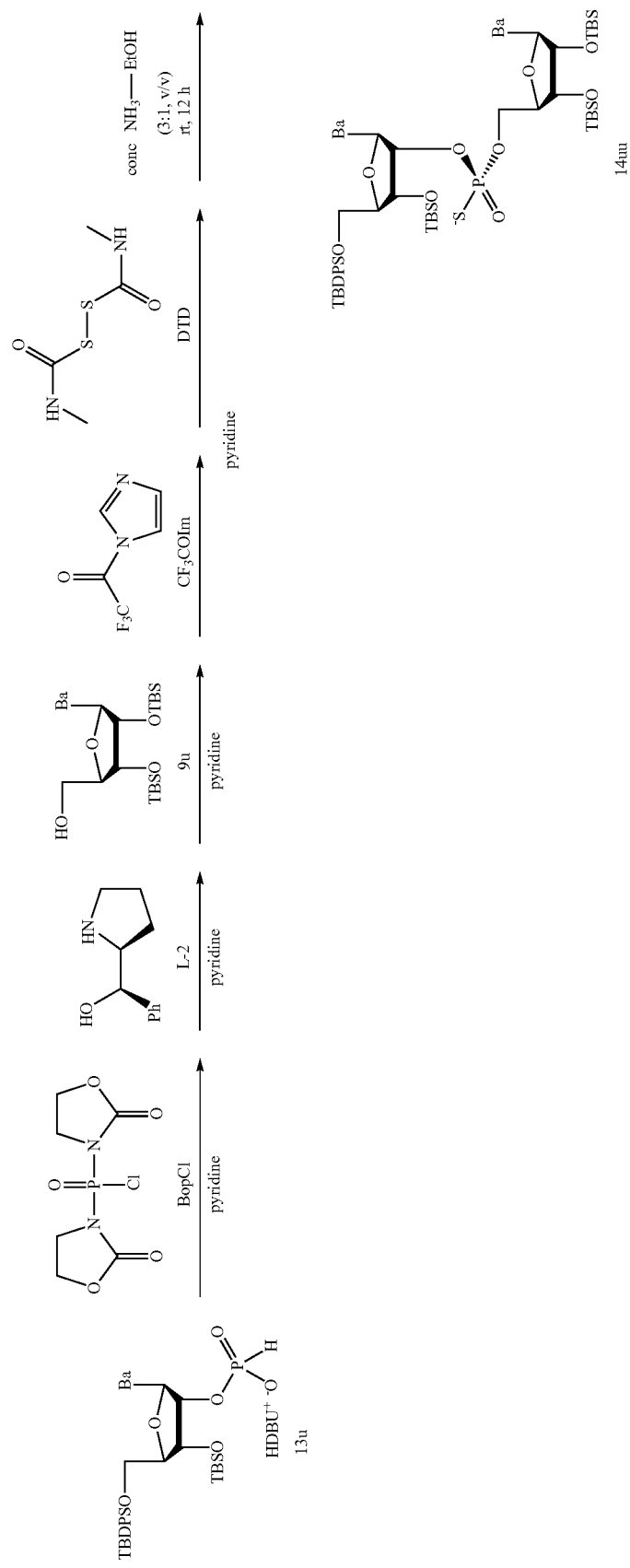

Example 33

Synthesis of (S$_P$)-1,8-Diazabicyclo[5.4.0]undec-7-enium 5'-O-(tert-butyldiphenylsilyl)-3'-O-(tert-butyldimethylsilyl)uridin-2'-yl 2',3'-O-bis(tert-butyldimethylsilyl)uridin-5'-yl phosphorothioate [(S$_P$)-14uu]

1,8-Diazabicyclo[5.4.0]undec-7-enium 5'-O-(tert-butyldiphenylsilyl)-3'-O-(tert-butyldimethylsilyl)uridin-3'-yl phosphonate (13u) (100 µmol) is dried by repeated coevaporations with dry pyridine and then dissolved in dry pyridine (1 mL). N,N'-Bis(2-oxo-3-oxazolidinyl)phosphinic chloride (BopCl; 500 µmol) is added, and the mixture is stirred for 5 min. To the mixture, a solution of amino alcohol (L-2) (100 µmol), which has been dried by repeated coevaportions with dry pyridine and dissolved in dry pyridine (1 mL), is added dropwise via syringe, and the mixture is stirred for 5 min under argon. 2',3'-O-bis(tert-butyldimethylsilyl)uridine 9u is dried by repeated coevaporations with dry pyridine and dissolved in 100 µmol pyridine. Then the above mixture is added via cannula into the solution of 2',3'-O-bis(tert-butyldimethylsilyl)uridine 9u (100 µmol). After 10 min, N-trifluoroacetyl imidazole (CF3COIm; 200 µmol) is added. After an additional 30 s, N,N'-dimethylthiuram disulfide (DTD; 120 µmol) is added. After an additional 3 min, the mixture is dried in vacuum. To the residue, conc NH3-EtOH (3:1, v/v, 10 mL) is added, and the mixture is stirred for 12 h, and then concentrated to dryness under reduced pressure. Then, the mixture is diluted with CHCl3 (5 mL), and washed with 0.2 M phosphate buffer (pH 7.0, 5 mL). The aqueous layers are back-extracted with CHCl3 (2×5 mL). The combined organic layers are dried over Na2SO4, filtered, and concentrated to dryness under reduced pressure. The residue is purified by PTLC. The product is dissolved in CHCl3 (5 mL), washed with 0.2 M 1,8-diazabicyclo[5.4.0]undec-7-enium bicarbonate buffer (5 mL) and back-extracted with CHCl3 (2×5 mL). The combined organic layers are dried over Na2SO4, filtered, and concentrated to dryness to afford (SP)-14uu.

Example 34

Synthesis of (S$_P$)-1,8-Diazabicyclo[5.4.0]undec-7-enium 6-N-benzoyl-5'-O-(tert-butyldiphenylsilyl)-3'-O-(tert-butyldimethylsilyl)adenosin-2'-yl 2',3'-O-bis(tert-butyldimethylsilyl)uridin-5'-yl phosphorothioate [(S$_P$)-14au]

(SP)-14au is produced as described in Example 33 using 1,8-diazabicyclo[5.4.0]undec-7-enium 6-N-benzoyl-5'-O-(tert-butyldiphenylsilyl)-3'-O-(tert-butyldimethylsilyl)adenosin-2'-yl phosphonate (13a) instead of 13u.

Example 35

Synthesis of (S$_P$)-1,8-Diazabicyclo[5.4.0]undec-7-enium 4-N-benzoyl-5'-O-(tert-butyldiphenylsilyl)-3'-O-(tert-butyldimethylsilyl)cytidin-2'-yl 2',3'-O-bis(tert-butyldimethylsilyl)uridin-5'-yl phosphorothioate [(S$_P$)-14cu]

(SP)-14cu is produced as described in Example 33 using 1,8-diazabicyclo[5.4.0]undec-7-enium 4-N-benzoyl-5'-O-(tert-butyldiphenylsilyl)-3'-O-(tert-butyldimethylsilyl)cytidin-2'-yl phosphonate (13c) instead of 13u.

Example 36

Synthesis of (S$_P$)-1,8-Diazabicyclo[5.4.0]undec-7-enium 2-N-phenoxyacetyl-5'-O-(tert-butyldiphenylsilyl)-3'-O-(tert-butyldimethylsilyl)guanosin-2'-yl 2',3'-O-bis(tert-butyldimethylsilyl)uridin-5'-yl phosphorothioate [(S$_P$)-14gu]

(SP)-14gu is produced as described in Example 33 using 1,8-diazabicyclo[5.4.0]undec-7-enium 2-N-phenoxyacetyl-5'-O-(tert-butyldiphenylsilyl)-3'-O-(tert-butyldimethylsilyl)guanosin-2'-yl phosphonate (13g) instead of 13u.

Example 37

Synthesis of (R$_P$)-1,8-Diazabicyclo[5.4.0]undec-7-enium 5'-O-(tert-butyldiphenylsilyl)-3'-O-(tert-butyldimethylsilyl)uridin-2'-yl 2',3'-O-bis(tert-butyldimethylsilyl)uridin-5'-yl phosphorothioate [(R$_P$)-14uu]

(R$_P$)-14uu is produced as described in Example 33 using chiral reagent D-2 instead of chiral reagent L-2.

Example 38

Synthesis of (R$_P$)-1,8-Diazabicyclo[5.4.0]undec-7-enium 6-N-benzoyl-5'-O-(tert-butyldiphenylsilyl)-3'-O-(tert-butyldimethylsilyl)adenosin-2'-yl 2',3'-O-bis(tert-butyldimethylsilyl)uridin-5'-yl phosphorothioate [(R$_P$)-14au]

(RP)-14au is produced as described in Example 33 using 13a instead of 13u and chiral reagent D-2 instead of chiral reagent L-2.

Example 39

Synthesis of (R$_P$)-1,8-Diazabicyclo[5.4.0]undec-7-enium 4-N-benzoyl-5'-O-(tert-butyldiphenylsilyl)-3'-O-(tert-butyldimethylsilyl)cytidin-2'-yl 2',3'-O-bis(tert-butyldimethylsilyl)uridin-5'-yl phosphorothioate [(R$_P$)-14cu]

(RP)-14cu is produced as described in Example 33 using 13c instead of 13u and chiral reagent D-2 instead of chiral reagent L-2.

Example 40

Synthesis of (R$_P$)-1,8-Diazabicyclo[5.4.0]undec-7-enium 2-N-phenoxyacetyl-5'-O-(tert-butyldiphenylsilyl)-3'-O-(tert-butyldimethylsilyl)guanosin-2'-yl 2',3'-O-bis(tert-butyldimethylsilyl)uridin-5'-yl phosphorothioate [(R$_P$)-14gu]

(RP)-14gu is produced as described in Example 33 using 13g instead of 13u and chiral reagent D-2 instead of chiral reagent L-2.

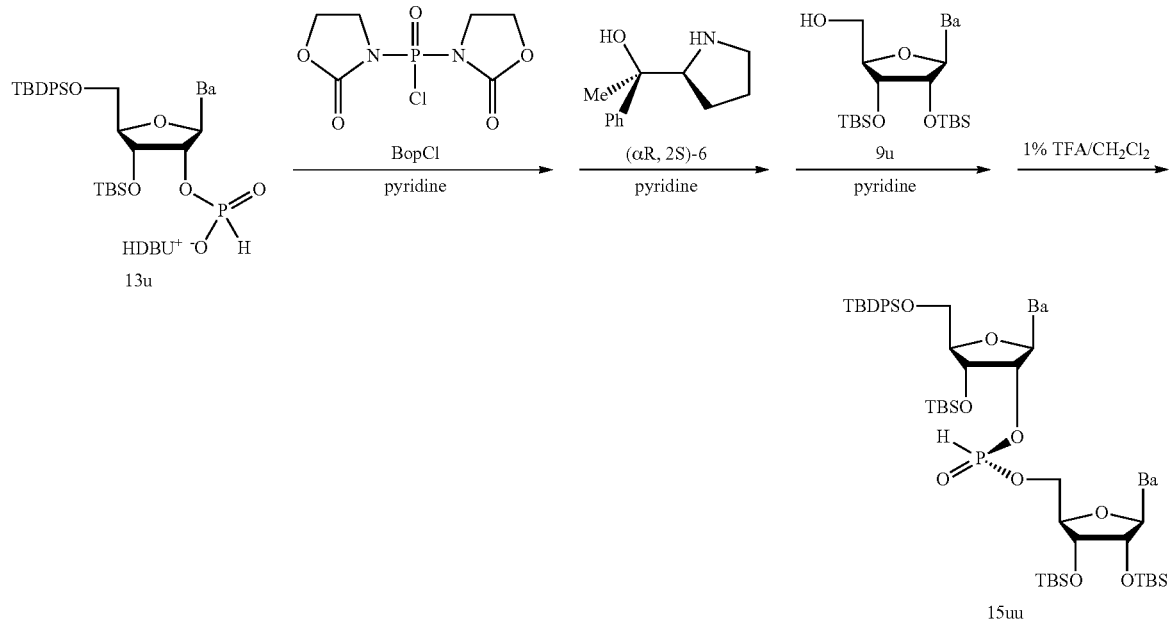

Scheme F

Example 41

Synthesis of (R_P)-5'-O-(tert-butyldiphenylsilyl)-3'-O-(tert-butyldimethylsilyl)uridin-2'-yl 2',3'-O-bis(tert-butyldimethylsilyl)uridin-5'-yl H-phosphonate [(R_P)-15uu]

13u (100 µmol) is dried by repeated coevaporations with dry pyridine and then dissolved in dry pyridine (1 mL). N,N'-Bis(2-oxo-3-oxazolidinyl)phosphinic chloride (BopCl; 500 µmol) is added, and the mixture is stirred for 5 min. To the mixture, a solution of amino alcohol ((αR,2S)-6) (100 µmol), which is dried by coevaportions with dry pyridine and dissolved in dry pyridine (1 mL), is added dropwise via syringe, and the mixture is stirred for 5 min under argon. Then the mixture is added via cannula into a solution of 9u (100 µmol), which is prepared by repeated coevaporations with dry pyridine and dissolution in pyridine. After 15 min, the mixture is concentrated under reduced pressure. The residue is diluted with CH2Cl2 (5 mL), and washed with saturated NaHCO3 (3×5 mL). The combined aqueous layers are back-extracted with CH2Cl2 (2×5 mL). The combined organic layers are dried over Na2SO4, filtered, and concentrated to ca. 1 mL under reduced pressure. The residue is added dropwise via a syringe to a stirred 1% trifluoroacetic acid (TFA) solution in dry CH2Cl2 (20 mL) at 0° C. After an additional 5 min, the mixture is diluted with dry CH2Cl2 (100 mL), and washed with saturated NaHCO3 aqueous solutions (2×100 mL). The combined aqueous layers are back-extracted with CH2Cl2 (2×100 mL). The combined organic layers are dried over Na2SO4, filtered, and concentrated to dryness under reduced pressure to afford crude (R_P)-15uu, which is analyzed by 31P NMR.

Example 42

Synthesis of (R_P)-6-N-Benzoyl-5'-O-(tert-butyldiphenylsilyl)-3'-O-(tert-butyldimethylsilyl)adenosin-2'-yl 2',3'-O-bis(tert-butyldimethylsilyl)uridin-5'-yl H-phosphonate [(R_P)-15 au]

Crude (RP)-15au is produced as described in Example 41 using 13a instead of 13u.

Example 43

Synthesis of (R_P)-4-N-Benzoyl-5'-O-(tert-butyldiphenylsilyl)-3'-O-(tert-butyldimethylsilyl)cytidin-2'-yl 2',3'-O-bis(tert-butyldimethylsilyl)uridin-5'-yl H-phosphonate [(R_P)-15cu]

Crude (RP)-15cu is produced as described in Example 41 using 13c instead of 13u.

Example 44

Synthesis of (R_P)-2-N-Phenoxyacetyl-5'-O-(tert-butyldiphenylsilyl)-3'-O-(tert-butyldimethylsilyl)guanosin-2'-yl 2',3'-O-bis(tert-butyldimethylsilyl)uridin-5'-yl H-phosphonate [(R_P)-15gu]

Crude (RP)-15gu is produced as described in Example 41 using 13g instead of 13u.

Example 45

Synthesis of (S_P)-5'-O-(tert-butyldiphenylsilyl)-3'-O-(tert-butyldimethylsilyl)uridin-2'-yl 2',3'-O-bis(tert-butyldimethylsilyl)uridin-5'-yl H-phosphonate [(S_P)-15uu]

Crude (SP)-15uu is produced as described in Example 41 using chiral reagent (αS,2R)-6 instead of chiral reagent (αR,2S)-6.

Example 46

Synthesis of (S$_P$)-6-N-Benzoyl-5'-O-(tert-butyldiphenylsilyl)-3'-O-(tert-butyldimethylsilyl)adenosin-2'-yl 2',3'-O-bis(tert-butyldimethylsilyl)uridin-5'-yl H-phosphonate [(S$_P$)-15 au]

Crude (SP)-15au is produced as described in Example 41 using 13a instead of 13u and chiral reagent (αS,2R)-6 instead of chiral reagent (αR,2S)-6.

Example 47

Synthesis of (S$_P$)-4-N-Benzoyl-5'-O-(tert-butyldiphenylsilyl)-3'-O-(tert-butyldimethylsilyl)cytidin-2'-yl 2',3'-O-bis(tert-butyldimethylsilyl)uridin-5'-yl H-phosphonate [(S$_P$)-15cu]

Crude (SP)-15cu is produced as described in Example 41 using 13c instead of 13u and chiral reagent (αS,2R)-6 instead of chiral reagent (αR,2S)-6.

Example 48

Synthesis of (S$_P$)-2-N-Phenoxyacetyl-5'-O-(tert-butyldiphenylsilyl)-3'-O-(tert-butyldimethylsilyl) guanosin-2'-yl 2',3'-O-bis(tert-butyldimethylsilyl) uridin-5'-yl H-phosphonate [(S$_P$)-15gu]

Crude (SP)-15gu is produced as described in Example 41 using 13g instead of 13u and chiral reagent (αS,2R)-6 instead of chiral reagent (αR,2S)-6.

Scheme G: Synthesis of S-acyl-2-thioethyl nucleic acid prodrugs.

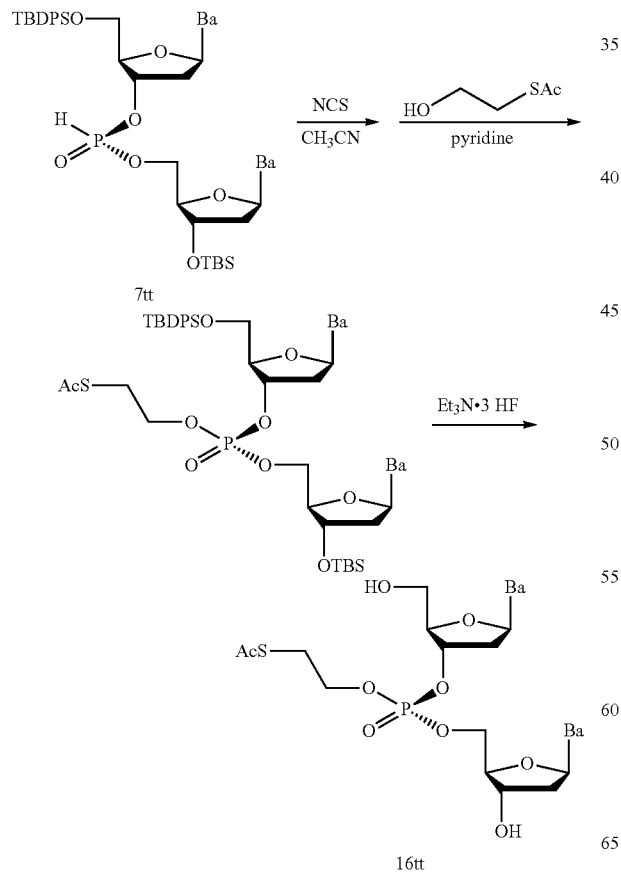

Example 49

Synthesis of the S-acyl-2-thioethyl nucleic acid prodrug of (R$_P$)-thymidin-3'-yl thymidin-5'-yl phosphonate [(R$_P$)-16tt] as described in Scheme G (RP)-5'-O-(tert-butyldiphenylsilyl)thymidin-3'-yl 3'-O-(tert-butyldimethylsilyl)thymidin-5'-yl H-phosphonate [(RP)-7tt] (100 µmol) is dried by repeated coevaporations with dry pyridine and then dissolved in dry pyridine (1 mL). N-chlorosuccinimide (0.1 mmol) is added, and the mixture is stirred for 2 hours at 0° C. The mixture is concentrated and dissolved in dry pyridine (1 mL). The above mixture is treated with 5-acetyl-2-thioethanol (100 µmol) in dry (100 µmol) pyridine. After 1 hour, the mixture is concentrated and then dissolved in triethylamine trihydrofluoride (500 µL). The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-16tt.

Example 50

Synthesis of the S-acyl-2-thioethyl pronucleotide of (R$_P$)-6-N-benzoyl-deoxyadenosin-3'-yl thymidin-5'-yl phosphonate [(R$_P$)-16at]

Crude (RP)-16 at is produced as described in Example 49 using (RP)-7at instead of (RP)-7tt.

Example 51

Synthesis of the S-acyl-2-thioethyl pronucleotide of (R$_P$)-4-N-benzoyl-deoxycytidin-3'-yl thymidin-5'-yl phosphonate [(R$_P$)-16ct]

Crude (RP)-16ct is produced as described in Example 49 using (RP)-7ct instead of (RP)-7tt.

Example 52

Synthesis of the S-acyl-2-thioethyl pronucleotide of (R$_P$)-2-N-phenoxyacetyl-deoxyguanosin-3'-yl thymidin-5'-yl phosphonate [(R$_P$)-16gt]

Crude (RP)-16gt is produced as described in Example 49 using (RP)-7g instead of (RP)-7tt.

Example 53

Synthesis of the S-acyl-2-thioethyl pronucleotide of (S$_P$)-thymidin-3'-yl thymidin-5'-yl phosphonate [(S$_P$)-16tt]

Crude (SP)-16tt is produced as described in Example 49 using (SP)-7tt instead of (RP)-7tt.

Example 54

Synthesis of the S-acyl-2-thioethyl pronucleotide of (S$_P$)-6-N-benzoyl-deoxyadenosin-3'-yl thymidin-5'-yl phosphonate [(S$_P$)-16at]

Crude (SP)-16 at is produced as described in Example 49 using (SP)-7at instead of (RP)-7tt.

Example 55

Synthesis of the S-acyl-2-thioethyl pronucleotide of (S$_P$)-4-N-benzoyl-deoxycytidin-3'-yl thymidin-5'-yl phosphonate [(S$_P$)-16ct]

Crude (SP)-16ct is produced as described in Example 49 using (SP)-7ct instead of (RP)-7tt.

Example 56

Synthesis of the S-acyl-2-thioethyl pronucleotide of (S$_P$)-2-N-phenoxyacetyl-deoxyguanosin-3'-yl thymidin-5'-yl phosphonate [(S$_P$)-16gt]

Crude (SP)-16gt is produced as described in Example 49 using (SP)-7gt instead of (RP)-7tt.

Example 57

Synthesis of the S-acyl-2-thioethyl pronucleotide of (R$_P$)-uridin-3'-yl uridin-5'-yl phosphonate [(R$_P$)-16uu]

Crude (RP)-16uu is produced as described in Example 49 using (RP)-12uu instead of (RP)-7tt.

Example 58

Synthesis of the S-acyl-2-thioethyl pronucleotide of (R$_P$)-6-N-Benzoyl-adenosin-3'-yl uridin-5'-yl phosphonate [(R$_P$)-16au]

Crude (RP)-16au is produced as described in Example 49 using (RP)-12au instead of (RP)-7tt.

Example 59

Synthesis of the S-acyl-2-thioethyl pronucleotide of (R$_P$)-4-N-Benzoyl-cytidin-3'-yl uridin-5'-yl phosphonate [(R$_P$)-16cu]

Crude (RP)-16cu is produced as described in Example 49 using (RP)-12cu instead of (RP)-7tt.

Example 60

Synthesis of the S-acyl-2-thioethyl pronucleotide of (R$_P$)-2-N-Phenoxyacetyl-guanosin-3'-yl uridin-5'-yl phosphonate [(R$_P$)-16gu]

Crude (RP)-16gu is produced as described in Example 49 using (RP)-12gu instead of (RP)-7tt.

Example 61

Synthesis of the S-acyl-2-thioethyl pronucleotide of (S$_P$)-uridin-3'-yl uridin-5'-yl phosphonate [(S$_P$)-16uu]

Crude (SP)-16uu is produced as described in Example 49 using (SP)-12uu instead of (RP)-7tt.

Example 62

Synthesis of the S-acyl-2-thioethyl pronucleotide of (S$_P$)-6-N-Benzoyl-adenosin-3'-yl uridin-5'-yl phosphonate [(S$_P$)-16au]

Crude (SP)-16au is produced as described in Example 49 using (SP)-12au instead of (RP)-7tt.

Example 63

Synthesis of the S-acyl-2-thioethyl pronucleotide of (S$_P$)-4-N-Benzoyl-cytidin-3'-yl uridin-5'-yl phosphonate [(S$_P$)-16cu]

Crude (SP)-16cu is produced as described in Example 49 using (SP)-12au instead of (RP)-7tt.

Example 64

Synthesis of the S-acyl-2-thioethyl pronucleotide of (S$_P$)-2-N-Phenoxyacetyl-guanosin-3'-yl uridin-5'-yl phosphonate [(S$_P$)-16gu]

Crude (SP)-16gu is produced as described in Example 49 using (SP)-12gu instead of (RP)-7tt.

Example 65

Synthesis of the S-acyl-2-thioethyl pronucleotide of (R$_P$)-uridin-2'-yl uridin-5'-yl phosphonate [(R$_P$)-17uu]

Crude (SP)-17uu is produced as described in Example 49 using (SP)-15uu instead of (RP)-7tt.

Example 66

Synthesis of the S-acyl-2-thioethyl pronucleotide of (R$_P$)-6-N-Benzoyl-adenosin-2'-yl uridin-5'-yl phosphonate [(R$_P$)-17au]

Crude (RP)-17au is produced as described in Example 49 using (SP)-15au instead of (RP)-7tt.

Example 67

Synthesis of the S-acyl-2-thioethyl pronucleotide of (R$_P$)-4-N-Benzoyl-cytidin-2'-yl uridin-5'-yl phosphonate [(R$_P$)-17cu]

Crude (RP)-17cu is produced as described in Example 49 using (SP)-15cu instead of (RP)-7tt.

Example 68

Synthesis of the S-acyl-2-thioethyl pronucleotide of ($R_P$)-2-N-Phenoxyacetyl-guanosin-2'-yl uridin-5'-yl H-phosphonate [($R_P$)-17gu]

Crude (RP)-17gu is produced as described in Example 49 using (SP)-15gu instead of (RP)-7tt.

Example 69

Synthesis of the S-acyl-2-thioethyl pronucleotide of ($S_P$)-uridin-2'-yl uridin-5'-yl phosphonate [($S_P$)-17uu]

Crude (SP)-17uu is produced as described in Example 49 using (SP)-15uu instead of (RP)-7tt.

Example 70

Synthesis of the S-acyl-2-thioethyl pronucleotide of ($S_P$)-6-N-Benzoyl-adenosin-2'-yl uridin-5'-yl phosphonate [($S_P$)-17au]

Crude (SP)-17au is produced as described in Example 49 using (SP)-15au instead of (RP)-7tt.

Example 71

Synthesis of the S-acyl-2-thioethyl pronucleotide of ($S_P$)-4-N-Benzoyl-cytidin-2'-yl uridin-5'-yl phosphonate [($S_P$)-17cu]

Crude (SP)-17cu is produced as described in Example 49 using (SP)-15cu instead of (RP)-7tt.

Example 72

Synthesis of the S-acyl-2-thioethyl pronucleotide of ($S_P$)-2-N-Phenoxyacetyl-guanosin-2'-yl uridin-5'-yl phosphonate [($S_P$)-17gu]

Crude (SP)-17gu is produced as described in Example 49 using (SP)-15gu instead of (RP)-7tt.

Scheme H: Synthesis of acyloxy pronucleotides.

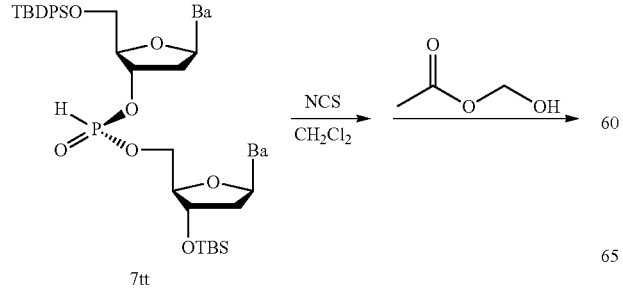

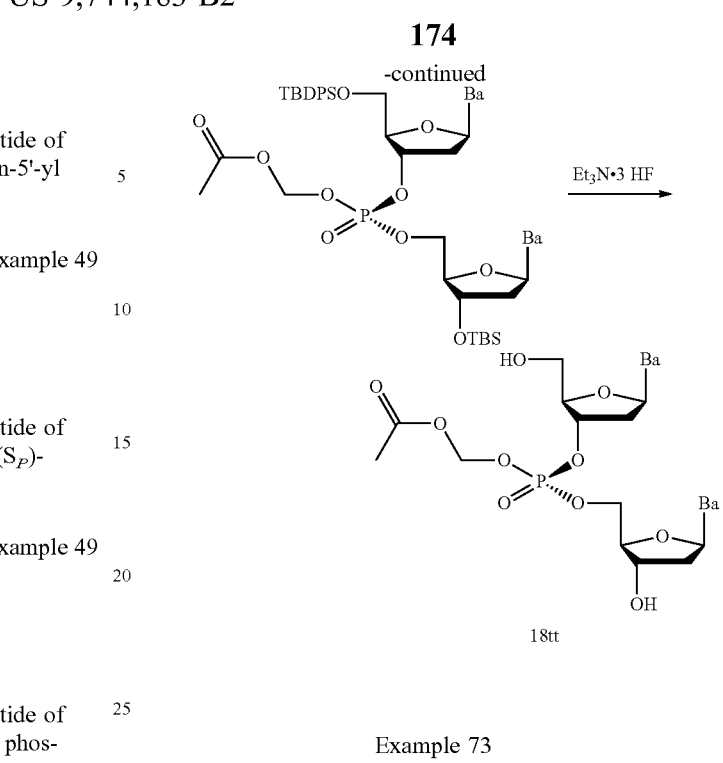

Example 73

Synthesis of the acyloxy pronucleotide of ($R_P$)-thymidin-3'-yl thymidin-5'-yl phosphonate [($R_P$)-18tt] as described in Scheme H (RP)-5'-O-(tert-butyldiphenylsilyl)thymidin-3'-yl 3'-O-(tert-butyldimethylsilyl)thymidin-5'-yl H-phosphonate [(RP)-7tt] (100 µmol) is dried by repeated coevaporations with dry pyridine and then dissolved in dry pyridine (1 mL). N-chlorosuccinimide (0.1 mmol) is added, and the mixture is stirred for 2 hours at 0° C. The mixture is concentrated and dissolved in dry pyridine (1 mL). The above mixture is treated with hydroxymethyl acetate, (100 µmol) in dry (100 µmol) methylene chloride. After 1 hour, the mixture is concentrated and then dissolved in triethylamine trihydrofluoride (500 µL). The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-18tt.

Example 74

Synthesis of the acyloxy pronucleotide of ($R_P$)-6-N-benzoyl-deoxyadenosin-3'-yl thymidin-5'-yl phosphonate [($R_P$)-18at]

Crude (RP)-18 at is produced as described in Example 73 using (RP)-7at instead of (RP)-7tt.

Example 75

Synthesis of the acyloxy pronucleotide of $(R_P)$-4-N-benzoyl-deoxycytidin-3'-yl thymidin-5'-yl phosphonate [$(R_P)$-18ct]

Crude (RP)-18ct is produced as described in Example 73 using (RP)-7ct instead of (RP)-7tt.

Example 76

Synthesis of the acyloxy pronucleotide of $(R_P)$-2-N-phenoxyacetyl-deoxyguanosin-3'-yl thymidin-5'-yl phosphonate [$(R_P)$-18gt]

Crude (RP)-18gt is produced as described in Example 73 using (RP)-7g instead of (RP)-7tt.

Example 77

Synthesis of the acyloxy pronucleotide of $(S_P)$-thymidin-3'-yl thymidin-5'-yl phosphonate [$(S_P)$-18tt]

Crude (SP)-18tt is produced as described in Example 73 using (SP)-7tt instead of (RP)-7tt.

Example 78

Synthesis of the acyloxy pronucleotide of $(S_P)$-6-N-benzoyl-deoxyadenosin-3'-yl thymidin-5'-yl phosphonate [$(S_P)$-18at]

Crude (SP)-18 at is produced as described in Example 73 using (SP)-7at instead of (RP)-7tt.

Example 79

Synthesis of the acyloxy pronucleotide of $(S_P)$-4-N-benzoyl-deoxycytidin-3'-yl thymidin-5'-yl phosphonate [$(S_P)$-18ct]

Crude (SP)-18ct is produced as described in Example 73 using (SP)-7ct instead of (RP)-7tt.

Example 80

Synthesis of the acyloxy pronucleotide of $(S_P)$-2-N-phenoxyacetyl-deoxyguanosin-3'-yl thymidin-5'-yl phosphonate [$(S_P)$-18gt]

Crude (SP)-18gt is produced as described in Example 73 using (SP)-7gt instead of (RP)-7tt.

Example 81

Synthesis of the acyloxy pronucleotide of $(R_P)$-uridin-3'-yl uridin-5'-yl phosphonate [$(R_P)$-18uu]

Crude (RP)-18uu is produced as described in Example 73 using (RP)-12uu instead of (RP)-7tt.

Example 82

Synthesis of the acyloxy pronucleotide of $(R_P)$-6-N-Benzoyl-adenosin-3'-yl uridin-5'-yl phosphonate [$(R_P)$-18au]

Crude (RP)-18au is produced as described in Example 73 using (RP)-12au instead of (RP)-7tt.

Example 83

Synthesis of the acyloxy pronucleotide of $(R_P)$-4-N-Benzoyl-cytidin-3'-yl uridin-5'-yl phosphonate [$(R_P)$-18cu]

Crude (RP)-18cu is produced as described in Example 73 using (RP)-12cu instead of (RP)-7tt.

Example 84

Synthesis of the acyloxy pronucleotide of $(R_P)$-2-N-Phenoxyacetyl-guanosin-3'-yl uridin-5'-yl phosphonate [$(R_P)$-18gu]

Crude (RP)-18gu is produced as described in Example 73 using (RP)-12gu instead of (RP)-7tt.

Example 85

Synthesis of the acyloxy pronucleotide of $(S_P)$-uridin-3'-yl uridin-5'-yl phosphonate [$(S_P)$-18uu]

Crude (SP)-18uu is produced as described in Example 73 using (SP)-12uu instead of (RP)-7tt.

Example 86

Synthesis of the acyloxy pronucleotide of $(S_P)$-6-N-Benzoyl-adenosin-3'-yl uridin-5'-yl phosphonate [$(S_P)$-18 au]

Crude (SP)-18au is produced as described in Example 73 using (SP)-12au instead of (RP)-7tt.

Example 87

Synthesis of the acyloxy pronucleotide of $(S_P)$-4-N-Benzoyl-cytidin-3'-yl uridin-5'-yl phosphonate [$(S_P)$-18cu]

Crude (SP)-18cu is produced as described in Example 73 using (SP)-12au instead of (RP)-7tt.

Example 88

Synthesis of the acyloxy pronucleotide of $(S_P)$-2-N-Phenoxyacetyl-guanosin-3'-yl uridin-5'-yl phosphonate [$(S_P)$-18gu]

Crude (SP)-18gu is produced as described in Example 73 using (SP)-12gu instead of (RP)-7tt.

Example 89

Synthesis of the acyloxy pronucleotide of ($R_P$)-uridin-2'-yl uridin-5'-yl phosphonate [($R_P$)-19uu]

Crude (SP)-19uu is produced as described in Example 73 using (SP)-15uu instead of (RP)-7tt.

Example 90

Synthesis of the acyloxy pronucleotide of ($R_P$)-6-N-Benzoyl-adenosin-2'-yl uridin-5'-yl phosphonate [($R_P$)-19au]

Crude (RP)-19au is produced as described in Example 73 using (SP)-15au instead of (RP)-7tt.

Example 91

Synthesis of the acyloxy pronucleotide of ($R_P$)-4-N-Benzoyl-cytidin-2'-yl uridin-5'-yl phosphonate [($R_P$)-19cu]

Crude (RP)-19cu is produced as described in Example 73 using (SP)-15cu instead of (RP)-7tt.

Example 92

Synthesis of the acyloxy pronucleotide of ($R_P$)-2-N-Phenoxyacetyl-guanosin-2'-yl uridin-5'-yl phosphonate [($R_P$)-19gu]

Crude (RP)-19gu is produced as described in Example 73 using (SP)-15gu instead of (RP)-7tt.

Example 93

Synthesis of the acyloxy pronucleotide of ($S_P$)-uridin-2'-yl uridin-5'-yl phosphonate [($S_P$)-19uu]

Crude (SP)-19uu is produced as described in Example 73 using (SP)-15uu instead of (RP)-7tt.

Example 94

Synthesis of the acyloxy pronucleotide of ($S_P$)-6-N-Benzoyl-adenosin-2'-yl uridin-5'-yl phosphonate [($S_P$)-19au]

Crude (SP)-19au is produced as described in Example 73 using (SP)-15au instead of (RP)-7tt.

Example 95

Synthesis of the acyloxy pronucleotide of ($S_P$)-4-N-Benzoyl-cytidin-2'-yl uridin-5'-yl phosphonate [($S_P$)-19cu]

Crude (SP)-19cu is produced as described in Example 73 using (SP)-15cu instead of (RP)-7tt.

Example 96

Synthesis of the acyloxy pronucleotide of ($S_P$)-2-N-Phenoxyacetyl-guanosin-2'-yl uridin-5'-yl phosphonate [($S_P$)-19gu]

Crude (SP)-19gu is produced as described in Example 73 using (SP)-15gu instead of (RP)-7tt.

Scheme I: Synthesis of thioacyloxy pronucleotides.

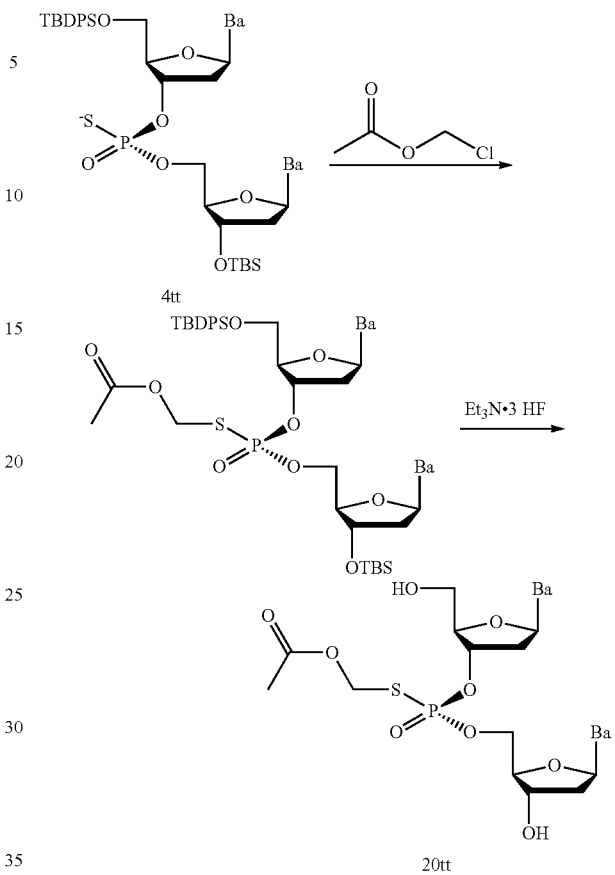

Example 97

Synthesis of the thioacyloxy pronucleotide of ($R_P$)-thymidin-3'-yl thymidin-5'-yl phosphorothioate [($R_P$)-20tt] as described in Scheme I (SP)-1,8-Diazabicyclo[5.4.0]undec-7-enium 5'-O-(tert-butyldiphenylsilyl)thymidin-3'-yl 3'-O-(tert-butyldimethylsilyl)thymidin-5'-yl phosphorothioate [(SP)-4tt] (100 μmol) is dried by repeated coevaporations with dry pyridine and then dissolved in dry methylene chloride (1 mL). The mixture is treated with chloromethyl acetate, prepared by the method of Bodor et al. J. Org. Chem. (1983), 48:5280, (100 μmol) in dry (100 μmol) methylene chloride. After 1 hour, the mixture is concentrated and then dissolved in triethylamine trihydrofluoride (500 μL). The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-20tt.

Example 98

Synthesis of the thioacyloxy pronucleotide of ($R_P$)-6-N-benzoyl-deoxyadenosin-3'-yl thymidin-5'-yl phosphorothioate [($R_P$)-20at]

Crude (RP)-20 at is produced as described in Example 97 using (RP)-4 at instead of (RP)-4tt.

Example 99

Synthesis of the thioacyloxy pronucleotide of ($R_P$)-4-N-benzoyl-deoxycytidin-3'-yl thymidin-5'-yl phosphorothioate [($R_P$)-20ct]

Crude (RP)-20 is produced as described in Example 97 using (RP)-4ct instead of (RP)-4tt.

Example 100

Synthesis of the thioacyloxy pronucleotide of ($R_P$)-2-N-phenoxyacetyl-deoxyguanosin-3'-yl thymidin-5'-yl phosphorothioate [($R_P$)-20gt]

Crude (RP)-20gt is produced as described in Example 97 using (RP)-4g instead of (RP)-4tt.

Example 101

Synthesis of the thioacyloxy pronucleotide of ($S_P$)-thymidin-3'-yl thymidin-5'-yl phosphorothioate [($S_P$)-20tt]

Crude (SP)-20tt is produced as described in Example 97 using (SP)-4tt instead of (RP)-4tt.

Example 102

Synthesis of the thioacyloxy pronucleotide of ($S_P$)-6-N-benzoyl-deoxyadenosin-3'-yl thymidin-5'-yl phosphorothioate [($S_P$)-20at]

Crude (SP)-20 at is produced as described in Example 97 using (SP)-4 at instead of (RP)-4tt.

Example 103

Synthesis of the thioacyloxy pronucleotide of ($S_P$)-4-N-benzoyl-deoxycytidin-3'-yl thymidin-5'-yl phosphorothioate [($S_P$)-20ct]

Crude (SP)-20ct is produced as described in Example 97 using (SP)-4ct instead of (RP)-4tt.

Example 104

Synthesis of the thioacyloxy pronucleotide of ($S_P$)-2-N-phenoxyacetyl-deoxyguanosin-3'-yl thymidin-5'-yl phosphorothioate [($S_P$)-20gt]

Crude (SP)-20gt is produced as described in Example 97 using (SP)-4gt instead of (RP)-4tt.

Example 105

Synthesis of the thioacyloxy pronucleotide of ($R_P$)-uridin-3'-yl uridin-5'-yl phosphorothioate [($R_P$)-20uu]

Crude (RP)-20uu is produced as described in Example 97 using (RP)-10uu instead of (RP)-4tt.

Example 106

Synthesis of the thioacyloxy pronucleotide of ($R_P$)-6-N-Benzoyl-adenosin-3'-yl uridin-5'-yl phosphorothioate [($R_P$)-20au]

Crude (RP)-20au is produced as described in Example 97 using (RP)-10au instead of (RP)-4tt.

Example 107

Synthesis of the thioacyloxy pronucleotide of ($R_P$)-4-N-Benzoyl-cytidin-3'-yl uridin-5'-yl phosphorothioate [($R_P$)-20cu]

Crude (RP)-20cu is produced as described in Example 97 using (RP)-10cu instead of (RP)-4tt.

Example 108

Synthesis of the thioacyloxy pronucleotide of ($R_P$)-2-N-Phenoxyacetyl-guanosin-3'-yl uridin-5'-yl phosphorothioate [($R_P$)-20gu]

Crude (RP)-20gu is produced as described in Example 97 using (RP)-10gu instead of (RP)-4tt.

Example 109

Synthesis of the thioacyloxy pronucleotide of ($S_P$)-uridin-3'-yl uridin-5'-yl phosphorothioate [(Sp)-20uu]

Crude (SP)-20uu is produced as described in Example 97 using (SP)-10uu instead of (RP)-4tt.

Example 110

Synthesis of the thioacyloxy pronucleotide of ($S_P$)-6-N-Benzoyl-adenosin-3'-yl uridin-5'-yl phosphorothioate [($S_P$)-20au]

Crude (SP)-20au is produced as described in Example 97 using (SP)-10au instead of (RP)-4tt.

Example 111

Synthesis of the thioacyloxy pronucleotide of ($S_P$)-4-N-Benzoyl-cytidin-3'-yl uridin-5'-yl phosphorothioate [($S_P$)-20cu]

Crude (SP)-20cu is produced as described in Example 97 using (SP)-10au instead of (RP)-4tt.

Example 112

Synthesis of the thioacyloxy pronucleotide of $(S_P)$-2-N-Phenoxyacetyl-guanosin-3'-yl uridin-5'-yl phosphorothioate $[(S_P)$-20gu]

Crude (SP)-20gu is produced as described in Example 97 using (SP)-10gu instead of (RP)-4tt.

Example 113

Synthesis of the thioacyloxy pronucleotide of $(R_P)$-uridin-2'-yl uridin-5'-yl phosphorothioate $[(R_P)$-21µl]

Crude (SP)-21uu is produced as described in Example 97 using (SP)-14uu instead of (RP)-4tt.

Example 114

Synthesis of the thioacyloxy pronucleotide of $(R_P)$-6-N-Benzoyl-adenosin-2'-yl uridin-5'-yl phosphorothioate $[(R_P)$-21au]

Crude (RP)-21au is produced as described in Example 97 using (SP)-14au instead of (RP)-4tt.

Example 115

Synthesis of the thioacyloxy pronucleotide of $(R_P)$-4-N-Benzoyl-cytidin-2'-yl uridin-5'-yl phosphorothioate $[(R_P)$-21cu]

Crude (RP)-21cu is produced as described in Example 97 using (SP)-14cu instead of (RP)-4tt.

Example 116

Synthesis of the thioacyloxy pronucleotide of $(R_P)$-2-N-Phenoxyacetyl-guanosin-2'-yl uridin-5'-yl phosphorothioate $[(R_P)$-21gu]

Crude (RP)-21gu is produced as described in Example 97 using (SP)-14gu instead of (RP)-4tt.

Example 117

Synthesis of the thioacyloxy pronucleotide of $(S_P)$-uridin-2'-yl uridin-5'-yl phosphorothioate $[(S_P)$-21uu]

Crude (SP)-21uu is produced as described in Example 97 using (SP)-14uu instead of (RP)-4tt.

Example 118

Synthesis of the thioacyloxy pronucleotide of $(S_P)$-6-N-Benzoyl-adenosin-2'-yl uridin-5'-yl phosphorothioate $[(S_P)$-21au]

Crude (SP)-21au is produced as described in Example 97 using (SP)-14au instead of (RP)-4tt.

Example 119

Synthesis of the thioacyloxy pronucleotide of $(S_P)$-4-N-Benzoyl-cytidin-2'-yl uridin-5'-yl phosphorothioate $[(S_P)$-21cu]

Crude (SP)-21cu is produced as described in Example 97 using (SP)-14cu instead of (RP)-4tt.

Example 120

Synthesis of the thioacyloxy pronucleotide of $(S_P)$-2-N-Phenoxyacetyl-guanosin-2'-yl uridin-5'-yl phosphorothioate $[(S_P)$-21gu]

Crude (SP)-21gu is produced as described in Example 97 using (SP)-14gu instead of (RP)-4tt.

Scheme J: Synthesis of 2-carboalkoxyethyl pronucleotides.

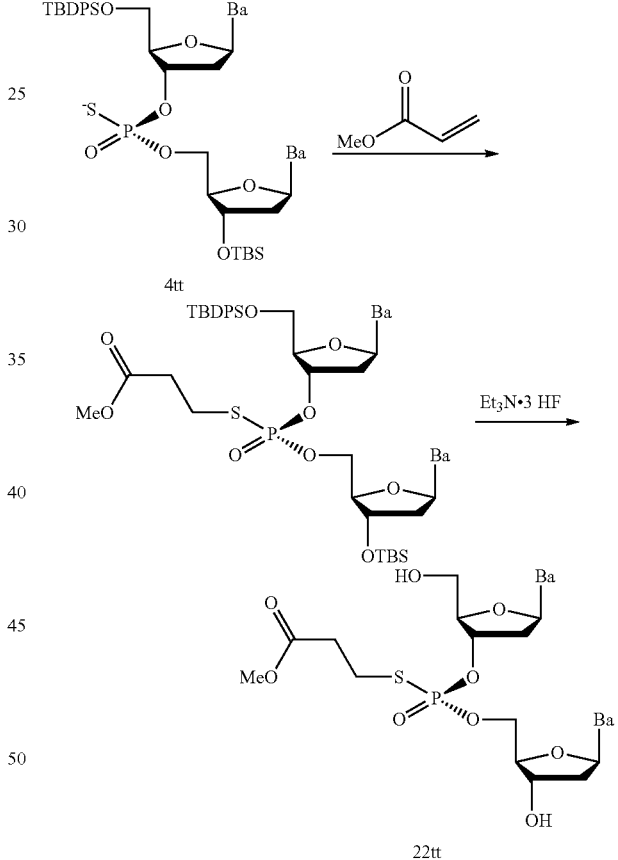

Example 121

Synthesis of the 2-carboalkoxyethyl pronucleotide of $(R_P)$-thymidin-3'-yl thymidin-5'-yl phosphorothioate $[(R_P)$-22tt] as described in Scheme J (SP)-1,8-Diazabicyclo[5.4.0]undec-7-enium 5'-O-(tert-butyldiphenylsilyl)thymidin-3'-yl 3'-O-(tert-butyldimethylsilyl)thymidin-5'-yl phosphorothioate [(SP)-4tt] (100 µmol) is dried by repeated coevaporations with dry pyridine and then dissolved in dry methylene chloride (1 mL). The mixture is treated with methyl acrylate (100 μmol) in dry (100 μmol) methylene chloride. After 1 hour, the mixture is concentrated and then dissolved in triethylamine trihydrofluoride (500 μL). The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-22tt.

Example 122

Synthesis of the 2-carboalkoxyethyl pronucleotide of $(R_P)$-6-N-benzoyl-deoxyadenosin-3'-yl thymidin-5'-yl phosphorothioate [$(R_P)$-22at]

Crude (RP)-22 at is produced as described in Example 121 using (RP)-4 at instead of (RP)-4tt.

Example 123

Synthesis of the 2-carboalkoxyethyl pronucleotide of $(R_P)$-4-N-benzoyl-deoxycytidin-3'-yl thymidin-5'-yl phosphorothioate [$(R_P)$-22ct]

Crude (RP)-22ct is produced as described in Example 121 using (RP)-4ct instead of (RP)-4tt.

Example 124

Synthesis of the 2-carboalkoxyethyl pronucleotide of $(R_P)$-2-N-phenoxyacetyl-deoxyguanosin-3'-yl thymidin-5'-yl phosphorothioate [$(R_P)$-22gt]

Crude (RP)-22gt is produced as described in Example 121 using (RP)-4g instead of (RP)-4tt.

Example 125

Synthesis of the 2-carboalkoxyethyl pronucleotide of $(S_P)$-thymidin-3'-yl thymidin-5'-yl phosphorothioate [$(S_P)$-22tt]

Crude (SP)-22tt is produced as described in Example 121 using (SP)-4tt instead of (RP)-4tt.

Example 126

Synthesis of the 2-carboalkoxyethyl pronucleotide of $(S_P)$-6-N-benzoyl-deoxyadenosin-3'-yl thymidin-5'-yl phosphorothioate [$(S_P)$-22at]

Crude (SP)-22 at is produced as described in Example 121 using (SP)-4 at instead of (RP)-4tt.

Example 127

Synthesis of the 2-carboalkoxyethyl pronucleotide of $(S_P)$-4-N-benzoyl-deoxycytidin-3'-yl thymidin-5'-yl phosphorothioate [$(S_P)$-22ct]

Crude (SP)-22ct is produced as described in Example 121 using (SP)-4ct instead of (RP)-4tt.

Example 128

Synthesis of the 2-carboalkoxyethyl pronucleotide of $(S_P)$-2-N-phenoxyacetyl-deoxyguanosin-3'-yl thymidin-5'-yl phosphorothioate [$(S_P)$-22gt]

Crude (SP)-22gt is produced as described in Example 121 using (SP)-4gt instead of (RP)-4tt.

Example 129

Synthesis of the 2-carboalkoxyethyl pronucleotide of $(R_P)$-uridin-3'-yl uridin-5'-yl phosphorothioate [$(R_P)$-22uu]

Crude (RP)-22uu is produced as described in Example 121 using (RP)-10uu instead of (RP)-4tt.

Example 130

Synthesis of the 2-carboalkoxyethyl pronucleotide of $(R_P)$-6-N-Benzoyl-adenosin-3'-yl uridin-5'-yl phosphorothioate [$(R_P)$-22au]

Crude (RP)-22au is produced as described in Example 121 using (RP)-10au instead of (RP)-4tt.

Example 131

Synthesis of the 2-carboalkoxyethyl pronucleotide of $(R_P)$-4-N-Benzoyl-cytidin-3'-yl uridin-5'-yl phosphorothioate [$(R_P)$-22cu]

Crude (RP)-22cu is produced as described in Example 121 using (RP)-10cu instead of (RP)-4tt.

Example 132

Synthesis of the 2-carboalkoxyethyl pronucleotide of $(R_P)$-2-N-Phenoxyacetyl-guanosin-3'-yl uridin-5'-yl phosphorothioate [$(R_P)$-22gu]

Crude (RP)-22gu is produced as described in Example 121 using (RP)-10gu instead of (RP)-4tt.

Example 133

Synthesis of the 2-carboalkoxyethyl pronucleotide of $(S_P)$-uridin-3'-yl uridin-5'-yl phosphorothioate [$(S_P)$-22uu]

Crude (SP)-22uu is produced as described in Example 121 using (SP)-10uu instead of (RP)-4tt.

Example 134

Synthesis of the 2-carboalkoxyethyl pronucleotide of $(S_P)$-6-N-Benzoyl-adenosin-3'-yl uridin-5'-yl phosphorothioate [$(S_P)$-22au]

Crude (SP)-22au is produced as described in Example 121 using (SP)-10au instead of (RP)-4tt.

Example 135

Synthesis of the 2-carboalkoxyethyl pronucleotide of ($S_P$)-4-N-Benzoyl-cytidin-3'-yl uridin-5'-yl phosphorothioate [($S_P$)-22cu]

Crude (SP)-22cu is produced as described in Example 121 using (SP)-10au instead of (RP)-4tt.

Example 136

Synthesis of the 2-carboalkoxyethyl pronucleotide of ($S_P$)-2-N-Phenoxyacetyl-guanosin-3'-yl uridin-5'-yl phosphorothioate [($S_P$)-22gu]

Crude (SP)-22gu is produced as described in Example 121 using (SP)-10gu instead of (RP)-4tt.

Example 137

Synthesis of the 2-carboalkoxyethyl pronucleotide of ($R_P$)-uridin-2'-yl uridin-5'-yl phosphorothioate [($R_P$)-23uu]

Crude (SP)-23uu is produced as described in Example 121 using (SP)-14uu instead of (RP)-4tt.

Example 138

Synthesis of the 2-carboalkoxyethyl pronucleotide of ($R_P$)-6-N-Benzoyl-adenosin-2'-yl uridin-5'-yl phosphorothioate [($R_P$)-23au]

Crude (RP)-23au is produced as described in Example 121 using (SP)-14au instead of (RP)-4tt.

Example 139

Synthesis of the 2-carboalkoxyethyl pronucleotide of ($R_P$)-4-N-Benzoyl-cytidin-2'-yl uridin-5'-yl phosphorothioate [($R_P$)-23cu]

Crude (RP)-23cu is produced as described in Example 121 using (SP)-14cu instead of (RP)-4tt.

Example 140

Synthesis of the 2-carboalkoxyethyl pronucleotide of ($R_P$)-2-N-Phenoxyacetyl-guanosin-2'-yl uridin-5'-yl phosphorothioate [($R_P$)-23gu]

Crude (RP)-23gu is produced as described in Example 121 using (SP)-14gu instead of (RP)-4tt.

Example 141

Synthesis of the 2-carboalkoxyethyl pronucleotide of ($S_P$)-uridin-2'-yl uridin-5'-yl phosphorothioate [($S_P$)-23uu]

Crude (SP)-23uu is produced as described in Example 121 using (SP)-14uu instead of (RP)-4tt.

Example 142

Synthesis of the 2-carboalkoxyethyl pronucleotide of ($S_P$)-6-N-Benzoyl-adenosin-2'-yl uridin-5'-yl phosphorothioate [($S_P$)-23au]

Crude (SP)-23au is produced as described in Example 121 using (SP)-14au instead of (RP)-4tt.

Example 143

Synthesis of the 2-carboalkoxyethyl pronucleotide of ($S_P$)-4-N-Benzoyl-cytidin-2'-yl uridin-5'-yl phosphorothioate [($S_P$)-23cu]

Crude (SP)-23cu is produced as described in Example 121 using (SP)-14cu instead of (RP)-4tt.

Example 144

Synthesis of the 2-carboalkoxyethyl pronucleotide of ($S_P$)-2-N-Phenoxyacetyl-guanosin-2'-yl uridin-5'-yl phosphorothioate [($S_P$)-23gu]

Crude (SP)-23gu is produced as described in Example 121 using (SP)-14gu instead of (RP)-4tt.

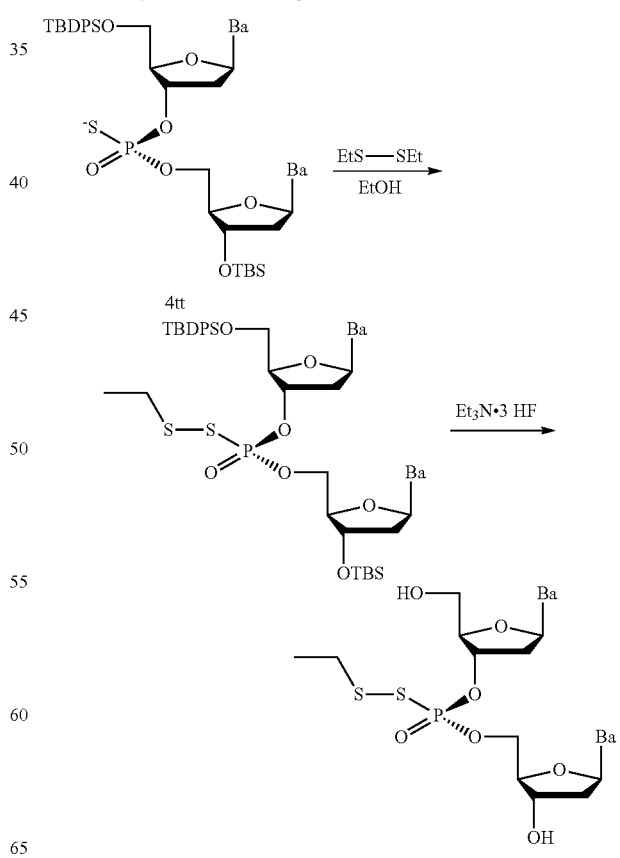

Scheme K: Synthesis of disulfide pronucleotides.

Example 145

Synthesis of the disulfide pronucleotide of $(R_P)$-thymidin-3'-yl thymidin-5'-yl phosphorothioate $[(R_P)$-24tt] as described in Scheme K (SP)-1,8-Diazabicyclo[5.4.0]undec-7-enium 5'-O-(tert-butyldiphenylsilyl)thymidin-3'-yl 3'-O-(tert-butyldimethylsilyl)thymidin-5'-yl phosphorothioate [(SP)-4tt] (100 μmol) is dried by repeated coevaporations with dry pyridine and then dissolved in dry ethanol (1 mL). The mixture is treated with diethyl disulfide (200 μmol) in dry (100 μmol) ethanol. After 1 hour, the mixture is concentrated and then dissolved in triethylamine trihydrofluoride (500 μL). The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-24tt.

Example 146

Synthesis of the disulfide pronucleotide of $(R_P)$-6-N-benzoyl-deoxyadenosin-3'-yl thymidin-5'-yl phosphorothioate $[(R_P)$-24at]

Crude (RP)-24 at is produced as described in Example 145 using (RP)-4 at instead of (RP)-4tt.

Example 147

Synthesis of the disulfide pronucleotide of $(R_P)$-4-N-benzoyl-deoxycytidin-3'-yl thymidin-5'-yl phosphorothioate $[(R_P)$-24ct]

Crude (RP)-24ct is produced as described in Example 145 using (RP)-4ct instead of (RP)-4tt.

Example 148

Synthesis of the disulfide pronucleotide of $(R_P)$-2-N-phenoxyacetyl-deoxyguanosin-3'-yl thymidin-5'-yl phosphorothioate $[(R_P)$-24gt]

Crude (RP)-24gt is produced as described in Example 145 using (RP)-4g instead of (RP)-4tt.

Example 149

Synthesis of the disulfide pronucleotide of $(S_P)$-thymidin-3'-yl thymidin-5'-yl phosphorothioate $[(S_P)$-24tt]

Crude (SP)-24tt is produced as described in Example 145 using (SP)-4tt instead of (RP)-4tt.

Example 150

Synthesis of the disulfide pronucleotide of $(S_P)$-6-N-benzoyl-deoxyadenosin-3'-yl thymidin-5'-yl phosphorothioate $[(S_P)$-24at]

Crude (SP)-24 at is produced as described in Example 145 using (SP)-4 at instead of (RP)-4tt.

Example 151

Synthesis of the disulfide pronucleotide of $(S_P)$-4-N-benzoyl-deoxycytidin-3'-yl thymidin-5'-yl phosphorothioate $[(S_P)$-24ct]

Crude (SP)-24ct is produced as described in Example 145 using (SP)-4ct instead of (RP)-4tt.

Example 152

Synthesis of the disulfide pronucleotide of $(S_P)$-2-N-phenoxyacetyl-deoxyguanosin-3'-yl thymidin-5'-yl phosphorothioate $[(S_P)$-24gt]

Crude (SP)-24gt is produced as described in Example 145 using (SP)-4gt instead of (RP)-4tt.

Example 153

Synthesis of the disulfide pronucleotide of $(R_P)$-uridin-3'-yl uridin-5'-yl phosphorothioate $[(R_P)$-24uu]

Crude (RP)-24uu is produced as described in Example 145 using (RP)-10uu instead of (RP)-4tt.

Example 154

Synthesis of the disulfide pronucleotide of $(R_P)$-6-N-Benzoyl-adenosin-3'-yl uridin-5'-yl phosphorothioate $[(R_P)$-24au]

Crude (RP)-24au is produced as described in Example 145 using (RP)-10au instead of (RP)-4tt.

Example 155

Synthesis of the disulfide pronucleotide of $(R_P)$-4-N-Benzoyl-cytidin-3'-yl uridin-5'-yl phosphorothioate $[(R_P)$-24cu]

Crude (RP)-24cu is produced as described in Example 145 using (RP)-10cu instead of (RP)-4tt.

Example 156

Synthesis of the disulfide pronucleotide of $(R_P)$-2-N-Phenoxyacetyl-guanosin-3'-yl uridin-5'-yl phosphorothioate $[(R_P)$-24gu]

Crude (RP)-24gu is produced as described in Example 145 using (RP)-10gu instead of (RP)-4tt.

Example 157

Synthesis of the disulfide pronucleotide of $(S_P)$-uridin-3'-yl uridin-5'-yl phosphorothioate [(Sp)-24uu]

Crude (SP)-24uu is produced as described in Example 145 using (SP)-10uu instead of (RP)-4tt.

Example 158

Synthesis of the disulfide pronucleotide of ($S_P$)-6-N-Benzoyl-adenosin-3'-yl uridin-5'-yl phosphorothioate [($S_P$)-24au]

Crude (SP)-24au is produced as described in Example 145 using (SP)-10au instead of (RP)-4tt.

Example 159

Synthesis of the disulfide pronucleotide of ($S_P$)-4-N-Benzoyl-cytidin-3'-yl uridin-5'-yl phosphorothioate [($S_P$)-24cu]

Crude (SP)-24cu is produced as described in Example 145 using (SP)-10au instead of (RP)-4tt.

Example 160

Synthesis of the disulfide pronucleotide of ($S_P$)-2-N-Phenoxyacetyl-guanosin-3'-yl uridin-5'-yl phosphorothioate [($S_P$)-24gu]

Crude (SP)-24gu is produced as described in Example 145 using (SP)-10gu instead of (RP)-4tt.

Example 161

Synthesis of the disulfide pronucleotide of ($R_P$)-uridin-2'-yl uridin-5'-yl phosphorothioate [($R_P$)-25uu]

Crude (SP)-25uu is produced as described in Example 145 using (SP)-14uu instead of (RP)-4tt.

Example 162

Synthesis of the disulfide pronucleotide of ($R_P$)-6-N-Benzoyl-adenosin-2'-yl uridin-5'-yl phosphorothioate [($R_P$)-25au]

Crude (RP)-25au is produced as described in Example 145 using (SP)-14au instead of (RP)-4tt.

Example 163

Synthesis of the disulfide pronucleotide of ($R_P$)-4-N-Benzoyl-cytidin-2'-yl uridin-5'-yl phosphorothioate [($R_P$)-25cu]

Crude (RP)-25cu is produced as described in Example 145 using (SP)-14cu instead of (RP)-4tt.

Example 164

Synthesis of the disulfide pronucleotide of ($R_P$)-2-N-Phenoxyacetyl-guanosin-2'-yl uridin-5'-yl phosphorothioate [($R_P$)-25gu]

Crude (RP)-25gu is produced as described in Example 145 using (SP)-14gu instead of (RP)-4tt.

Example 165

Synthesis of the disulfide pronucleotide of ($S_P$)-uridin-2'-yl uridin-5'-yl phosphorothioate [(Sp)-25uu]

Crude (SP)-25uu is produced as described in Example 145 using (SP)-14uu instead of (RP)-4tt.

Example 166

Synthesis of the disulfide pronucleotide of ($S_P$)-6-N-Benzoyl-adenosin-2'-yl uridin-5'-yl phosphorothioate [($S_P$)-25au]

Crude (SP)-25au is produced as described in Example 145 using (SP)-14au instead of (RP)-4tt.

Example 167

Synthesis of the disulfide pronucleotide of ($S_P$)-4-N-Benzoyl-cytidin-2'-yl uridin-5'-yl phosphorothioate [($S_P$)-25cu]

Crude (SP)-25cu is produced as described in Example 145 using (SP)-14cu instead of (RP)-4tt.

Example 168

Synthesis of the disulfide pronucleotide of ($S_P$)-2-N-Phenoxyacetyl-guanosin-2'-yl uridin-5'-yl phosphorothioate [($S_P$)-25gu]

Crude (SP)-25gu is produced as described in Example 145 using (SP)-14gu instead of (RP)-4tt.

Scheme L: Synthesis of thioacetal pronucleotides.

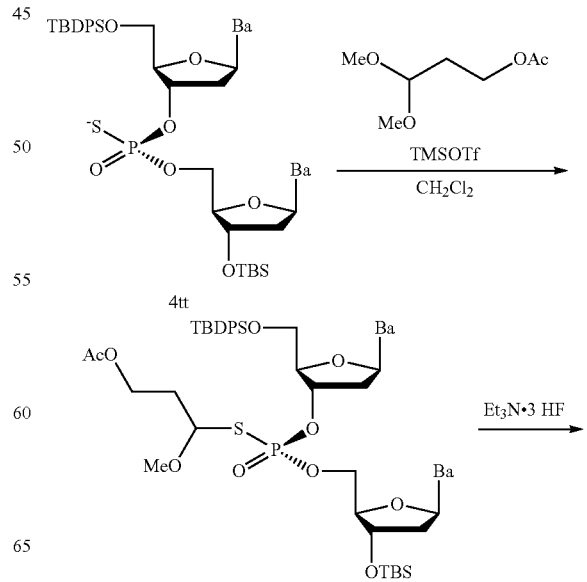

-continued

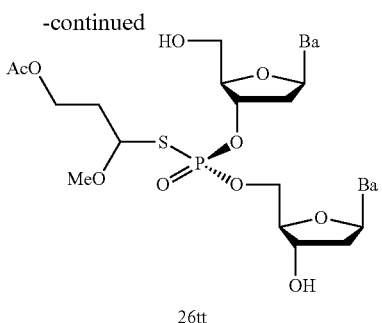

26tt

Example 169

Synthesis of the thioacetal pronucleotide of ($R_P$)-thymidin-3'-yl thymidin-5'-yl phosphorothioate [($R_P$)-26tt] as described in Scheme L 3,3-Dimethoxypropyl acetate (100 μmol) is added to a solution of trimethylsilyltriflate (100 μmol) in methylene chloride (1 mL) at −78° C. After stirring at −78° C. for 30 min, (SP)-1,8-Diazabicyclo[5.4.0]undec-7-enium 5'-O-(tert-butyldiphenylsilyl)thymidin-3'-yl 3'-O-(tert-butyldimethylsilyl)thymidin-5'-yl phosphorothioate [(SP)-4tt] (100 μmol) is added in dry methylene chloride (1 mL). The mixture is allowed to slowly warm to room temperature. After 1 hour, the mixture is concentrated and then dissolved in triethylamine trihydrofluoride (500 μL). The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-26tt.

Example 170

Synthesis of the thioacetal pronucleotide of ($R_P$)-6-N-benzoyl-deoxyadenosin-3'-yl thymidin-5'-yl phosphorothioate [($R_P$)-26at]

Crude (RP)-26 at is produced as described in Example 169 using (RP)-4 at instead of (RP)-4tt.

Example 171

Synthesis of the thioacetal pronucleotide of ($R_P$)-4-N-benzoyl-deoxycytidin-3'-yl thymidin-5'-yl phosphorothioate [($R_P$)-26ct]

Crude (RP)-26ct is produced as described in Example 169 using (RP)-4ct instead of (RP)-4tt.

Example 172

Synthesis of the thioacetal pronucleotide of ($R_P$)-2-N-phenoxyacetyl-deoxyguanosin-3'-yl thymidin-5'-yl phosphorothioate [($R_P$)-26gt]

Crude (RP)-26gt is produced as described in Example 169 using (RP)-4g instead of (RP)-4tt.

Example 173

Synthesis of the thioacetal pronucleotide of ($S_P$)-thymidin-3'-yl thymidin-5'-yl phosphorothioate [($S_P$)-26tt]

Crude (SP)-26tt is produced as described in Example 169 using (SP)-4tt instead of (RP)-4tt.

Example 174

Synthesis of the thioacetal pronucleotide of ($S_P$)-6-N-benzoyl-deoxyadenosin-3'-yl thymidin-5'-yl phosphorothioate [($S_P$)-26at]

Crude (SP)-26 at is produced as described in Example 169 using (SP)-4 at instead of (RP)-4tt.

Example 175

Synthesis of the thioacetal pronucleotide of ($S_P$)-4-N-benzoyl-deoxycytidin-3'-yl thymidin-5'-yl phosphorothioate [($S_P$)-26ct]

Crude (SP)-26ct is produced as described in Example 169 using (SP)-4ct instead of (RP)-4tt.

Example 176

Synthesis of the thioacetal pronucleotide of ($S_P$)-2-N-phenoxyacetyl-deoxyguanosin-3'-yl thymidin-5'-yl phosphorothioate [($S_P$)-26gt]

Crude (SP)-26gt is produced as described in Example 169 using (SP)-4gt instead of (RP)-4tt.

Example 177

Synthesis of the thioacetal pronucleotide of ($R_P$)-uridin-3'-yl uridin-5'-yl phosphorothioate [($R_P$)-26uu]

Crude (RP)-26uu is produced as described in Example 169 using (RP)-10uu instead of (RP)-4tt.

Example 178

Synthesis of the thioacetal pronucleotide of ($R_P$)-6-N-Benzoyl-adenosin-3'-yl uridin-5'-yl phosphorothioate [($R_P$)-26au]

Crude (RP)-26au is produced as described in Example 169 using (RP)-10au instead of (RP)-4tt.

Example 179

Synthesis of the thioacetal pronucleotide of ($R_P$)-4-N-Benzoyl-cytidin-3'-yl uridin-5'-yl phosphorothioate [($R_P$)-26cu]

Crude (RP)-26cu is produced as described in Example 169 using (RP)-10cu instead of (RP)-4tt.

Example 180

Synthesis of the thioacetal pronucleotide of $(R_P)$-2-N-Phenoxyacetyl-guanosin-3'-yl uridin-5'-yl phosphorothioate [$(R_P)$-26gu]

Crude (RP)-26gu is produced as described in Example 169 using (RP)-10gu instead of (RP)-4tt.

Example 181

Synthesis of the thioacetal pronucleotide of $(S_P)$-uridin-3'-yl uridin-5'-yl phosphorothioate [(Sp)-26uu]

Crude (SP)-26uu is produced as described in Example 169 using (SP)-10uu instead of (RP)-4tt.

Example 182

Synthesis of the thioacetal pronucleotide of $(S_P)$-6-N-Benzoyl-adenosin-3'-yl uridin-5'-yl phosphorothioate [$(S_P)$-26au]

Crude (SP)-26au is produced as described in Example 169 using (SP)-10au instead of (RP)-4tt.

Example 183

Synthesis of the thioacetal pronucleotide of $(S_P)$-4-N-Benzoyl-cytidin-3'-yl uridin-5'-yl phosphorothioate [$(S_P)$-26cu]

Crude (SP)-26cu is produced as described in Example 169 using (SP)-10au instead of (RP)-4tt.

Example 184

Synthesis of the thioacetal pronucleotide of $(S_P)$-2-N-Phenoxyacetyl-guanosin-3'-yl uridin-5'-yl phosphorothioate [$(S_P)$-26gu]

Crude (SP)-26gu is produced as described in Example 169 using (SP)-10gu instead of (RP)-4tt.

Example 185

Synthesis of the thioacetal pronucleotide of $(R_P)$-uridin-2'-yl uridin-5'-yl phosphorothioate [$(R_P)$-27uu]

Crude (SP)-27uu is produced as described in Example 169 using (SP)-14uu instead of (RP)-4tt.

Example 186

Synthesis of the thioacetal pronucleotide of $(R_P)$-6-N-Benzoyl-adenosin-2'-yl uridin-5'-yl phosphorothioate [$(R_P)$-27au]

Crude (RP)-27au is produced as described in Example 169 using (SP)-14au instead of (RP)-4tt.

Example 187

Synthesis of the thioacetal pronucleotide of $(R_P)$-4-N-Benzoyl-cytidin-2'-yl uridin-5'-yl phosphorothioate [$(R_P)$-27cu]

Crude (RP)-27cu is produced as described in Example 169 using (SP)-14cu instead of (RP)-4tt.

Example 188

Synthesis of the thioacetal pronucleotide of $(R_P)$-2-N-Phenoxyacetyl-guanosin-2'-yl uridin-5'-yl phosphorothioate [$(R_P)$-27gu]

Crude (RP)-27gu is produced as described in Example 169 using (SP)-14gu instead of (RP)-4tt.

Example 189

Synthesis of the thioacetal pronucleotide of $(S_P)$-uridin-2'-yl uridin-5'-yl phosphorothioate [(Sp)-27uu]

Crude (SP)-27uu is produced as described in Example 169 using (SP)-14uu instead of (RP)-4tt.

Example 190

Synthesis of the thioacetal pronucleotide of $(S_P)$-6-N-Benzoyl-adenosin-2'-yl uridin-5'-yl phosphorothioate [$(S_P)$-27au]

Crude (SP)-27au is produced as described in Example 169 using (SP)-14au instead of (RP)-4tt.

Example 191

Synthesis of the thioacetal pronucleotide of $(S_P)$-4-N-Benzoyl-cytidin-2'-yl uridin-5'-yl phosphorothioate [$(S_P)$-27cu]

Crude (SP)-27cu is produced as described in Example 169 using (SP)-14cu instead of (RP)-4tt.

Example 192

Synthesis of the thioacetal pronucleotide of $(S_P)$-2-N-Phenoxyacetyl-guanosin-2'-yl uridin-5'-yl phosphorothioate [$(S_P)$-27gu]

Crude (SP)-27gu is produced as described in Example 169 using (SP)-14gu instead of (RP)-4tt.

Scheme M: Synthesis of C3 enol ester pronucleotides.

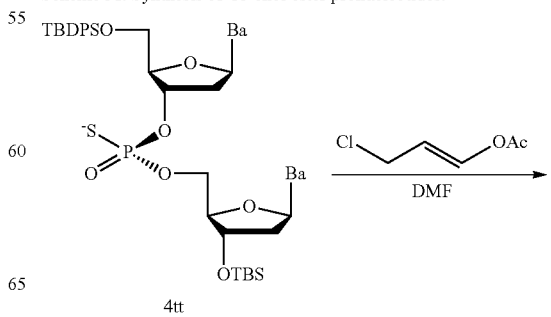

4tt

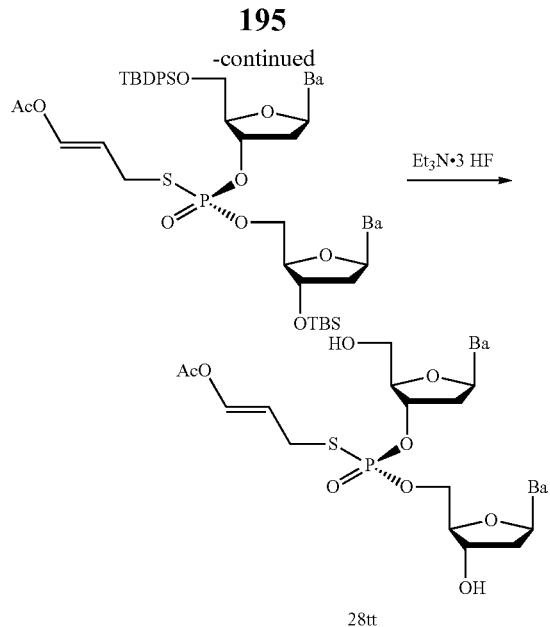

28tt

Example 193

Synthesis of the C3 enol ester pronucleotide of (R$_P$)-thymidin-3'-yl thymidin-5'-yl phosphorothioate [(R$_P$)-28tt] as described in Scheme M To a solution of (E)-3-chloroprop-1-enyl acetate (100 μmol) in DMF (1 mL) is added (SP)-1,8-Diazabicyclo[5.4.0]undec-7-enium 5'-O-(tert-butyldiphenylsilyl)thymidin-3'-yl 3'-O-(tert-butyldimethylsilyl)thymidin-5'-yl phosphorothioate [(SP)-4tt] (100 μmol). After 1 hour, the mixture is concentrated and then dissolved in triethylamine trihydrofluoride (500 μL). The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-28tt.

Example 194

Synthesis of the C3 enol ester pronucleotide of (R$_P$)-6-N-benzoyl-deoxyadenosin-3'-yl thymidin-5'-yl phosphorothioate [(R$_P$)-28at]

Crude (RP)-28 at is produced as described in Example 193 using (RP)-4 at instead of (RP)-4tt.

Example 195

Synthesis of the C3 enol ester pronucleotide of (R$_P$)-4-N-benzoyl-deoxycytidin-3'-yl thymidin-5'-yl phosphorothioate [(R$_P$)-28ct]

Crude (RP)-28ct is produced as described in Example 193 using (RP)-4ct instead of (RP)-4tt.

Example 196

Synthesis of the C3 enol ester pronucleotide of (R$_P$)-2-N-phenoxyacetyl-deoxyguanosin-3'-yl thymidin-5'-yl phosphorothioate [(R$_P$)-28gt]

Crude (RP)-28gt is produced as described in Example 193 using (RP)-4g instead of (RP)-4tt.

Example 197

Synthesis of the C3 enol ester pronucleotide of (S$_P$)-thymidin-3'-yl thymidin-5'-yl phosphorothioate [(S$_P$)-28tt]

Crude (SP)-28tt is produced as described in Example 193 using (SP)-4tt instead of (RP)-4tt.

Example 198

Synthesis of the C3 enol ester pronucleotide of (S$_P$)-6-N-benzoyl-deoxyadenosin-3'-yl thymidin-5'-yl phosphorothioate [(S$_P$)-28at]

Crude (SP)-28 at is produced as described in Example 193 using (SP)-4 at instead of (RP)-4tt.

Example 199

Synthesis of the C3 enol ester pronucleotide of (S$_P$)-4-N-benzoyl-deoxycytidin-3'-yl thymidin-5'-yl phosphorothioate [(S$_P$)-28ct]

Crude (SP)-28ct is produced as described in Example 193 using (SP)-4ct instead of (RP)-4tt.

Example 200

Synthesis of the C3 enol ester pronucleotide of (S$_P$)-2-N-phenoxyacetyl-deoxyguanosin-3'-yl thymidin-5'-yl phosphorothioate [(S$_P$)-28gt]

Crude (SP)-28gt is produced as described in Example 193 using (SP)-4gt instead of (RP)-4tt.

Example 201

Synthesis of the C3 enol ester pronucleotide of (R$_P$)-uridin-3'-yl uridin-5'-yl phosphorothioate [(R$_P$)-28uu]

Crude (RP)-28uu is produced as described in Example 193 using (RP)-10uu instead of (RP)-4tt.

Example 202

Synthesis of the C3 enol ester pronucleotide of (R$_P$)-6-N-Benzoyl-adenosin-3'-yl uridin-5'-yl phosphorothioate [(R$_P$)-28au]

Crude (RP)-28au is produced as described in Example 193 using (RP)-10au instead of (RP)-4tt.

Example 203

Synthesis of the C3 enol ester pronucleotide of (R$_P$)-4-N-Benzoyl-cytidin-3'-yl uridin-5'-yl phosphorothioate [(R$_P$)-28cu]

Crude (RP)-28cu is produced as described in Example 193 using (RP)-10cu instead of (RP)-4tt.

Example 204

Synthesis of the C3 enol ester pronucleotide of (R$_P$)-2-N-Phenoxyacetyl-guanosin-3'-yl uridin-5'-yl phosphorothioate [(R$_P$)-28gu]

Crude (RP)-28gu is produced as described in Example 193 using (RP)-10gu instead of (RP)-4tt.

Example 205

Synthesis of the C3 enol ester pronucleotide of (S$_P$)-uridin-3'-yl uridin-5'-yl phosphorothioate [(Sp)-28uu]

Crude (SP)-28uu is produced as described in Example 193 using (SP)-10uu instead of (RP)-4tt.

Example 206

Synthesis of the C3 enol ester pronucleotide of (S$_P$)-6-N-Benzoyl-adenosin-3'-yl uridin-5'-yl phosphorothioate [(S$_P$)-28au]

Crude (SP)-28au is produced as described in Example 193 using (SP)-10au instead of (RP)-4tt.

Example 207

Synthesis of the C3 enol ester pronucleotide of (S$_P$)-4-N-Benzoyl-cytidin-3'-yl uridin-5'-yl phosphorothioate [(S$_P$)-28cu]

Crude (SP)-28cu is produced as described in Example 193 using (SP)-10au instead of (RP)-4tt.

Example 208

Synthesis of the C3 enol ester pronucleotide of (S$_P$)-2-N-Phenoxyacetyl-guanosin-3'-yl uridin-5'-yl phosphorothioate [(S$_P$)-28gu]

Crude (SP)-28gu is produced as described in Example 193 using (SP)-10gu instead of (RP)-4tt.

Example 209

Synthesis of the C3 enol ester pronucleotide of (R$_P$)-uridin-2'-yl uridin-5'-yl phosphorothioate [(R$_P$)-29uu]

Crude (SP)-29uu is produced as described in Example 193 using (SP)-14uu instead of (RP)-4tt.

Example 210

Synthesis of the C3 enol ester pronucleotide of (R$_P$)-6-N-Benzoyl-adenosin-2'-yl uridin-5'-yl phosphorothioate [(R$_P$)-29au]

Crude (RP)-29au is produced as described in Example 193 using (SP)-14au instead of (RP)-4tt.

Example 211

Synthesis of the C3 enol ester pronucleotide of (R$_P$)-4-N-Benzoyl-cytidin-2'-yl uridin-5'-yl phosphorothioate [(R$_P$)-29cu]

Crude (RP)-29cu is produced as described in Example 193 using (SP)-14cu instead of (RP)-4tt.

Example 212

Synthesis of the C3 enol ester pronucleotide of (R$_P$)-2-N-Phenoxyacetyl-guanosin-2'-yl uridin-5'-yl phosphorothioate [(R$_P$)-29gu]

Crude (RP)-29gu is produced as described in Example 193 using (SP)-14gu instead of (RP)-4tt.

Example 213

Synthesis of the C3 enol ester pronucleotide of (S$_P$)-uridin-2'-yl uridin-5'-yl phosphorothioate [(S$_P$)-29uu]

Crude (SP)-29uu is produced as described in Example 193 using (SP)-14uu instead of (RP)-4tt.

Example 214

Synthesis of the C3 enol ester pronucleotide of (S$_P$)-6-N-Benzoyl-adenosin-2'-yl uridin-5'-yl phosphorothioate [(S$_P$)-29au]

Crude (SP)-29au is produced as described in Example 193 using (SP)-14au instead of (RP)-4tt.

Example 215

Synthesis of the C3 enol ester pronucleotide of (S$_P$)-4-N-Benzoyl-cytidin-2'-yl uridin-5'-yl phosphorothioate [(S$_P$)-29cu]

Crude (SP)-29cu is produced as described in Example 193 using (SP)-14cu instead of (RP)-4tt.

Example 216

Synthesis of the C3 enol ester pronucleotide of (S$_P$)-2-N-Phenoxyacetyl-guanosin-2'-yl uridin-5'-yl phosphorothioate [(S$_P$)-29gu]

Crude (SP)-29gu is produced as described in Example 193 using (SP)-14gu instead of (RP)-4tt.

Scheme N: Synthesis of C4 enol ester pronucleotides.

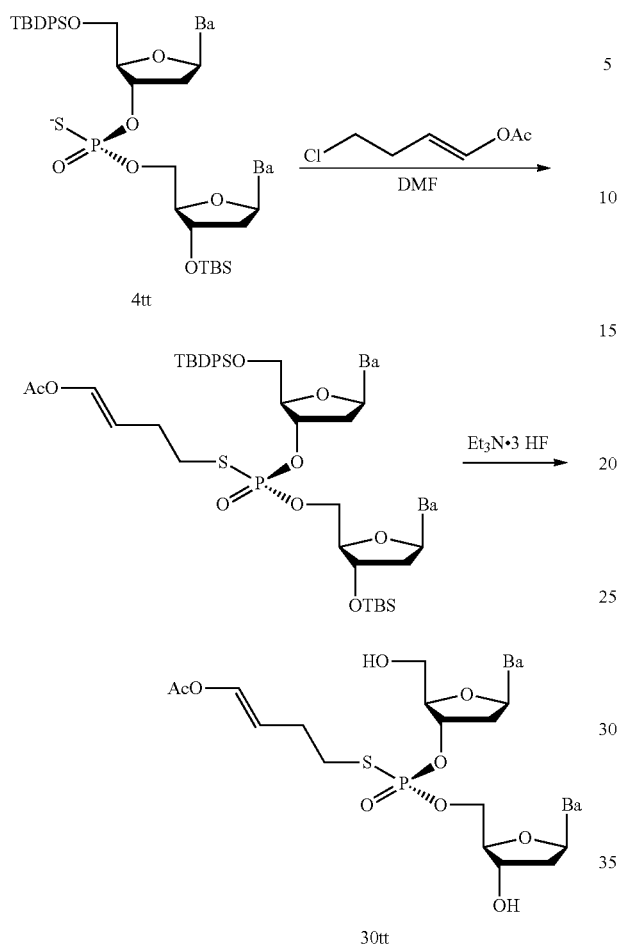

Example 217

Synthesis of the C4 enol ester pronucleotide of ($R_P$)-thymidin-3'-yl thymidin-5'-yl phosphorothioate [($R_P$)-30tt] as described in Scheme N To a solution of (E)-4-chlorobut-1-enyl acetate (100 µmol) in DMF (1 mL) is added (SP)-1,8-Diazabicyclo[5.4.0]undec-7-enium 5'-O-(tert-butyldiphenylsilyl)thymidin-3'-yl 3'-O-(tert-butyldimethylsilyl)thymidin-5'-yl phosphorothioate [(SP)-4tt] (100 µmol). After 1 hour, the mixture is concentrated and then dissolved in triethylamine trihydrofluoride (500 µL). The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-30tt.

Example 218

Synthesis of the C4 enol ester pronucleotide of ($R_P$)-6-N-benzoyl-deoxyadenosin-3'-yl thymidin-5'-yl phosphorothioate [($R_P$)-30at]

Crude (RP)-30 at is produced as described in Example 217 using (RP)-4 at instead of (RP)-4tt.

Example 219

Synthesis of the C4 enol ester pronucleotide of ($R_P$)-4-N-benzoyl-deoxycytidin-3'-yl thymidin-5'-yl phosphorothioate [($R_P$)-30ct]

Crude (RP)-30ct is produced as described in Example 217 using (RP)-4ct instead of (RP)-4tt.

Example 220

Synthesis of the C4 enol ester pronucleotide of ($R_P$)-2-N-phenoxyacetyl-deoxyguanosin-3'-yl thymidin-5'-yl phosphorothioate [($R_P$)-30gt]

Crude (RP)-30gt is produced as described in Example 217 using (RP)-4g instead of (RP)-4tt.

Example 221

Synthesis of the C4 enol ester pronucleotide of ($S_P$)-thymidin-3'-yl thymidin-5'-yl phosphorothioate [($S_P$)-30tt]

Crude (SP)-30tt is produced as described in Example 217 using (SP)-4tt instead of (RP)-4tt.

Example 222

Synthesis of the C4 enol ester pronucleotide of ($S_P$)-6-N-benzoyl-deoxyadenosin-3'-yl thymidin-5'-yl phosphorothioate [($S_P$)-30at]

Crude (SP)-30 at is produced as described in Example 217 using (SP)-4 at instead of (RP)-4tt.

Example 223

Synthesis of the C4 enol ester pronucleotide of ($S_P$)-4-N-benzoyl-deoxycytidin-3'-yl thymidin-5'-yl phosphorothioate [($S_P$)-30ct]

Crude (SP)-30ct is produced as described in Example 217 using (SP)-4ct instead of (RP)-4tt.

Example 224

Synthesis of the C4 enol ester pronucleotide of ($S_P$)-2-N-phenoxyacetyl-deoxyguanosin-3'-yl thymidin-5'-yl phosphorothioate [($S_P$)-30gt]

Crude (SP)-30gt is produced as described in Example 217 using (SP)-4gt instead of (RP)-4tt.

Example 225

Synthesis of the C4 enol ester pronucleotide of ($R_P$)-uridin-3'-yl uridin-5'-yl phosphorothioate [($R_P$)-30uu]

Crude (RP)-30uu is produced as described in Example 217 using (RP)-10uu instead of (RP)-4tt.

Example 226

Synthesis of the C4 enol ester pronucleotide of ($R_P$)-6-N-Benzoyl-adenosin-3'-yl uridin-5'-yl phosphorothioate [($R_P$)-30au]

Crude (RP)-30au is produced as described in Example 217 using (RP)-10au instead of (RP)-4tt.

Example 227

Synthesis of the C4 enol ester pronucleotide of ($R_P$)-4-N-Benzoyl-cytidin-3'-yl uridin-5'-yl phosphorothioate [($R_P$)-30cu]

Crude (RP)-30cu is produced as described in Example 217 using (RP)-10cu instead of (RP)-4tt.

Example 228

Synthesis of the C4 enol ester pronucleotide of ($R_P$)-2-N-Phenoxyacetyl-guanosin-3'-yl uridin-5'-yl phosphorothioate [($R_P$)-30gu]

Crude (RP)-30gu is produced as described in Example 217 using (RP)-10gu instead of (RP)-4tt.

Example 229

Synthesis of the C4 enol ester pronucleotide of ($S_P$)-uridin-3'-yl uridin-5'-yl phosphorothioate [($S_P$)-30uu]

Crude (SP)-30uu is produced as described in Example 217 using (SP)-10uu instead of (RP)-4tt.

Example 230

Synthesis of the C4 enol ester pronucleotide of ($S_P$)-6-N-Benzoyl-adenosin-3'-yl uridin-5'-yl phosphorothioate [($S_P$)-30au]

Crude (SP)-30au is produced as described in Example 217 using (SP)-10au instead of (RP)-4tt.

Example 231

Synthesis of the C4 enol ester pronucleotide of ($S_P$)-4-N-Benzoyl-cytidin-3'-yl uridin-5'-yl phosphorothioate [($S_P$)-30cu]

Crude (SP)-30cu is produced as described in Example 217 using (SP)-10au instead of (RP)-4tt.

Example 232

Synthesis of the C4 enol ester pronucleotide of ($S_P$)-2-N-Phenoxyacetyl-guanosin-3'-yl uridin-5'-yl phosphorothioate [($S_P$)-30gu]

Crude (SP)-30gu is produced as described in Example 217 using (SP)-10gu instead of (RP)-4tt.

Example 233

Synthesis of the C4 enol ester pronucleotide of ($R_P$)-uridin-2'-yl uridin-5'-yl phosphorothioate [($R_P$)-31uu]

Crude (SP)-31uu is produced as described in Example 217 using (SP)-14uu instead of (RP)-4tt.

Example 234

Synthesis of the C4 enol ester pronucleotide of ($R_P$)-6-N-Benzoyl-adenosin-2'-yl uridin-5'-yl phosphorothioate [($R_P$)-31au]

Crude (RP)-31au is produced as described in Example 217 using (SP)-14au instead of (RP)-4tt.

Example 235

Synthesis of the C4 enol ester pronucleotide of ($R_P$)-4-N-Benzoyl-cytidin-2'-yl uridin-5'-yl phosphorothioate [($R_P$)-31cu]

Crude (RP)-31cu is produced as described in Example 217 using (SP)-14cu instead of (RP)-4tt.

Example 236

Synthesis of the C4 enol ester pronucleotide of ($R_P$)-2-N-Phenoxyacetyl-guanosin-2'-yl uridin-5'-yl phosphorothioate [($R_P$)-31gu]

Crude (RP)-31gu is produced as described in Example 217 using (SP)-14gu instead of (RP)-4tt.

Example 237

Synthesis of the C4 enol ester pronucleotide of ($S_P$)-uridin-2'-yl uridin-5'-yl phosphorothioate [($S_P$)-31uu]

Crude (SP)-31uu is produced as described in Example 217 using (SP)-14uu instead of (RP)-4tt.

Example 238

Synthesis of the C4 enol ester pronucleotide of ($S_P$)-6-N-Benzoyl-adenosin-2'-yl uridin-5'-yl phosphorothioate [($S_P$)-31au]

Crude (SP)-31au is produced as described in Example 217 using (SP)-14au instead of (RP)-4tt.

Example 239

Synthesis of the C4 enol ester pronucleotide of ($S_P$)-4-N-Benzoyl-cytidin-2'-yl uridin-5'-yl phosphorothioate [($S_P$)-31cu]

Crude (SP)-31cu is produced as described in Example 217 using (SP)-14cu instead of (RP)-4tt.

Example 240

Synthesis of the C4 enol ester pronucleotide of ($S_P$)-2-N-Phenoxyacetyl-guanosin-2'-yl uridin-5'-yl phosphorothioate [($S_P$)-31gu]

Crude (SP)-31gu is produced as described in Example 217 using (SP)-14gu instead of (RP)-4tt.

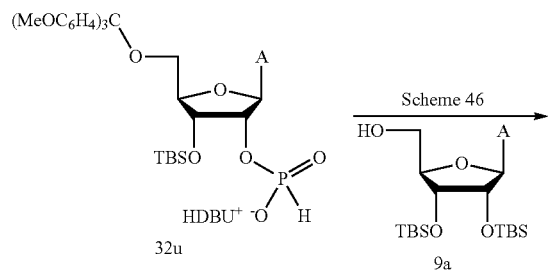

Scheme O: Synthesis of protected 2'-5'-A₃ H-phosphonate

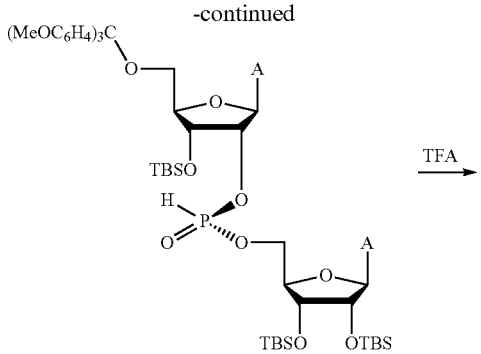

Example 241

The synthesis of a 5'-O-(methoxytrityl) protected 2'-5'-A₃ H-phosphonate is illustrated in Scheme O-a 5'-O-(Methoxytrityl) protected compound 32 is coupled with 9a as described in Scheme 6, Example 41. The resulting H-phosphonate 33 is subjected to 5'-O-(methoxytrityl) deprotection by treatment with 1% TFA in $CH_2Cl_2$ to give 5'-OH compound 34. Coupling of 34 with 32, as described in Scheme 6, Example 41, gives the H-phosphonate trinucleotide 35. Deprotection of the 5'-OH group with 1% TFA in $CH_2Cl_2$ to gives H-phosphonate trinucleotide 36.

Scheme O-b: Synthesis of a 2′-5′-A$_3$ S-acetyl-2-thioethyl pronucleotide
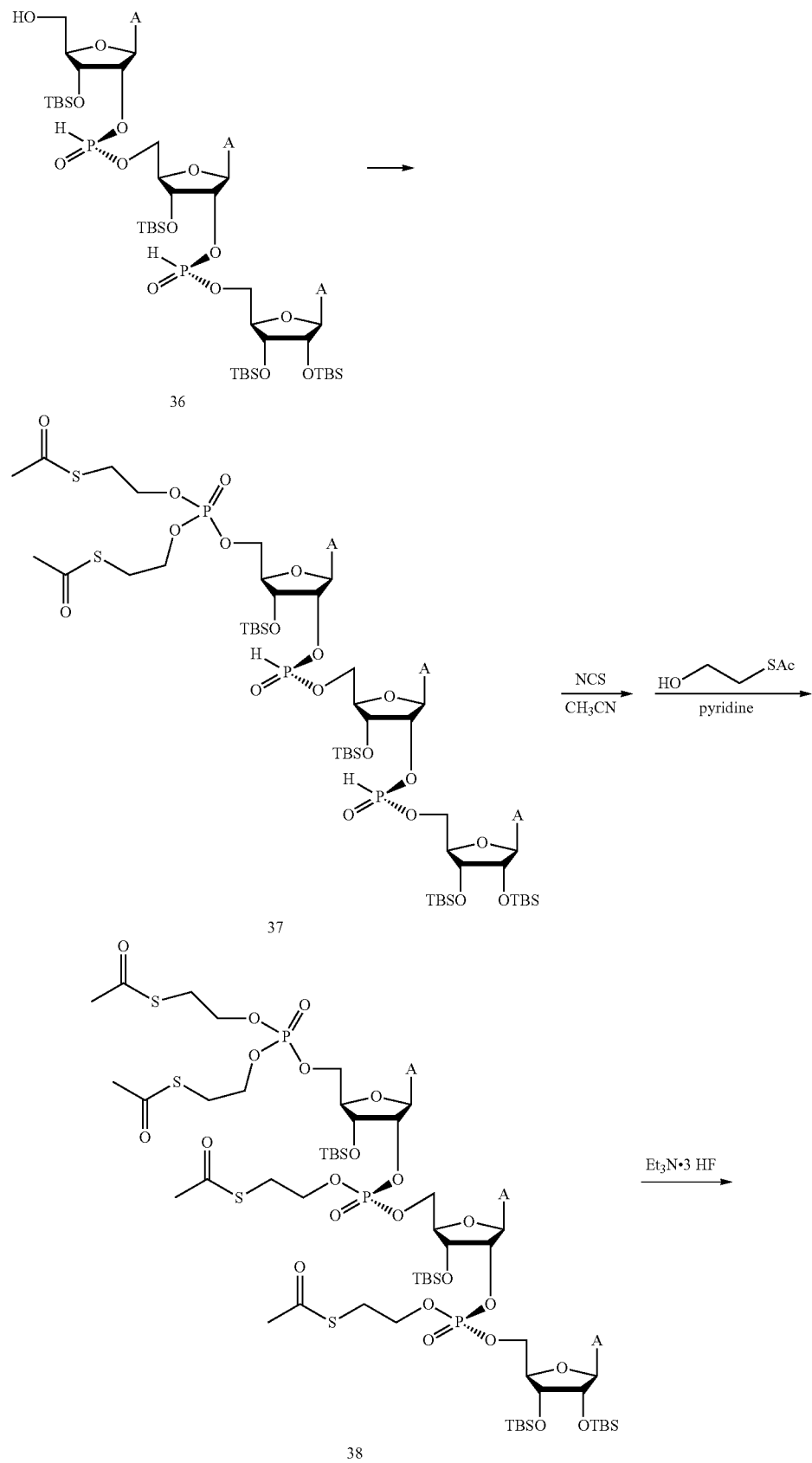

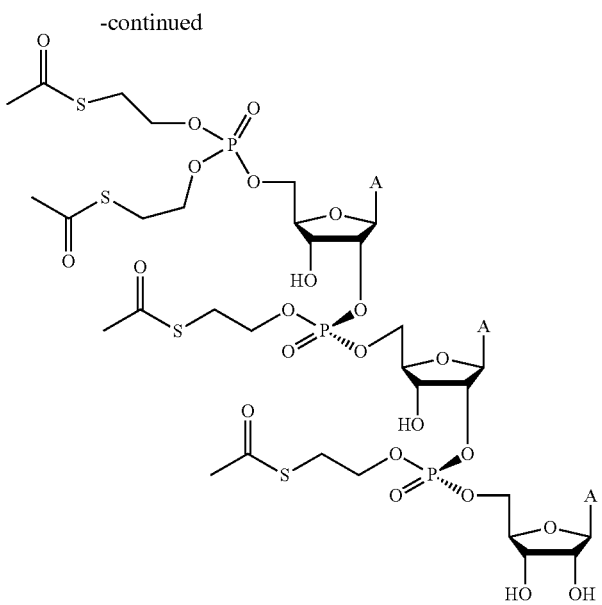

39

Example 242

Synthesis a 2'-5'-A₃ S-acetyl-2-thioethyl pronucleotide is illustrated in Scheme O-b 5'-OH H-phosphonate trinucleotide compound 36 is converted to the S-acetyl-2-thioethyl prodrug by the method of Eldrup, as described in U.S. Pat. No. 7,202,224. To 36 (1 mmol) is added 1H-tetrazole (1.1 mmol) and the mixture dried overnight over P2O5. To this mixture is added dry acetonitrile (10 mL) followed by bis(S-acetyl-2-thioethyl) N,N-diisopropylphosphoramidite (1.1 mmol) and the resulting mixture is stirred at room temperature for 2 hours. The solvent is removed, the residue cooled to −40° C. and a solution of m-CPBA (1.0 mmol) in dichloromethane (10 mL) is added. After stirring at room temperature for 1 hour, aq. NaHSO3 is added and the organic layer separated and product 37 is isolated by chromatography.

Compound 37 is converted into the final product 39 following the procedure of Scheme 7, Example 49. Compound 37 (100 μmol) is dried by repeated coevaporations with dry pyridine and then dissolved in dry pyridine (1 mL). N-chlorosuccinimide (0.1 mmol) is added, and the mixture is stirred for 2 hours at 0° C. The mixture is concentrated and dissolved in dry pyridine (1 mL). The above mixture is treated with S-acetyl-2-thioethanol (100 μmol) in dry (100 μmol) pyridine. After 1 hour, the mixture is concentrated and then dissolved in triethylamine trihydrofluoride (500 μL). The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford 39.

Scheme P: Synthesis of trimethylammoniumethyl nucleic acid prodrugs.

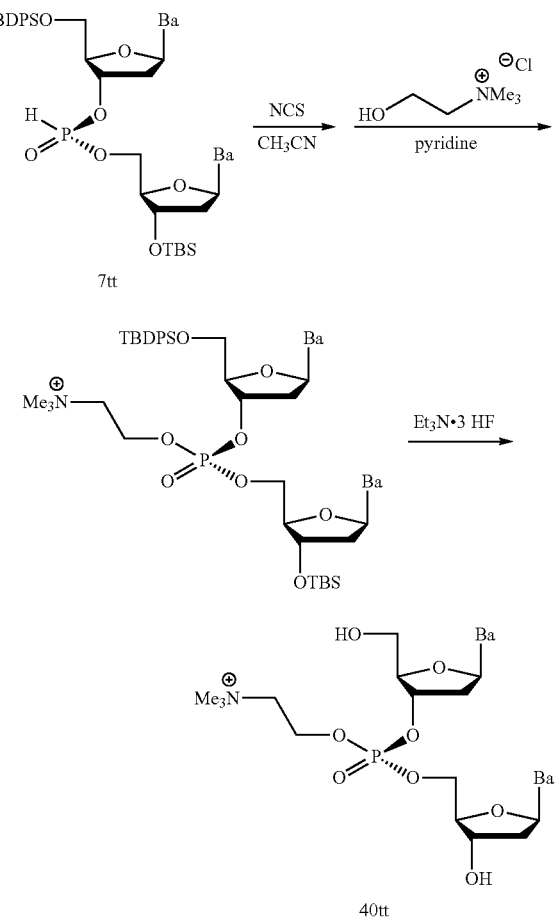

Example 243

Synthesis of the trimethylammoniumethyl nucleic acid prodrug of ($R_P$)-thymidin-3'-yl thymidin-5'-yl phosphonate [($R_P$)-16tt] as described in Scheme P (RP)-5'-O-(tert-butyldiphenylsilyl)thymidin-3'-yl 3'-O-(tert-butyldimethylsilyl)thymidin-5'-yl H-phosphonate [(RP)-7tt] (100 μmol) is dried by repeated coevaporations with dry pyridine and then dissolved in dry pyridine (1 mL). N-chlorosuccinimide (0.1 mmol) is added, and the mixture is stirred for 2 hours at 0° C. The mixture is concentrated and dissolved in dry pyridine (1 mL). The above mixture is treated with 1-(2-hydroxy)-ethyl-trimethylammonium chloride (100 μmol) in dry (100 μmol) pyridine. After 1 hour, the mixture is concentrated and then dissolved in triethylamine trihydrofluoride (500 μL). The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-40tt.

Example 244

Synthesis of the trimethylammoniumethyl pronucleotide of ($R_P$)-6-N-benzoyl-deoxyadenosin-3'-yl thymidin-5'-yl phosphonate [($R_P$)-40at]

Crude (RP)-40 at is produced as described in Example 243 using (RP)-7at instead of (RP)-7tt.

Example 245

Synthesis of the trimethylammoniumethyl pronucleotide of ($R_P$)-4-N-benzoyl-deoxycytidin-3'-yl thymidin-5'-yl phosphonate [($R_P$)-40ct]

Crude (RP)-40ct is produced as described in Example 49 using (RP)-7ct instead of (RP)-7tt.

Example 246

Synthesis of the trimethylammoniumethyl pronucleotide of ($R_P$)-2-N-phenoxyacetyl-deoxyguanosin-3'-yl thymidin-5'-yl phosphonate [($R_P$)-40gt]

Crude (RP)-40gt is produced as described in Example 49 using (RP)-7g instead of (RP)-7tt.

Example 247

Synthesis of the trimethylammoniumethyl pronucleotide of ($S_P$)-thymidin-3'-yl thymidin-5'-yl phosphonate [($S_P$)-40tt]

Crude (SP)-40tt is produced as described in Example 49 using (SP)-7tt instead of (RP)-7tt.

Example 248

Synthesis of the trimethylammoniumethyl pronucleotide of ($S_P$)-6-N-benzoyl-deoxyadenosin-3'-yl thymidin-5'-yl phosphonate [($S_P$)-40at]

Crude (SP)-40 at is produced as described in Example 49 using (SP)-7at instead of (RP)-7tt.

Example 249

Synthesis of the trimethylammoniumethyl pronucleotide of ($S_P$)-4-N-benzoyl-deoxycytidin-3'-yl thymidin-5'-yl phosphonate [($S_P$)-40ct]

Crude (SP)-40ct is produced as described in Example 49 using (SP)-7ct instead of (RP)-7tt.

Example 250

Synthesis of the trimethylammoniumethyl pronucleotide of ($S_P$)-2-N-phenoxyacetyl-deoxyguanosin-3'-yl thymidin-5'-yl phosphonate [($S_P$)-40gt]

Crude (SP)-40gt is produced as described in Example 49 using (SP)-7gt instead of (RP)-7tt.

Example 251

Synthesis of the trimethylammoniumethyl pronucleotide of ($R_P$)-uridin-3'-yl uridin-5'-yl phosphonate [($R_P$)-40uu]

Crude (RP)-40uu is produced as described in Example 49 using (RP)-12uu instead of (RP)-7tt.

Example 252

Synthesis of the trimethylammoniumethyl pronucleotide of ($R_P$)-6-N-Benzoyl-adenosin-3'-yl uridin-5'-yl phosphonate [($R_P$)-40au]

Crude (RP)-40au is produced as described in Example 49 using (RP)-12au instead of (RP)-7tt.

Example 253

Synthesis of the trimethylammoniumethyl pronucleotide of ($R_P$)-4-N-Benzoyl-cytidin-3'-yl uridin-5'-yl phosphonate [($R_P$)-40cu]

Crude (RP)-16cu is produced as described in Example 49 using (RP)-12cu instead of (RP)-7tt.

Example 254

Synthesis of the trimethylammoniumethyl pronucleotide of ($R_P$)-2-N-Phenoxyacetyl-guanosin-3'-yl uridin-5'-yl phosphonate [($R_P$)-40gu]

Crude (RP)-40gu is produced as described in Example 49 using (RP)-12gu instead of (RP)-7tt.

Example 255

Synthesis of the trimethylammoniumethyl pronucleotide of ($S_P$)-uridin-3'-yl uridin-5'-yl phosphonate [($S_P$)-40uu]

Crude (SP)-40uu is produced as described in Example 49 using (SP)-12uu instead of (RP)-7tt.

Example 256

Synthesis of the trimethylammoniumethyl pronucleotide of ($S_P$)-6-N-Benzoyl-adenosin-3'-yl uridin-5'-yl phosphonate [($S_P$)-40au]

Crude (SP)-40au is produced as described in Example 49 using (SP)-12au instead of (RP)-7tt.

Example 257

Synthesis of the trimethylammoniumethyl pronucleotide of ($S_P$)-4-N-Benzoyl-cytidin-3'-yl uridin-5'-yl phosphonate [($S_P$)-40cu]

Crude (SP)-40cu is produced as described in Example 49 using (SP)-12au instead of (RP)-7tt.

Example 258

Synthesis of the trimethylammoniumethyl pronucleotide of ($S_P$)-2-N-Phenoxyacetyl-guanosin-3'-yl uridin-5'-yl phosphonate [($S_P$)-40gu]

Crude (SP)-40gu is produced as described in Example 49 using (SP)-12gu instead of (RP)-7tt.

Example 259

Synthesis of the trimethylammoniumethyl pronucleotide of ($R_P$)-uridin-2'-yl uridin-5'-yl phosphonate [($R_P$)-41uu]

Crude (RP)-41uu is produced as described in Example 49 using (RP)-15uu instead of (RP)-7tt.

Example 260

Synthesis of the trimethylammoniumethyl pronucleotide of ($R_P$)-6-N-Benzoyl-adenosin-2'-yl uridin-5'-yl phosphonate [($R_P$)-41au]

Crude (RP)-41au is produced as described in Example 49 using (SP)-15au instead of (RP)-7tt.

Example 261

Synthesis of the trimethylammoniumethyl pronucleotide of ($R_P$)-4-N-Benzoyl-cytidin-2'-yl uridin-5'-yl phosphonate [($R_P$)-41cu]

Crude (RP)-41cu is produced as described in Example 49 using (SP)-15cu instead of (RP)-7tt.

Example 262

Synthesis of the trimethylammoniumethyl pronucleotide of ($R_P$)-2-N-Phenoxyacetyl-guanosin-2'-yl uridin-5'-yl H-phosphonate [($R_P$)-41gu]

Crude (RP)-41gu is produced as described in Example 49 using (SP)-15gu instead of (RP)-7tt.

Example 263

Synthesis of the trimethylammoniumethyl pronucleotide of ($S_P$)-uridin-2'-yl uridin-5'-yl phosphonate [($S_P$)-41uu]

Crude (SP)-41uu is produced as described in Example 49 using (SP)-15uu instead of (RP)-7tt.

Example 264

Synthesis of the trimethylammoniumethyl pronucleotide of ($S_P$)-6-N-Benzoyl-adenosin-2'-yl uridin-5'-yl phosphonate [($S_P$)-41au]

Crude (SP)-41au is produced as described in Example 49 using (SP)-15au instead of (RP)-7tt.

Example 265

Synthesis of the trimethylammoniumethyl pronucleotide of ($S_P$)-4-N-Benzoyl-cytidin-2'-yl uridin-5'-yl phosphonate [($S_P$)-41cu]

Crude (SP)-41cu is produced as described in Example 49 using (SP)-15cu instead of (RP)-7tt.

Example 266

Synthesis of the trimethylammoniumethyl pronucleotide of ($S_P$)-2-N-Phenoxyacetyl-guanosin-2'-yl uridin-5'-yl phosphonate [($S_P$)-41gu]

Crude (SP)-41gu is produced as described in Example 49 using (SP)-15gu instead of (RP)-7tt.

Scheme Q: Synthesis of alkylhydroxamate nucleic acid prodrugs.

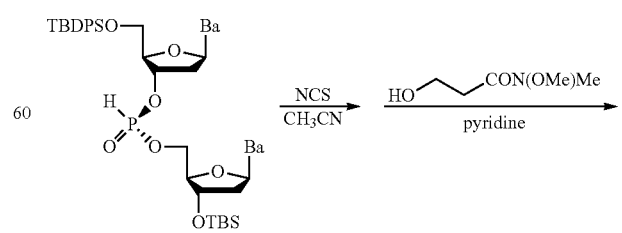

-continued

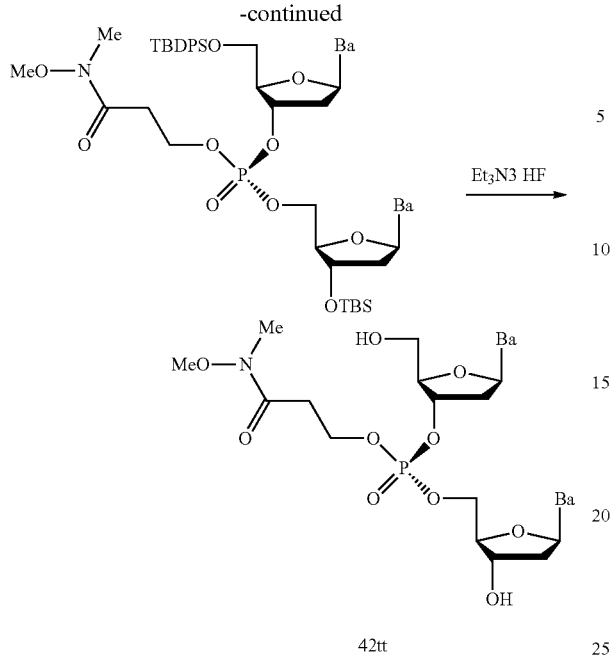

42tt

Example 267

Synthesis of the alkylhydroxamate nucleic acid prodrug of $(R_P)$-thymidin-3'-yl thymidin-5'-yl phosphonate $[(R_P)$-42tt] as described in Scheme Q (RP)-5'-O-(tert-butyldiphenylsilyl)thymidin-3'-yl 3'-O-(tert-butyldimethylsilyl)thymidin-5'-yl H-phosphonate [(RP)-7tt] (100 µmol) is dried by repeated coevaporations with dry pyridine and then dissolved in dry pyridine (1 mL). N-chlorosuccinimide (0.1 mmol) is added, and the mixture is stirred for 2 hours at 0° C. The mixture is concentrated and dissolved in dry pyridine (1 mL). The above mixture is treated with N-methoxy-N-methyl-3-hydroxypropionamide (100 µmol) in dry (100 µmol) pyridine. After 1 hour, the mixture is concentrated and then dissolved in triethylamine trihydrofluoride (500 µL). The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-42tt.

Example 268

Synthesis of the alkylhydroxamate pronucleotide of $(R_P)$-6-N-benzoyl-deoxyadenosin-3'-yl thymidin-5'-yl phosphonate $[(R_P)$-42at]

Crude (RP)-42 at is produced as described in Example 267 using (RP)-7at instead of (RP)-7tt.

Example 269

Synthesis of the alkylhydroxamate pronucleotide of $(R_P)$-4-N-benzoyl-deoxycytidin-3'-yl thymidin-5'-yl phosphonate $[(R_P)$-42ct]

Crude (RP)-42ct is produced as described in Example 267 using (RP)-7ct instead of (RP)-7tt.

Example 270

Synthesis of the alkylhydroxamate pronucleotide of $(R_P)$-2-N-phenoxyacetyl-deoxyguanosin-3'-yl thymidin-5'-yl phosphonate $[(R_P)$-42gt]

Crude (RP)-42gt is produced as described in Example 267 using (RP)-7g instead of (RP)-7tt.

Example 271

Synthesis of the alkylhydroxamate pronucleotide of $(S_P)$-thymidin-3'-yl thymidin-5'-yl phosphonate $[(S_P)$-42tt]

Crude (SP)-42tt is produced as described in Example 267 using (SP)-7tt instead of (RP)-7tt.

Example 272

Synthesis of the alkylhydroxamate pronucleotide of $(S_P)$-6-N-benzoyl-deoxyadenosin-3'-yl thymidin-5'-yl phosphonate $[(S_P)$-42at]

Crude (SP)-42 at is produced as described in Example 267 using (SP)-7at instead of (RP)-7tt.

Example 273

Synthesis of the alkylhydroxamate pronucleotide of $(S_P)$-4-N-benzoyl-deoxycytidin-3'-yl thymidin-5'-yl phosphonate $[(S_P)$-42ct]

Crude (SP)-42ct is produced as described in Example 267 using (SP)-7ct instead of (RP)-7tt.

Example 274

Synthesis of the alkylhydroxamate pronucleotide of $(S_P)$-2-N-phenoxyacetyl-deoxyguanosin-3'-yl thymidin-5'-yl phosphonate $[(S_P)$-42gt]

Crude (SP)-42gt is produced as described in Example 267 using (SP)-7gt instead of (RP)-7tt.

Example 275

Synthesis of the alkylhydroxamate pronucleotide of $(R_P)$-uridin-3'-yl uridin-5'-yl phosphonate $[(R_P)$-42uu]

Crude (RP)-42uu is produced as described in Example 267 using (RP)-12uu instead of (RP)-7tt.

Example 276

Synthesis of the alkylhydroxamate pronucleotide of $(R_P)$-6-N-Benzoyl-adenosin-3'-yl uridin-5'-yl phosphonate [$(R_P)$-42au]

Crude (RP)-42au is produced as described in Example 267 using (RP)-12au instead of (RP)-7tt.

Example 277

Synthesis of the alkylhydroxamate pronucleotide of $(R_P)$-4-N-Benzoyl-cytidin-3'-yl uridin-5'-yl phosphonate [$(R_P)$-42cu]

Crude (RP)-42cu is produced as described in Example 267 using (RP)-12cu instead of (RP)-7tt.

Example 278

Synthesis of the alkylhydroxamate pronucleotide of $(R_P)$-2-N-Phenoxyacetyl-guanosin-3'-yl uridin-5'-yl phosphonate [$(R_P)$-42gu]

Crude (RP)-42gu is produced as described in Example 267 using (RP)-12gu instead of (RP)-7tt.

Example 279

Synthesis of the alkylhydroxamate pronucleotide of $(S_P)$-uridin-3'-yl uridin-5'-yl phosphonate [(Sp)-42uu]

Crude (SP)-42uu is produced as described in Example 267 using (SP)-12uu instead of (RP)-7tt.

Example 280

Synthesis of the alkylhydroxamate pronucleotide of $(S_P)$-6-N-Benzoyl-adenosin-3'-yl uridin-5'-yl phosphonate [$(S_P)$-42au]

Crude (SP)-42au is produced as described in Example 267 using (SP)-12au instead of (RP)-7tt.

Example 281

Synthesis of the alkylhydroxamate pronucleotide of $(S_P)$-4-N-Benzoyl-cytidin-3'-yl uridin-5'-yl phosphonate [$(S_P)$-42cu]

Crude (SP)-42cu is produced as described in Example 267 using (SP)-12au instead of (RP)-7tt.

Example 282

Synthesis of the alkylhydroxamate pronucleotide of $(S_P)$-2-N-Phenoxyacetyl-guanosin-3'-yl uridin-5'-yl phosphonate [$(S_P)$-42gu]

Crude (SP)-42gu is produced as described in Example 267 using (SP)-12gu instead of (RP)-7tt.

Example 283

Synthesis of the alkylhydroxamate pronucleotide of $(R_P)$-uridin-2'-yl uridin-5'-yl phosphonate [$(R_P)$-43uu]

Crude (RP)-43uu is produced as described in Example 267 using (RP)-15uu instead of (RP)-7tt.

Example 284

Synthesis of the alkylhydroxamate pronucleotide of $(R_P)$-6-N-Benzoyl-adenosin-2'-yl uridin-5'-yl phosphonate [$(R_P)$-43au]

Crude (RP)-43au is produced as described in Example 267 using (SP)-15au instead of (RP)-7tt.

Example 285

Synthesis of the alkylhydroxamate pronucleotide of $(R_P)$-4-N-Benzoyl-cytidin-2'-yl uridin-5'-yl phosphonate [$(R_P)$-43cu]

Crude (RP)-43cu is produced as described in Example 267 using (SP)-15cu instead of (RP)-7tt.

Example 286

Synthesis of the alkylhydroxamate pronucleotide of $(R_P)$-2-N-Phenoxyacetyl-guanosin-2'-yl uridin-5'-yl H-phosphonate [$(R_P)$-43gu]

Crude (RP)-43gu is produced as described in Example 267 using (SP)-15gu instead of (RP)-7tt.

Example 287

Synthesis of the alkylhydroxamate pronucleotide of $(S_P)$-uridin-2'-yl uridin-5'-yl phosphonate [$(S_P)$-43uu]

Crude (SP)-43uu is produced as described in Example 267 using (SP)-15uu instead of (RP)-7tt.

Example 288

Synthesis of the alkylhydroxamate pronucleotide of $(S_P)$-6-N-Benzoyl-adenosin-2'-yl uridin-5'-yl phosphonate [$(S_P)$-43au]

Crude (SP)-43au is produced as described in Example 267 using (SP)-15au instead of (RP)-7tt.

Example 289

Synthesis of the alkylhydroxamate pronucleotide of $(S_P)$-4-N-Benzoyl-cytidin-2'-yl uridin-5'-yl phosphonate [$(S_P)$-43cu]

Crude (SP)-43cu is produced as described in Example 267 using (SP)-15cu instead of (RP)-7tt.

Example 290

Synthesis of the alkylhydroxamate pronucleotide of ($S_P$)-2-N-Phenoxyacetyl-guanosin-2'-yl uridin-5'-yl phosphonate [($S_P$)-43gu]

Crude (SP)-43gu is produced as described in Example 267 using (SP)-15gu instead of (RP)-7tt.

Scheme R: Synthesis of acylhydroxamate nucleic acid prodrugs.

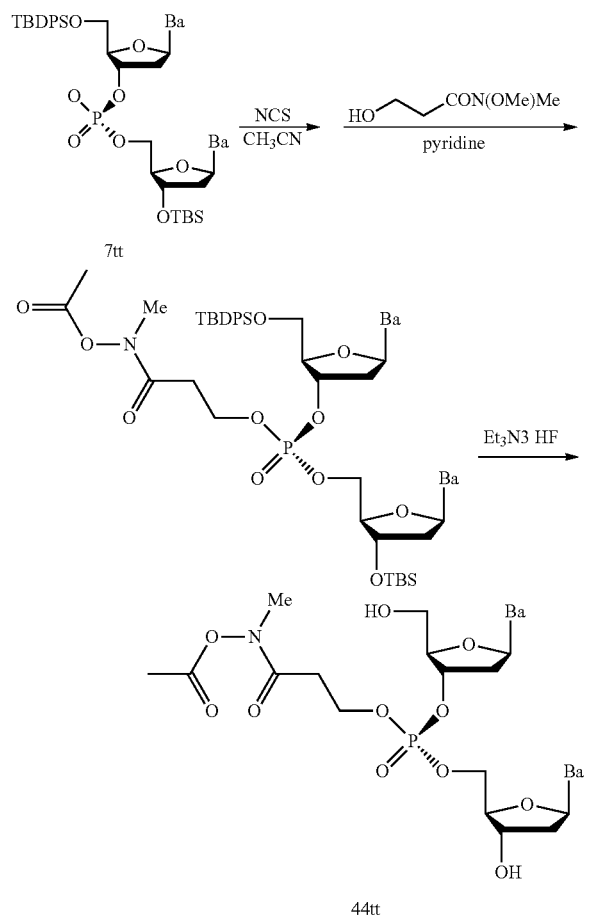

Example 291

Synthesis of the acylhydroxamate nucleic acid prodrug of ($R_P$)-thymidin-3'-yl thymidin-5'-yl phosphonate [($R_P$)-44tt] as described in Scheme R (RP)-5'-O-(tert-butyldiphenylsilyl)thymidin-3'-yl 3'-O-(tert-butyldimethylsilyl)thymidin-5'-yl H-phosphonate [(RP)-7tt] (100 μmol) is dried by repeated coevaporations with dry pyridine and then dissolved in dry pyridine (1 mL). N-chlorosuccinimide (0.1 mmol) is added, and the mixture is stirred for 2 hours at 0° C. The mixture is concentrated and dissolved in dry pyridine (1 mL). The above mixture is treated with N-acyloxy-N-methyl-3-hydroxypropionamide (100 μmol) in dry (100 μmol) pyridine. After 1 hour, the mixture is concentrated and then dissolved in triethylamine trihydrofluoride (500 μL). The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-44tt.

Example 292

Synthesis of the acylhydroxamate pronucleotide of ($R_P$)-6-N-benzoyl-deoxyadenosin-3'-yl thymidin-5'-yl phosphonate [($R_P$)-44at]

Crude (RP)-40 at is produced as described in Example 291 using (RP)-7at instead of (RP)-7tt.

Example 293

Synthesis of the acylhydroxamate pronucleotide of ($R_P$)-4-N-benzoyl-deoxycytidin-3'-yl thymidin-5'-yl phosphonate [($R_P$)-44ct]

Crude (RP)-44ct is produced as described in Example 291 using (RP)-7ct instead of (RP)-7tt.

Example 294

Synthesis of the acylhydroxamate pronucleotide of ($R_P$)-2-N-phenoxyacetyl-deoxyguanosin-3'-yl thymidin-5'-yl phosphonate [($R_P$)-44gt]

Crude (RP)-44gt is produced as described in Example 291 using (RP)-7g instead of (RP)-7tt.

Example 295

Synthesis of the acylhydroxamate pronucleotide of ($S_P$)-thymidin-3'-yl thymidin-5'-yl phosphonate [($S_P$)-44tt]

Crude (SP)-44tt is produced as described in Example 291 using (SP)-7tt instead of (RP)-7tt.

Example 296

Synthesis of the acylhydroxamate pronucleotide of ($S_P$)-6-N-benzoyl-deoxyadenosin-3'-yl thymidin-5'-yl phosphonate [($S_P$)-44at]

Crude (SP)-44 at is produced as described in Example 291 using (SP)-7at instead of (RP)-7tt.

Example 297

Synthesis of the acylhydroxamate pronucleotide of ($S_P$)-4-N-benzoyl-deoxycytidin-3'-yl thymidin-5'-yl phosphonate [($S_P$)-44ct]

Crude (SP)-44ct is produced as described in Example 291 using (SP)-7ct instead of (RP)-7tt.

Example 298

Synthesis of the acylhydroxamate pronucleotide of (S$_P$)-2-N-phenoxyacetyl-deoxyguanosin-3'-yl thymidin-5'-yl phosphonate [(S$_P$)-44gt]

Crude (SP)-44gt is produced as described in Example 291 using (SP)-7gt instead of (RP)-7tt.

Example 299

Synthesis of the acylhydroxamate pronucleotide of (R$_P$)-uridin-3'-yl uridin-5'-yl phosphonate [(R$_P$)-44uu]

Crude (RP)-44uu is produced as described in Example 291 using (RP)-12uu instead of (RP)-7tt.

Example 300

Synthesis of the acylhydroxamate pronucleotide of (R$_P$)-6-N-Benzoyl-adenosin-3'-yl uridin-5'-yl phosphonate [(R$_P$)-44au]

Crude (RP)-44au is produced as described in Example 291 using (RP)-12au instead of (RP)-7tt.

Example 301

Synthesis of the acylhydroxamate pronucleotide of (R$_P$)-4-N-Benzoyl-cytidin-3'-yl uridin-5'-yl phosphonate [(R$_P$)-44cu]

Crude (RP)-44cu is produced as described in Example 291 using (RP)-12cu instead of (RP)-7tt.

Example 302

Synthesis of the acylhydroxamate pronucleotide of (R$_P$)-2-N-Phenoxyacetyl-guanosin-3'-yl uridin-5'-yl phosphonate [(R$_P$)-44gu]

Crude (RP)-40gu is produced as described in Example 291 using (RP)-12gu instead of (RP)-7tt.

Example 303

Synthesis of the acylhydroxamate pronucleotide of (S$_P$)-uridin-3'-yl uridin-5'-yl phosphonate [(Sp)-44uu]

Crude (SP)-44uu is produced as described in Example 291 using (SP)-12uu instead of (RP)-7tt.

Example 304

Synthesis of the acylhydroxamate pronucleotide of (S$_P$)-6-N-Benzoyl-adenosin-3'-yl uridin-5'-yl phosphonate [(S$_P$)-44au]

Crude (SP)-44au is produced as described in Example 291 using (SP)-12au instead of (RP)-7tt.

Example 305

Synthesis of the acylhydroxamate pronucleotide of (S$_P$)-4-N-Benzoyl-cytidin-3'-yl uridin-5'-yl phosphonate [(S$_P$)-44cu]

Crude (SP)-44cu is produced as described in Example 291 using (SP)-12au instead of (RP)-7tt.

Example 306

Synthesis of the acylhydroxamate pronucleotide of (S$_P$)-2-N-Phenoxyacetyl-guanosin-3'-yl uridin-5'-yl phosphonate [(S$_P$)-44gu]

Crude (SP)-44gu is produced as described in Example 291 using (SP)-12gu instead of (RP)-7tt.

Example 307

Synthesis of the acylhydroxamate pronucleotide of (R$_P$)-uridin-2'-yl uridin-5'-yl phosphonate [(R$_P$)-45uu]

Crude (RP)-45uu is produced as described in Example 291 using (RP)-15uu instead of (RP)-7tt.

Example 308

Synthesis of the acylhydroxamate pronucleotide of (R$_P$)-6-N-Benzoyl-adenosin-2'-yl uridin-5'-yl phosphonate [(R$_P$)-45au]

Crude (RP)-45au is produced as described in Example 291 using (SP)-15au instead of (RP)-7tt.

Example 309

Synthesis of the acylhydroxamate pronucleotide of (R$_P$)-4-N-Benzoyl-cytidin-2'-yl uridin-5'-yl phosphonate [(R$_P$)-45cu]

Crude (RP)-45cu is produced as described in Example 291 using (SP)-15cu instead of (RP)-7tt.

Example 310

Synthesis of the acylhydroxamate pronucleotide of (R$_P$)-2-N-Phenoxyacetyl-guanosin-2'-yl uridin-5'-yl H-phosphonate [(R$_P$)-45gu]

Crude (RP)-45gu is produced as described in Example 291 using (SP)-15gu instead of (RP)-7tt.

Example 311

Synthesis of the acylhydroxamate pronucleotide of (S$_P$)-uridin-2'-yl uridin-5'-yl phosphonate [(Sp)-45uu]

Crude (SP)-45uu is produced as described in Example 291 using (SP)-15uu instead of (RP)-7tt.

Example 312

Synthesis of the acylhydroxamate pronucleotide of $(S_P)$-6-N-Benzoyl-adenosin-2'-yl uridin-5'-yl phosphonate [$(S_P)$-45au]

Crude (SP)-45au is produced as described in Example 291 using (SP)-15au instead of (RP)-7tt.

Example 313

Synthesis of the acylhydroxamate pronucleotide of $(S_P)$-4-N-Benzoyl-cytidin-2'-yl uridin-5'-yl phosphonate [$(S_P)$-45cu]

Crude (SP)-45cu is produced as described in Example 291 using (SP)-15cu instead of (RP)-7tt.

Example 314

Synthesis of the acylhydroxamate pronucleotide of $(S_P)$-2-N-Phenoxyacetyl-guanosin-2'-yl uridin-5'-yl phosphonate [$(S_P)$-45gu]

Crude (SP)-45gu is produced as described in Example 291 using (SP)-15gu instead of (RP)-7tt.

Scheme S: Synthesis of thiotrialkylammoniumethyl pronucleotides.

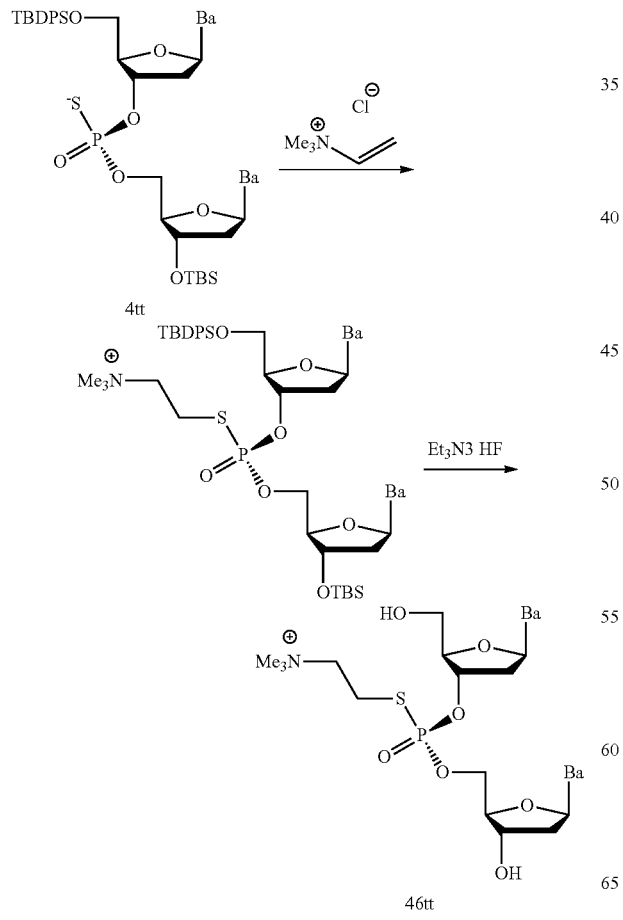

Example 315

Synthesis of the thiotrialkylammoniumethyl pronucleotide of $(R_P)$-thymidin-3'-yl thymidin-5'-yl phosphorothioate [$(R_P)$-46tt] as described in Scheme S (SP)-1,8-Diazabicyclo[5.4.0]undec-7-enium 5'-O-(tert-butyldiphenylsilyl)thymidin-3'-yl 3'-O-(tert-butyldimethylsilyl)thymidin-5'-yl phosphorothioate [(SP)-4tt] (100 μmol) is dried by repeated coevaporations with dry pyridine and then dissolved in dry methylene chloride (1 mL). The mixture is treated with vinyltrimethylammonium chloride (100 μmol) in dry (100 μmol) methylene chloride. After 1 hour, the mixture is concentrated and then dissolved in triethylamine trihydrofluoride (500 μL). The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-46tt.

Example 316

Synthesis of the thiotrialkylammoniumethyl pronucleotide of $(R_P)$-6-N-benzoyl-deoxyadenosin-3'-yl thymidin-5'-yl phosphorothioate [$(R_P)$-46at]

Crude (RP)-46 at is produced as described in Example 315 using (RP)-4 at instead of (RP)-4tt.

Example 317

Synthesis of the thiotrialkylammoniumethyl pronucleotide of $(R_P)$-4-N-benzoyl-deoxycytidin-3'-yl thymidin-5'-yl phosphorothioate [$(R_P)$-46ct]

Crude (RP)-46ct is produced as described in Example 315 using (RP)-4ct instead of (RP)-4tt.

Example 318

Synthesis of the thiotrialkylammoniumethyl pronucleotide of $(R_P)$-2-N-phenoxyacetyl-deoxyguanosin-3'-yl thymidin-5'-yl phosphorothioate [$(R_P)$-46gt]

Crude (RP)-46gt is produced as described in Example 315 using (RP)-4g instead of (RP)-4tt.

Example 319

Synthesis of the thiotrialkylammoniumethyl pronucleotide of $(S_P)$— thymidin-3'-yl thymidin-5'-yl phosphorothioate [$(S_P)$-46tt]

Crude (SP)-46tt is produced as described in Example 315 using (SP)-4tt instead of (RP)-4tt.

Example 320

Synthesis of the thiotrialkylammoniumethyl pronucleotide of ($S_P$)-6-N-benzoyl-deoxyadenosin-3'-yl thymidin-5'-yl phosphorothioate [($S_P$)-46at]

Crude (SP)-46 at is produced as described in Example 315 using (SP)-4 at instead of (RP)-4tt.

Example 321

Synthesis of the thiotrialkylammoniumethyl pronucleotide of ($S_P$)-4-N-benzoyl-deoxycytidin-3'-yl thymidin-5'-yl phosphorothioate [($S_P$)-46ct]

Crude (SP)-46ct is produced as described in Example 315 using (SP)-4ct instead of (RP)-4tt.

Example 322

Synthesis of the thiotrialkylammoniumethyl pronucleotide of ($S_P$)-2-N-phenoxyacetyl-deoxyguanosin-3'-yl thymidin-5'-yl phosphorothioate [($S_P$)-46gt]

Crude (SP)-46gt is produced as described in Example 315 using (SP)-4gt instead of (RP)-4tt.

Example 323

Synthesis of the thiotrialkylammoniumethyl pronucleotide of ($R_P$)-uridin-3'-yl uridin-5'-yl phosphorothioate [($R_P$)-46uu]

Crude (RP)-46uu is produced as described in Example 315 using (RP)-10uu instead of (RP)-4tt.

Example 324

Synthesis of the thiotrialkylammoniumethyl pronucleotide of ($R_P$)-6-N-Benzoyl-adenosin-3'-yl uridin-5'-yl phosphorothioate [($R_P$)-46au]

Crude (RP)-46au is produced as described in Example 315 using (RP)-10au instead of (RP)-4tt.

Example 325

Synthesis of the thiotrialkylammoniumethyl pronucleotide of ($R_P$)-4-N-Benzoyl-cytidin-3'-yl uridin-5'-yl phosphorothioate [($R_P$)-46cu]

Crude (RP)-46cu is produced as described in Example 315 using (RP)-10cu instead of (RP)-4tt.

Example 326

Synthesis of the thiotrialkylammoniumethyl pronucleotide of ($R_P$)-2-N-Phenoxyacetyl-guanosin-3'-yl uridin-5'-yl phosphorothioate [($R_P$)-46gu]

Crude (RP)-46gu is produced as described in Example 315 using (RP)-10gu instead of (RP)-4tt.

Example 327

Synthesis of the thiotrialkylammoniumethyl pronucleotide of ($S_P$)-uridin-3'-yl uridin-5'-yl phosphorothioate [($S_P$)-46uu]

Crude (SP)-46uu is produced as described in Example 315 using (SP)-10uu instead of (RP)-4tt.

Example 328

Synthesis of the thiotrialkylammoniumethyl pronucleotide of ($S_P$)-6-N-Benzoyl-adenosin-3'-yl uridin-5'-yl phosphorothioate [($S_P$)-46au]

Crude (SP)-46au is produced as described in Example 315 using (SP)-10au instead of (RP)-4tt.

Example 329

Synthesis of the thiotrialkylammoniumethyl pronucleotide of ($S_P$)-4-N-Benzoyl-cytidin-3'-yl uridin-5'-yl phosphorothioate [($S_P$)-46cu]

Crude (SP)-46cu is produced as described in Example 315 using (SP)-10au instead of (RP)-4tt.

Example 330

Synthesis of the thiotrialkylammoniumethyl pronucleotide of ($S_P$)-2-N-Phenoxyacetyl-guanosin-3'-yl uridin-5'-yl phosphorothioate [($S_P$)-46gu]

Crude (SP)-46gu is produced as described in Example 315 using (SP)-10gu instead of (RP)-4tt.

Example 331

Synthesis of the thiotrialkylammoniumethyl pronucleotide of ($R_P$)-uridin-2'-yl uridin-5'-yl phosphorothioate [($R_P$)-47uu]

Crude (SP)-47uu is produced as described in Example 315 using (SP)-14uu instead of (RP)-4tt.

Example 332

Synthesis of the thiotrialkylammoniumethyl pronucleotide of ($R_P$)-6-N-Benzoyl-adenosin-2'-yl uridin-5'-yl phosphorothioate [($R_P$)-47au]

Crude (RP)-47au is produced as described in Example 315 using (SP)-14au instead of (RP)-4tt.

Example 333

Synthesis of the thiotrialkylammoniumethyl pronucleotide of ($R_P$)-4-N-Benzoyl-cytidin-2'-yl uridin-5'-yl phosphorothioate [($R_P$)-47cu]

Crude (RP)-47cu is produced as described in Example 315 using (SP)-14cu instead of (RP)-4tt.

Example 334

Synthesis of the thiotrialkylammoniumethyl pronucleotide of (R$_P$)-2-N-Phenoxyacetyl-guanosin-2'-yl uridin-5'-yl phosphorothioate [(R$_P$)-47gu]

Crude (RP)-47gu is produced as described in Example 315 using (SP)-14gu instead of (RP)-4tt.

Example 335

Synthesis of the thiotrialkylammoniumethyl pronucleotide of (S$_P$)-uridin-2'-yl uridin-5'-yl phosphorothioate [(S$_P$)-47uu]

Crude (SP)-47uu is produced as described in Example 315 using (SP)-14uu instead of (RP)-4tt.

Example 336

Synthesis of the thiotrialkylammoniumethyl pronucleotide of (S$_P$)-6-N-Benzoyl-adenosin-2'-yl uridin-5'-yl phosphorothioate [(S$_P$)-47au]

Crude (SP)-47au is produced as described in Example 315 using (SP)-14au instead of (RP)-4tt.

Example 337

Synthesis of the thiotrialkylammoniumethyl pronucleotide of (S$_P$)-4-N-Benzoyl-cytidin-2'-yl uridin-5'-yl phosphorothioate [(S$_P$)-47cu]

Crude (SP)-47cu is produced as described in Example 315 using (SP)-14cu instead of (RP)-4tt.

Example 338

Synthesis of the thiotrialkylammoniumethyl pronucleotide of (S$_P$)-2-N-Phenoxyacetyl-guanosin-2'-yl uridin-5'-yl phosphorothioate [(S$_P$)-47gu]

Crude (SP)-47gu is produced as described in Example 315 using (SP)-14gu instead of (RP)-4tt.

Scheme T: Synthesis of thio N-alkylhydroxamate pronucleotides.

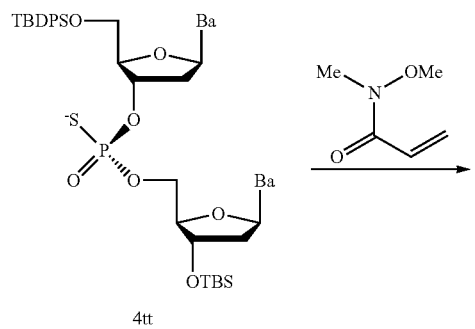

4tt

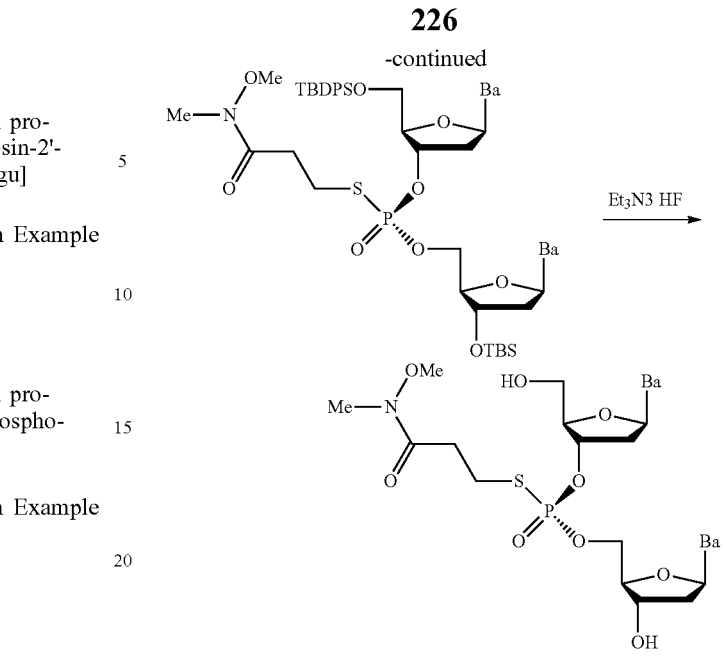

48tt

Example 339

Synthesis of the thio N-alkylhydroxamate pronucleotide of (R$_P$)-thymidin-3'-yl thymidin-5'-yl phosphorothioate [(R$_P$)-48tt] as described in Scheme T (SP)-1,8-Diazabicyclo[5.4.0]undec-7-enium 5'-O-(tert-butyldiphenylsilyl)thymidin-3'-yl 3'-O-(tert-butyldimethylsilyl)thymidin-5'-yl phosphorothioate [(SP)-4tt] (100 μmol) is dried by repeated coevaporations with dry pyridine and then dissolved in dry methylene chloride (1 mL). The mixture is treated with N,O-dimethylacrylamide (100 μmol) in dry (100 μmol) methylene chloride. After 1 hour, the mixture is concentrated and then dissolved in triethylamine trihydrofluoride (500 μL). The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-48tt.

Example 340

Synthesis of the thio N-alkylhydroxamate pronucleotide of (R$_P$)-6-N-benzoyl-deoxyadenosin-3'-yl thymidin-5'-yl phosphorothioate [(R$_P$)-48at]

Crude (RP)-48 at is produced as described in Example 339 using (RP)-4 at instead of (RP)-4tt.

Example 341

Synthesis of the thio N-alkylhydroxamate pronucleotide of ($R_P$)-4-N-benzoyl-deoxycytidin-3'-yl thymidin-5'-yl phosphorothioate [($R_P$)-48ct]

Crude (RP)-48ct is produced as described in Example 339 using (RP)-4ct instead of (RP)-4tt.

Example 342

Synthesis of the thio N-alkylhydroxamate pronucleotide of ($R_P$)-2-N-phenoxyacetyl-deoxyguanosin-3'-yl thymidin-5'-yl phosphorothioate [($R_P$)-48gt]

Crude (RP)-48gt is produced as described in Example 339 using (RP)-4g instead of (RP)-4tt.

Example 343

Synthesis of the thio N-alkylhydroxamate pronucleotide of ($S_P$)-thymidin-3'-yl thymidin-5'-yl phosphorothioate [($S_P$)-48tt]

Crude (SP)-48tt is produced as described in Example 339 using (SP)-4tt instead of (RP)-4tt.

Example 344

Synthesis of the thio N-alkylhydroxamate pronucleotide of ($S_P$)-6-N-benzoyl-deoxyadenosin-3'-yl thymidin-5'-yl phosphorothioate [($S_P$)-48at]

Crude (SP)-48 at is produced as described in Example 339 using (SP)-4 at instead of (RP)-4tt.

Example 345

Synthesis of the thio N-alkylhydroxamate pronucleotide of ($S_P$)-4-N-benzoyl-deoxycytidin-3'-yl thymidin-5'-yl phosphorothioate [($S_P$)-48ct]

Crude (SP)-48ct is produced as described in Example 339 using (SP)-4ct instead of (RP)-4tt.

Example 346

Synthesis of the thio N-alkylhydroxamate pronucleotide of ($S_P$)-2-N-phenoxyacetyl-deoxyguanosin-3'-yl thymidin-5'-yl phosphorothioate [($S_P$)-48gt]

Crude (SP)-48gt is produced as described in Example 339 using (SP)-4gt instead of (RP)-4tt.

Example 347

Synthesis of the thio N-alkylhydroxamate pronucleotide of ($R_P$)-uridin-3'-yl uridin-5'-yl phosphorothioate [($R_P$)-48uu]

Crude (RP)-48uu is produced as described in Example 339 using (RP)-10uu instead of (RP)-4tt.

Example 348

Synthesis of the thio N-alkylhydroxamate pronucleotide of ($R_P$)-6-N-Benzoyl-adenosin-3'-yl uridin-5'-yl phosphorothioate [($R_P$)-48au]

Crude (RP)-48au is produced as described in Example 339 using (RP)-10au instead of (RP)-4tt.

Example 349

Synthesis of the thio N-alkylhydroxamate pronucleotide of ($R_P$)-4-N-Benzoyl-cytidin-3'-yl uridin-5'-yl phosphorothioate [($R_P$)-48cu]

Crude (RP)-48cu is produced as described in Example 339 using (RP)-10cu instead of (RP)-4tt.

Example 350

Synthesis of the thio N-alkylhydroxamate pronucleotide of ($R_P$)-2-N-Phenoxyacetyl-guanosin-3'-yl uridin-5'-yl phosphorothioate [($R_P$)-48gu]

Crude (RP)-48gu is produced as described in Example 339 using (RP)-10gu instead of (RP)-4tt.

Example 351

Synthesis of the thio N-alkylhydroxamate pronucleotide of ($S_P$)-uridin-3'-yl uridin-5'-yl phosphorothioate [($S_P$)-48uu]

Crude (SP)-48uu is produced as described in Example 339 using (SP)-10uu instead of (RP)-4tt.

Example 352

Synthesis of the thio N-alkylhydroxamate pronucleotide of ($S_P$)-6-N-Benzoyl-adenosin-3'-yl uridin-5'-yl phosphorothioate [($S_P$)-48au]

Crude (SP)-48au is produced as described in Example 339 using (SP)-10au instead of (RP)-4tt.

Example 353

Synthesis of the thio N-alkylhydroxamate pronucleotide of ($S_P$)-4-N-Benzoyl-cytidin-3'-yl uridin-5'-yl phosphorothioate [($S_P$)-48cu]

Crude (SP)-48cu is produced as described in Example 339 using (SP)-10au instead of (RP)-4tt.

Example 354

Synthesis of the thio N-alkylhydroxamate pronucleotide of ($S_P$)-2-N-Phenoxyacetyl-guanosin-3'-yl uridin-5'-yl phosphorothioate [($S_P$)-48gu]

Crude (SP)-48gu is produced as described in Example 339 using (SP)-10gu instead of (RP)-4tt.

Example 355

Synthesis of the thio N-alkylhydroxamate pronucleotide of $(R_P)$-uridin-2'-yl uridin-5'-yl phosphorothioate $[(R_P)$-49uu]

Crude (SP)-49uu is produced as described in Example 339 using (SP)-14uu instead of (RP)-4tt.

Example 356

Synthesis of the thio N-alkylhydroxamate pronucleotide of $(R_P)$-6-N-Benzoyl-adenosin-2'-yl uridin-5'-yl phosphorothioate $[(R_P)$-49au]

Crude (RP)-49au is produced as described in Example 339 using (SP)-14au instead of (RP)-4tt.

Example 357

Synthesis of the thio N-alkylhydroxamate pronucleotide of $(R_P)$-4-N-Benzoyl-cytidin-2'-yl uridin-5'-yl phosphorothioate $[(R_P)$-49cu]

Crude (RP)-49cu is produced as described in Example 339 using (SP)-14cu instead of (RP)-4tt.

Example 358

Synthesis of the thio N-alkylhydroxamate pronucleotide of $(R_P)$-2-N-Phenoxyacetyl-guanosin-2'-yl uridin-5'-yl phosphorothioate $[(R_P)$-49gu]

Crude (RP)-49gu is produced as described in Example 339 using (SP)-14gu instead of (RP)-4tt.

Example 359

Synthesis of the thio N-alkylhydroxamate pronucleotide of $(S_P)$-uridin-2'-yl uridin-5'-yl phosphorothioate $[(S_P)$-49uu]

Crude (SP)-49uu is produced as described in Example 339 using (SP)-14uu instead of (RP)-4tt.

Example 360

Synthesis of the thio N-alkylhydroxamate pronucleotide of $(S_P)$-6-N-Benzoyl-adenosin-2'-yl uridin-5'-yl phosphorothioate $[(S_P)$-49au]

Crude (SP)-49au is produced as described in Example 339 using (SP)-14au instead of (RP)-4tt.

Example 361

Synthesis of the thio N-alkylhydroxamate pronucleotide of $(S_P)$-4-N-Benzoyl-cytidin-2'-yl uridin-5'-yl phosphorothioate $[(S_P)$-49cu]

Crude (SP)-49cu is produced as described in Example 339 using (SP)-14cu instead of (RP)-4tt.

Example 362

Synthesis of the thio N-alkylhydroxamate pronucleotide of $(S_P)$-2-N-Phenoxyacetyl-guanosin-2'-yl uridin-5'-yl phosphorothioate $[(S_P)$-49gu]

Crude (SP)-49gu is produced as described in Example 339 using (SP)-14gu instead of (RP)-4tt.

Scheme U: Synthesis of thio N-acetoxyhydroxamate pronucleotides.

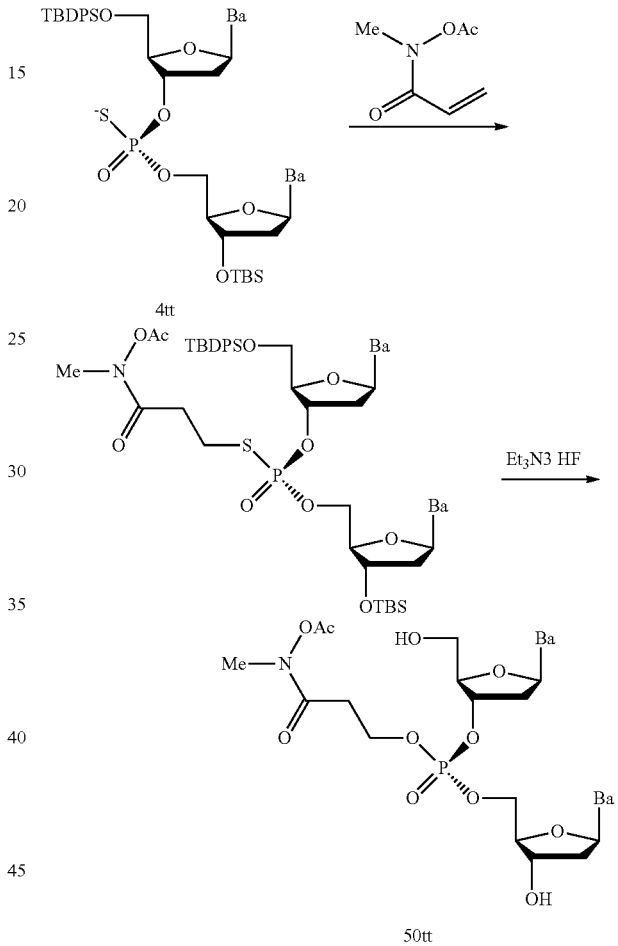

Example 363

Synthesis of the thio N-acetoxyhydroxamate pronucleotide of $(R_P)$-thymidin-3'-yl thymidin-5'-yl phosphorothioate $[(R_P)$-50tt] as described in Scheme U (SP)-1,8-Diazabicyclo[5.4.0]undec-7-enium 5'-O-(tert-butyldiphenylsilyl)thymidin-3'-yl 3'-O-(tert-butyldimethylsilyl)thymidin-5'-yl phosphorothioate [(SP)-4tt] (100 µmol) is dried by repeated coevaporations with dry pyridine and then dissolved in dry methylene chloride (1 mL). The mixture is treated with N-methyl-N-acetoxy-acrylamide (100 µmol) in dry (100 µmol) methylene chloride. After 1 hour, the mixture is concentrated and then dissolved in triethylamine trihydrofluoride (500 µL). The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-50tt.

Example 364

Synthesis of the thio N-acetoxyhydroxamate pronucleotide of $(R_P)$-6-N-benzoyl-deoxyadenosin-3'-yl thymidin-5'-yl phosphorothioate [$(R_P)$-50at]

Crude (RP)-50 at is produced as described in Example 363 using (RP)-4 at instead of (RP)-4tt.

Example 365

Synthesis of the thio N-acetoxyhydroxamate pronucleotide of $(R_P)$-4-N-benzoyl-deoxycytidin-3'-yl thymidin-5'-yl phosphorothioate [$(R_P)$-50ct]

Crude (RP)-50ct is produced as described in Example 363 using (RP)-4ct instead of (RP)-4tt.

Example 366

Synthesis of the thio N-acetoxyhydroxamate pronucleotide of $(R_P)$-2-N-phenoxyacetyl-deoxyguanosin-3'-yl thymidin-5'-yl phosphorothioate [$(R_P)$-50gt]

Crude (RP)-50gt is produced as described in Example 363 using (RP)-4g instead of (RP)-4tt.

Example 367

Synthesis of the thio N-acetoxyhydroxamate pronucleotide of $(S_P)$-thymidin-3'-yl thymidin-5'-yl phosphorothioate [$(S_P)$-50tt]

Crude (SP)-50tt is produced as described in Example 363 using (SP)-4tt instead of (RP)-4tt.

Example 368

Synthesis of the thio N-acetoxyhydroxamate pronucleotide of $(S_P)$-6-N-benzoyl-deoxyadenosin-3'-yl thymidin-5'-yl phosphorothioate [$(S_P)$-50at]

Crude (SP)-50 at is produced as described in Example 363 using (SP)-4 at instead of (RP)-4tt.

Example 369

Synthesis of the thio N-acetoxyhydroxamate pronucleotide of $(S_P)$-4-N-benzoyl-deoxycytidin-3'-yl thymidin-5'-yl phosphorothioate [$(S_P)$-50ct]

Crude (SP)-50ct is produced as described in Example 363 using (SP)-4ct instead of (RP)-4tt.

Example 370

Synthesis of the thio N-acetoxyhydroxamate pronucleotide of $(S_P)$-2-N-phenoxyacetyl-deoxyguanosin-3'-yl thymidin-5'-yl phosphorothioate [$(S_P)$-50gt]

Crude (SP)-50gt is produced as described in Example 363 using (SP)-4gt instead of (RP)-4tt.

Example 371

Synthesis of the thio N-acetoxyhydroxamate pronucleotide of $(R_P)$-uridin-3'-yl uridin-5'-yl phosphorothioate [$(R_P)$-50uu]

Crude (RP)-50uu is produced as described in Example 363 using (RP)-10uu instead of (RP)-4tt.

Example 372

Synthesis of the thio N-acetoxyhydroxamate pronucleotide of $(R_P)$-6-N-Benzoyl-adenosin-3'-yl uridin-5'-yl phosphorothioate [$(R_P)$-50au]

Crude (RP)-50au is produced as described in Example 363 using (RP)-10au instead of (RP)-4tt.

Example 373

Synthesis of the thio N-acetoxyhydroxamate pronucleotide of $(R_P)$-4-N-Benzoyl-cytidin-3'-yl uridin-5'-yl phosphorothioate [$(R_P)$-50cu]

Crude (RP)-50cu is produced as described in Example 363 using (RP)-10cu instead of (RP)-4tt.

Example 374

Synthesis of the thio N-acetoxyhydroxamate pronucleotide of $(R_P)$-2-N-Phenoxyacetyl-guanosin-3'-yl uridin-5'-yl phosphorothioate [$(R_P)$-50gu]

Crude (RP)-50gu is produced as described in Example 363 using (RP)-10gu instead of (RP)-4tt.

Example 375

Synthesis of the thio N-acetoxyhydroxamate pronucleotide of $(S_P)$-uridin-3'-yl uridin-5'-yl phosphorothioate [$(S_P)$-50uu]

Crude (SP)-50uu is produced as described in Example 363 using (SP)-10uu instead of (RP)-4tt.

Example 376

Synthesis of the thio N-acetoxyhydroxamate pronucleotide of $(S_P)$-6-N-Benzoyl-adenosin-3'-yl uridin-5'-yl phosphorothioate [$(S_P)$-50au]

Crude (SP)-50au is produced as described in Example 363 using (SP)-10au instead of (RP)-4tt.

Example 377

Synthesis of the thio N-acetoxyhydroxamate pronucleotide of $(S_P)$-4-N-Benzoyl-cytidin-3'-yl uridin-5'-yl phosphorothioate [$(S_P)$-50cu]

Crude (SP)-50cu is produced as described in Example 363 using (SP)-10au instead of (RP)-4tt.

Example 378

Synthesis of the thio N-acetoxyhydroxamate pronucleotide of $(S_P)$-2-N-Phenoxyacetyl-guanosin-3'-yl uridin-5'-yl phosphorothioate [$(S_P)$-50gu]

Crude (SP)-50gu is produced as described in Example 363 using (SP)-10gu instead of (RP)-4tt.

Example 379

Synthesis of the thio N-acetoxyhydroxamate pronucleotide of $(R_P)$-uridin-2'-yl uridin-5'-yl phosphorothioate [$(R_P)$-51uu]

Crude (SP)-51uu is produced as described in Example 363 using (SP)-14uu instead of (RP)-4tt.

Example 380

Synthesis of the thio N-acetoxyhydroxamate pronucleotide of $(R_P)$-6-N-Benzoyl-adenosin-2'-yl uridin-5'-yl phosphorothioate [$(R_P)$-51 au]

Crude (RP)-51au is produced as described in Example 363 using (SP)-14au instead of (RP)-4tt.

Example 381

Synthesis of the thio N-acetoxyhydroxamate pronucleotide of $(R_P)$-4-N-Benzoyl-cytidin-2'-yl uridin-5'-yl phosphorothioate [$(R_P)$-51cu]

Crude (RP)-51cu is produced as described in Example 363 using (SP)-14cu instead of (RP)-4tt.

Example 382

Synthesis of the thio N-acetoxyhydroxamate pronucleotide of $(R_P)$-2-N-Phenoxyacetyl-guanosin-2'-yl uridin-5'-yl phosphorothioate [$(R_P)$-51gu]

Crude (RP)-51gu is produced as described in Example 363 using (SP)-14gu instead of (RP)-4tt.

Example 383

Synthesis of the thio N-acetoxyhydroxamate pronucleotide of $(S_P)$-uridin-2'-yl uridin-5'-yl phosphorothioate [$(S_P)$-51uu]

Crude (SP)-51uu is produced as described in Example 363 using (SP)-14uu instead of (RP)-4tt.

Example 384

Synthesis of the thio N-acetoxyhydroxamate pronucleotide of $(S_P)$-6-N-Benzoyl-adenosin-2'-yl uridin-5'-yl phosphorothioate [$(S_P)$-51 au]

Crude (SP)-51au is produced as described in Example 363 using (SP)-14au instead of (RP)-4tt.

Example 385

Synthesis of the thio N-acetoxyhydroxamate pronucleotide of $(S_P)$-4-N-Benzoyl-cytidin-2'-yl uridin-5'-yl phosphorothioate [$(S_P)$-51cu]

Crude (SP)-51cu is produced as described in Example 363 using (SP)-14cu instead of (RP)-4tt.

Example 386

Synthesis of the thio N-acetoxyhydroxamate pronucleotide of $(S_P)$-2-N-Phenoxyacetyl-guanosin-2'-yl uridin-5'-yl phosphorothioate [$(S_P)$-51gu]

Crude (SP)-51gu is produced as described in Example 363 using (SP)-14gu instead of (RP)-4tt.

Scheme V: Synthesis of thiotrialkylammoniumethyl pronucleotides

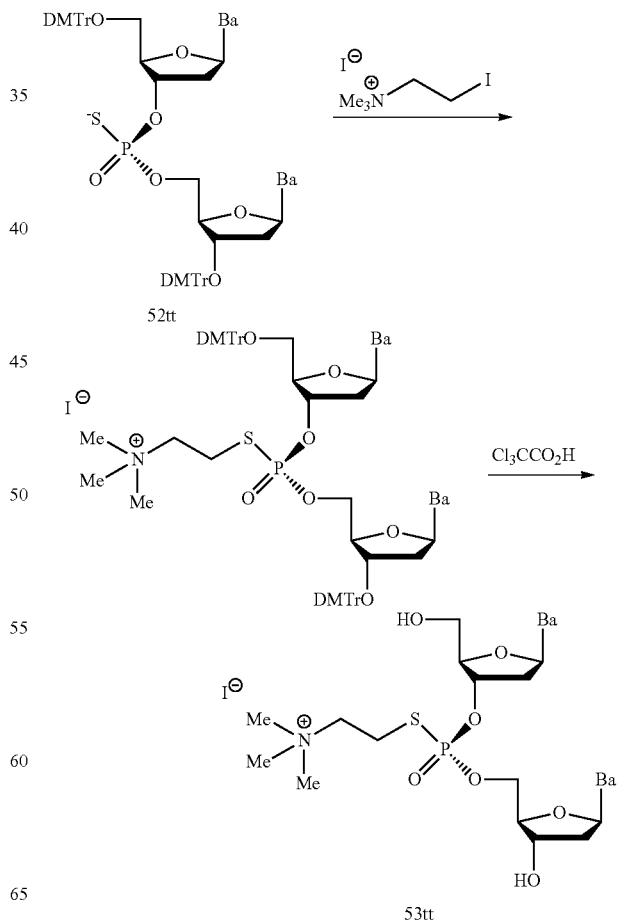

Example 387

Synthesis of the thiotrialkylammoniumethyl pronucleotide of (R$_P$)-thymidin-3'-yl thymidin-5'-yl phosphorothioate [(R$_P$)-53tt] as described in Scheme V (SP)-1,8-Diazabicyclo[5.4.0]undec-7-enium 5'-O-(dimethoxytrity)thymidin-3'-yl 3'-O-(dimethoxytrity)thymidin-5'-yl phosphorothioate [(SP)-52tt] is prepared by the same method used for the preparation of compound 4tt in Example 1 (Scheme A). Compound (SP)-52tt (100 µmol) is dried by repeated coevaporations with dry pyridine and then dissolved in dry dimethylformamide (1 mL). The mixture is treated with 2-iodoethyl trimethylammonium iodide (100 µmol) in dry DMF (0.5 mL). After 1 hour, the mixture is concentrated and then dissolved in CH$_2$Cl$_2$ (1000 µL) and trichloroacetic acid (50 µmol) is added. The mixture is stirred for 15 h at room temperature. A 0.1 M ammonium acetate buffer (2.5 mL) is then added to the mixture and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-53tt.

Scheme W: Synthesis of thiotrialkylammoniumethyl pronucleotides

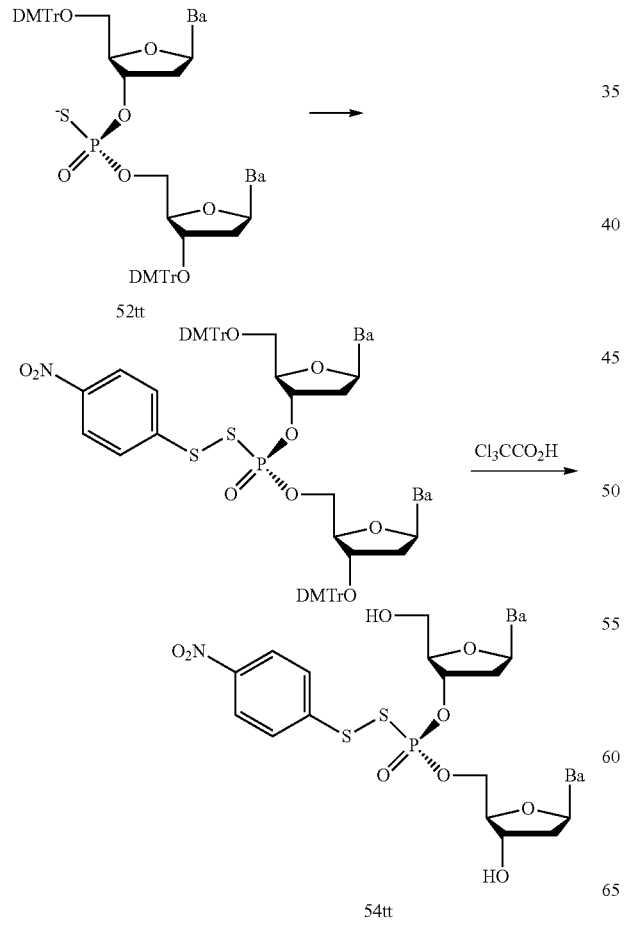

Example 388

Synthesis of the disulfide pronucleotide of (R$_P$)-thymidin-3'-yl thymidin-5'-yl phosphorothioate [(R$_P$)-54tt] as described in Scheme W Compound (SP)-52tt (100 µmol) is dried by repeated coevaporations with dry pyridine and then dissolved in dry ethanol (1 mL). The mixture is treated with p-nitrobenezene sulfenyl chloride (200 µmol) in dry (100 µmol) ethanol. After 1 hour, the mixture is concentrated and then dissolved in CH$_2$Cl$_2$ (1000 µL) and trichloroacetic acid (50 µmol) is added. The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-54tt.

Scheme X: Synthesis of 2-thiopivalylethyl nucleic acid prodrugs.

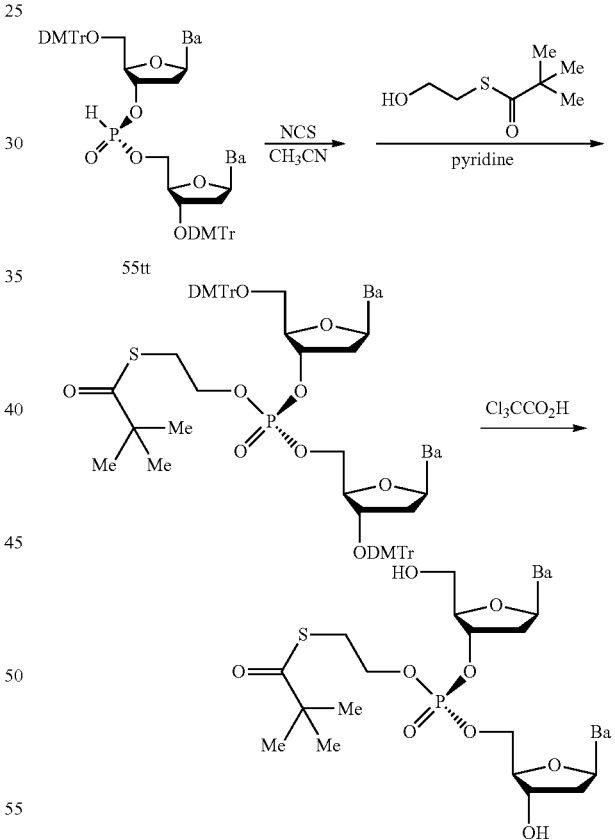

Example 389

Synthesis of the 2-thiopivalylethyl nucleic acid prodrug of (R$_P$)-thymidin-3'-yl thymidin-5'-yl phosphonate [(R$_P$)-56tt] as described in Scheme X (RP)-5'-O-(dimethoxytrityl)thymidin-3'-yl 3'-O-(dimethoxytrityl)thymidin-5'-yl H-phosphonate [(RP)-55tt] is prepared by the same method used for the preparation of compound 7tt in Example 8 (Scheme B). Compound (RP)-55tt (100 μmol) is dried by repeated coevaporations with dry pyridine and then dissolved in dry pyridine (1 mL). N-Chlorosuccinimide (0.1 mmol) is added, and the mixture is stirred for 2 hours at 0° C. The mixture is concentrated and dissolved in dry pyridine (1 mL). The above mixture is treated with 2-hydroxyethylthiopivalate (100 μmol) in dry (100 μmol) pyridine. After 1 hour, the mixture is concentrated and then dissolved in $CH_2Cl_2$ (1000 μL) and trichloroacetic acid (50 μmol) is added. The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-56tt.

pyridine (1 mL). N-Chlorosuccinimide (0.1 mmol) is added, and the mixture is stirred for 2 hours at 0° C. The mixture is concentrated and dissolved in dry pyridine (1 mL). The above mixture is treated with ethyl 2-hydroxyethylpropionate (100 μmol) in dry (100 μmol) pyridine. After 1 hour, the mixture is concentrated and then dissolved in $CH_2Cl_2$ (1000 μL) and trichloroacetic acid (50 μmol) is added. The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-57tt.

Scheme Y: Synthesis of 2-carboethoxyethyl nucleic acid prodrugs.

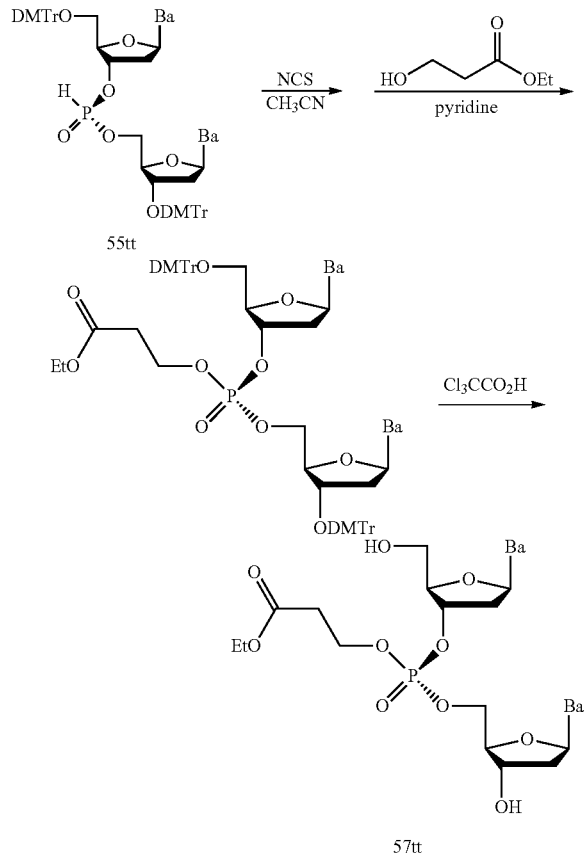

Scheme Z: Synthesis of thio(cyclohexyl)acyloxy pronucleotides

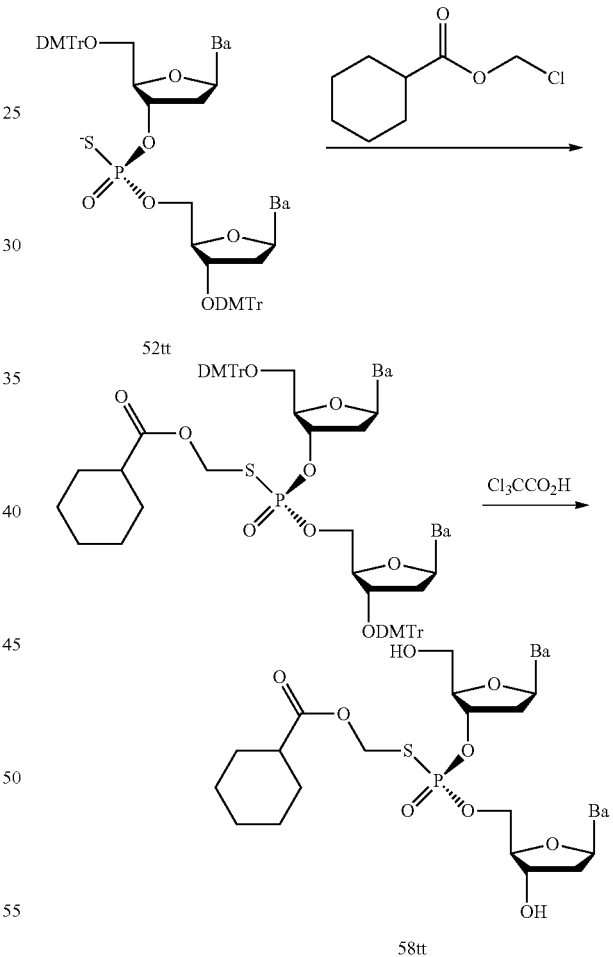

Example 390

Synthesis of the 2-carboethoxyethyl nucleic acid prodrug of $(R_P)$-thymidin-3'-yl thymidin-5'-yl phosphonate [$(R_P)$-57tt] as described in Scheme Y Compound (RP)-55tt (100 μmol) is dried by repeated coevaporations with dry pyridine and then dissolved in dry Example 391

Synthesis of the thio(cyclohexyl)acyloxy pronucleotide of $(R_P)$-thymidin-3'-yl thymidin-5'-yl phosphorothioate [$(R_P)$-58tt] as described in Scheme Z Compound (SP)-52tt (100 μmol) is dried by repeated coevaporations with dry pyridine and then dissolved in dry methylene chloride (1 mL). The mixture is treated with chloromethylcyclohexylacetate acetate (100 µmol) in dry (100 µmol) methylene chloride. After 1 hour, the mixture is concentrated and then dissolved in CH$_2$Cl$_2$ (1000 µL) and trichloroacetic acid (50 µmol) is added. The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-58tt.

the mixture is concentrated and then dissolved in CH$_2$Cl$_2$ (1000 µL) and trichloroacetic acid (50 µmol) is added. The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-59tt.

Scheme AA: Synthesis of 2-carboxyethyl nucleic acid prodrugs.

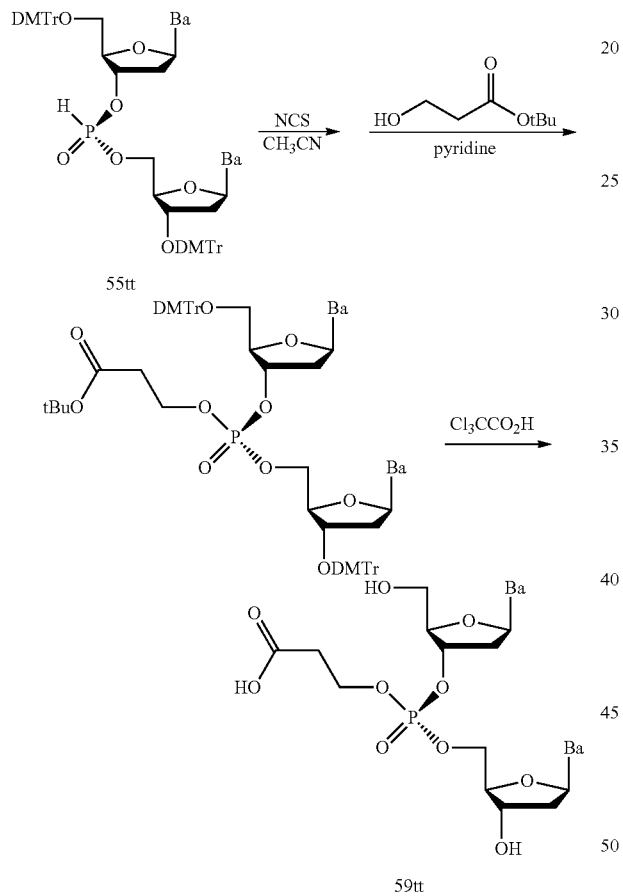

Scheme BB: Synthesis of 2-((2-hydroxyethyl)disulfide)ethyl nucleic acid prodrugs.

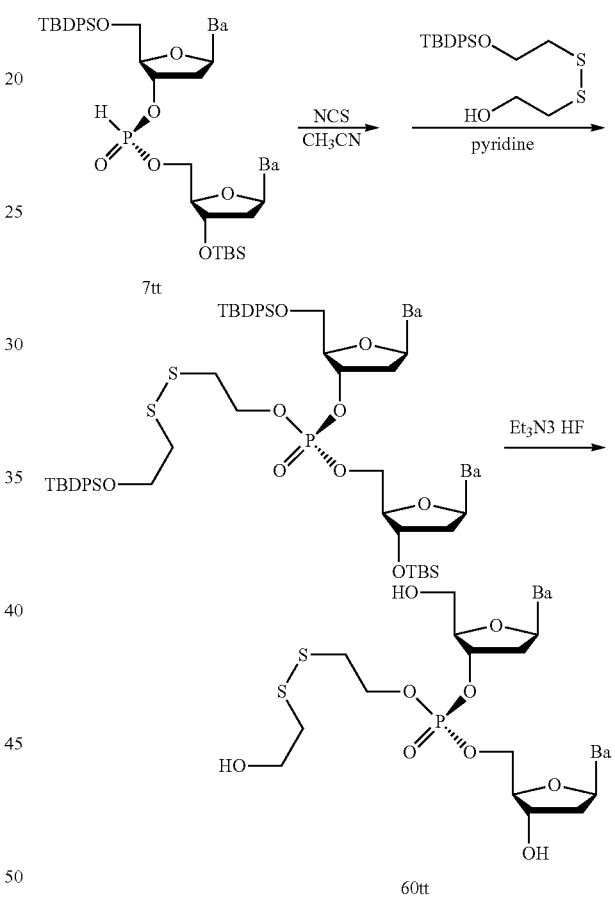

Example 392

Synthesis of the 2-carboxyethyl nucleic acid prodrug of (R$_P$)-thymidin-3'-yl thymidin-5'-yl phosphonate [(R$_P$)-59tt] as described in Scheme AA Compound (RP)-55tt (100 µmol) is dried by repeated coevaporations with dry pyridine and then dissolved in dry pyridine (1 mL). N-Chlorosuccinimide (0.1 mmol) is added, and the mixture is stirred for 2 hours at 0° C. The mixture is concentrated and dissolved in dry pyridine (1 mL). The above mixture is treated with tert-butyl 2-hydroxyethylpropionate (100 µmol) in dry (100 µmol) pyridine. After 1 hour, Example 393

Synthesis of the 2-((2-hydroxyethyl)disulfide)ethyl nucleic acid prodrug of (R$_P$)-thymidin-3'-yl thymidin-5'-yl phosphonate [(R$_P$)-60tt] as described in Scheme BB Compound (RP)-7tt (100 µmol) is dried by repeated coevaporations with dry pyridine and then dissolved in dry pyridine (1 mL). N-Chlorosuccinimide (0.1 mmol) is added, and the mixture is stirred for 2 hours at 0° C. The mixture is concentrated and dissolved in dry pyridine (1 mL). The above mixture is treated with 2-((2-(tert-butyldiphenylsilyloxy)ethyl)disulfanyl)ethanol (100 µmol) in dry (100 µmol)

pyridine. After 1 hour, the mixture is concentrated and then dissolved in triethylamine trihydrofluoride (500 μL). The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-60tt.

1 hour, the mixture is concentrated and then dissolved in CH$_2$Cl$_2$ (1000 μL) and trichloroacetic acid (50 μmol) is added. The mixture is stirred for 15 h at room temperature. A 0.1 M ammonium acetate buffer (2.5 mL) is then added to the mixture, and the mixture is washed with Et2O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford (RP)-61tt.

Scheme DD

Synthesis of Prodrug Molecules from H-Phosphonate Thymidine Dimer

Chemoselectivity and stereospecificity of iodine mediated oxidative couplings using separate diastereomers of dinucleoside H-phosphonate and O-nucleophiles to prepare phosphotriesters are known in the art (Nucleosides, Nucleotides & Nucleic Acids 2003 Vol. 22, Nos. 5-8, 1467-1469). The products were purified by silica gel chromatography and characterized by 31P and $^1$H NMR spectroscopy. The products were further purified by reverse phase HPLC for kinetic studies.

Scheme CC: Synthesis of 2-(methanesulfonothioate)ethyl nucleic acid prodrugs.

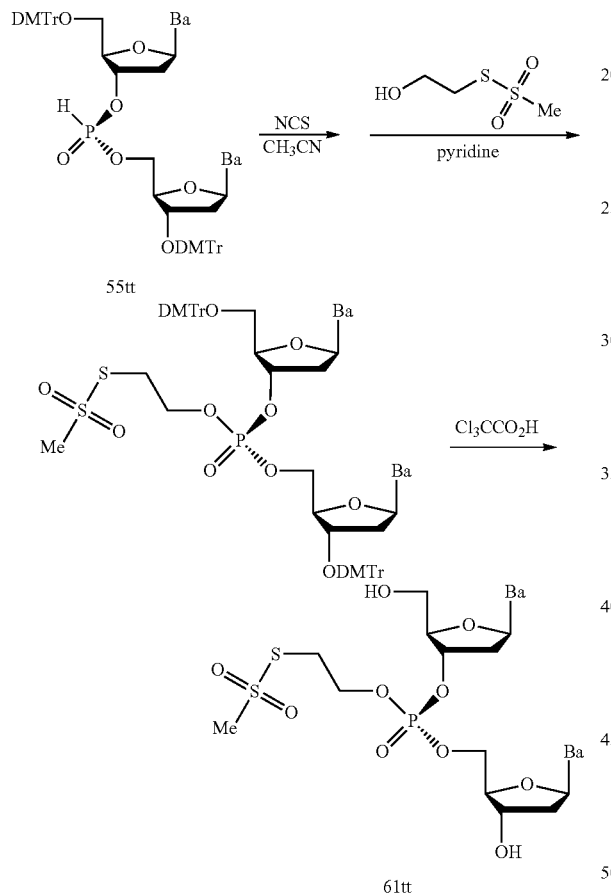

Example 394

Synthesis of the 2-(methanesulfonothioate)ethyl nucleic acid prodrug of (R$_P$)-thymidin-3'-yl thymidin-5'-yl phosphonate [(R$_P$)-61tt] as described in Scheme CC Compound (RP)-55tt (100 μmol) is dried by repeated coevaporations with dry pyridine and then dissolved in dry pyridine (1 mL). N-Chlorosuccinimide (0.1 mmol) is added, and the mixture is stirred for 2 hours at 0° C. The mixture is concentrated and dissolved in dry pyridine (1 mL). The above mixture is treated with S-2-hydroxyethyl methanesulfonothioate (100 μmol) in dry (100 μmol) pyridine. After Scheme DD

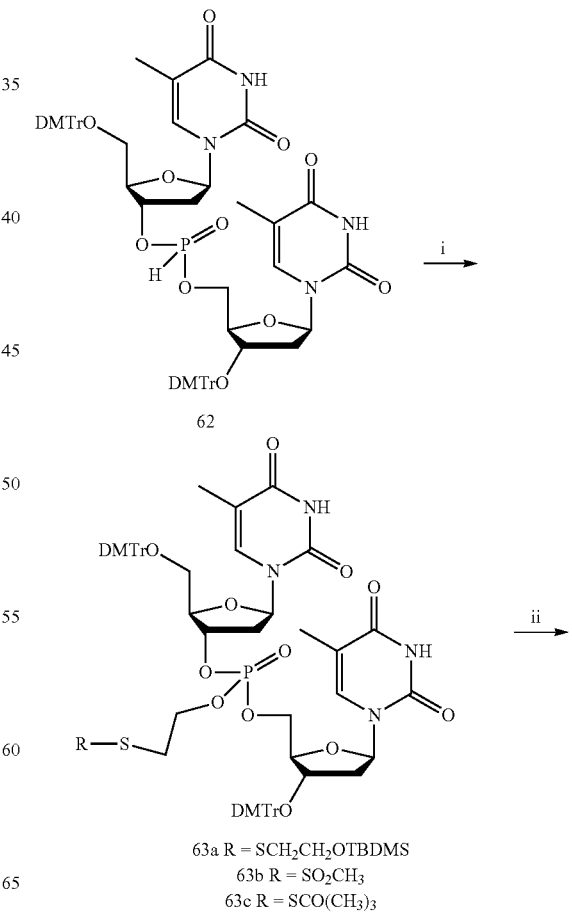

-continued

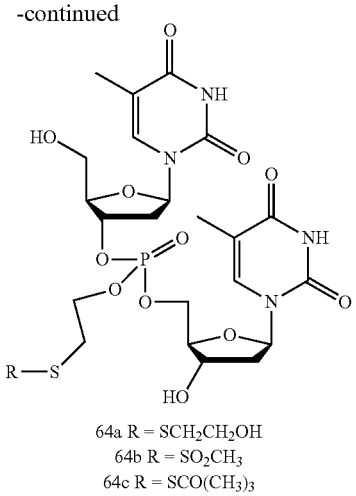

64a R = SCH₂CH₂OH
64b R = SO₂CH₃
64c R = SCO(CH₃)₃ i) I₂, ACN:Py (3:2), TBDPSCl and 2-((2-((tert-butyldimethylsilyl)oxy)ethyl)disulfanyl)ethanol for 63a; 2-hydroxyethyl mehanesulfonate for 63b and 63c) 2-Hydroxyethylthiopivalate
ii) 3% DCA/DCM Example 395

General Procedure for Synthesis of 63a, 63b and 63c (Scheme DD)

(RP,SP)-5'-O-(4,4'-dimethoxytrityl)thymidin-3'-yl 3'-O-(4,4'-dimethoxytrityl)thymidin-5'-yl H-phosphonate (62) (113.5 mg, 100 μmol) was dried under high vacuum overnight and dissolved in ACN (2 ml) and pyridine (2 ml). tert-Butyldiphenylsilyl chloride (52 μL, 200 μmol) and 12 (76 mg, 300 moles) were added. The reaction mixture was cooled in ice and respective alkylating reagent (1 mmol) dissolved in ACN (2 mL) was added drop wise to reaction mixture. The mixture was stirred for 10 min under argon. TLC of the crude reaction mixture showed quantitative conversion to product. The solvents were evaporated and residue was dissolved in ethyl acetate and washed with 5% Na2S2O3, brine and dried over Na2SO4. The ethyl acetate layer was concentrated under reduced pressure. The residue was purified by silica gel column chromatography to afford (RP,SP)-5'-O-(4,4'-dimethoxytrityl)thymidin-3'-yl 3'-O-(4,4'-dimethoxytrityl)thymidin-5'-yl phosphotriester 63a, 63b and 63c in 80-90% yield.

General Procedure for Synthesis of 64a, 64b and 64c

3% DCA/DCM was added slowly to DMTr protected triester and reaction was left for stirring at room temperature for 30 min. Reaction was quenched with methanol, solvents were evaporated and residue was purified by silica column. In case of compound 63a, TBDMS deprotection occurred simultaneously. Compounds 64a, 64b and 64c were obtained in quantitative yields.

Compound 63a: 1H NMR (400 MHz, CDCl3) δ 7.58-7.18 (m, 20H), 6.87-6.78 (m, 8H), 6.49-6.27 (m, 2H), 5.11-5.07 (m, 1H), 4.2-4.05 (m, 3H), 3.99-3.87 (m, 1H), 3.85-3.73 (m, 13H), 3.73-3.56 (m, 1H), 3.54-3.26 (m, 2H), 2.94-2.66 (m, 8H), 1.97-1.78 (m, 4H), 1.76-1.54 (m, 1H), 1.43-1.3 (m, 3H), 0.94-0.78 (m, 9H), 0.11-0.03 (m, 6H). $^{31}$P NMR (162 MHz, CDCl3) δ −1.19, −1.26 (two diastereomers).

Compound 63b: 1H NMR (400 MHz, CDCl3+trace amount of Py-D5) δ 9.72-9.45 (m, 2H), 7.62-7.18 (m, 20H), 6.90-6.81 (m, 8H), 6.48-6.31 (m, 2H), 5.18-5.10 (m, 1H), 4.31-4.09 (m, 3H), 4.03-3.91 (m, 1H), 3.88-3.74 (m, 15H), 3.74-3.62 (m, 1H), 3.54-3.31 (m, 2H), 2.89-2.76 (m, 4H), 2.67-2.31 (m, 2H), 1.98-1.89 (m, 1H), 1.88, 1.85 (2s, 3H, diastereomers), 1.76-1.64 (m, 1H), 1.39 (s, 3H). $^{31}$P NMR (162 MHz, CDCl3) δ −1.24, −1.27 (two diastereomers).

Compound 63c: 1H NMR (400 MHz, CDCl3+trace amount of Py-D5) δ 7.6-7.16 (m, 20H), 6.9-6.77 (m, 8H), 6.49-6.27 (m, 2H), 5.18-5.06 (m, 1H), 4.32-4.04 (m, 2H), 4.0-3.85 (m 3H), 3.82-3.71 (m, 12H), 3.71-3.57 (m, 1H), 3.55-3.27 (m, 2H), 3.07-2.88 (m, 2H), 2.62-2.24 (m, 2H), 1.97-1.89 (m, 1H), 1.89-1.81 (m, 3H), 1.78-1.59 (m, 3H), 1.45-1.32 (m, 3H), 1.22-1.14 (m, 9H). $^{31}$P NMR (162 MHz, CDCl₃) δ −1.23, −1.27 (two diastereomers).

Compound 64a: 1H NMR (400 MHz, D2O) δ 7.52 (s, 1H), 7.42 (s, 1H), 6.28-6.07 (m, 2H), 5.07-4.87 (m, 1H), 4.54-4.38 (m, 1H), 4.37-4.19 (m, 3H), 4.19-3.95 (m, 2H), 3.80-3.50 (m, 4H), 2.99-2.62 (2m, 4H), 2.60-2.17 (m, 4H), 1.85-1.60 (m, 6H). $^{31}$P NMR (162 MHz, CD3OD) δ −1.37, −1.41 (two diastereomers). Calculated mass=682.66, Observed mass in ESI−ve mode=681.22

Compound 64b: 1H NMR (400 MHz, CD3OD) δ 7.74, 7.49 (2s, 2H), 6.28-6.19 (m, 2H), 5.10-5.04 (m, 1H), 4.41-4.23 (m, 4H), 4.19-4.15 (m, 1H), 4.04-3.98 (m, 1H), 3.78-3.69 (m, 4H), 3.00-2.77 (m, 4H), 2.55-2.21 (m, 4H), 1.86, 1.83 (2s, 6H). $^{31}$P NMR (162 MHz, CD3OD) δ −1.37, −1.41 (two diastereomers). Calculated mass=684.63, Observed mass in ESI+ve mode=683.14

Compound 64c: 1H NMR (400 MHz, CD3OD) δ 7.799 (s, 1H), 7.54 (s, 1H), 6.32-6.24 (m, 2H), 5.17-5.07 (m, 1H), 4.48-4.26 (m, 3H), 4.26-4.12 (m, 3H), 4.08-3.99 (m, 1H), 3.21-3.15 (m, 2H), 2.61-2.48 (m, 1H), 2.46-2.16 (m, 3H), 1.9 (s, 3H), 1.87 (s, 3H), 1.27-1.19 (d, 9H). $^{31}$P NMR (162 MHz, CD3OD) δ-1.53, −1.60 (two diastereomers). Calculated mass=690.66, Observed mass in ESI−ve mode=689.53

HPLC purification of 64a, 64b and 64c

Reverse phase purification was carried out using Waters 2525 BGM combined with 2487 UV detector, Phenomenex Luna 5u C18 (2) 100 Å, 250×10 mm column and MassLynx v4.1. A gradient of Water and acetonitrile was used with flow rate of 5 ml/min.

Gradient used for compound 64a and 64b: 10 to 50% B in 30 min

Gradient used for compound 64c: 20 to 60% B in 30 min

The product peaks were monitored at 254 and 280 nm.

Analytical HPLC Conditions

Quantitative analysis was done by reverse-phase HPLC employing an automated Alliance Waters e2695 HPLC instrument in combination with Empower software. An XBridge C18 3.5 um, 4.6×150 mm, Waters part#186003034A was fitted and detection was done by UV (254 nm and 280 nm). A gradient elution system was developed (Table 1) enabling the resolution of prodrug, intermediate and the released drug within the same chromatogram; mobile phase A consisting of 20 mM ammonium acetate in water; mobile phase B was acetonitrile.

TABLE 1

| Column temperature: 60° C. | | | | |
|---|---|---|---|---|
| Time | Flow | % A | % B | Curve |
| 0.01 | 1.00 | 99.0 | 1.0 | |
| 5.00 | 1.00 | 99.0 | 1.0 | 1 |

TABLE 1-continued

| | Column temperature: 60° C. | | | |
|---|---|---|---|---|
| Time | Flow | % A | % B | Curve |
| 30.00 | 1.00 | 75.0 | 25.0 | 6 |
| 30.50 | 1.00 | 10.0 | 90.0 | 6 |
| 35.00 | 1.00 | 10.0 | 90.0 | 1 |
| 35.50 | 1.00 | 99.0 | 1.0 | 6 |
| 42.00 | 1.00 | 99.0 | 1.0 | 1 |

Example 396

Glutathione Assisted Prodrug Release

To 20 µL of 64 in water (2 O.D.), 100 µL of 10×PBS, and 630 µL of H2O were mixed. Kept the mixture in a hot plate set at 37° C. 250 µL of freshly prepared 20 mM reduced L-glutathione was added to above mixture which gave 5 mM GSH concentration in the reaction mixture which is equal to cytosol concentration. 100 µl aliquots were take at time intervals of 10 min, 20 min, 30 min, 40 min, 50 min, 60 min, 1.5 hr, 2 hr and 2.5 hr. Each aliquot was immediately quenched with 400 µl of 100 mM citrate buffer (pH 4) and analyzed by reversed-phase HPLC and LC/MS.

Scheme EE: Mechanism of Glutathione Cleavage

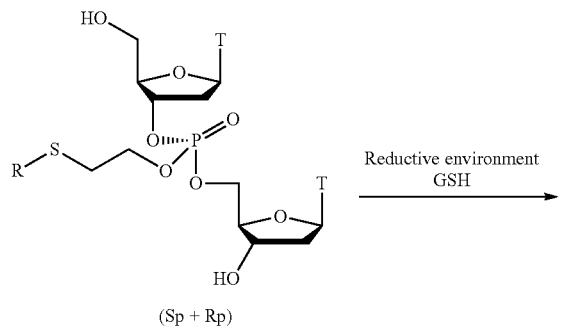

(Sp + Rp)
64a, R = SCH$_2$CH$_2$OH
64b, R = SO$_2$CH$_3$

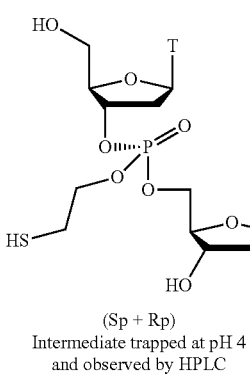

(Sp + Rp)
Intermediate trapped at pH 4
and observed by HPLC

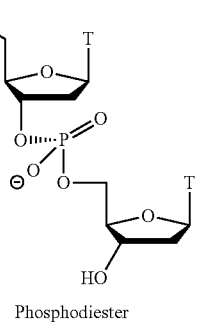

Phosphodiester

LCMS of Reaction Mixture of Compound 64b+GSH at 20 min Time Point

Waters Acquity HPLC and SDS were used to characterize the products formed during prodrug release. XBridge c18 3.5 um, 4.6×150 mm, Waters part#186003034 was used with solvent system A: 5 mM ammonium formate/water and B: acetonitrile with linear gradient as shown in Table 2.

TABLE 2

| Time | Flow | % A | % B | Curve |
|---|---|---|---|---|
| 0.0 | 1.00 | 99.0 | 1.0 | |
| 5.00 | 1.00 | 80 | 20 | 6 |
| 7 | 1.00 | 5 | 95 | 6 |
| 7.5 | 1.00 | 99 | 1 | 6 |
| 9 | 1.00 | 99 | 1 | 1 |

In FIG. 1 is provided a representative HPLC profile of compound 64a+GSH.

Figure 2:
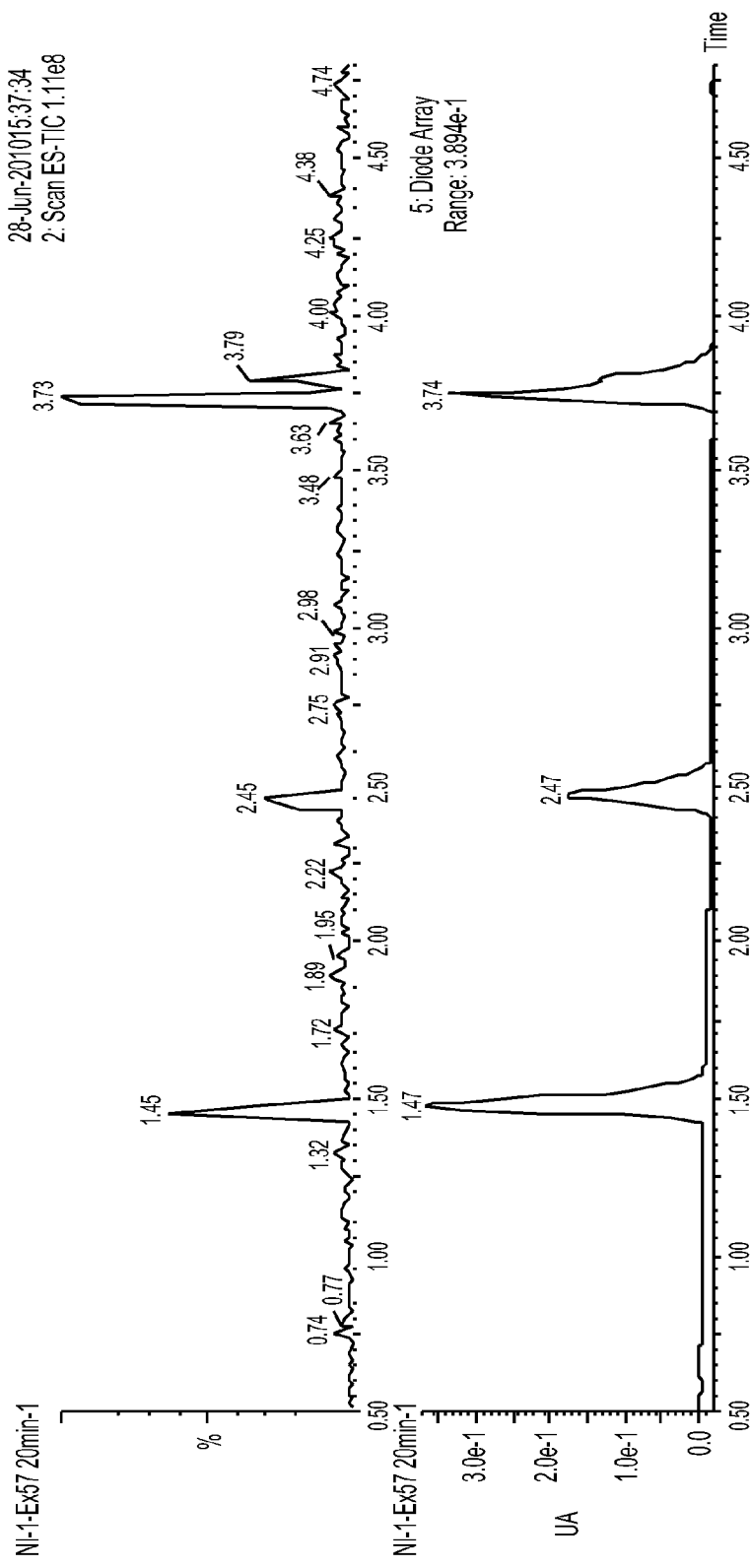
FIG. 2 provides provided a representative HPLC profile of compound 64a, a glutathione adduct, and the final product after release from the pro-moeity.
Figure 2:
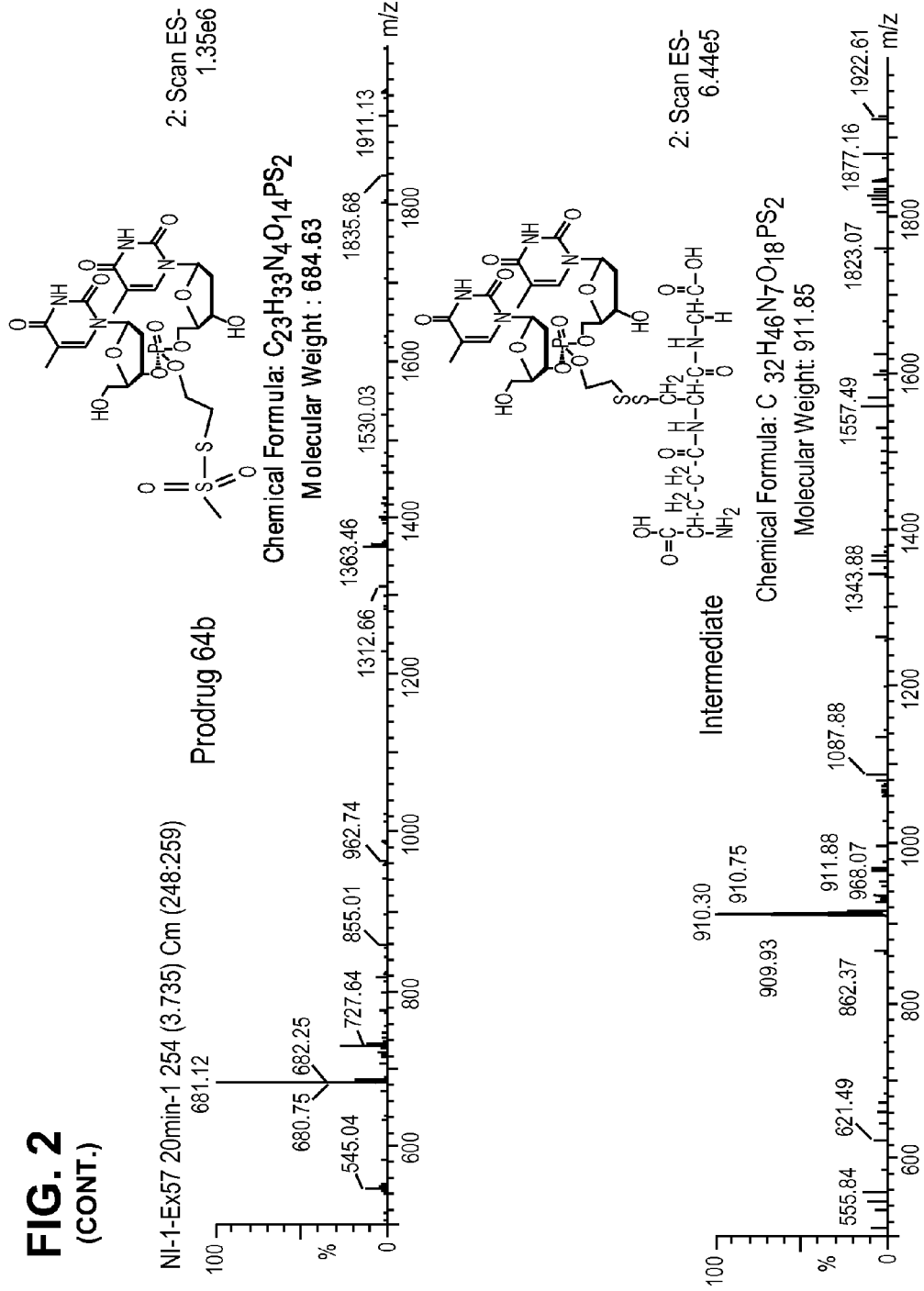
Figure 2:
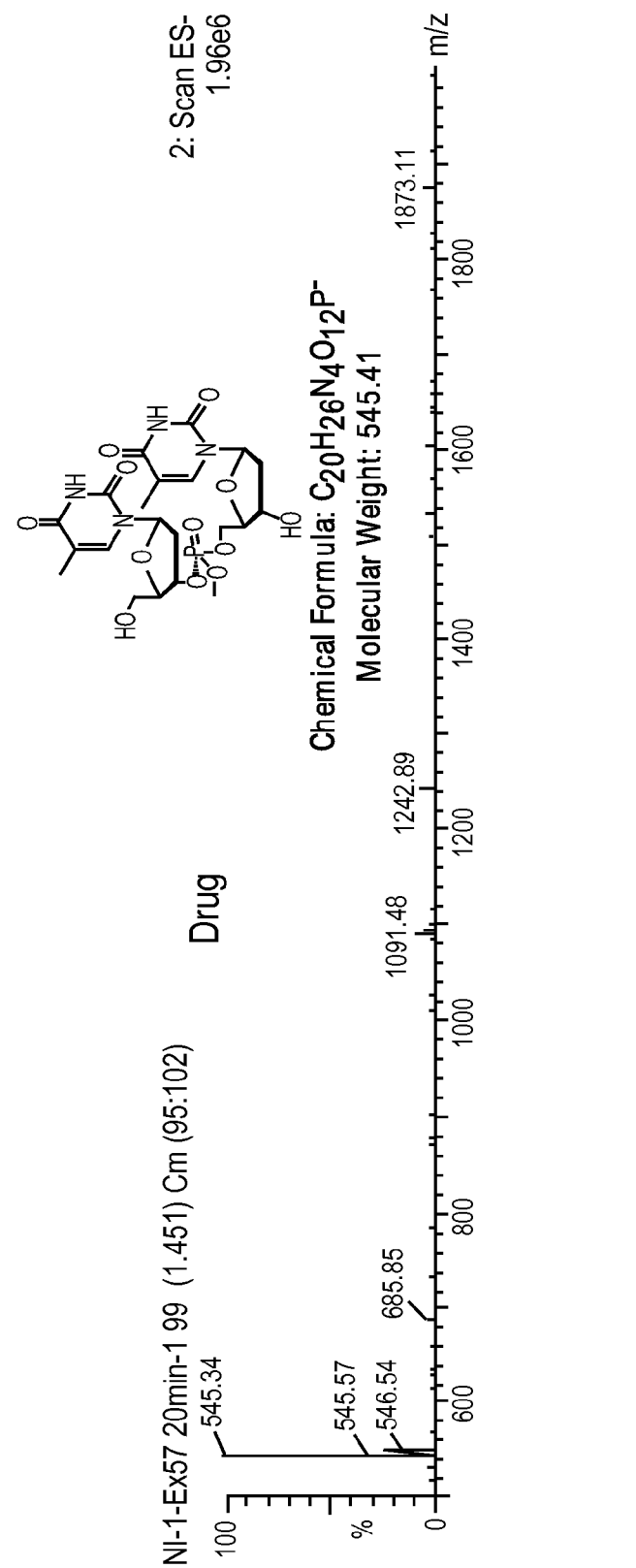

In FIG. 2 is provided a representative HPLC profile of compound 64a, a glutathione adduct, and the final product after release from the pro-moeity.

Figure 3:
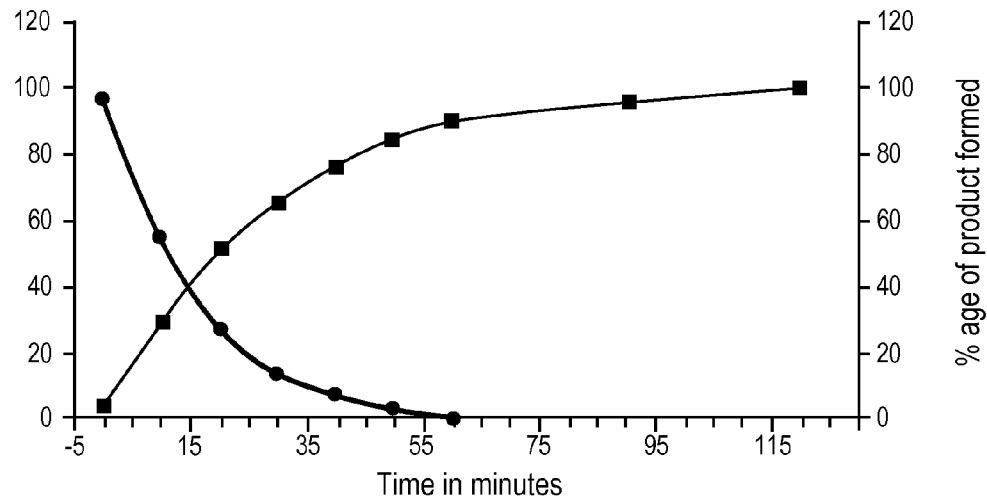
FIG. 3 provides a plot of conversion over time for compound 64a and 64b.
Figure 3:
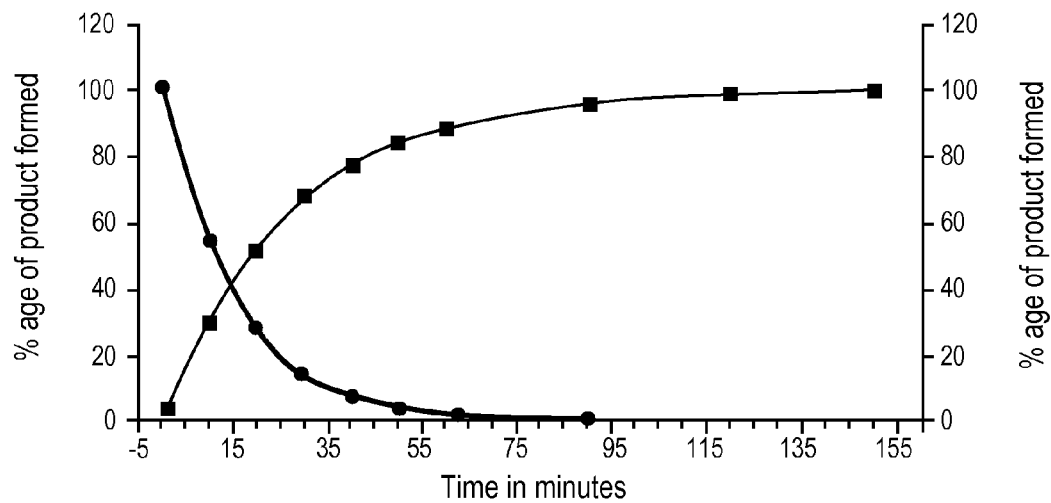
Figure 4:
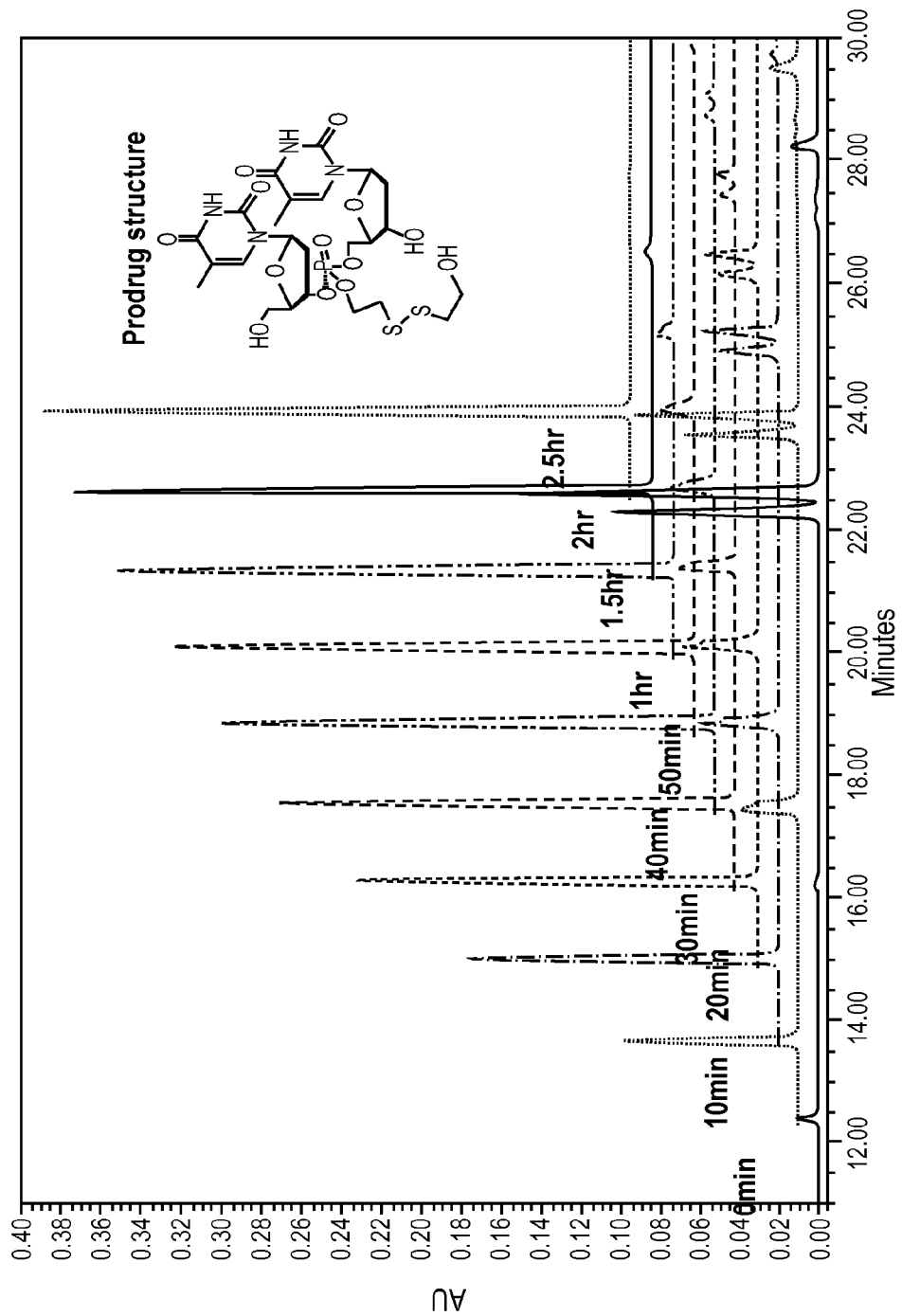

In FIG. 3, compounds 64a and 64b show a pseudo first order kinetics because glutathione concentration is in great excess compared to substrate and thus remains effectively constant during the course of reaction. The curves for depleting starting material and forming product are not mirror images because of accumulation of intermediate which is characterized as Glutathione adduct of dinucleoside triester (see FIG. 2 and FIG. 4).

Example 397

Carboxyesterase Assisted Cleavage of Compound 64c

Scheme FF

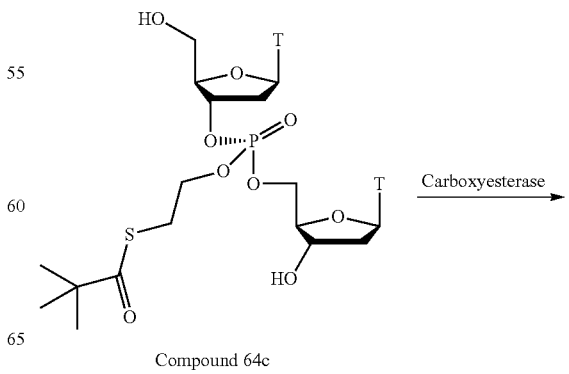

Compound 64c

-continued

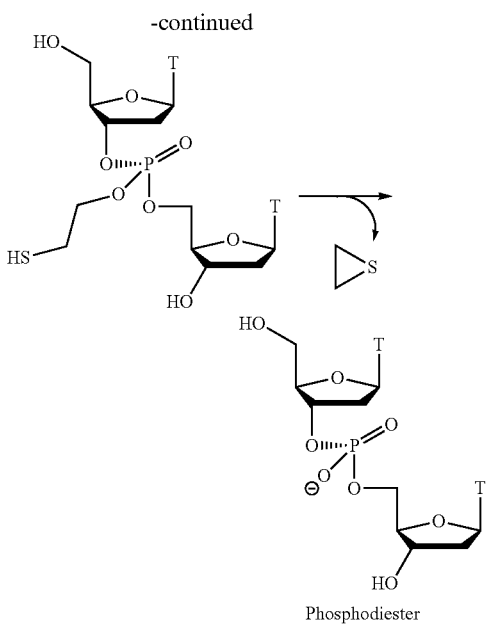

Phosphodiester

Porcine Liver esterase (Sigma Aldrich, product number: E2884) was a suspension in 3.2M ammonium sulfate pH=8.0, concentration 36 mg protein/mL and 154 units/mg protein. According to product specifications, one unit will hydrolyse 1 μM of ethyl butyrate to butyric acid and ethanol per minute at pH=8.0 at 25° C. Compound 64c (0.10.D, 5.5 nmoles) in 10 μL 1×PBS was incubated at 37° C. for 10 min. Serial dilutions of PLE were made in ten vials with conc in units from 1, 10-1, 10-2, 10-3, 10-4, 10-5, 10-6, 10-7, 10-8, 10-9 each in 10 μL 1×PBS. The protein solution was incubated at 37° C. for 10 min and then each added to ten vials containing compound 64c. The mixtures were stored at 37° C. for 30 min and analysed by analytical HPLC and LCMS. The 64c was completely converted to phosphodiester in vials with protein conc. from 1, 10-1 and 10-2. No side reactions were observed. There was no reaction in vials with protein conc. from 10-6 to 10-9. There was some product seen in the vials containing protein conc. 10-3 and 10-4. This suggests that these concentrations are appropriate to study the kinetics of prodrug release using PLE. Time dependent kinetics will be studied using conc. within the range of 10-3 to 10-4/~6 nmoles of compound 64c.

Compound 64c (5 O.D., 2.9 μmoles) dissolved in 900 μL of 1×PBS was incubated at 37° C. for 10 min. Porcine Liver Esterase (1U) in 100 μL 1×PBS was added to above mixture and was stored at 37° C. Aliquots of 100 μL were withdrawn at 0 min, 15 min and 45 min, quenched with 100 μL acetonitrile and samples were cooled in ice-bath. The samples were analyzed by HPLC SQD on XBridge C-18 3.5 μm, 4.6×150 mm, with solvent system A: 5 mM ammonium formate/water and B: acetonitrile with linear gradient as shown in Table 3. At zero minutes, only compound 64c was observed, at 15 min nearly 50% of the product was formed and reaction was complete at 45 minutes. Thus TpT diester 64c was released by carboxyesterase treatment without detectable accumulation of any intermediates.

TABLE 3

| Time | Flow | % A | % B | Curve |
|---|---|---|---|---|
| 0.0 | 1.00 | 99.0 | 1.0 | |
| 2.0 | 1.00 | 99.0 | 1.0 | 1 |

TABLE 3-continued

| Time | Flow | % A | % B | Curve |
|---|---|---|---|---|
| 7.0 | 1.00 | 60.0 | 40.0 | 6 |
| 9.0 | 1.00 | 5.0 | 95.00 | 6 |
| 9.5 | 1.00 | 99.0 | 1.0 | 6 |
| 11.0 | 1.00 | 99.0 | 1.0 | 1 |

Example 398

Treatment of Pancreatic Cancer

A method for treating a subject having pancreatic cancer comprising administering to the subject a therapeutically effective amount of a composition comprising the 2'-5'-A3 S-acetyl-2-thioethyl pronucleotide of Example 242 is contemplated. Treatment is expected to achieve increased tumor inhibition compared with gemcitabine administered as a single agent or gemcitabine and erlotinib administered in combination.

Example 399

Cell Penetration Assay $P^{32}$-Labeled Nucleic Acid Drugs

Prepare labeled nucleic acid prodrug and parent drug using [$^{32}$P]dNTP radionucleotide (Fisher Scientific, Pittsburgh, Pa.) to synthesize nucleic acid molecules comprising chiral phosphorous moieties and corresponding parent drugs as described herein.

Cell Culture and Penetration Testing

Select culture of either HeLa (adherent human cervical cancer) cells grown in DMEM-10% FBS or BxPC-3 (adherent human pancreas adenocarcinoma) cells grown in 90% RPMI 1640-10% FBS. For plating of cell cultures, trypsinize cells with 0.05% trypsin-EDTA. Assay for viability and cell counting via standard Trypan Blue in phosphate buffered saline (PBS) staining. Dilute cells and seed at 1×105 cells/well in a 6-well format. Incubate at 37° C. in a 5% CO2 atmosphere for 16 hours or until cells adhere and grow to at least 80% confluency.

Add labeled prodrug mixture to prodrug experimental wells to achieve final predetermined range of concentrations (e.g., 1 μM, 5 μM, and 10 μM). Add labeled parent drug mixture to parent drug experimental wells to achieve final predetermined range of concentrations (e.g., 1 μM, 5 μM, and 10 μM). Reserve untreated wells for negative control. Incubate cells with experimental treatments for predetermined ranges of time (e.g., 15 minutes, 1 hour, 4 hours, and 8 hours).

$P^{32}$ Detection and Determination of Prodrug Penetration

To harvest, wash wells 3 times with serum-free media and apply non-denaturing TRIS-HCl lysis buffer with 1% Triton X100 (Cell Signaling Technology, Inc., Boston, Mass.) and sonicate briefly. Collect cytosolic and nuclear fractions via standard collection techniques.

Measurement of drug penetration is performed using standard radiation detection techniques. For detection via scintillation counter, add 50 μL of sample to 5 mL of scintillation cocktail and measure beta-emission via liquid scintillation counting. Aliquots of each sample are assayed via Bradford colorimetric assays to normalize radiation counts by total protein concentration.

Example 400

Functional Cell Penetration Assay Using Reporter Gene

Assembly of Fusion Gene Vector and Transfection of Cell Line

When nucleic acid prodrugs are used to inhibit specific gene expression, for example, antisense oligonucleotides or antigene oligonucleotides, a functional penetration assay may be desirable. Culture HeLa (adherent human cervical cancer) cells in DMEM-10% FBS. Clone gene of interest into a commercially available vector such as the Living Colors® Fluorescent Protein Vector, Clontech, Mountain View, Calif. Transfection of cells with DNA construct and selection for stable transfectants are performed using standard techniques. The result is constitutive expression of gene of interest and a fluorescent reporter (e.g., the protein AcGFP1).

Nucleic Acid Drugs Inhibiting Specific Gene Expression

Prepare nucleic acid molecules comprising chiral phosphorous moieties and corresponding parent drugs as described herein to disrupt the vector's gene promoter sequence.

Cell Culture and Penetration Testing

Prepare transfected culture by first trypsinizing cells for plating with 0.05% trypsin-EDTA. Assay for viability and cell counting via standard Trypan Blue in phosphate buffered saline (PBS) staining. Dilute cells and seed at 1×105 cells/well in a 6-well format. Incubate at 37° C. in a 5% CO2 atmosphere for 16 hours or until cells adhere and grow to at least 80% confluency.

Fluorescent signal is first detected 8-12 hours after transfection. Add prodrug mixture to prodrug experimental wells to achieve final predetermined range of concentrations (e.g., 1 µM, 5 µM, and 10 µM). Add parent drug mixture to parent drug experimental wells to achieve final predetermined range of concentrations (e.g., 1 µM, 5 µM, and 10 µM). Reserve untreated wells for negative control. Incubate cells with experimental treatments for predetermined ranges of time (e.g., 15 minutes, 1 hour, 4 hours, and 8 hours).

Reporter Gene Expression Determination of Prodrug Penetration

To harvest, wash each well 3 times with serum-free media and retrypsinize Measurement of drug penetration is performed using standard fluorescence detection techniques. For qualitative fluorescence measurement with microscopy and quantitative measurement with flow cytometry, use the wavelength that is excitatory for the fluorescent reporter (e.g., 488 nm for AcGFP1).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. An oligonucleotide composition comprising a plurality of oligonucleotides of the following structure:

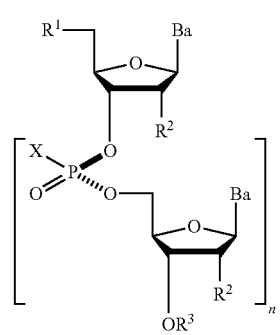

Formula 1 wherein:
each X-phosphonate independently has an Rp or Sp configuration;
$R^1$ is —OH, —SH, —NR$^d$R$^d$, —N$_3$, halogen, hydrogen, alkyl, alkenyl, alkynyl, alkyl-Y$^1$—, alkenyl-Y$^1$—, alkynyl-Y$^1$—, aryl-Y$^1$—, heteroaryl-Y$^1$—, —P(O)(R$^e$)$_2$, —HP(O)(R$^e$), —OR$^a$ or —SR$^c$;
$Y^1$ is O, NR$^d$, S, or Se;
$R^a$ is a blocking group;
$R^c$ is a blocking group;
each instance of $R^d$ is independently hydrogen, alkyl, alkenyl, alkynyl, aryl, acyl, substituted silyl, carbamate, —P(O)(R$^e$)$_2$, or —HP(O)(R$^e$);
each instance of $R^e$ is independently hydrogen, alkyl, aryl, alkenyl, alkynyl, alkyl-Y$^2$—, alkenyl-Y$^2$—, alkynyl-Y$^2$—, aryl-Y$^2$—, or heteroaryl-Y$^2$—, or a cation which is Na$^{+1}$, Li$^{+1}$, or K$^{+1}$;
$Y^2$ is O, S, or NR$^d$ wherein R$^d$ is hydrogen, alkyl, alkenyl, alkynyl, aryl, acyl, substituted silyl, or carbamate;
each instance of $R^2$ is independently hydrogen, —OH, —SH, —NR$^d$R$^d$, —N$_3$, halogen, alkyl, alkenyl, alkynyl, alkyl-Y$^1$—, alkenyl-Y$^1$—, alkynyl-Y$^1$—, aryl-Y$^1$—, heteroaryl-Y$^1$—, —OR$^b$, or —SR$^c$, wherein R$^b$ is a blocking group;
each instance of Ba is independently a blocked or unblocked adenine, cytosine, guanine, thymine, uracil or modified nucleobase, wherein each modified nucleobase is independently adenine, cytosine, guanine, thymine or uracil, modified by one or more modifications by which:
(1) a nucleobase is modified by one or more groups independently selected from acyl, halogen, amino, azide, alkyl, alkenyl, alkynyl, aryl, heteroalkyl, heteroalkenyl, heteroalkynyl, heterocyclyl, heteroaryl, carboxyl, hydroxyl, biotin, avidin, streptavidin, substituted silyl, and combinations thereof;
(2) one or more atoms of a nucleobase are independently replaced with a different atom selected from carbon, nitrogen or sulfur;

(3) one or more double bonds in a nucleobase are independently hydrogenated; or
(4) one or more aryl or heteroaryl rings are independently inserted into a nucleobase; or is selected from:
uracil, thymine, adenine, cytosine, and guanine having their respective amino groups protected by acyl groups, 2-fluorouracil, 2-fluorocytosine, 5-bromouracil, 5-iodouracil, 2,6-diaminopurine, azacytosine, pseudoisocytosine, pseudouracil, 8-substituted purines, xanthine, hypoxanthine,

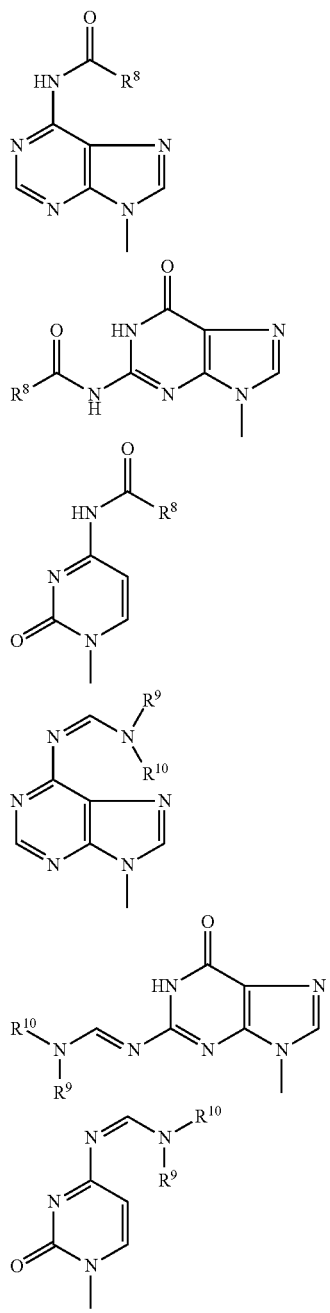

wherein:
$R^8$ is a linear or branched alkyl, aryl, aralkyl, or aryloxylalkyl group having 1 to 15 carbon atoms, and
each of $R^9$ and $R^{10}$ represents a linear or branched alkyl group having 1 to 4 carbon atoms;

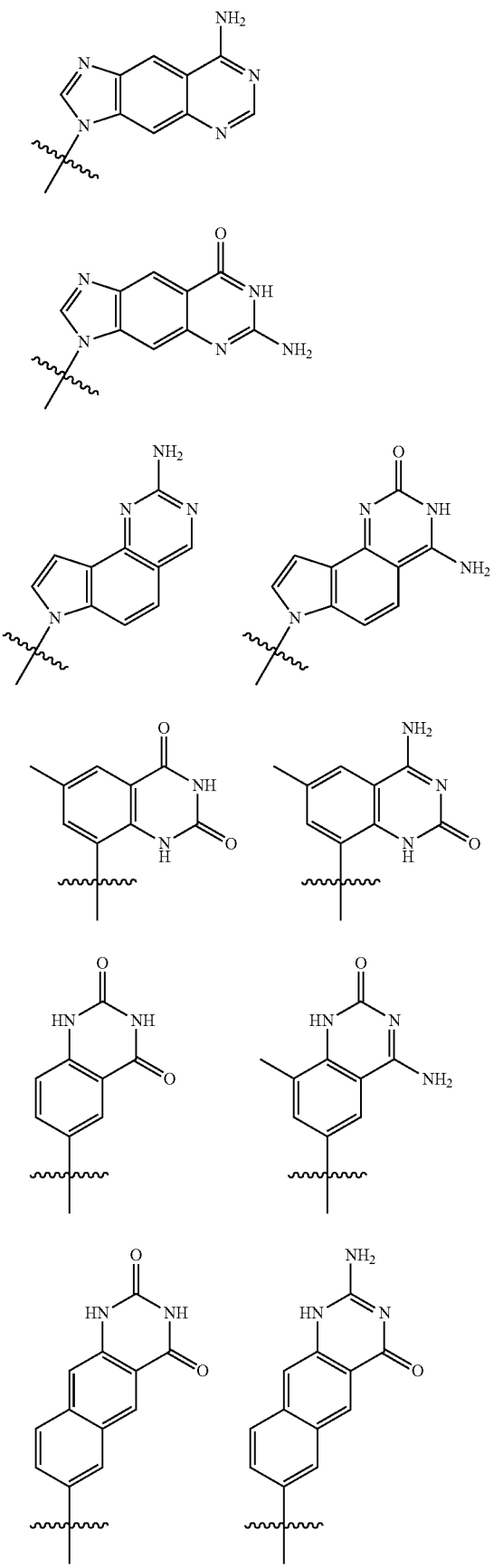

-continued

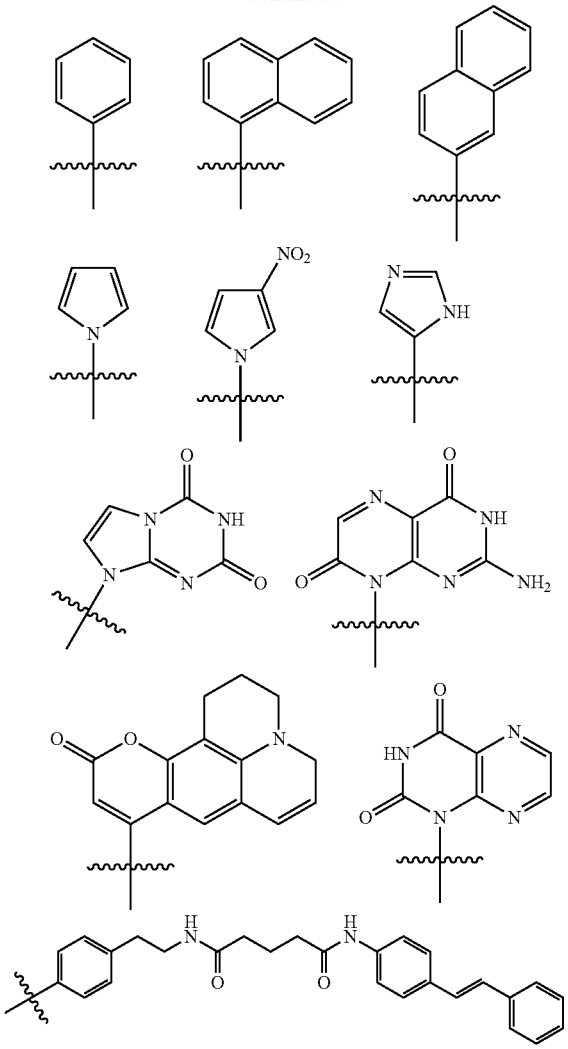

corrin or porphyrin, each optionally modified by one or more groups independently selected from acyl, halogen, amino, azide, alkyl, alkenyl, alkynyl, aryl, heteroalkyl, heteroalkenyl, heteroalkynyl, heterocyclyl, heteroaryl, carboxyl, hydroxyl, biotin, avidin, streptavidin, substituted silyl, and combinations thereof;

phenanthrene, pyrene, stillbene, isoxanthine, isozanthopterin, terphenyl, terthiophene, benzoterthiophene, coumarin, lumazine, tethered stillbene, benzo-uracil, or naphtho-uracil, each optionally modified by one or more groups independently selected from acyl, halogen, amino, azide, alkyl, alkenyl, alkynyl, aryl, heteroalkyl, heteroalkenyl, heteroalkynyl, heterocyclyl, heteroaryl, carboxyl, hydroxyl, biotin, avidin, streptavidin, substituted silyl, and combinations thereof;

3-nitropyrrole, 5-bromouracil, 5-iodouracil, or 2,6-diaminopurine, or a nucleobase of 4-acetylcytidine; 5-(carboxyhydroxylmethyl)uridine; 2'-O-methylcytidine; 5-carboxymethylaminomethyl-2-thiouridine; 5-carboxymethylaminomethyluridine; dihydrouridine; 2'-O-methylpseudouridine; beta,D-galactosylqueosine; 2'-O-methylguanosine; N6-isopentenyladenosine; 1-methyladenosine; 1-methylpseudouridine; 1-methylguanosine; 1-methylinosine; 2,2-dimethylguanosine; 2-methyladenosine; 2-methylguanosine; N7-methylguanosine; 3-methyl-cytidine; 5-methylcytidine; N6-methyladenosine; 7-methylguanosine; 5-methylaminoethyluridine; 5-methoxyaminomethyl-2-thiouridine; beta,D-mannosylqueosine; 5-methoxycarbonylmethyluridine; 5-methoxyuridine; 2-methylthio-N6-isopentenyladenosine; N-((9-beta,D-ribofuranosyl-2-methylthiopurine-6-yl)carbamoyl)threonine; N-((9-beta,D-ribofuranosylpurine-6-yl)-N-methylcarbamoyl) threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; or 2'-O-methyluridine; and heteroaryl or heterocyclyl optionally substituted with one or more groups independently selected from acyl, halogen, amino, azide, alkyl, alkenyl, alkynyl, aryl, heteroalkyl, heteroalkenyl, heteroalkynyl, heterocyclyl, heteroaryl, carboxyl, hydroxyl, biotin, avidin, streptavidin, substituted silyl, and combinations thereof;

each instance of X is H or —OCH$_2$CH$_2$S—S(O)$_2$R$_{10}$, —OCH$_2$CH$_2$S—SCH$_2$CH$_2$OH, —OCH$_2$CH$_2$CO$_2$H,

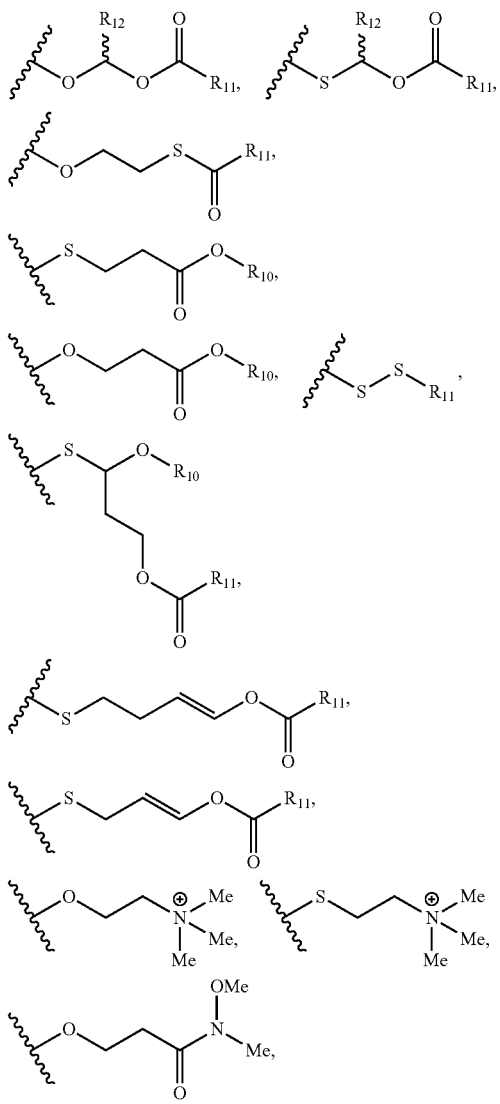

-continued

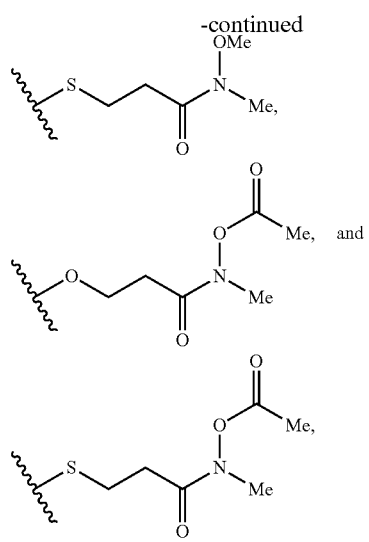

wherein at least 25% of X moieties present in the oligonucleotide are not H;

wherein $R_{10}$ is an alkyl group having 1 to 4 carbon atoms; $R_{11}$ is alkyl, aryl, heteroaryl, heterocyclyl, or cycloalkyl; and $R_{12}$ is hydrogen or alkyl;

$R^3$ is hydrogen, a blocking group, a linking moiety connected to a solid support or a linking moiety connected to a nucleic acid;

n is an integer of 10 to about 200; and wherein the composition is stereodefined in that each X-phosphonate moiety is more than 98% diastereomerically pure within the composition.

2. The composition of claim 1 wherein the diastereomeric purity is determined by $^{31}P$ NMR spectroscopy or reverse-phase HPLC.

3. The composition of claim 1 wherein each X-phosphonate moiety has an $R_P$ configuration.

4. The composition of claim 1 wherein each X-phosphonate moiety has an $S_P$ configuration.

5. The composition of claim 1, wherein at least 90% of the X moieties of the oligonucleotide are independently selected from —OCH$_2$CH$_2$S—S(O)$_2$R$_{10}$, —OCH$_2$CH$_2$S—SCH$_2$CH$_2$OH, —OCH$_2$CH$_2$CO$_2$H,

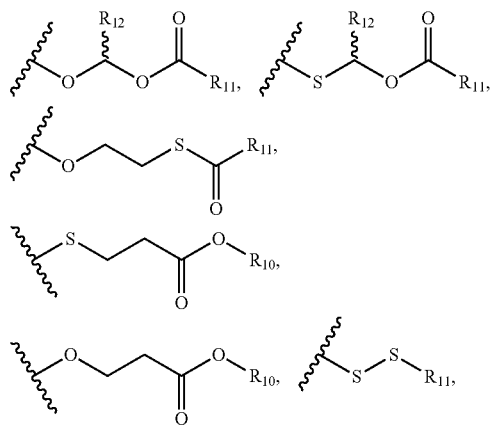

-continued

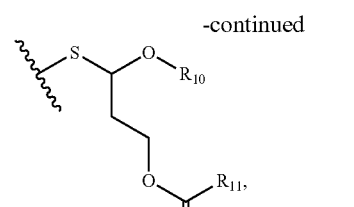

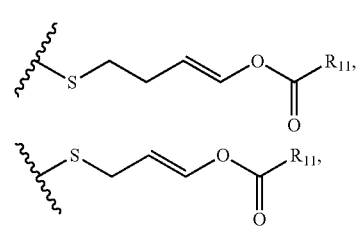

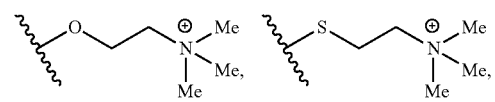

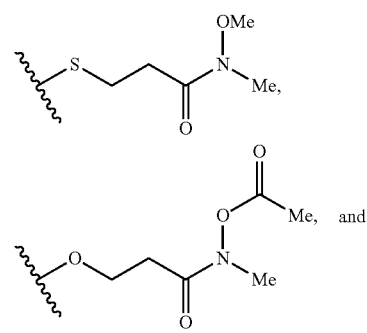

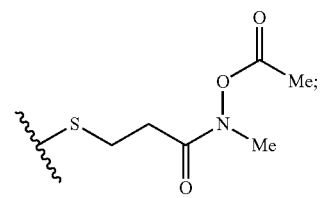

wherein $R_{10}$ is an alkyl group having 1 to 4 carbon atoms; $R_{11}$ is alkyl, aryl, heteroaryl, heterocyclyl, or cycloalkyl; and $R_{12}$ is hydrogen or alkyl.

6. The composition of claim 1, wherein each instance of X is independently selected from —OCH$_2$CH$_2$S—S(O)$_2$R$_{10}$, —OCH$_2$CH$_2$S—SCH$_2$CH$_2$OH, —OCH$_2$CH$_2$CO$_2$H,

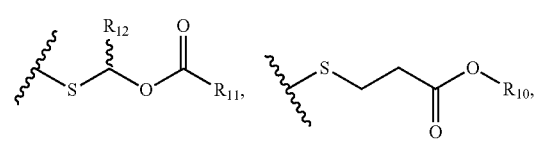

-continued

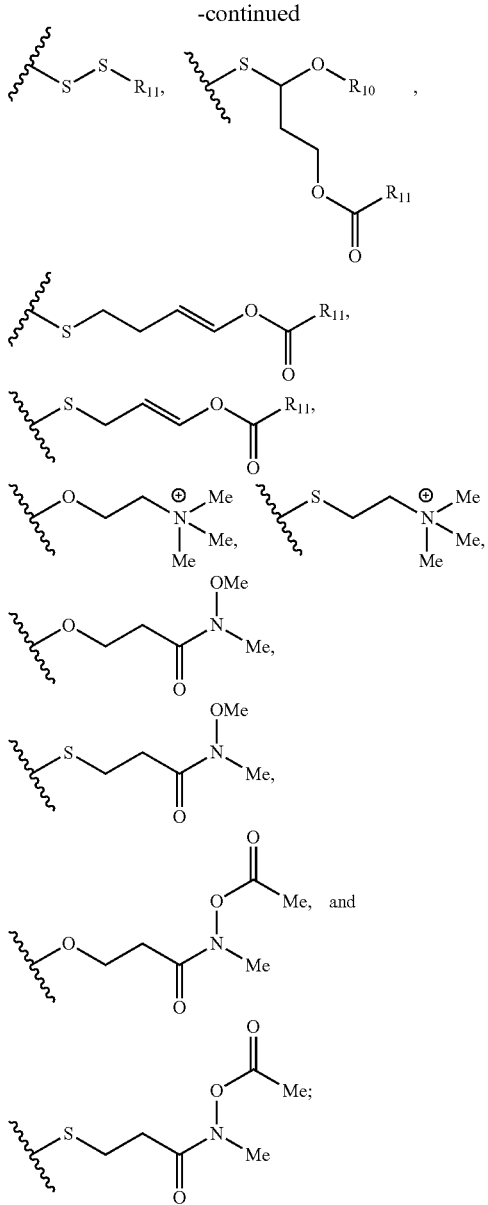

wherein $R_{10}$ is an alkyl group having 1 to 4 carbon atoms; $R_{11}$ is alkyl, aryl, heteroaryl, heterocyclyl, or cycloalkyl; and $R_{12}$ is hydrogen or alkyl.

7. The composition of claim 1, wherein $R_{10}$ is methyl.

8. The composition of claim 1, wherein $R_{11}$ is methyl.

9. The composition of claim 1, wherein $R_{12}$ is methyl.

10. The composition of claim 1, wherein n is an integer of 15 to about 200.

11. The composition of claim 1, wherein n is an integer of 20 to about 200.

12. The composition of claim 1, wherein each instance of Ba is independently a blocked or unblocked adenine, cytosine, guanine, thymine, uracil or 5-methylcytosine.

13. The composition of claim 1, wherein $Y^1$ is O.

14. The composition of claim 13, wherein:
$R^1$ is —OH, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, or —$OR^a$;
each instance of $R^2$ is independently hydrogen, —OH, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, or —$OR^b$, wherein $R^b$ is a blocking group; and
$R^3$ is hydrogen or a blocking group.

15. The composition of claim 14, wherein each instance of Ba is independently a blocked or unblocked adenine, cytosine, guanine, thymine, uracil or 5-methylcytosine.

16. The composition of claim 1, wherein each instance of $R^d$ is independently hydrogen, alkyl, alkenyl, alkynyl, aryl, or acyl.

17. The composition of claim 16, wherein each instance of Ba is independently a blocked or unblocked adenine, cytosine, guanine, thymine, uracil or 5-methylcytosine.

18. The composition of claim 1, wherein $Y^2$ is O or S.

19. The composition of claim 18, wherein each instance of Ba is independently a blocked or unblocked adenine, cytosine, guanine, thymine, uracil or 5-methylcytosine.

20. A pharmaceutical composition comprising a therapeutically effective amount of a composition of claim 1 and a pharmaceutically acceptable excipient.

21. The composition of claim 1, wherein:
$R^1$ is —OH or —$OR^a$;
each instance of $R^2$ is independently hydrogen, —OH, halogen, or —$OR^b$; and
$R^3$ is hydrogen or a blocking group;
each instance of Ba is independently adenine, cytosine, guanine, thymine, uracil or 5-methylcytosine.

22. A pharmaceutical composition comprising a therapeutically effective amount of a composition of claim 15 and a pharmaceutically acceptable excipient.

23. A pharmaceutical composition comprising a therapeutically effective amount of a composition of claim 21 and a pharmaceutically acceptable excipient.

* * * * *